(12) United States Patent
Bower et al.

(10) Patent No.: US 7,449,317 B2
(45) Date of Patent: Nov. 11, 2008

(54) PHYTASE ENZYMES, NUCLEIC ACID SEQUENCES ENCODING PHYTASE ENZYMES AND VECTORS AND HOST CELLS INCORPORATING SAME

(75) Inventors: Benjamin Bower, Newark, CA (US); Frits Goedegebuur, Vlaardingen (NL); Kathleen A. Clarkson, San Francisco, CA (US); Scott D. Power, San Bruno, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 11/698,523

(22) Filed: Jan. 26, 2007

(65) Prior Publication Data

US 2007/0207525 A1   Sep. 6, 2007

Related U.S. Application Data

(62) Division of application No. 10/492,782, filed as application No. PCT/US02/34256 on Oct. 25, 2002, now Pat. No. 7,220,445.

(60) Provisional application No. 60/339,552, filed on Oct. 26, 2001.

(51) Int. Cl.
  C12N 9/16 (2006.01)
  C12N 1/20 (2006.01)
  C12N 15/00 (2006.01)
  C07H 21/04 (2006.01)

(52) U.S. Cl. ............... 435/196; 435/252.3; 435/320.1; 536/23.2

(58) Field of Classification Search .............. 436/196, 436/252.3, 320.1; 536/23.2
See application file for complete search history.

(56) References Cited

U.S. PATENT DOCUMENTS

| 4,469,863 A | 9/1984 | Ts'o et al. |
| 4,683,202 A | 7/1987 | Mullis |
| 5,034,506 A | 7/1991 | Summerton et al. |
| 5,216,141 A | 6/1993 | Benner |
| 5,235,033 A | 8/1993 | Summerton et al. |
| 5,268,526 A | 12/1993 | Hershey et al. |
| 5,386,023 A | 1/1995 | Sanghvi et al. |
| 5,510,471 A | 4/1996 | Lebrun et al. |
| 5,538,880 A | 7/1996 | Lundquist et al. |
| 5,571,706 A | 11/1996 | Baker et al. |
| 5,589,615 A | 12/1996 | De Clercq et al. |
| 5,597,945 A | 1/1997 | Jaynes et al. |
| 5,602,240 A | 2/1997 | De Mesmaeker et al. |
| 5,610,049 A | 3/1997 | Clark |
| 5,637,684 A | 6/1997 | Cook et al. |
| 5,644,048 A | 7/1997 | Yau |
| 5,677,175 A | 10/1997 | Hodges et al. |
| 5,747,285 A | 5/1998 | Bovenberg et al. |
| 5,750,386 A | 5/1998 | Conkling et al. |
| 5,750,871 A | 5/1998 | Moloney et al. |
| 5,773,269 A | 6/1998 | Somers et al. |
| 5,780,708 A | 7/1998 | Lundquist et al. |
| 5,907,080 A | 5/1999 | Karatzas et al. |
| 5,942,435 A | 8/1999 | Wheeler |
| 5,998,697 A | 12/1999 | Devlin |
| 6,066,725 A | 5/2000 | DeBoer et al. |
| 6,153,418 A | 11/2000 | Lehmann |
| 6,262,336 B1 | 7/2001 | Lubon et al. |
| 6,268,545 B1 | 7/2001 | Houdebine et al. |
| 6,271,436 B1 | 8/2001 | Piedrahita et al. |
| 6,475,762 B1 | 11/2002 | Stafford et al. |
| 6,720,174 B1 * | 4/2004 | Lehmann ............... 435/196 |

FOREIGN PATENT DOCUMENTS

| EP | 0684313 A2 | 11/1995 |
| EP | 0 897 010 A | 2/1999 |
| EP | 0420358 B1 | 5/1999 |
| JP | 6-38745 | 3/1992 |
| WO | WO 01/12792 A1 | 2/2001 |

OTHER PUBLICATIONS

Sequence search alignment between Applicant's SEQ ID No. 8 and SEQ ID No. 12 from USP 6,720,174-B1.*
Al-Batshan, H.A. et al., "Duodenal Calcium Uptake, Femur Ash, and Eggshell Quality Decline with Age and Increase Following Molt,", Poultry Science, vol. 73, No. 10, pp. 1590-1596, 1994.
Altschul, Stephen F. et al., "Basic Local Alignment Search Tool," J. Mol. Biol., vol. 215, pp. 403-410, 1990.
Altschul, Stephen F. et al., "Gapped BLAST and PSI-BLAST: a new generation of protein database search programs," Nucleic Acids Research, vol. 25, No. 17, pp. 3389-3402, 1997.
Aplin, John D. et al., "Preparation, Properties, and Applications of Carbohydrate Conjugates of Proteins and Lipids," Crit. Rev. Biochem., pp. 259-306, May, 1981.
Ausubel et al., *Current Protocols in Molecular Biology*, 3rd, ed., John Wiley & Sons, Inc. Book not sent.
Beaton, Graham et al., *Synthesis of oligonucleotide phosphorodithioates and Analogues, A Practical Approach*, F. Eckstein, ed., Oxford University Press, pp. 109-134, 1991.
Beaucage, Serge et al. "The Functionalization of Oligonucleotides via Phosphoramidite Derivatives," Tetrahedron Report No. 329, Tetrahedron, vol. 49, No. 10, pp. 1925-1963, 1993.
Bennett & Lasure, *More Gene Manipulations in Fungi*, Academic Press, San Diego, pp. 70-76, 1991.
Benton, W. et al., "Screening Agt Recombinant Clones by Hybridization to Single Plaques in situ," Science, vol. 196, pp. 180-182, 1977.

(Continued)

*Primary Examiner*—Tekchand Saidha
(74) *Attorney, Agent, or Firm*—Danisco A/S, Genencor Division

(57) ABSTRACT

DNA is provided which encodes an enzyme having phytase activity isolated from *Penicillium, Fusarium, Humicola* and *Emericella*. Also provided for is a method of isolating DNA encoding an enzyme having phytase activity from organisms which possess such DNA, transformation of the DNA into a suitable host organism, expression of the transformed DNA and the use of the expressed phytase protein in feed as a supplement.

12 Claims, 28 Drawing Sheets

OTHER PUBLICATIONS

Birnboim, H.C. et al., "A rapid alkaline extraction for screening recombinant plasmid DNA," Nucleic Acids Research, vol. 7, No. 6, pp. 1513-1523, 1979.

Botstein, David et al., "Strategies and Applications of in Vitro Mutagenesis," Science, vol. 229, No. 4719, pp. 1193-1201, Sep. 20, 1985.

Brill, Wolfgang K. D., et al., "Synthesis of Oligodeoxynucleoside Phosphorodithioates via Thioamidtes," J. A. Chem. Soc., vol. 111, pp. 2321-2322, 1989.

Brisson, N. et al., "Expression of a bactrial gene in plants by using a viral vector," Nature, vol. 310, pp. 511-514, Aug. 9, 1984.

Brogile, Richard et al., "Light-Regulated Expression of a Pea Ribulose-1,5-Bisphosphate Carboxylase Small subunit Gene in Transformed Plant Cells," Science, vol. 224, pp. 838-843.

Cadwell, R.C., et al., "Randomization of Genes by PCR Mutagenesis," PCR Methods ad Applications, vol. 2, pp. 28-33, 1992.

Carlsson, Christina et al., "Screening for genetic mutations," Nature, vol. 380, pp. 207, Mar. 21, 1996.

Clunies, M. et al., "Effect of dietary calcium level on plasma proteins and calcium flux occuring during a 24 h ovulatory cycle," Canadian Journal on Animal Science, vol. 75, No. 3, pp. 439-444, 1995.

Committee on Food Chemicals Codex, Institute of Medicine, Food Chemicals Codex, 4th ed., National Academy Press, Washington, D.C., 1996.

Coruzzi, Gloria et al., "Tissue-specific and light-regulated expression of a pea nuclear gene encoding the small subunit of ribulose-1, 5-biphosphate carboxylase," The EMBO Journal, vol. 3, No. 8, pp. 1671-1679, 1984.

Creighton, T. E., *Proteins: Structure and Molecular Principles*, W. H. Freeman and Company, San Francisco, pp. 79-86, 1983.

Cromwell, G.L. et al., "Efficacy of Phytase in Improving the Bioavailability of Phosphorus in Soybean meal and Corn-Soybean Meal Diets for Pigs," J. Anim. Sci., vol. 71, pp. 1831-1840.

Damron, B. L. et al., "Calcium Supplementation of Hen Drinking Water," Poultry Science, vol. 74, No. 5, pp. 784-787, 1995.

Dayhoff, M. O. et al., "A Model of Evolutionary Change in Proteins," *Atlas of Protein Sequence and Structure*, vol. 5, suppl. 3, Dayhoff, M. O. ed., Natl. Biomed Res. Foundation, Washington, D.C., vol. 5, suppl. 3, pp. 345-352.

De Groot, Marcel et al., "Agrobacterium tumefaciens-mediated transformation of filamentous fungi," Nature Biotechnology, vol. 16, pp. 839-842, 1998.

De Mesmaeker, Alain et al., Bioorganic & Medicinal Chemistry Letters, vol. 4, No. 3, pp. 395-398, 1994.

Dempcy, Robert O. et al., "Synthesis of a thymidyl pentamer of deoyribonucleic guanidine and binding studies with DNA homopolynucleotides," Proc. Natl. Acad. Sci., USA, vol. 92, pp. 6097-6101, 1995.

Deutscher, Murray P., "Rethinking Your Purification Procedure," *Methods in Enzymology*, Academic Press, vol. 182, pp. 779-780, 1990.

Dieffenbach, C. W. et al., PCR Primer, a Laboratory Manual, Cold Spring Harbor Press, Plainview, N.Y. (1995) Book not sent.

Eckert, Kristin A. et al., "DNA Polymerase Fidelity and the Polymerase Chain Reaction," PCR Methods and Applications, Cold Spring Harbor Laboratory Press, pp. 17-24-, 1991.

Edge, Albert S. et al., "Deglycosylation of Glycoproteins by Trifluoromethanesulfonic Acid," Analytical Biochemistry, vol. 118, pp. 131-137, 1981.

Egholm, Michael et al., "Peptide Nucleic Acids (PNA). Oligonecleotide Analogues with an Achiral Peptide Backbone," J. A. Chem. Soc., vol. 114, pp. 1895-1897, 1992.

Egholm, Michael et al., "PNA hybridizes to complementary oligonucleotides obeying the Watson-Crick hydrogen-bonding rules," Nature, vol. 365, pp. 566-568, Oct. 7, 1993.

Ehrlich, Kenneth C. et al., "Identification and cloning of a second phytase gene *(phyB)*, from *Aspergillus niger (ficuum)*," Biochemical and Biophysical Research Communications, vol. 195, No. 1, pp. 53-57, Aug. 31, 1993.

Ehrlich, Kenneth C. et al., "An Acid Phosphatase From *Aspergillus ficuum* has Homology to *Penicillium chrysogenum* PHOA, " Biochemical and Biophysical Research Communications, vol. 1, pp. 63-68, 1994.

Elander, R. P., Microbial Screening, Selection and Strain Improvement, *Basic Biology*, Academic Press, Harcourt, Brace Jovanovich, Pub., Bulock, John et al. Ed., New York, pp. 217-251, 1987.

Evan, Gerard I. et al., "Isolation of Monoclonal Antibodies Specific for Human c-myc Proto-Oncogene Product," Molecular and Cellular Biology, vol. 5, No. 12, pp. 3610-3616, Dec., 1985.

Field, Jeffrey et al., "Purifcation of a RAS-Responsive Adenylyl Cyclase Complex from Saccharomyces cerevisiae by Use of an Epitope Addition Method," Molecular and Cellular Biology, vol. 8, No. 5, pp. 2159-2165, May, 1988.

Finkelstein, David B. et al., "Biotechnology of Filamentous Fungi, technology and Products," Butterworth-Heinemann, David Finkelstein, ed., pp. 113-156, 1992.

Fiske, Cyrus H. et al., "The Colorimetric Determination of Phosphorus," The Journal of Biological Chemistry, vol. 66, No. 2, pp. 375-392, 1925.

Fungaro, Maria H. P. et al., "Transformation of Aspergillus nidulans by microprojectile bombardment on intact conidia," FEMS Microbiology Letters, vol. 125, pp. 293-298, 1995.

Gao, Xiaolian et al., "Unusual conformation of a 3'-thioformacetal linkage in a DNA duplex," Journal of Biomolecular NMR, vol. 4, pp. 17-34, 1994.

Gelvin, Stanton B. et al., "vir Genes Influence Conjugal Transfer of the Ti Plasmid of *Agrobacterium tumefaciens*," Journal of Bacteriology, vol. 172, No. 3, pp. 1600-1608, 1990.

Gish, Warren et al., "Identification of protein coding regions by database similarity search," Nature Genetics, vol. 3, pp. 266-272, 1993.

Glover, D. M. et al., DNA Cloning 1: A Practicle Approach, Oxford University Press, Oxford, 1995.

Glover, D. M. et al., DNA Cloning 2: A Practicle Approach, Oxford University Press, Oxford, 1995.

Grunstein, Michael et al., "Colony hybridication: A method for the isolation of cloned dans that contain a specific gene," Nat. Acad. Sci, USA, vol. 72, No. 10, pp. 3961-3965, 1975.

Hale & Markman, The Harper Collins Dictionary of Biology, Harper Perennial, NY, 1991.

Henikoff, Steven et al., "Amino acid substitution matrices from protein blocks," Proc. Natl. Acad. Sci., USA, vol. 89, pp. 10915-10919, 1992.

Higgins, Desmond G. et al., "Clustal V: improved software for mutiple sequence alignment," Comput. Appl. Biosci., vol. 8, No. 2, pp. 189-191, 1992.

Hopp, Thomas P. et al., "Short Polypeptide Marker Sequence Useful for Recombinant Protein Identification and Purification," Bio/technology, vol. 6, pp. 1204-1210, 1988.

Jenkins, Gareth N. et al., "The Biosynthesis of Carbocyclic Nucleosides," Chemical Society Reviews, pp. 169-176, 1995.

Jeroch, Von H. et al., "Zur Wirksamkeit Mikrobieller Phytase Zu Legehennerationen auf Mais-bzw. Weizenbasis," Bodenkultur, vol. 45, No. 4, pp. 361-368, 1994.

Jung, Paul M. et al., "Hybridization of Alternating Cationic/Anionic Olgonucleotides to RNA Segments," Nucleosides & Nucleotides, vol. 13, Nos. 6 & 7, pp. 1597-1605, 1994.

Karlin, Samuel et al., "Applications and statistics for multiple high-scoring segments in molecular sequences," Proc. Natl. Acad. Sci., USA, vol. 90, pp. 5873-5877, 1993.

Kerovuo, Janne et al., "Isolation, Characterization, Molecular Gene Cloning, and Sequencing of a Novel Phytase from Bacillus subtilis," Applied and Environemental Microbiology, vol. 64, No. 6, pp. 2079-2085, 1998.

Kornegay, E. T. et al., "Response of broilers to graded levels of Microbial phytase added to maize-soyabean-meal-based diets containing three levels of non-phytate posporus," British Journal of Nutrition, vol. 75, pp. 839-852, 1996.

Letsinger, Robert L. et al., "Cationic Oligonucleotides," J. Am. Chem. Soc. vol. 110, pp. 4470-4471, 1988.

Letsinger, Robert L. et al., "Effects of pendent groups at phosphorus on binding properties of d-ApA analogues," Nucleic Acids Research, vol. 14, No. 8, pp. 3487-3499, 1986.

Letsinger, Robert et al., "Phosphoramidate Analogs of Oligonucleotides," J. Org. Chem., vol. 35, No. 11, pp. 3800-3803, 1970.

Leung, David W. et al., "A Method for Random Mutagenesis of a Defined DNASegment Using a Modified Polymerase Chain Reaction," Technique-A Journal of Methods in Cell and Molecular Biology, vol. 1, No. 1, pp. 11-15, 1989.

Lutz-Geyermuth, Carol et al., "Quantitative determination that one of two potential RNA-binding domains of the A protein component of the U1 small nuclear ribonucleoprotein complex binds with high affinity to stem-loop II of U1 RNA," Proc. Natl. Acad. Sci., USA, vol. 87, pp. 6393-6397, 1990.

Madden, Thomas L. et al., "Applications of Network BLAST Server," Methods in Enzymology, Academic Press, vol. 266, pp. 131-141, 1996.

Mag, Matthias et al., "Synthesis and selective cleavage of an oligodeoxynucleotide containing a bridged internucleotide 5'-phosphorothioate linkage," Nucleic Acids Research, vol. 19, No. 7, pp. 1437-1441, 1991.

Martin, George et al., "GAP Domains Responsible for RAS p21-Dependent Inhibition of Muscarinic Atrial $K^+$Channel Currents," Science, vol. 255, pp. 192-194, 1992.

Meier, Chris et al., "Peptide Nucleic Acids (PNAs)-Unusual Properties of Nonionic Oligonucleotide Analogues," Angew. Chem. Into. Ed. Engl., vol. 31, No. 8, pp. 1008-1010, 1992.

The Merck Veterinary Manual, Merck & Co., Inc. Rahway, N.J., 7th ed., pp. 1268-1269, 1991.

Mitchell, David B. et al., "The phytase subfamily of histidine acid phosphatases : isolation of genes for two novel phytases from the fungi Aspergillus terreus and Myceliophthrora thermophila, " Microbiology, vol. 143, pp. 245-252, 1997.

Mullaney, E.J. et al., "Positive identification of a lamba gt11 clone containing a region of fungal phytase gene by immunoprobe and sequence verification," Applied Microbiology Biotechnology, vol. 35, 611-614, 1991.

Murry, Lynn, McGraw Hill Yearbook of Science and Technology, McGraw Hill, New york, NY, pp. 191-196, 1992.

Myers, Richmond M. et al., "A General Method for Saturation Mutagenesis of Cloned DNA Fragments," Science vol. 229, pp. 242-247, 1985.

Needleman, Saul B. et al., "A General Method Applicable to the Search for Similarities in the Amino Acid Sequence of Two Proteins," J. Mol. Biol. vol. 48, pp. 443-43, 1970.

Oakley, Berl R. et al., "Cloning, mapping and molecular analysis of the pyrG (orotidine-5'-phosphate decarboxylase) gene of Aspergillus nidulans," Gene, vol. 61, pp. 385-399, 1987.

Paborsky, Lisa R. et al., "Mammalian cell transient expression of tissue factor for the production of antigene," Protein Engineering, vol. 3, No. 6, pp. 547-553, 1990.

Pasamontes, Luis et al., "Cloning of the phytases from Emericella nidulans and the thermophilic fungus Talaromyces thermophilus, " Biochemica et Biophysica Acta 1353, pp. 217-223, 1997.

Pasamontes, Luis et al., "Gene Cloning, Purification, and Characterization of a Heat-Stable Phytase from the Fungus Aspergillus fumigatus, " Applied and Environmental Microbiology, vol. 63, No. 5, pp. 1696-1700, 1997.

Pasamontes, Luis et al., "Gene Cloning, Purification, and Characterization of a Heat-Stable Phytase from the Fungus Aspergillus fumigatus, " Applied and Environmental Microbiology, vol. 63, No. 5, pp. 1696-1700, 1997.

Pauwels, R. et al., "Biological Activity of New 2-5A Analogues," Chemica Scripta, vol. 26, pp. 141-145, 1986.

Pearson, William R. et al., "improved tools for biological sequence comparison, " Proc. Natl. Acad. Sci. USA, vol. 85, pp. 2444-2448, 1988.

Piddington, C.S. et al., "The cloning and sequencing of the genes encoding phytase (phy) and pH 2.5-optimum acid phosphate (aph) from Aspergillus niger var. awamori," Gene, vol. 133, pp. 55-62, 1993.

Power V. K. et al., "Purification and Properties of Phytate-Specific Phosphatase from Bacillus subtills, " Journal of Bacteriology, vol. 151, No. 3, pp. 1102-1108, 1982.

Rawls, Rebecca L., "Optimistic about Antisense," C&E News, pp. 35-39, Jun. 2, 1997.

Rogers, Stephen G. et al., "Gene Transfer in Plants: Production of Transformed Plants Using Ti Plasmid Vectors," Methods for Plants Molecular Biology, Academic Press, New York, NY pp. 421-463, 1988.

Roland, D. A., Sr. et al., "Influence of Calcium and Environmental Temperature on Performance of First-Cycle (Phase 1) Commercial Leghorns," Poultry Science, vol. 75, No. 1, pp. 62-68, 1996.

Sambrook J., et al., et al., Molecular Cloning, A Laboratory Manual, $2^{nd}$ ed., Cold Spring Harbor Press, 1989.

Sambrook J. et al., et al., Molecular Cloning, A Laboratory Manual, 3rd ed., Cold Spring Harbor Press, 1989.

Sanchez, Olivia et al., "Efficient Transformation of Aspergillus nidulans electroporation of Germinated Conidia," Fungal Genetics Newsletter, vol. 43, pp. 48-51, 1996.

Sanger, F. et al., "DNA sequencing with chain-terminating inhibitors," Proc. Natl. Acad. Sci. USA, vol. 74, No. 12, pp. 5463-5467, 1977.

Sanghvi, Yogesh S. et al., ed., Carbohydrate Modifications in Antisense Research, ACS Symposium Series 580, Chapters 2, 3, 6 and 7, American Chemical Society, Washington, DC, 1994.

Sawai, Hiroaki, "Synthesis and Proteins of Oligoadenylic Acids Containing 2'-5' Phosphoramide Linkage," Chem. Lett., pp. 805-808, 1984.

Schwartz, R. M. et al., "Matrices for Detecting Distant Relationships," Atlas of Protein Sequence and Structure, Dayoff, M., ed., vol. 5, Supplemental 3, 1978.

Scopes, Protein Purification: Principles and Practice, Springer-Verlag, New York, 1982.

Segueilha, L. et al., "Purification and Properties of the Phytase from Schwanniomyces castellii," Journal of Fermentation and Bioengineering, vol. 74, No. 1, pp. 7-11, 1992.

Shimizu, Mikio, "Purification and Characterization of Phytase from Bacillus subtilis (natto) N-77," Biosci. Biotech. Biochem., vol. 56, No. 8, pp. 1266-1269, 1992.

Singleton et al., Dictionary of Microbiology and Molecular Biology, $2^{nd}$ ed., John Wiley and sons, New York, 1994.

Skinner, Richard H. et al., "Use of the Glu-Glu-Phe C-terminal Epitope for Rapid Purification of the Catalytic Domain of Normal and Mutant ras GTPase-activating Proteins," Journal of Biological Chemistry, vol. 266, No. 22, pp. 14163-14166, 1991.

Smith, Temple F. et al., "Comparison of Biosequences," Advances in Applied Mathematics, vol. 2, pp. 482-489, 1981.

Sojar, Hakimuddin T. et al., "A Chemical Method for the Deglycosylation of Proteins," Archives of Biochemistry and Biophysics, vol. 259, No. 1, pp. 52-57, 1987.

Sprinzl, Mathias et al., "Enzymatic Incorporation of ATP and CTP analogues into the 3' End of tRNA," Eur. J. Biochem., vol. 81, pp. 579-589, 1977.

Takamatsu, Nobuhiko et al., "Expression of bacterial chloramphenicol acetyltransferase gene in tobacco plants mediated by TMV-RNA," The EMBO Journal, vol. 6, No. 2, pp. 307-311, 1987.

Tseng, V.-H. et al., "Isolation and Characterization of a Novel Phytase from Penicillium simplicissimum," Folia Microbiol., vol. 45, No. 2, pp. 121-127, 2000.

Thotakura, Nagaware R. et al., "Enzymatic Deglycosylation of Glycoproteins," Methods in Enzymology, vol. 138, Complex Carbohydrates, Part E, Victor Ginsburg, ed., Academic Press, Inc., 1987.

Ullah, Abul, H. J. et al., "Extracellular Phytase (E. C. 3.1.3.8) from Aspergillus Ficuum NRRL 315: Purification and Characterization," Preparative Biochemistry, vol. 17, No 1, pp. 63-91, 1987.

Van Hartingsveldt, Wim et al., "Cloning, characterization and overexpression of the phytase-encoding gene (phyA) of Aspergillus niger," Gene, vol. 127, pp. 87-94, 1993.

Von Kiedrowski, Gunter et al., "Paraboloic Growth of a Self-Replicating Hexadeoxynucleotide Bearing a 3'-5-Phosphoamidate Linkage," Angew. Chem. Int. Ed. Engl., vol. 30, No. 4, pp. 423-428, 1991.

Weber, Kristy L. et al., "Rapid Acquisition of Unknown DNA Sequence Adjacent to a Known Segment by Multiplex Restriction Site PCR," BioTechniques, vol. 25, No. 3, pp. 415-419, 1998.

Weidner, Gerhard et al., "Development of a homologous transformation system for the human pathogenic fungus *Aspergillus fumigatus* based on the pyrG gene encoding orotidine 5'-monophosphate decarboxylase," Curr. Genet., vol. 33, pp. 378-385, 1998.

Winter, Jill et al., "The Expression of Heat Shock Protein and Cognate Genes During Plant Development," *Heat Shock and Development*, Hightower, L. ed., Springer-Verlag, pp. 85-105, 1991.

Yamada, Koichi et al., "Phytase from *Aspergillus terreus*," Agr. Biol. Chem., vol. 32, No. 10, pp. 1275-1282, 1968.

\* cited by examiner

FIG. 1

TGCACTACTGTCGATGGCGGTTACCAATGCAATTCCGAGCTCTCACACAAGTGGGGCCAGTATTCGCCCTATTTCTCTCT
TTCCGAAGAATCATCCATCTCGAATGAGGTACCTCATGATTGTCAGATCACTTTTGCTCAAGTGATCTCCCGTCATGGTG
CTCGATTCCCGTCCGCGAAGAAGAGCAAGGTATATGCCAAGCTCATTGAAAATATCCAAGCGAACGCGACTGCATACAAT
GGCAACACGAAGTTCCTCCGCTCATACAAGTACACCATGGGCGGTGATGATTTGGTACCCTTCGGAGTGAACCAGACGGT
GGACTCGGGGACCAAATTCTACCAGCGCTACGAGGCGTTGGCGAAGAAAGCTGTGCCCTTCATTCGGTCATCTGACTCAG
GGCGGGTTGTGGCTTCAGGCGTGAACTTTATCAAGGGATTCCAGCAGGCAAAGTTGGATGATAAAAATGCCAATCACCGT
CAGCCAAGCCCCAAAACCAACGTCATCATCTCAGAAGAGTCTGGCACCAACAACACTCTGAACCACAGCGAGATCTGTCC
TAAGTTCGAAGACAATGAGCTGGGCGACAAGGTCGAAGAAAAATACATGAAAATCTTTGTGCCGCCCATCCGAGCTCGTC
TCGAGGCCGATCTCCCTGGCGTTAAACTTGAAGACATCGATGTTGTCAGTCTGATGGACATCTGCCCTTTCGAGACAGTG
TCTTCAAGTGACGACGCAGCCGAGCTATCTCCATTCTGCGACCTCTTCACCCCGACCGAATGGAGCCAATATGACTACCT
CCAGTCGTTAAGCAAGTACTATGGTTATGGCGCCGGCAATCCTCTCGGCCCGACCCAGGGTGTCGGTTTCGTAAACGAAC
TGATTGCCCGACTCACTCGCCACCCAGTGAGAGACCACACAAGCACAAACCGTGCGCTCGATGCCCCGGCGCTGCGACA
TTCCCCCTCAACTACACCATGTATGCCGACTTCACGCATGACAACGGAATGATCCCGTTCTTCTTTGCTTTGGGGCTGTA
CAACGGCACCGCTCCACTCTCGCTCACCCACGTCCAGTCTCCTAGCCAAACAGACGGGTTCTCATCCGCCTGGACAGTCC
CCTTCGGTGCTCGGGCTTATGTTGAGATGATGCAATGTCGTCGGGAACCTGAGCCGCTCGTGCGAGTCCTCGTTAATGAC
CGTGTTATTCCGCTGCACGGTTGCCCGGTGGATAAACTTGGCCGTTGTCGCCGTCGTGATTTCGTGAAAGGGCTTACTTT
CGCACGCTCTGGCGGCGACTGGGCCAGGTGTTATAAA

FIG. 2

CTTVDGGYQCNSELSHKWGQYSPYFSLSEESSISNEVPHDCQITFAQVISRHGARFPSAKKSKVYAKLIENIQANATAYN
GNTKFLRSYKYTMGGDDLVPFGVNQTVDSGTKFYQRYEALAKKAVPFIRSSDSGRVVASGVNFIKGFQQAKLDDKNANHR
QPSPKTNVIISEESGTNNTLNHSEICPKFEDNELGDKVEEKYMKIFVPPIRARLEADLPGVKLEDIDVVSLMDICPFETV
SSSDDAAELSPFCDLFTPTEWSQYDYLQSLSKYYGYGAGNPLGPTQGVGFVNELIARLTRHPVRDHTSTNRALDAPGAAT
FPLNYTMYADFTHDNGMIPFFFALGLYNGTAPLSLTHVQSPSQTDGFSSAWTVPFGARAYVEMMQCRREPEPLVRVLVND
RVIPLHGCPVDKLGRCRRRDFVKGLTFARSGGDWARCYK

FIG. 3

ASRNQSTCTTVDGGYQCNSELSHKWGQYSPYFSLSEESSISNEVPHDCQITFAQVISRHGARFPSAKKSKVYAKLIENIQ
ANATAYNGNTKFLRSYKYTMGGDDLVPFGVNQTVDSGTKFYQRYEALAKKAVPFIRSSDSGRVVASGVNFIKGFQQAKLD
DKNANHRQPSPKTNVIISEESGTNNTLNHSEICPKFEDNELGDKVEEKYMKIFVPPIRARLEADLPGVKLEDIDVVSLMD
ICPFETVSSSDDAAELSPFCDLFTPTEWSQYDYLQSLSKYYGYGAGNPLGPTQGVGFVNELIARLTRHPVRDHTSTNRAL
DAPGAATFPLNYTMYADFTHDNGMIPFFFALGLYNGTAPLSLTHVQSPSQTDGFSSAWTVPFGARAYVEMMQCRREPEPL
VRVLVNDRVIPLHGCPVDKLGRCRRRDFVKGLTFARSGGDWARCYK

FIG. 4

TGTGAGTATGACGGGAGCTGTAATGACATCTCTCGGCTCTGGGGACAGTACTCTGCATACTTCCCAATCCCGTCTGAGCT
TGATGCCTCAACACCAGACGATTGTGATGTGACTTTTGCACTCGTCTTGTCCCGCCATGGAGCCAGGTACCCAACGGACA
GCAAGTCTGCAGCATACAACGCTACCATTGCCCGCATTCAAAAGTCTGCTACCATGTACGGCAAGAACTACAAGTGGCTT
AAGGAGTATACCTACAGTCTCGGCGCTGAAGACCTGACTGAGTTTGGCCAGCGGCAGATGGTCGACTCTGGTAGGGCCTT
TTATGAGCGGTACATGAGTCTCGCTGAGAAGACTGAGCCTTTTGTTCGGGCATCGGGCTCAGATCGGGTCATCATGTCGT
CTTACAATTTTACGCAAGGCTTTTACGCATCGCGAGGAGAGTCTGGAGACGATTATACTCAGGATGTTCTTATCATCCCT
GAAGAACCTGGCATCAACAACACCATGTTGCATGGATCGTGCGCCTCATTCGAAAGCGACAGAGTTCCTAAAGACGCAGA
TGAAAAGGCCGAGGTTGCATGGGGAGCAAGATTCCTCCCCGAGATTCGAAATAGGTTGAACCACCACCTGCCAGGAGTCA
ACCTGACGCTGGAGGAAACCATCTACATGATGGACATGTGTCCGTTCCTCGCGGCTGACACACCTGATGGCGCTGGTCAC
TCGAGGTTCTGCGACCTCTTCACCAAGGCAGACTGGCGAAGTTACGACTACTACATGACTCTGAGCAAGTTCTACAAGTT
TGGCAATGGCAATGCCATGGGACCGACACAAGGTGTTGGATATGTCAACGAACTCATCTCACGCTTGACTGGGAAGCCTG
TTGACGACCACACCACGACCAACAGCACATTGGACTCATCGCCAAAGACGTTCCCTCTTGACAGGGCTCTATATGCGGAT
TTTAGCCACGACAACAGCATGGTCTCCATCTTCTCAGCACTGGGCTTGTACAACTCGACTACCCTGCTACCAAAGGACCA
TATTGTGCCCGCGATCAAGGCGCACGGCTACTCATCGACATGGGTAGTCCCCTTTGGAGCCAGAATGTACGTCGAGAAGC
TCGAGTGTGGTGCCAGCAGGAATGAAAAGAGAGACGAGTACGTGCGAGTCCTGGTCAACGACCGAGTGATGTCGCTCGAA
ACCTGCGGAGGCGACGAGTACGGGCTCTGCAGACTAGAAAACTTTGTGGAGAGTCTGTCGTTTGCCGCCTCGGGAGGAAA
CTGGGATCAATGCGGTGGA

FIG. 5

CEYDGSCNDISRLWGQYSAYFPIPSELDASTPDDCDVTFALVLSRHGARYPTDSKSAAYNATIARIQKSATMYGKNYKWL
KEYTYSLGAEDLTEFGQRQMVDSGRAFYERYMSLAEKTEPFVRASGSDRVIMSSYNFTQGFYASRGESGDDYTQDVLIIP
EEPGINNTMLHGSCASFESDRVPKDADEKAEVAWGARFLPEIRNRLNHHLPGVNLTLEETIYMMDMCPFLAADTPDGAGH
SRFCDLFTKADWRSYDYYMTLSKFYKFGNGNAMGPTQGVGYVNELISRLTGKPVDDHTTTNSTLDSSPKTFPLDRALYAD
FSHDNSMVSIFSALGLYNSTTLLPKDHIVPAIKAHGYSSTWVVPFGARMYVEKLECGASRNEKRDEYVRVLVNDRVMSLE
TCGGDEYGLCRLENFVESLSFAASGGNWDQCGG

FIG. 6

ASRNQSTCEYDGSCNDISRLWGQYSAYFPIPSELDASTPDDCDVTFALVLSRHGARYPTDSKSAAYNATIARIQKSATMY
GKNYKWLKEYTYSLGAEDLTEFGQRQMVDSGRAFYERYMSLAEKTEPFVRASGSDRVIMSSYNFTQGFYASRGESGDDYT
QDVLIIPEEPGINNTMLHGSCASFESDRVPKDADEKAEVAWGARFLPEIRNRLNHHLPGVNLTLEETIYMMDMCPFLAAD
TPDGAGHSRFCDLFTKADWRSYDYYMTLSKFYKFGNGNAMGPTQGVGYVNELISRLTGKPVDDHTTTNSTLDSSPKTFPL
DRALYADFSHDNSMVSIFSALGLYNSTTLLPKDHIVPAIKAHGYSSTWVVPFGARMYVEKLECGASRNEKRDEYVRVLVN
DRVMSLETCGGDEYGLCRLENFVESLSFAASGGNWDQCGG

FIG. 7

GCGGATTTTAGGCACGATAATAGTCTGACCTCGATATACGCTGCTCTTGGTCTGTATAACGGCACAAAGCAACTATCCAA
ATCGAGGATAGAATCGACAAACCAGACAAATGGCTATTCTGCTGGCTGGACAGTTCCATTTGGAGCAAGGGCGTATGTTG
AGATGATGCAATGCCCCTCGGGGGATGAACCTCTGATTCGAGTTCTGGTGAACGATCGCGTCAT

FIG. 8

ADFRHDNSLTSIYAALGLYNGTKQLSKSRIESTNQTNGYSAGWTVPFGARAYVEMMQCPSGDEPLIRVLVNDRV

FIG. 9

TGCGACTCTGTCGACAGAGGCTTCTGGTGCGCCGCCGACATCTCCCACTCCTGGGGACAGTACTCACCATACTTCTCCGT
CCCCTCTGACATTGACCCGGGTTTCCCCAAGGGCTGCAATGTGACGTTCGCACAGGTCCTCTCACGCCACGGCGCCCGCG
CCCCAACTACGGGCCGGGCCGCCTACTACGTCGACGTGATTGACCGCGTCCAGCGTCAGGCGACCTCGTACGGCCCCGGC
CACGCGTTCCTGCGCTCCTACCGCTACACCCTCGGCGCCAACGAGCTTACCCCGATGGGAGAGCGGCAGCTGGCGTATTC
CGGCGCAAGGTTTTACCATCGCTATCGCGAACTTGCGCGCGTCGAGGCGCCCTTCGTGCGGTCCAGTGGCGTAAGCCGCG
TTGTAGCCTCAGCTGTCAATTTCACCCAGGGCTTCCACCAGGCGCGGCTCGCCGACCGCGGCGCCACGTTGCCCCGCCA
ACACTGCCCTATGACATGGTGATCATCTCGTCAGACGACACCGCCAACAACACCTTGCACCACGGTCTCTGCACGGTCTT
CGAGGAGGGGCCCTATGCCGACATTGGCGACAAGGCGCAGAAAGAATACCTCTCCAAGTTTGTCGGTCCCATCGTGGAGC
GCATTAACGCGCAGCTGCCCGGCGCGAATCTCAACGCGACGGACATCATCGCGCTGATGGACCTGTGCCCGTTCGAGACG
GTCGCGTTCCCAGAAGGCACGAAGCTGTCGCCCTTCTGCCGGCTCTTCACGGCCGCCGAATGGCGGGCCTACGACCGGTA
CCAGGACGTCGGCAAATGGTTCGGCTACGGCCCGGGCAATCCGCTCGGCCCGACTCAGGGGGTCGGGTTCGTCAACGAGC
TGATCGCGCGGCTGTCCGGCCAGCCGGTGAGCGATGGGACCAGCACGAACCGCACGCTGGATGAGAACCCGGAGACCTTC
CCGCTCGGGAGGAGGCTGTATGCGGATTTCAGCCATGATAACGACATGGTGGGCATCCTCAGCGCCTTGGGGTTGTGGGA
CAACCATGAAGAACCTGGGAATGAAATGCCCGCTGAGGGGGAGGAGGACGACAATGGTCGGTTCTCGACTGCTAGGGCCG
TGCCGTTCGGGGCGCGGGTGTATGTCGAAAAGCTGCGGTGTGGGGATCGGAGGAGGATGAAGAAATGGTGCGCGTGTTG
GTCAATGACCGGGTGATGCCCCTTGCACAGTGCGGAGGGGACAAGAGGGGAATGTGCACCCTCAGCCGGTTCGTTGAAAG
CTTGAAGTTTGCGCGGAACAACGGGAGGTGGGACATGTGTTTTGAA

FIG. 10

CDSVDRGFWCAADISHSWGQYSPYFSVPSDIDPGFPKGCNVTFAQVLSRHGARAPTTGRAAYYVDVIDRVQRQATSYGPG
HAFLRSYRYTLGANELTPMGERQLAYSGARFYHRYRELARVEAPFVRSSGVSRVVASAVNFTQGFHQARLADRGATLPPP
TLPYDMVIISSDDTANNTLHHGLCTVFEEGPYADIGDKAQKEYLSKFVGPIVERINAQLPGANLNATDIIALMDLCPFET
VAFPEGTKLSPFCRLFTAAEWRAYDRYQDVGKWFGYGPGNPLGPTQGVGFVNELIARLSGQPVSDGTSTNRTLDENPETF
PLGRRLYADFSHDNDMVGILSALGLWDNHEEPGNEMPAEGEEDDNGRFSTARAVPFGARVYVEKLRCGGSEEDEEMVRVL
VNDRVMPLAQCGGDKRGMCTLSRFVESLKFARNNGRWDMCFE

FIG. 11

ASRNQSTCDSVDRGFWCAADISHSWGQYSPYFSVPSDIDPGFPKGCNVTFAQVLSRHGARAPTTGRAAYYVDVIDRVQRQ
ATSYGPGHAFLRSYRYTLGANELTPMGERQLAYSGARFYHRYRELARVEAPFVRSSGVSRVVASAVNFTQGFHQARLADR
GATLPPPTLPYDMVIISSDDTANNTLHHGLCTVFEEGPYADIGDKAQKEYLSKFVGPIVERINAQLPGANLNATDIIALM
DLCPFETVAFPEGTKLSPFCRLFTAAEWRAYDRYQDVGKWFGYGPGNPLGPTQGVGFVNELIARLSGQPVSDGTSTNRTL
DENPETFPLGRRLYADFSHDNDMVGILSALGLWDNHEEPGNEMPAEGEEDDNGRFSTARAVPFGARVYVEKLRCGGSEED
EEMVRVLVNDRVMPLAQCGGDKRGMCTLSRFVESLKFARNNGRWDMCFE

FIG. 12

ATGGGCGTCTCTGCTGTTCTACTTCCTTTGTATCTCCTAGCTGGGTATGCTAAGCACCGCTATCTAAGTCTGATAAGGAC
CCTCTCTGCCGAGGGCCCCTGAAGCTCGGACTGTGTGGGACTACTGATCGCTGACAATCTGTGCAGAGTCACCTCCGGAC
TGGCAGTCCCCGCCTCGAGAAATCAATCCACT

FIG. 13

MGVSAVLLPLYLLAGVTSGLAVPASRNQST

FIG. 14A

```
A. niger        1 ASRNQSSCDTVDQGYQCFSETSHLWGQYAPFFSLANESVISPEVPAGCRV 50
                  ||||||·| ||| |||| || || ||||·|:|||· || || |||   |·:
P. chrysogenum  1 ASRNQSTCTTVDGGYQCNSELSHKWGQYSPYFSLSEESSISNEVPHDCQI 50

51 TFAQVLSRHGARYPTDSKGKKYSALIEEIQQNATTFDGKYAFLKTYNYSL 100
                  |||||:||||||:|·   | | |· ||| || |||  :·|   ||:·| |·:
               51 TFAQVISRHGARFPSAKKSKVYAKLIENIQANATAYNGNTKFLRSYKYTM 100

101 GADDLTPFGEQELVNSGIKFYQRYESLTRNIVPFIRSSGSSRVIASGKKF 150
                  | ||| |||   : |·|| ||||||·|  :   ||||||| | ||:||| |
              101 GGDDLVPFGVNQTVDSGTKFYQRYEALAKKAVPFIRSSDSGRVVASGVNF 150

151 IEGFQSTKLKDPRAQPGQSSPKIDVVISEASSSNNTLDPG.TCTVFEDSE 199
                  |·|||  || |    | |||  -|:|||  | ·||||·    |  |||·|
              151 IKGFQQAKLDDKNANHRQPSPKTNVIISEESGTNNTLNHSEICPKFEDNE 200

200 LADTVEANFTATFVPSIRQRLENDLSGVTLTDTEVTYLMDMCSFDTISTS 249
                  | | ||   :   ||| || ||| || || ||  | | |  :| |||·| |:|:|·|
              201 LGDKVEEKYMKIFVPPIRARLEADLPGVKLEDIDVVSLMDICPFETVSSS 250

250 TVDTKLSPFCDLFTHDEWINYDYLQSLKKYYGHGAGNPLGPTQGVGYANE 299
                  ·|||||||||  ||  ||||||||  |||||:|||||||||||||||: ||
              251 DDAAELSPFCDLFTPTEWSQYDYLQSLSKYYGYGAGNPLGPTQGVGFVNE 300

300 LIARLTHSPVHDDTSSNHTLDS.SPATFPLNSTLYADFSHDNGIISILFA 348
                  ||||||  || | ||·| ||·       ||||||  |:||||·||||·|  ||
              301 LIARLTRHPVRDHTSTNRALDAPGAATFPLNYTMYADFTHDNGMIPFFFA 350

349 LGLYNGTKPLSTTTVENITQTDGFSSAWTVPFASRLYVEMMQCQAEQEPL 398
                  ||||||| ||| | |:·  ·||||||||||| ·| |||||||||·  | |||
              351 LGLYNGTAPLSLTHVQSPSQTDGFSSAWTVPFGARAYVEMMQCRREPEPL 400

399 VRVLVNDRVVPLHGCPVDALGRCTRDSFVRGLSFARSGGDWAECFA 444
                  ||||||||||:|||||||||| |||| ||:||·|||||||||| |:
              401 VRVLVNDRVIPLHGCPVDKLGRCRRRDFVKGLTFARSGGDWARCYK 446
```

FIG. 14B

```
(P.c.):    1 ASRNQSTCTTVDGGYQCNSELSHKWGQYSPYFSLSEESSISNEVPHDCQITFAQVISRHG  60
             +S   +C TVD GYQC+    SH WGQYSP+FSL +E S+S+++P DC+IT  QV+SRHG
(A.f.):  407 SSAGSKSCDTVDLGYQCSPATSHLWGQYSPFFSLEDELSVSSKLPKDCRITLVQVLSRHG 586

:  61 ARFPSAKKSKVYAKLIENIQANATAYNGNTKFLRSYKYTMGGDDLVPFGVNQTVDSGTKF 120
             AR+P++ KSK Y KL+  IQANAT + G   FL++Y YT+G DDL PFG  Q V+SG KF
        : 587 ARYPTSSKSKKYKKLVTAIQANATDFKGKFAFLKTYNYTLGADDLTPFGEQQLVNSGIKF 766

: 121 YQRYEALAKKAVPFIRSSDSGRVVASGVNFIKGFQQAKLDDKNANHRQPSPKTNVIISEE 180
             YQRY+ALA+   VPFIR+S S  RV+ASG  FI+GFQQAKL D  A  +R  +P  +VII E
        : 767 YQRYKALARSVVPFIRASGSDRVIASGEKFIEGFQQAKLADPGATNR-AAPAISVIIPES 943

: 181 SGTNNTLNHSEICPKFEDNELGDKVEEKYMKIFVPPIRARLEADLPGVKLEDIDVVSLMD 240
                 NNTL+H  +C KFE ++LGD+V   + +F P IRAR E  LPGV L D DVVSLMD
        : 944 ETFNNTLDHG-VCTKFEASQLGDEVAANFTALFAPDIRARAEKHLPGVTLTDEDVVSLMD 1120

: 241 ICPFETVSSSDDAAELSPFCDLFTPTEWSQYDYLQSLSKYYGYGAGNPLGPTQGVGFVNE 300
             +C F+TV+ + DA++LSPFC LFT  EW +Y+YLQSL KYYGYGAGNPLGP QG+GF NE
        :1121 MCSFDTVARTSDASQLSPFCQLFTHNEWKKYNYLQSLGKYYGYGAGNPLGPAQGIGFTNE 1300

: 301 LIARLTRHPVRDHTSTNRALDAPGAATFPLNYTMYADFTHDNGMIPFFFALGLYNGTAPL 360
             LIARLTR PV+DHTSTN  L     ATFPLN TMY DF+HDN M+  FFALGLYNGT PL
        :1301 LIARLTRSPVQDHTSTNSTL-VSNPATFPLNATMYVDFSHDNSMVSIFFALGLYNGTEPL 1477

: 361 SLTHVQSPSQTDGFSSAWTVPFGARAYVEMMQCRREPEPLVRVLVNDRVIPLHGCPVDKL 420
               S T V+S  + DG+S++W VPFGARAY E MQC+ E EPLVR L+NDRV+PLHGC VDKL
        :1478 SRTSVESAKELDGYSASWVVPFGARAYFETMQCKSEKEPLVRALINDRVVPLHGCDVDKL 1657

: 421 GRCRRDFVKGLTFARSGGDWARCY 445
             GRC+  DFVKGL++ARSGG+W  C+
        :1658 GRCKLNDFVKGLSWARSGGNWGECF 1732
```

FIG. 14C

```
(P.c.):   4 NQSTCTTVDGGYQCNSELSHKWGQYSPYFSLSEESSISNEVPHDCQITFAQVISRHGARF  63
            N S CT+VD GYQC  ELSHKWG Y+PYFSL +ES     +VP DC ITF QV++RHGAR
(A.t.): 411 NHSDCTSVDRGYQCFPELSHKWGLYAPYFSLQDESPFPLDVPDDCHITFVQVLARHGARS 590

:  64 PSAKKSKVYAKLIENIQANATAYNGNTKFLRSYKYTMGGDDLVPFGVNQTVDSGTKFYQR 123
              P+  K+K YA  I IQ NATA  G    FL+SY Y+MG ++L PFG NQ  D G +FY+R
        : 591 PTDSKTKAYAATIAAIQKNATALPGKYAFLKSYNYSMGSENLNPFGRNQLQDLGAQFYRR 770

: 124 YEALAKKAVPFIRSSDSGRVVASGVNFIKGFQQAKLDDKNANHRQPSPKTNVIISEESGT 183
              Y+  L +    PF+R++DS RV  S    F++GFQ A+   D +AN  QPSP+ +V+I E  +
        : 771 YDTLTRHINPFVRAADSSRVHESAEKFVEGFQNARQGDPHANPHQPSPRVDVVIPEGTAY 950

: 184 NNTLNHSEICPKFEDNELGDKVEEKYMKIFVPPIRARLEADLPGVKLEDIDVVSLMDICP 243
              NNTL HS IC  FE + +GD  + +  +F P I  RLEADLPGV+L   DVV+LM +CP
        : 951 NNTLEHS-ICTAFEASTVGDAAADNFTAVFAPAIAKRLEADLPGVQLSADDVVNLMAMCP 1127

: 244 FETVSSSDDAAELSPFCDLFTPTEWSQYDYLQSLSKYYGYGAGNPLGPTQGVGFVNELIA 303
              FETVS +DDA  LSPFCDLFT  EW+QY+YL SL KYYGYG GNPLGP QGVG+ NELIA
        :1128 FETVSLTDDAHTLSPFCDLFTAAEWTQYNYLLSLDKYYGYGGGNPLGPVQGVGWANELIA 1307

: 304 RLTRHPVRDHTSTNRALDAPGAATFPLNYTMYADFTHDNGMIPFFFALGLYNGTAPLSLT 363
              RLTR PV DHT  N   LDA    ATFPLN T+YADF+HD+ ++  F+ALGLYNGT PLS T
        :1308 RLTRSPVHDHTCVNNTLDA-NPATFPLNATLYADFSHDSNLVSIFWALGLYNGTKPLSQT 1484

: 364 HVQSPSQTDGFSSAWTVPFGARAYVEMMQCRREPEPLVRVLVNDRVIPLHGCPVDKLGRC 423
              V+   ++TDG+++ AWTVPF ARAY+EMMQCR E +PLVRVLVNDRV+PLHGC VD LGRC
        :1485 TVEDITRTDGYAAAWTVPFAARAYIEMMQCRAEKQPLVRVLVNDRVMPLHGCAVDNLGRC 1664

: 424 RRRDFVKGLTFARSGGDWARCY 445
              +R DFV+GL+FAR+GG+WA C+
        :1665 KRDDFVEGLSFARAGGNWAECF 1730
```

FIG. 14D

```
(P.c.):    7 TCTTVDGGYQCNSELSHKWGQYSPYFSLSEESSISNEVPHDCQITFAQVISRHGARFPSA   66
             +C T DGGYQC   +SH WGQYSPYFS+ +ES+IS +VPH C++TF QV+SRHGAR+P+
(E.n.):  293 SCNTADGGYQCFPNVSHVWGQYSPYFSIEQESAISEDVPHGCEVTFVQVLSRHGARYPTE  472

:         67 KKSKVYAKLIENIQANATAYNGNTKFLRSYKYTMGGDDLVPFGVNQTVDSGTKFYQRYEA  126
             KSK Y+ LIE IQ NAT++ G   FL SY YT+G DDL  FG NQ VDSG KFY+RY+
:        473 SKSKAYSGLIEAIQKNATSFWGQYAFLESYNYTLGADDLTIFGENQMVDSGAKFYRRYKN  652

:        127 LAKKAVPFIRSSDSGRVVASGVNFIKGFQQAKLDDKNANHRQPSPKTNVIISEESGTNNT  186
             LA+K  PFIR+S S RVVAS   FI GF++A+L D  +  ++ +P  NVII E G NNT
:        653 LARKNTPFIRASGSDRVVASAEKFINGFRKAQLHDHGS--KRATPVVNVIIPEIDGFNNT  826

:        187 LNHSEICPKFEDNELGDKVEEKYMKIFVPPIRARLEADLPGVKLEDIDVVSLMDICPFET  246
             L+HS  C   FE++E D++E +   I  PPIR RLE DLPG+KL + +V+ LMD+C F+T
:        827 LDHS-TCVSFENDERADEIEANFTAIMGPPIRKRLENDLPGIKLTNENVIYLMDMCSFDT 1003

:        247 VSSSDDAAELSPFCDLFTPTEWSQYDYLQSLSKYYGYGAGNPLGPTQGVGFVNELIARLT  306
             ++ +     ELSPFC +FT  EW QYDYLQSLSKYYGYGAG+PLGP QG+GF NELIARLT
:       1004 MARTAHGTELSPFCAIFTEKEWLQYDYLQSLSKYYGYGAGSPLGPAQGIGFTNELIARLT 1183

:        307 RHPVRDHTSTNRALDAPGAATFPLNYTMYADFTHDNGMIPFFFALGLYNGTAPLSLTHVQ  366
             + PV+D+TSTN  LD+   ATFPL+ +YADF+HDN MI  FFA+GLYNGT PLS+  V+
:       1184 QSPVQDNTSTNHTLDS-NPATFPLDRKLYADFSHDNSMISIFFAMGLYNGTQPLSMDSVE 1360

:        367 SPSQTDGFSSAWTVPFGARAYVEMMQCRREPEPLVRVLVNDRVIPLHGCPVDKLGRCRRR  426
             S   + DG++++WTVPFGARAY E+MQC ++ EPLVRVLVNDRV+PLHGC VDK GRC
:       1361 SIQEMDGYAASWTVPFGARAYFELMQCEKK-EPLVRVLVNDRVVPLHGCAVDKFGRCTLD 1537

:        427 DFVKGLTFARSGGDWARCY                                          445
             D+V+GL FARSGG+W  C+
:       1538 DWVEGLNFARSGGNWKTCF                                         1594
```

FIG. 15A

```
A. niger        1 ASRNQSSCDTVDQGYQCFSETSHLWGQYAPFFSLANESVISPEVPAGCRV 50
                  ||||||·|:          .:||||||.:|:.|   :   |  ||
F. javanicum    1 ASRNQSTCEYDGS....CNDISRLWGQYSAYFPIPSE..LDASTPDDCDV 44

51 TFAQVLSRHGARYPTDSKGKKYSALIEEIQQNATTFDGKYAFLKTYNYSL 100
                  |||  ||||||||||||||||  |·|  |  ||··||  :  | ·|| | |||
               45 TFALVLSRHGARYPTDSKSAAYNATIARIQKSATMYGKNYKWLKEYTYSL 94

101 GADDLTPFGEQELVNSGIKFYQRYESLTRNIVPFIRSSGSSRVIASGKKF 150
                  ||:|||  ||:.::|·||    ||:||  ||       ||:|·|||  ||| |        |
               95 GAEDLTEFGQRQMVDSGRAFYERYMSLAEKTEPFVRASGSDRVIMSSYNF 144

151 IEGFQSTKLKDPRAQPGQSSPKIDVVISEASSSNNTLDPGTCTVFEDSEL 200
                  :||  ..      |:|    .  .:||      |||:  |·|  || .
              145 TQGFYAS.....RGESGDDYTQDVLIIPEEPGINNTMLHGSCASFESDRV 189

201 A....DTVEANFTATFVPSIRQRLENDLSGVTLTDTEVTYLMDMCSFDTI 246
                  :  |  .||·|||||·|||||  .|||||  |   |:||||   |
              190 PKDADEKAEVAWGARFLPEIRNRLNHHLPGVNLTLEETIYMMDMCPFLAA 239

247 STSTVDTKLSPFCDLFTHDEWINYDYLQSLKKYYGHGAGNPLGPTQGVGY 296
                  |       ||||||| :|·|||  ·||:| ||·:|||||||||
              240 DTPD.GAGHSRFCDLFTKADWRSYDYYMTLSKFYKFGNGNAMGPTQGVGY 288

297 ANELIARLTHSPVHDDTSSNHTLDSSPATFPLNSTLYADFSHDNGIISIL 346
                  ||||·||||||  |||  |·|   ·||||||:|||| :||||||||  ·:||
              289 VNELISRLTGKPVDDHTTTNSTLDSSPKTFPLDRALYADFSHDNSMVSIF 338

347 FALGLYNGTKPLSTTTVENITQTDGFSSAWTVPFASRLYVEMMQCQA... 393
                  ||||||  |    |:||  |||·|:||| ::|  |
              339 SALGLYNSTTLLPKDHIVPAIKAHGYSSTWVVPFGARMYVEKLECGASRN 388

394     EQEPLVRVLVNDRVVPLHGCPVDALGRCTRDSFVRGLSFARSGGDWAEC 442
                      ..:|||||||||·| | | | |  :·||  ||||·|||·|·|:|
              389 EKRDEYVRVLVNDRVMSLETCGGDEYGLCRLENFVESLSFAASGGNWDQC 438

```
F. javanicum    1 ..................ASRNQSTCEYDGSCN...DISRLWGQYS  25
                                    .| |    ||      .:|  .|||||
E. nidulans     1 MAFFTVALSLYYLLSRVSAQAPVVQNHSCNTADGGYQCFPNVSHVWGQYS  50

26 AYFPIPSE..LDASTPDDCDVTFALVLSRHGARYPTDSKSAAYNATIARI  73
                  || | |  :     |  |:|||  |||||||||||:||| ||.  | |
               51 PYFSIEQESAISEDVPHGCEVTFVQVLSRHGARYPTESKSKAYSGLIEAI 100

74 QKSATMYGKNYKWLKEYTYSLGAEDLTEFGQRQMVDSGRAFYERYMSLAE 123
                  ||.||  :   | .|. |  |.|||:|||  ||: ||||||  || ||.||
              101 QKNATSFWGQYAFLESYNYTLGADDLTIFGENQMVDSGAKFYRRYKNLAR 150

124 KTEPFVRASGSDRVIMSSYNFTQGF.YASRGESGDDYTQDV..LIIPEEP 170
                  |  ||:|||||||:  |.  |  ||  | :|        | .||||
              151 KNTPFIRASGSDRVVASAEKFINGFRKAQLHDGSKRATPVVNVIIPEID  200

171 GINNTMLHGSCASFESDRVPKDADEKAEVAWGARFLPEIRNRLNHHLPGV 220
                  | |||: | .| |||.|    :   :.|  .|   | || ||  .|||:
              201 GFNNTLDHSTCVSFEND....ERADEIEANFTAIMGPPIRKRLENDLPGI 246

221 NLTLEETIYMMDMCPF.LAADTPDGAGHSRFCDLFTKADWRSYDYYMTLS 269
                  || |  ||:|||| | | |  | |:||.:|  ||| .||
              247 KLTNENVIYLMDMCSFDTMARTAHGTELSPFCAIFTEKEWLQYDYLQSLS 296

270 KFYKFGNGNAMGPTQGVGYVNELISRLTGKPVDDHTTTNSTLDSSPKTFP 319
                  |:| :| |. :|| ||:|: ||||.||| || |.|.|| |||| |·| |||
              297 KYYGYGAGSPLGPAQGIGFTNELIARLTQSPVQDNTSTNHTLDSNPATFP 346

320 LDRALYADFSHDNSMVSIFSALGLYNSTTLLPKDHIVPAIKAHGYSSTWV 369
                  ||| ||||||||||:|| |:||||||| ||  |  |  :   ||...|
              347 LDRKLYADFSHDNSMISIFFAMGLYNGTQPLSMDSVESIQEMDGYAASWT 396

370 VPFGARMYVEKLECGASRNEKRDEYVRVLVNDRVMSLETCGGDEYGLCRL 419
                  |||||| | | ::|    ||::   ||||||||||·| | | |·:| | |
              397 VPFGARAYFELMQC.....EKKEPLVRVLVNDRVVPLHGCAVDKFGRCTL 441

420 ENFVESLSFAASGGNWDQCGG. 440
                  :..|| |·|| ||||| |
              442 DDWVEGLNFARSGGNWKTCFTL 463
```

FIG. 15C

```
(F.j.): 17   ISRLWGQYSAYFPIPSELDASTPDDCDVTFALVLSRHGARYPTDSKSAAYNATIARIQKS 76
             IS  WGQYS YF +PSELDAS PDDC+VTFA VLSRHGAR PT  ++A+Y   I RI
(M.t.): 2379 ISHFWGQYSPYFSVPSELDASIPDDCEVTFAQVLSRHGARAPTLKRAASYVDLIDRIHHG 2558

:   77 ATMYGKNYKWLKEYTYSLGAEDLTEFGQRQMVDSGRAFYERYMSLAEKTEPFVRASGSDR 136
             A  YG  Y++L+  Y Y+LGA++LT  GQ+QMV+SG  FY RY +LA K+ PFVR +G DR
      : 2559 AISYGPGYEFLRTYDYTLGADELTRTGQQQMVNSGIKFYRRYRALARKSIPFVRTAGQDR 2738

:  137 VIMSSYNFTQGFY----ASRGES-GDDYTQDVLIIPEEPGINNTMLHGSCASFESDRVPK 191
             V+ S+ NFTQGF+     A RG +        D+++IPE G NNT+ +   C  +FE
      : 2739 VVHSAENFTQGFHSALLADRGSTVRPTLPYDMVVIPETAGANNTLHNDLCTAFEEGPYST 2918

:  192 DADEKAEVAWGARFLPEIRNRLNHHLPGVNLTLEETIYMMDMCPF--LAADTPD------ 243
             D+ A+  + + F    I  R+N +LPG NLT  +T+  +MD+CPF  +A+  + D
      : 2919 IGDD-AQDTYLSTFAGPITARVNANLPGANLTDADTVALMDLCPFETVASSSSDPATADA 3095

:  244 GAGHSR----FCDLFTKADWRSYDYYMTLSKFYKFGNGNAMGPTQGVGYVNELISRLTGK 299
             G G+ R    FC LF++++WR+YDY  ++ K+Y +G GN +GPTQGVG+VNEL++RL G
      : 3096 GGGNGRPLSPFCRLFSESEWRAYDYLQSVGKWYGYGPGNPLGPTQGVGFVNELLARLAGV 3275

:  300 PVDDHTTTNSTLDSSPKTFPLDRALYADFSHDNSMVSIFSALGLYNSTTLLPKDHIVPAI 359
             PV D T+TN TLD  P+TFPL R LYADFSHDN M+ +  ALG Y+     L K
      : 3276 PVRDGTSTNRTLDGDPRTFPLGRPLYADFSHDNDMMGVLGALGAYDGVPPLDKTARRDPE 3455

:  360 KAHGYSSTWVVPFGARMYVEKLEC---------GASRNEKRDEYVRVLVNDRVMSLETCG 410
             +  GY+++ W VPF AR+YVEK+ C         G  R EK +E VRVLVNDRVM+L+ CG
      : 3456 ELGGYAASWAVPFAARIYVEKMRCSGGGGGGGGGEGRQEKDEEMVRVLVNDRVMTLKGCG 3635

:  411 GDEYGLCRLENFVESLSFAASGGNWDQC 438
             DE G+C LE F+ES++FA   G WD C
      : 3636 ADERGMCTLERFIESMAFARGNGKWDLC 3719
```

FIG. 16A

```
H. grisea       1 .................ASRNQSTCDSVDRGFWCAADISHSWGQYSPYF  32
                                   ||.|  ||  |    |||  ||||||||
M. thermophila  1 MTGLGVMVVMVGFLAIASLQSESRPCDTPDLGFQCGTAISHFWGQYSPYF  50

33 SVPSDIDPGFPKGCNVTFAQVLSRHGARAPTTGRAAYYVDVIDRVQRQAT  82
                  ||||::|   |   | |||||||||||||||||  ||| |||·|||:   |
               51 SVPSELDASIPDDCEVTFAQVLSRHGARAPTLKRAASYVDLIDRIHHGAI 100

83 SYGPGHAFLRSYRYTLGANELTPMGERQLAYSGARFYHRYRELARVEAPF 132
                  |||||: |||·| |||||·|||  |:·|:   ||  :|| ||| |||   ||
              101 SYGPGYEFLRTYDYTLGADELTRTGQQQMVNSGIKFYRRYRALARKSIPF 150

133 VRSSGVSRVVASAVNFTQGFHQARLADRGATLPPPTLPYDMVIISSDDTA 182
                  ||··|  ||| ||  |||||||| | |||||·|·  ||||||||:|    |
              151 VRTAGQDRVVHSAENFTQGFHSALLADRGSTV.RPTLPYDMVVIPETAGA 199

183 NNTLHHGLCTVFEEGPYADIGDKAQKEYLSKFVGPIVERINAQLPGANLN 232
                  |||||· ||| ||||||·  ||| ||   |||  |  ||| | |||  |:|| ||||||
              200 NNTLHNDLCTAFEEGPYSTIGDDAQDTYLSTFAGPITARVNANLPGANLT 249

233 ATDIIALMDLCPFETVAFP...........EGTKLSPFCRLFTAAEWRA 270
                  |   :||||||||||||||    |   ||||||||·  ·||||
              250 DADTVALMDLCPFETVASSSSDPATADAGGGNGRPLSPFCRLFSESEWRA 299

271 YDRYQDVGKWFGYGPGNPLGPTQGVGFVNELIARLSGQPVSDGTSTNRTL 320
                  ||  |  ||||:|||||||||||||||||||||||:|||·| ||  ||||||||||
              300 YDYLQSVGKWYGYGPGNPLGPTQGVGFVNELLARLAGVPVRDGTSTNRTL 349

321 DENPETFPLGRRLYADFSHDNDMVGILSALGLWDNHEEPGNEMPAEGEED 370
                  |  ·|  ||||||  ||||||||||||·|:|  |||   :|  |   :  | :  :
              350 DGDPRTFPLGRPLYADFSHDNDMMGVLGALGAYDG..VPPLDKTARRDPE 397

371 DNGRFSTARAVPFGARVYVEKLRCGG...........SEEDEEMVRVLVN 409
                  :|:·· |||| ||:||||:||  |   |·|||||||||||
              398 ELGGYAASWAVPFAARIYVEKMRCSGGGGGGGGGEGRQEKDEEMVRVLVN 447

410 DRVMPLAQCGGDKRGMCTLSRFVESLKFARNNGRWDMCFE 449
                  ||||  |  ||  |·||||||  ||:||:  |||  ||:||:||
              448 DRVMTLKGCGADERGMCTLERFIESMAFARGNGKWDLCFA 487
```

FIG. 16B

```
A. niger      1 ASRNQSSCDTVDQGYQCFSETSHLWGQYAPFFSLANESVISPEVPAGCRV 50
                ||||||.||.||.|: | .: || ||||.|:||. .:  | |  | ||  |
H. grisea     1 ASRNQSTCDSVDRGFWCAADISHSWGQYSPYFSVPSD..IDPGFPKGCNV 48

51 TFAQVLSRHGARYPTDSKGKGKKYSALIEEIQQNATTFDGKYAFLKTYNYSL 100
                |||||||||||| ||  :   | .|: :|. ||.:   :|||:.| |.|
             49 TFAQVLSRHGARAPTTGRAAYYVDVIDRVQRQATSYGPGHAFLRSYRYTL 98

101 GADDLTPFGEQELVNSGIKFYQRYESLTRNIVPFIRSSGSSRVIASGKKF 150
                ||.:||| ||.:|  || :|| ||   | ||:||||  |||:||  |
             99 GANELTPMGERQLAYSGARFYHRYRELARVEAPFVRSSGVSRVVASAVNF 148

151 IEGFQSTKLKDPRAQ.PGQSSPKIDVVISEASSSNNTLDPGTCTVFED.. 197
                :||   :|||  | |  .|  |:|| ..||||  | |||||:
            149 TQGFHQARLADRGATLPPPTLPYDMVIISSDDTANNTLHHGLCTVFEEGP 198

198 .SELADTVEANFTATFVPSIRQRLENDLSGVTLTDTEVTYLMDMCSFDTI 246
                 .::  |  :  .  ||  |  :|:     || |   |  |::   |||:| |:|:
            199 YADIGDKAQKEYLSKFVGPIVERINAQLPGANLNATDIIALMDLCPFETV 248

247 STSTVDTKLSPFCDLFTHDEWINYDLQSLKKYYGHGAGNPLGPTQGVGY 296
                .       |||||||  |||  ||  ||    |  .  |::|:|  |||||||||||:
            249 AFPE.GTKLSPFCRLFTAAEWRAYDRYQDVGKWFGYGPGNPLGPTQGVGF 297

297 ANELIARLTHSPVHDDTSSNHTLDSSPATFPLNSTLYADFSHDNGIISIL 346
                |||||||.  || | ||.| ||| .| ||||      |||||||||| -: ||
            298 VNELIARLSGQPVSDGTSTNRTLDENPETFPLGRRLYADFSHDNDMVGIL 347

347 FALGLY.NGTKPLSTTTVENITQTDG.FSSAWTVPFASRLYVEMMQC...Q 392
                ||||: |  .|  .   |    .|  ||.| |||  .|.|||  :.|
            348 SALGLWDNHEEPGNEMPAEGEEDDNGRFSTARAVPFGARVYVEKLRCGGS 397

393 AEQEPLVRVLVNDRVVPLHGCPVDALGRCTRDSFVRGLSFARSGGDWAEC 442
                | |  :|||||||||.||  |   |  |   ||   || | |||. ||| |
            398 EEDEEMVRVLVNDRVMPLAQCGGDKRGMCTLSRFVESLKFARNNGRWDMC 447

```
(H.g.):    8 CDSVDRGFWCAADISHSWGQYSPYFSVPSDIDPGFPKGCNVTFAQVLSRHGARAPTTGRA   67
             CD+ D GF C   ISH WGQYSPYFSVPS++D    P  C VTFAQVLSRHGARAPT  RA
(M.t.): 2340 CDTPDLGFQCGTAISHFWGQYSPYFSVPSELDASIPDDCEVTFAQVLSRHGARAPTLKRA 2519

:   68 AYYVDVIDRVQRQATSYGPGHAFLRSYRYTLGANELTPMGERQLAYSGARFYHRYRELAR  127
               A YVD+IDR+   A SYGPG+ FLR+Y YTLGA+ELT  G++Q+   SG +FY RYR LAR
        : 2520 ASYVDLIDRIHHGAISYGPGYEFLRTYDYTLGADELTRTGQQQMVNSGIKFYRRYRALAR 2699

:  128 VEAPFXXXXXXXXXXXXXXXXNFTQGFHQARLADRGATLPPPTLPYDMVIISSDDTANNTLH  187
                   PF                NFTQGFH A LADRG+T+   PTLPYDMV+I     ANNTLH
        : 2700 KSIPFVRTAGQDRVVHSAENFTQGFHSALLADRGSTV-RPTLPYDMVVIPETAGANNTLH 2876

:  188 HGLCTVFEEGPYADIGDKAQKEYLSKFVGPIVERINAQLPGANLNATDIIALMDLCPFET  247
               + LCT FEEGPY+ IGD AQ  YLS F GPI  R+ NA LPGANL   D +ALMDLCPFET
        : 2877 NDLCTAFEEGPYSTIGDDAQDTYLSTFAGPITARVNANLPGANLTDADTVALMDLCPFET 3056

:  248 VAFP-----------EGTKLSPFCRLFTAAEWRAYDRYQDVGKWFGYGPGNPLGPTQGV  295
               VA             G  LSPFCRLF+ +EWRAYD Q VGKW+GYGPGNPLGPTQGV
        : 3057 VASSSSDPATADAGGGNGRPLSPFCRLFSESEWRAYDYLQSVGKWYGYGPGNPLGPTQGV 3236

:  296 GFVNELIARLSGQPVSDGTSTNRTLDENPETFPLGRRLYADFSHDNDMVGILSALGLWDN  355
               GFVNEL+ARL+G PV DGTSTNRTLD +P TFPLGR LYADFSHDNDM+G+L ALG +D
        : 3237 GFVNELLARLAGVPVRDGTSTNRTLDGDPRTFPLGRPLYADFSHDNDMMGVLGALGAYDG 3416

:  356 HEEPGNEMPAEGEEDDNGRFSTARAVPFGARVYVEKLRCGG----------SEEDEEMV  404
                   P   + A  + ++   G ++ + AVPF AR+YVEK+RC G           E+DEMV
        : 3417 --VPPLDKTARRDPEELGGYAASWAVPFAARIYVEKMRCSGGGGGGGGGEGRQEKDEEMV 3590

:  405 RVLVNDRVMPLAQCGGDKRGMCTLSRFVESLKFARNNGRWDMCF                448
               RVLVNDRVM L   CG D+RGMCTL RF+ES+ FAR NG+WD+CF
        : 3591 RVLVNDRVMTLKGCGADERGMCTLERFIESMAFARGNGKWDLCF                3722
```

FIG. 17A

ATGGTTCTTTTCACGGTCTCCCTTTCGCTGTACTACCTACTTACGAGGTGAGATCTCTACAGTAGCTG
CTTGTTTAGTTGAGTTGGTACTTACCTACACAGCGTCTCTGCTCAGGCCGTGGTGGCGCAGGAATAT
TCATGTAATTCGGCCGACGCTGGGTATCAATGTTTCCCCAATGTCTCGCACGTCTGGGGCCAGTACT
CGCCGTACTTCTCACTCGAGCATGAGTCTGCCATTTCTCAGGACGTGCCTCATGGCTGTGAGGTTAC
CTTCGTGCAGGTGCTCTCGCGACATGGGGCTAGATATcCTTCGGAGTCAAAAAGCAAGGCGTATGCG
AAGTTGATTGACGCTATCAAGAAGAATGCTACTTCGTTTTCGGGACAGTATGCTTTTCTGGAGAGTT
ATAATTATACTCTCGGCGCGGAAGACTTGACTACTTTTGGTGAGAACCAGATGGTCGACTCGGGTGC
CAAGTTTTACCGGCGGTATAAGAATTTGGCCAGGAAAAATACTCCATTCATACGTGCATCAGGGTCT
GACCGTGTCGTTGCGTCCGCGGAGAAGTTTATTGACGGACTTCGAGACGCCCAGACCCACGACCAG
GGCTCCAAACGTGTTGCCCCAGTTGTCAATGTGGTTATCCCTGAAACTGATGGATTTAACAACACCC
TGGATCATAGCACTTGCGTGTCTTTTGAGAATGATGAGCGGGCGGACGAAATTGAAGCCAACTTCGC
CGCGATCATTGGACCTCCGAtTCGCAAACGTCTGGAAAACGACCTTCCTGGCGTTGAGCTTACAAAT
GAGCATGTGGAATACTTGATGGATATGTgctcgttcgacaccatggcgcgcaccgcccatggaaccgagctgtctccatt
ctgcgccatcttcactgaaaaggagtggctgcagtacgacTACCTACAATCTCTGtCAAAGTACTACGGCTACGGTGC
CGGGAACCCCCTTGGCCCAGCTCAGGGAATTGGCTTCACCAACGAGCTGATTGCcCGACTGA
CGCAGTCGCCTGTCCAGGACAACACGAGCACCAACCACACTCTAGACTCTGACCCGGCCACGTTCC
CCCTCGACAGGAAGCTCTACGCCGACTTCTCCCACGACAATAACATGATTTCTATATTCTTCGCCAT
GGGCCTGTACAACGGCACCCAGCCGCTGTCCATGGACACTGTGGAGTCGATTGAGGAGATGGATGG
CTACGCGGCGTCTTGGACTGTCCCGTTTGGTGCGAGGGCTTACTTTGAGGTGATGCAGTGCCAAAAA
AAGAAGGAGCCACTTGTGCGGGTATTAGTGAATGATCGCGTTGTTCCTCTCCATGGCTGTGCTGTTG
ACAAGCTCGGACGATGCACTTTGGACGATTGGGTCGAGGGCTTGAGTTTTGCGAGGGCCGGTGGGA
ACTGGAAGGCTTGTTTTACTGCCTAA

FIG. 17B

MVLFTVSLSLYYLLTSVSAQAVVAQEYSCNSADAGYQCFPNVSHVWGQYSPYFSLEHESAISQDVPHGCE
VTFVQVLSRHGARYPSESKSKAYAKLIDAIKKNATSFSGQYAFLESYNYTLGAEDLTTFGENQMVDSGAKF
YRRYKNLARKNTPFIRASGSDRVVASAEKFIDGLRDAQTHDQGSKRVAPVVNVVIPETDGFNNTLDHSTCV
SFENDERADEIEANFAADGPPIRKRLENDLPGVELTNEHVEYLMDMCSFDTMARTAHGTELSPFCAIFTEKE
WLQYDYLQSLSKYYGYGAGNPLGPAQGIGFTNELIARLTQSPVQDNTSTNHTLDSDPATFPLDRKLYADFS
HDNNMISIFFAMGLYNGTQPLSMDTVESIEEMDGYAASWTVPFGARAYFEVMQCQKKKEPLVRVLVNDR
VVPLHGCAVDKLGRCTLDDWVEGLSFARAGGNWKACFTA.

FIG. 18A

```
                    Dra I
TTAAGACTGCCTAGAGCAGCTTTTTAAATACGAATCGCCTAGTGCGATCTATTATTCTCAAGATATTTATTGACTCACATGAAGTGAAGT
                                                                                          90

Ppu10 I
                Nsi I
                 Sph I           BsrD I                              Bsg I           Bsm I
TGAATGAGAGAAGATGTCTGAGTGAATCATGCATGCGTGGCCGAGACATTGCGTGGTGCAGGGTATTTACAAGCCAAGCGATGAATGCGT
                                                                                          180

Vsp I                                Mun I
CCATCACTCAGAGTTTAAGCTAATTGAATCCACTCAATTAATCAACCTTGACAGAAACATCGGACATATTCTTCAATTGACTTTCAAGTA
                                                                                          270

BsrG I                        Bsg I
TAAAATCAAAATCACAGCACAAGACGCCCTTGTACATCAACTCATGTGCAGGGTGCTCAAAGTGGCTGACAAAGTGCCTCGTTCGTTGAC
                                                                                          360

BstX I
   Pml I       Bbs I                                                          Bpu10 I
CAACCACGTGGTCCACCTCAAGGCCATGTCTTCAACGTCAAACATTCAGGGATAGCCGAGCAGCTCGTTCATCTCATTCACCCTCAGCCC
                                                                                          450

BssH II
CGCAACCTGACTCGATGGAACCATCCCTTGACAATCACATTAACGCGCGCGACTCTACAGCATCTTTTACTGAAATTCAATCAGCCAGAG
                                                                                          540

Bpu1102 I    Bsa I    Nhe I
CTGCTGAGCTGATGGGTCTCGCCGCCAGTGGGAGCTAGCATATCCCTGTCACGATTACCGAATCACTGGAGATGGTGCATCTTGGGCGGC
                                                                                          630

Ear I           Bbs I                                       BspLU11 I    BsaB I
GCGACGGCGAAGAGGAAGACGCGCCTCCCATCGCGGATCATCGGGACGACGACAACGACGACATGTCTGATTCTGATCCCGAGAGGGGAC
                                                                                          720

Bpu1102 I
                                 BsrB I    BsrB I                                    BsmB I
GCCTGCTTCATAATGACGACGATGATGGTGTTGATACTGAGAGCCGCTCGGACGCTGAGCGGCTTGAGAGCTGGCATGAGGAGCACCGAC
                                                                                          810

Aat II
 BseR I
  BsmB I     Bcg I                                Bcl I
GTCGTGAGACGAGACGATGGAGTTACCTCGTCATGGTCATCAGCACCATCGCATTGATCACAGTTCTTGGATTTTGGGTCCAGAATGGGT
                                                                                          900
                              ┌──── 289F ────▶
                              M  V  I  S  T  I  A  L  I  T  V  L  G  F  W  V  Q  N  G─
```

FIG. 18B

```
                BsaB I    Dra I
GAGTTATATGAGTTGATGCTCATCTTTTAAATCAAACTGACACGCCTGATAGAACTCGACCGGCTGGGTGTGAGTATGACGGGAGCTGTA
                                                                                          990
                                              T  R  P  A  G  C  E  Y  D  G  S  C

Sca I
ATGACATCTCTCGGCTCTGGGGACAGTACTCTGCATACTTCCCAATCCCGTCTGAGCTTGATGCCTCAACACCAGACGATTGTGATGTGA
                                                                                          1080
 N  D  I  S  R  L  W  G  Q  Y  S  A  Y  F  P  I  P  S  E  L  D  A  S  T  P  D  D  C  D  V

Nco I    Acc65 I              Pst I           BsrD I    Bsm I
CTTTTGCACTCGTCTTGTCCCGCCATGGAGCCAGGTACCCAACGGACAGCAAGTCTGCAGCATACAACGCTACCATTGCCCGCATTCAAA
                                                                                          1170
 T  F  A  L  V  L  S  R  H  G  A  R  Y  P  T  D  S  K  S  A  A  Y  N  A  T  I  A  R  I  Q

Bal I
                          Afl II       Bst1107 I                      Bbs I      Eco57 I
AGTCTGCTACCATGTACGGCAAGAACTACAAGTGGCTTAAGGAGTATACCTACAGTCTCGGCGCTGAAGACCTGACTGAGTTTGGCCAGC
                                                                                          1260
 K  S  A  T  M  Y  G  K  N  Y  K  W  L  K  E  Y  T  Y  S  L  G  A  E  D  L  T  E  F  G  Q

Sal I                      BsrB I                     Bbs I
GGCAGATGGTCGACTCTGGTAGGGCCTTTTATGAGCGGTACATGAGTCTCGCTGAGAAGACTGAGCCTTTTGTTCGGGCATCGGGCTCAG
                                                                                          1350
 R  Q  M  V  D  S  G  R  A  F  Y  E  R  Y  M  S  L  A  E  K  T  E  P  F  V  R  A  S  G  S

Nru I    BsmBI    BseR I
ATCGGGTCATCATGTCGTCTTACAATTTTACGCAAGGCTTTTACGCATCGCGAGGAGAGTCTGGAGACGATTATACTCAGGATGTTCTTA
                                                                                          1440
 D  R  V  I  M  S  S  Y  N  F  T  Q  G  F  Y  A  S  R  G  E  S  G  D  D  Y  T  Q  D  V  L

Eco57 I
TCATCCCTGAAGAACCTGGCATCAACAACACCATGTTGCATGGATCGTGCGCCTCATTCGAAAGCGACAGAGTTCCTAAAGACGCAGATG
                                                                                          1530
 I  I  P  E  E  P  G  I  N  N  T  M  L  H  G  S  C  A  S  F  E  S  D  R  V  P  K  D  A  D

BspM I
AAAAGGCCGAGGTTGCATGGGGAGCAAGATTCCTCCCCGAGATTCGAAATAGGTTGAACCACCACCTGCCAGGAGTCAACCTGACGCTGG
                                                                                          1620
 E  K  A  E  V  A  W  G  A  R  F  L  P  E  I  R  N  R  L  N  H  H  L  P  G  V  N  L  T  L

BspLU11 I
       Xcm I    PshA I                                                                 Ear I
AGGAAACCATCTACATGATGGACATGTGTCCGTTCCTCGCGGCTGACACACCTGATGGCGCTGGTCACTCGAGGTTCTGCGACCTCTTCA
                                                                                          1710
 E  E  T  I  Y  M  M  D  M  C  P  F  L  A  A  D  T  P  D  G  A  G  H  S  R  F  C  D  L  F
```

FIG. 18C

```
                                                              BsrD I
                                                               Nco I
                                                               BsrD I      Dra III
CCAAGGCAGACTGGCGAAGTTACGACTACTACATGACTCTGAGCAAGTTCTACAAGTTTGGCAATGGCAATGCCATGGGACCGACACAAG
                                                                                          1800
 T  K  A  D  W  R  S  Y  D  Y  Y  M  T  L  S  K  F  Y  K  F  G  N  G  N  A  M  G  P  T  Q

Xcm I
GTGTTGGATATGTCAACGAACTCATCTCACGCTTGACTGGGAAGCCTGTTGACGACCACACCACGACCAACAGCACATTGGACTCATCGC
                                                                                          1890
 V  V  G  Y  V  N  E  L  I  S  R  L  T  G  K  P  V  D  D  H  T  T  T  N  S  T  L  D  S  S

Bsa I,           Bcg I
                                                                           BsrG I
CAAAGACGTTCCCTCTTGACAGGGCTCTATATGCGGATTTTAGCCACGACAACAGCATGGTCTCCATCTTCTCAGCACTGGGCTTGTACA
                                                                                          1980
 P  K  T  F  P  L  D  R  A  L  Y  A  D  F  S  H  D  N  S  M  V  S  I  F  S  A  L  G  L  Y

ACTCGACTACCCTGCTACCAAAGGACCATATTGTGCCCGCGATCAAGGCGCACGGCTACTCATCGACATGGGTAGTCCCCTTTGGAGCCA
                                                                                          2070
 N  S  T  T  L  L  P  K  D  H  I  V  P  A  I  K  A  H  G  Y  S  S  T  V  V  P  F  G  A

Bcg I                                BsmBI
GAATGTACGTCGAGAAGCTCGAGTGTGGTGCCAGCAGGAATGAAAAGAGAGACGAGTACGTGCGAGTCCTGGTCAACGACCGAGTGATGT
                                                                                          2160
 R  M  Y  / E  K  L  E  C  G  A  S  R  N  E  K  R  D  E  Y  V  R  V  L  V  N  D  R  V  M

BspM I                     Pst I
CGCTCGAAACCTGCGGAGGCGACGAGTACGGGCTCTGCAGACTAGAAAACTTTGTGGAGAGTCTGTCGTTTGCCGCCTCGGGAGGAAACT
                                                                                          2250
                                                                                    ⟵29
 S  L  E  T  C  G  G  D  E  Y  G  L  C  R  L  E  N  F  V  E  S  L  S  F  A  A  S  G  G  N

GGGATCAATGCGGTGGATAA
─────────────────── 2270
      290R
 W  D  Q  C  G  G
```

FIG. 19A

```
                    Xma I
                    Sma I
     Mlu I   Sal I  Srf I                              Bsm I
                                                       Ear I
ACTATAGGGCACGCGTGGTCGACGGCCCGGGCTGGTAAATATGAACTGGTTTTCCCCTCTTCGCATTCTATATGCTCACAGGTGTCACGG
                                                                                          90

Age I
                         SgrA I                      Nco I  Ear I
Spe I
ACTAGTCAAGCTGTGATTTCGTGTATTCACCGGTGTGATGGCGGCTTTCTCTAAAAACCATGGAGAGGAAGAGGGCCTTCTCGGAGAGAA
                                                                                         180

Drd I
ACAAGAGCGACGCTGGAAACAGCAACGCCAGCAATCTTCCCGAAGATGGACAGCGTTGACCATCATGTCCCTGCTGGGCACTTTCGCCCT
                                                                                         270
                                                           ┌──────291F──────→
                                                           M  S  L  L  G  T  F  A  L

Pml I
                                            |  Fsp I                            BspLU11 I
     Nru I            BseR I                |                                   Ear I
GGTTGTGTACTTCGCGAAGGGAACCCAGTGCAACCCTCCTCCACGTGCGCACAACCCAGCCTGACCTACCTCTGACTTCCCCCGTGAACA
                                                                                         360
                                                            ┌──── presumed intron ────
V  V  Y  F  A  K  G  T  Q  C  N  P  P  P Bsg I   Bgl II                   BstE II  Bcg I         Sac I
TGTCGAAGAGATCTGACTGCACTACTGTCGATGGCGGTTACCAATGCAATTCCGAGCTCTCACACAAGTGGGGCCAGTATTCGCCCTATT
                                                                                         450
┌presumed in┐ S  D  C  T  T  V  D  G  G  Y  Q  C  N  S  E  L  S  H  K  V  G  Q  Y  S  P  Y Acc65 I
                      |  BspH I
TCTCTCTTTCCGAAGAATCATCCATCTCGAATGAGGTACCTCATGATTGTCAGATCACTTTTGCTCAAGTGATCTCCCGTCATGGTGCTC
                                                                                         540
F  S  L  S  E  E  S  S  I  S  N  E  V  P  H  D  C  Q  I  T  F  A  Q  V  I  S  R  H  G  A Ear I
   Sap I
GATTCCCGTCCGCGAAGAAGAGCAAGGTATATGCCAAGCTCATTGAAAATATCCAAGCGAACGCGACTGCATACAATGGCAACACGAAGT
                                                                                         630
R  F  P  S  A  K  K  S  K  V  Y  A  K  L  I  E  N  I  Q  A  N  A  T  A  Y  N  G  N  T  K BsrB I         Nco I           Acc65 I
TCCTCCGCTCATACAAGTACACCATGGGCGGTGATGATTTGGTACCCTTCGGAGTGAACCAGACGGTGGACTCGGGGACCAAATTCTACC
                                                                                         720
F  L  R  S  Y  K  Y  T  M  G  G  D  D  L  V  P  F  G  V  N  Q  T  V  D  S  G  T  K  F  Y Eco47 III                                     Eco57 I
AGCGCTACGAGGCGTTGGCGAAGAAAGCTGTGCCCTTCATTCGGTCATCTGACTCAGGGCGGGTTGTGGCTTCAGGCGTGAACTTTATCA
                                                                                         810
Q  R  Y  E  A  L  A  K  K  A  V  P  F  I  R  S  S  D  S  G  R  V  V  A  S  G  V  N  F  I
```

FIG. 19B

```
                                                         Bsg I
AGGGATTCCAGCAGGCAAAGTTGGATGATAAAAATGCCAATCACCGTCAGCCAAGCCCCAAAACCAACGTCATCATCTCAGAAGAGTCTG
                                                                                            900
 K  G  F  Q  Q  A  K  L  D  D  K  N  A  N  H  R  Q  P  S  P  K  T  N  V  I  I  S  E  E  S

BstE II  Bcg I            Sac I
GCACCAACAACACTCTGAACCACAGCGAGATCTGTCCTAAGTTCGAAGACAATGAGCTGGGCGACAAGGTCGAAGAAAAATACATGAAAA
                                                                                            990
 G  T  N  N  T  L  N  H  S  E  I  C  P  K  F  E  D  N  E  L  G  D  K  V  E  E  K  Y  M  K

Acc65 I
            Sac I                                                        BspH I
TCTTTGTGCCGCCCATCCGAGCTCGTCTCGAGGCCGATCTCCCTGGCGTTAAACTTGAAGACATCGATGTTGTCAGTCTGATGGACATCT
                                                                                            1080
 I  F  V  P  P  I  R  A  R  L  E  A  D  L  P  G  V  K  L  E  D  I  D  V  V  S  L  M  D  I

Ear I
                                                   Sap I
GCCCTTTCGAGACAGTGTCTTCAAGTGACGACGCAGCCGAGCTATCTCCATTCTGCGACCTCTTCACCCCGACCGAATGGAGCCAATATG
                                                                                            1170
 C  P  F  E  T  V  S  S  S  D  D  A  A  E  L  S  P  F  C  D  L  F  T  P  T  E  W  S  Q  Y

BsrB I           Nco I           Acc65 I
ACTACCTCCAGTCGTTAAGCAAGTACTATGGTTATGGCGCCGGCAATCCTCTCGGCCCGACCCAGGGTGTCGGTTTCGTAAACGAACTGA
                                                                                            1260
 D  Y  L  Q  S  L  S  K  Y  Y  G  Y  G  A  G  N  P  L  G  P  T  Q  G  V  G  F  V  N  E  L

Eco47 III
TTGCCCGACTCACTCGCCACCCAGTGAGAGACCACACAAGCACAAACCGTGCGCTCGATGCCCCCGGCGCTGCGACATTCCCCCTCAACT
                                                                                            1350
 I  A  R  L  T  R  H  P  V  R  D  H  T  S  T  N  R  A  L  D  A  P  G  A  A  T  F  P  L  N

Eco57 I
ACACCATGTATGCCGACTTCACGCATGACAACGGAATGATCCCGTTCTTCTTTGCTTTGGGGCTGTACAACGGCACCGCTCCACTCTCGC
                                                                                            1440
 Y  T  M  Y  A  D  F  T  H  D  N  G  M  I  P  F  F  F  A  L  G  L  Y  N  G  T  A  P  L  S

Acc65 I
            Sac I                                                        BspH I
TCACCCACGTCCAGTCTCCTAGCCAAACAGACGGGTTCTCATCCGCCTGGACAGTCCCCTTCGGTGCTCGGGCTTATGTTGAGATGATGC
                                                                                            1530
 L  T  H  V  Q  S  P  S  Q  T  D  G  F  S  S  A  W  T  V  P  F  G  A  R  A  Y  V  E  M  M

Ear I
                                                   Sap I
AATGTCGTCGGGAACCTGAGCCGCTCGTGCGAGTCCTCGTTAATGACCGTGTTATTCCGCTGCACGGTTGCCCGGTGGATAAACTTGGCC
                                                                                            1620
 Q  C  R  R  E  P  E  P  L  V  R  V  L  V  N  D  R  V  I  P  L  H  G  C  P  V  D  K  L  G
```

FIG. 20A

```
          Nhe I                          BspM I           BseR I
GCCGCTAGCCATCGTCACAAAGAAAACCTGCTTCGGCAGCTCCCACGTCGTCTGCGGATTCCTCCTCCCCTATTTCCCCATCGGCTCTTT
|_____| 90

Stu I
ACGTGACCACCTTCTCCAACCTGACTTCCACACCGCCACCGCCCTGACCTTCTTCATGTTAGGCCTCGTCGCCGTCACTTTCTTGTGAGT
|_____| 180
                                                       M  L  G  L  V  A  V  T  F  L

Tth111 I
                                                                    Sal I
TTGGGCTCCCTTTTCTGCCATCGCTGGTGAACTAACCGTTCGGAAGGCAACAACCGCACCACTCTTGCGACTCTGTCGACAGAGGCTTCT
|_____| 270
                                    Q  Q  P  H  H  S  C  D  S  V  D  R  G  F

Sca I                                     Xma I
                                                                  Sma I
GGTGCGCCGCCGACATCTCCCACTCCTGGGGACAGTACTCACCATACTTCTCCGTCCCCTCTGACATTGACCCGGGTTTCCCCAAGGGCT
|_____| 360
V  C  A  A  D  I  S  H  S  V  G  Q  Y  S  P  Y  F  S  V  P  S  D  I  D  P  G  F  P  K  G

BsrD I                      Kas I                                  Sal I        Tth111 I
GCAATGTGACGTTCGCACAGGTCCTCTCACGCCACGGCGCCCGCGCCCCAACTACGGGCCGGGCCGCCTACTACGTCGACGTGATTGACC
|_____| 450
C  N  V  T  F  A  Q  V  L  S  R  H  G  A  R  A  P  T  T  G  R  A  A  Y  Y  V  D  V  I  D

BsiW I         Mlu I                               Kas I
GCGTCCAGCGTCAGGCGACCTCGTACGGCCCCGGCCACGCGTTCCTGCGCTCCTACCGCTACACCCTCGGCGCCAACGAGCTTACCCCGA
|_____| 540
R  V  Q  R  Q  A  T  S  Y  G  P  G  H  A  F  L  R  S  Y  R  Y  T  L  G  A  N  E  L  T  P

BsrB I Pvu II                           Nru I    BssH II  Kas I
TGGGAGAGCGGCAGCTGGCGTATTCCGGCGCAAGGTTTTACCATCGCTATCGCGAACTTGCGCGCGTCGAGGCGCCCTTCGTGCGGTCCA
|_____| 630
M  G  E  R  Q  L  A  Y  S  G  A  R  F  Y  H  R  Y  R  E  L  A  R  V  E  A  P  F  V  R  S

Bpu10 I                                                     Sac II
             Pvu II                                                     Kas I
GTGGCGTAAGCCGCGTTGTAGCCTCAGCTGTCAATTTCACCCAGGGCTTCCACCAGGCGCGGCTCGCCGACCGCGGCGCCACGTTGCCCC
|_____| 720
S  G  V  S  R  V  V  A  S  A  V  N  F  T  Q  G  F  H  Q  A  R  L  A  D  R  G  A  T  L  P

Bbs I
                                                                 Bsa I
                Bcl I                              Bsg I         Eco31 I
CGCCAACACTGCCCTATGACATGGTGATCATCTCGTCAGACGACACCGCCAACAACACCTTGCACCACGGTCTCTGCACGGTCTTCGAGG
|_____| 810
P  P  T  L  P  Y  D  M  V  I  I  S  S  D  D  T  A  N  N  T  L  H  H  G  L  C  T  V  F  E

Bsp120 I
     Bcg I
      BseR I                                                                          Pvu II
AGGGGCCCTATGCCGACATTGGCGACAAGGCGCAGAAAGAATACCTCTCCAAGTTTGTCGGTCCCATCGTGGAGCGCATTAACGCGCAGC
|_____| 900
E  G  P  Y  A  D  I  G  D  K  A  Q  K  E  Y  L  S  K  F  V  G  P  I  V  E  R  I  N  A  Q
```

FIG. 20B

```
                                                              BsmBI
                                                              Esp3 I
TGCCCGGCGCGAATCTCAACGCGACGGACATCATCGCGCTGATGGACCTGTGCCCGTTCGAGACGGTCGCGTTCCCAGAAGGCACGAAGC
                                                                                              990
 L  P  G  A  N  L  N  A  T  D  I  I  A  L  M  D  L  C  P  F  E  T  V  A  F  P  E  G  T  K

Xma I
                                                                                   Sma I
            NgoM I      Ear I                                                      Srf I
                        Sap I              Age I           Aat II                  Bcg I
TGTCGCCCTTCTGCCGGCTCTTCACGGCCGCCGAATGGCGGGCCTACGACCGGTACCAGGACGTCGGCAAATGGTTCGGCTACGGCCCGG
                                                                                              1080
 L  S  P  F  C  R  L  F  T  A  A  E  V  R  A  Y  D  R  Y  Q  D  V  G  K  W  F  G  Y  G  P

BsrB I         Bcg I
GCAATCCGCTCGGCCCGACTCAGGGGGTCGGGTTCGTCAACGAGCTGATCGCGCGGCTGTCCGGCCAGCCGGTGAGCGATGGGACCAGCA
                                                                                              1170
 G  N  P  L  G  P  T  Q  G  V  G  F  V  N  E  L  I  A  R  L  S  G  Q  P  V  S  D  G  T  S

Bsa I
               Eco31 I        BsrB I              BseR I
CGAACCGCACGCTGGATGAGAACCCGGAGACCTTCCCGCTCGGGAGGAGGCTGTATGCGGATTTCAGCCATGATAACGACATGGTGGGCA
                                                                                              1260
 T  N  R  T  L  D  E  N  P  E  T  F  P  L  G  R  R  L  Y  A  D  F  S  H  D  N  D  M  V  G

PshA I
Bpu10 I                     Xcm I                    Bpu10 I                 BseR I
TCCTCAGCGCCTTGGGGTTGTGGGACAACCATGAAGAACCTGGGAATGAAATGCCCGCTGAGGGGGAGGAGGACGACAATGGTCGGTTCT
                                                                                              1350
 I  L  S  A  L  G  L  W  D  N  H  E  E  P  G  N  E  M  P  A  E  G  E  E  D  D  N  G  R  F

BseR I
CGACTGCTAGGGCCGTGCCGTTCGGGGCGCGGGTGTATGTCGAAAAGCTGCGGTGTGGGGGATCGGAGGAGGATGAAGAAATGGTGCGCG
                                                                                              1440
 S  T  A  R  A  V  P  F  G  A  R  V  Y  V  E  K  L  R  C  G  G  S  E  E  D  E  E  M  V  R

ApaL I  Bpu10 I         Hind III
TGTTGGTCAATGACCGGGTGATGCCCCTTGCACAGTGCGGAGGGGACAAGAGGGGAATGTGCACCCTCAGCCGGTTCGTTGAAAGCTTGA
                                                                                              1530
 V  L  V  N  D  R  V  M  P  L  A  Q  C  G  G  D  K  R  G  M  C  T  L  S  R  F  V  E  S  L BspLU11 I                        Bpu10 I
AGTTTGCGCGGAACAACGGGAGGTGGGACATGTGTTTTGAATGATGAGAGATGACACAGGCTCAGGTTGGGGAGGCGCGTTGTGAGTTTT
                                                                                              1620
 K  F  A  R  N  N  G  R  W  D  M  C  F  E GGAGTATGGAGTATGGCGGCAGGAATTGGATACCTGATACCTTTTGGATAGAGCTTTTTGCGAGGGGAAAACGCAGTGGTTTGAATACTC
                                                                                              1710

Cla I
GGAGATTCTTTGATGATGTAAGTTGATCGATTTCAGTTGTGAGGTGTAGGACATAAGGATATACAGCAAGTTCAGGGTAAGGGTTCGGAG
                                                                                              1800

Hind III                                              Eco57 I           Xcm I
ATCGGGAAGCTTGCCCGGATCTGCGGCTTGGCAGCGGGGCTGAAGTAGCCGTTTTCAGAGGTCTGCAACGGCCAAAGCCACACTGGGCTG
                                                                                              1890
```

FIG. 20C

```
                                     Bsa I
                                     Eco31 I
CGGCGTCACCCAACTTGATGCAACTTGTTGGAGGTTCCAGGTTCCCTTTCGATCCGAGACCCCTCCATGCCACGAAATCCCTCCTTCTT
                                                                                          1980

EcoR I
CGTTTCCCAGATTTCCCAGGCGCAAACCCGTCCARACGTGCTCGGAATTC
                                                  2030
```

FIG. 21

```
GCGGATTTTAGGCACGATAATAGTCTGACCTCGATATACGCTGCTCTTGGTCTGTATAACGGCACAAAGCAACTATCC
 A  D  F  R  H  D  N  S  L  T  S  I  Y  A  A  L  G  L  Y  N  G  T  K  Q  L  S
              BstX I
AAATCGAGGATAGAATCGACAAACCAGACAAATGGCTATTCTGCTGGCTGGACAGTTCCATTTGGAGCAAGGGCGTATGTTGAGATGATG
 K  S  R  I  E  S  T  N  Q  T  N  G  Y  S  A  G  W  T  V  P  F  G  A  R  A  Y  V  E  M  M
    BsrD I                                    Pvu I
CAATGCCCCTCGGGGATGAACCTCTGATTCGAGTTCTGGTGAACGATCGCGTCAT
 Q  C  P  S  G  D  E  P  L  I  R  V  L  V  N  D  R  V  I
```

FIG. 22

```
                                           GSP2rev.frt036
TATCCTTCGGAGTCAGAAAGCAAGGCGTATGCGAAGTTGATTGACGCTATCAAGAAGAATGCTACTTCGT    70
 Y  P  S  E  S  E  S  K  A  Y  A  K  L  I  D  A  I  K  K  N  A  T  S
       GFP1rev.fr1037
TTTCGGGACAGTATGCTTTTCTGGAGAGTTATAATTATACTCTCGGCGCGGAAGACTTGACTACTTTTGG   140
 F  S  G  Q  Y  A  F  L  E  S  Y  N  Y  T  L  G  A  E  D  L  T  T  F  G TGAGAACCAGATGGTCGACTCGGGTGCCAAGTTTTACCGGCGGTATAAGAATTTGGCCAGGAAAAATACT   210
 E  N  Q  M  V  D  S  G  A  K  F  Y  R  R  Y  K  N  L  A  R  K  N  T CCATTCATACGTGCATCAGGGTCTGACCGTGTCGTTGCGTCCGCGGAGAAGTTTATTGACGGACTTCGAG   280
 P  P  I  R  A  S  G  S  D  R  V  V  A  S  A  E  K  F  I  D  G  L  R ACGCCCAGACCCACGACCAGGGCTCCAAACGTGTTGCCCCAGTTGTCAATGTGGTTATCCCTGAAACTGA   350
 D  A  Q  T  H  D  Q  G  S  K  R  V  A  P  V  V  N  V  V  I  P  E  T  D TGGATTTAACAACACCCTGGATCATAGCACTTGCGTGTCTTTTGAGAATGATGAGCGGGCGGACGAAATT   420
 G  F  N  N  T  L  D  H  S  T  C  V  S  F  E  N  D  E  R  A  D  E  I GAAGCAACTTCGCCGCGATCATTGGACCTCCGATTCGCAAACGTCTGGAAAACGACCTTCCTGGCGTTG   490
 E  A  N  F  A  A  I  I  G  P  P  I  R  K  R  L  E  N  D  L  P  G  V AGCTTACAAATGAGCATGTGGAATACTTGATGGATATGTGCTCGTTCGACACCATGGCGCGCACCGCCA   560
 E  L  T  N  E  H  V  E  Y  L  M  D  M  C  S  F  D  T  M  A  R  T  A  H TGGAACCGAGCTGTCTCCATTCTGCGCCATCTTCACTGAAAAGGAGTGGCTGCAGTACGACTACCTACAA   630
 G  T  E  L  S  P  F  C  A  I  F  T  E  K  E  W  L  Q  Y  D  Y  L  Q TCTCTGTCAAAGTACTACGGCTACGGTGCCGGGAACCCCCTTGGCCCAGCTCAGGGAATTGGCTTCACCA   700
 S  L  S  K  Y  Y  G  Y  G  A  G  N  P  L  G  P  A  Q  G  I  G  F  T ACGAGCTGATTGCCCGACTGACGCAGTCGCCTGTCCAGGACAACACGAGCACCAACCACACTCTAGACTC   770
 N  E  L  I  A  R  L  T  Q  S  P  V  Q  D  N  T  S  T  N  H  T  L  D  S TGACCCGGCCACGTTCCCCCTCGACAGGAAGCTCTACGCCGACTTCTCCCACGACAATAACATGATTTCT   840
 D  P  A  T  F  P  L  D  R  K  L  Y  A  D  F  S  H  D  N  N  M  I  S ATATTCTTCGCCATGGGCCTGTACAACGGCACCCAGCCGCTGTCCATGGACACTGTGGAGTCGATTGAGG   910
 I  F  F  A  M  G  L  Y  N  G  T  Q  P  L  S  M  D  T  V  E  S  I  E AGATGGATGGCTACGCGGCGTCTTGGACTGTCCCGTTTGGTGCGAGGGCTTACTTTGAGGTGATGCAGTG   980
 E  M  D  G  Y  A  A  S  W  T  V  P  F  G  A  R  A  Y  F  E  V  M  Q  C CCAAAAAAAGAAGGAGCCACTTGTGCGGGTATTAGTGAATGATCGCGTTGTTCCTCTCCATGGCTGTGCT  1050
 Q  K  K  K  E  P  L  V  R  V  L  V  N  D  R  V  V  P  L  H  G  C  A GTTGACAAGCTCGGACGATGCACTTTGGACGATTGGGTCGAGGGCTTGAGTTTTGCCAGGGCCGGTGGGA  1120
 V  D  K  L  G  R  C  T  L  D  D  W  V  E  G  L  S  F  A  R  A  G  G ACTGGAAGGCTTGTTTTACTGCCTAA                                              1146
 N  W  K  A  C  F  T  A  .
```

FIG. 23

```
                                                          CSP3rev,fy1033
CAGTACTCTGCATACTTCCCAATCCCGTCTGAGCTTGATGCCTCAACACCAGACGATTGTGATGTGACTT        70
 Q  Y  S  A  I  P  P  I  P  S  E  L  D  A  S  T  P  D  D  C  D  V  T
                      CSP1rev,fy1039
TTGCACTCGTCTTGTCCCGCCATGGAGCCAGGTACCCAACGGACAGCAAGTCTGCAGCATACAACGCTAC       140
 F  A  L  V  L  S  R  H  G  A  R  T  P  T  D  S  K  S  A  A  Y  N  A  T CATTGCCCGCATTCAAAAGTCTGCTACCATGTACGGCAAGAACTACAAGTGGCTTAAGGAGTATACCTAC       210
 I  A  R  I  Q  K  S  A  T  M  Y  G  K  N  Y  K  W  L  K  E  Y  T  Y AGTCTCGGCGCTGAAGACCTGACTGAGTTTGGCCAGCGGCAGATGGTCGACTCTGCTAGGCCTTTTATG       280
 S  L  G  A  E  D  L  T  E  F  G  Q  R  Q  M  V  D  S  G  R  A  F  Y AGCGGTACATGAGTCTCGCTGAGAAGACTGAGCCTTTTGTTCGGGCATCGGGCTCAGATCGGGTCATCAT      350
 E  R  Y  M  S  L  A  E  K  T  E  P  P  V  R  A  S  G  E  D  R  V  I  M GTCCTCTTACAATTTTACGCAAGGCTTTTACGCATCGCGAGGAGAGTCTGGAGACGATTATACTCAGGAT      420
 S  S  Y  N  F  T  Q  G  F  Y  A  S  R  G  E  S  G  D  D  Y  T  Q  D GTTCTTATCATCCCTGAAGAACCTGGCATCAACAACACCATGTTGCATGGATCGTGCGCCTCATTCGAAA      490
 V  L  I  I  P  E  E  P  G  I  N  N  T  M  L  H  G  S  C  A  S  F  E GCGACAGAGTTCCTAAAGACGCAGATGAAAAGGCCGAGGTTGCATGGGAGCAAGATTCCTCCCCGAGAT      560
 S  D  R  V  P  K  D  A  D  E  K  A  E  V  A  W  G  A  R  F  L  P  E  I TCGAAATAGGTTGAACCACCACCTGCCACGAGTCAACCTGACGCTGGAGGAAACCATCTACATGATGGAC      630
 R  N  R  L  N  H  H  L  P  G  V  N  L  T  L  E  E  T  I  Y  M  M  D ATGTGTCCGTTCCTCGCGGCTGACACACCTGATGGCGCTGGTCACTCGAGGTTCTGCGACCTCTTCACCA      700
 M  C  P  P  L  A  A  D  T  P  D  G  A  G  H  S  R  F  C  D  L  F  T AGGCAGACTGGCCAAGTTACGACTACTACATGACTCTGAGCAAGTTCTACAAGTTTGGCAATGGCAATGC      770
 K  A  D  W  R  S  Y  D  Y  Y  M  T  L  S  K  F  Y  K  F  G  N  G  N  A CATGGGACCGACACAAGGTGTTCCATATGTCAACGAACTCATCTCACGCTTGACTGGGAAGCCTGTTGAC      840
 M  G  P  T  Q  G  V  V  N  E  L  I  S  R  L  T  G  K  P  V  D GACCACACCACGACCAACAGCACATTGGACTCATCGCCAAAGACGTTCCCTCTTGACAGGGCTCTATATG      910
 D  H  T  T  T  N  S  T  L  D  S  S  P  K  T  F  P  L  D  R  A  L  Y CGGATTTTAGCCACGACAACAGCATGGTCTCCATCTTCTCAGCACTGGGCTTCTACAACTCGACTACCCT      980
 A  D  F  S  H  D  N  S  M  V  S  I  F  S  A  L  G  L  Y  N  S  T  T  L GCTACCAAAGGACCATATTGTGCCCGCGATCAAGGCGCACGGCTACTCATCGACATGGGTAGTCCCCTTT     1050
 L  P  K  D  H  I  V  P  A  I  K  A  H  G  Y  S  S  T  W  V  V  P  F CGACCCAGAATGTACGTCGAGAAGCTCGAGTGTGGCGCCAGCAGGAATGAAAAGAGAGACCGAGTACGTGC     1120
 G  A  R  M  Y  V  E  K  L  E  C  G  A  S  R  N  E  K  R  D  E  Y  V GAGTCCTGGTCAACGACCGAGTGATGTCGCTCGAAACCTGCGGAGGCGACGAGTACGGCTCTGCAGACT     1190
 R  V  L  V  N  D  R  V  M  S  L  E  T  C  G  G  D  E  Y  G  L  C  R  L AGAAAACTTTGTGGAGAGTCTGTCGTTTGCCGCCTCGGGAGGAAACTGGGATCAATGCGGTGGATAA    1257
 E  N  F  V  E  S  L  S  F  A  A  S  G  G  N  W  D  Q  C  G  G
```

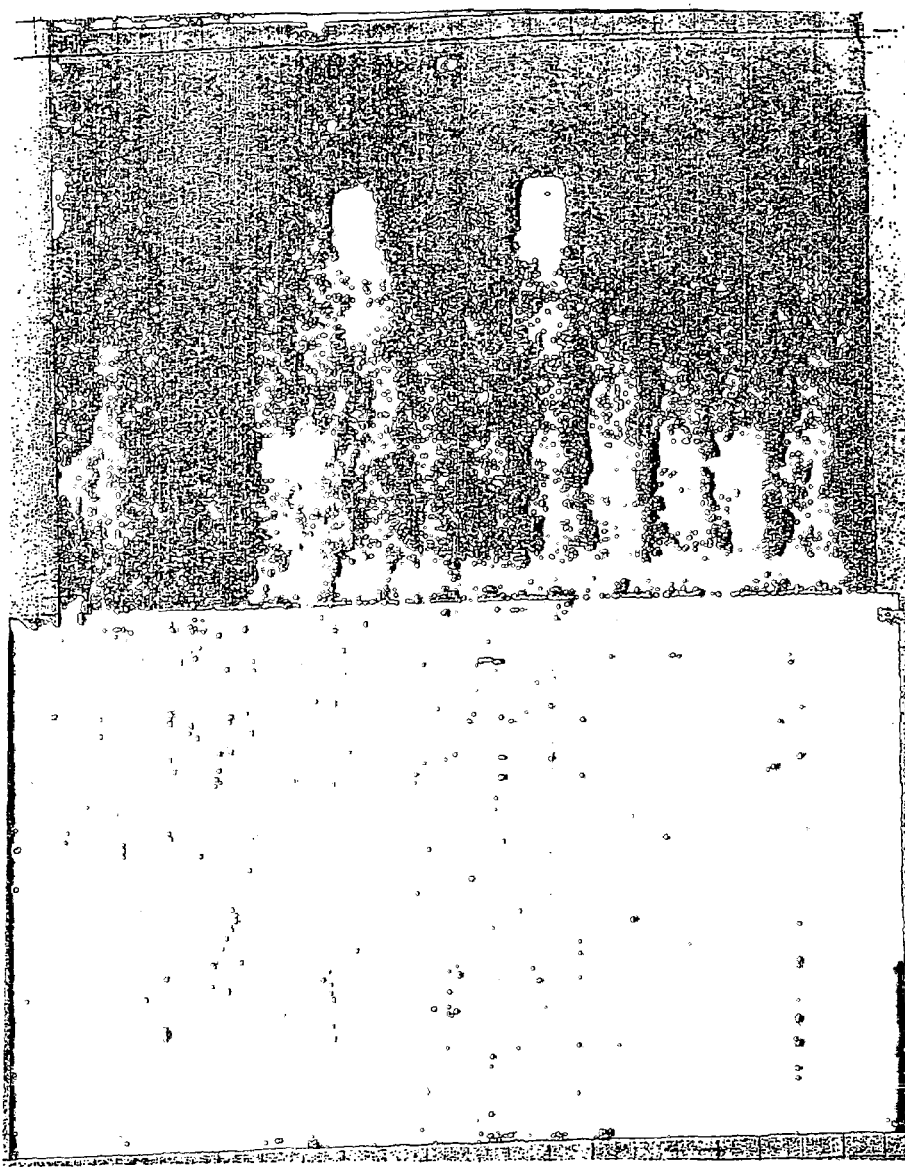

SEQUENCE LISTING

```
<160> NUMBER OF SEQ ID NOS: 80

<210> SEQ ID NO 1
<211> LENGTH: 1317
<212> TYPE: DNA
<213> ORGANISM: Penicillium chrysogenum

<400> SEQUENCE: 1
tgcactactg tcgatggcgg ttaccaatgc aattccgagc tctcacacaa gtggggccag      60
tattcgccct atttctctct ttccgaagaa tcatccatct cgaatgaggt acctcatgat     120
tgtcagatca cttttgctca agtgatctcc cgtcatggtg ctcgattccc gtccgcgaag     180
```

```
aagagcaagg tatatgccaa gctcattgaa aatatccaag cgaacgcgac tgcatacaat    240
ggcaacacga agttcctccg ctcatacaag tacaccatgg gcggtgatga tttggtaccc    300
ttcggagtga accagacggt ggactcgggg accaaattct accagcgcta cgaggcgttg    360
gcgaagaaag ctgtgccctt cattcggtca tctgactcag ggcgggttgt ggcttcaggc    420
gtgaacttta tcaagggatt ccagcaggca agttggatg ataaaaatgc caatcaccgt    480
cagccaagcc ccaaaaccaa cgtcatcatc tcagaagagt ctggcaccaa caacactctg    540
aaccacagcg agatctgtcc taagttcgaa gacaatgagc tgggcgacaa ggtcgaagaa    600
aaatacatga aaatctttgt gccgcccatc cgagctcgtc tcgaggccga tctccctggc    660
gttaaacttg aagacatcga tgttgtcagt ctgatggaca tctgcccttt cgagacagtg    720
tcttcaagtg acgacgcagc cgagctatct ccattctgcg acctcttcac cccgaccgaa    780
tggagccaat atgactacct ccagtcgtta agcaagtact atggttatgg cgccggcaat    840
cctctcggcc cgacccaggg tgtcggtttc gtaaacgaac tgattgcccg actcactcgc    900
cacccagtga gagaccacac aagcacaaac cgtgcgctcg atgccccgg cgctgcgaca    960 ttcccctca actacaccat gtatgccgac ttcacgcatg acaacggaat gatcccgttc   1020
ttctttgctt tggggctgta caacggcacc gctccactct cgctcaccca cgtccagtct   1080
cctagccaaa cagacgggtt ctcatccgcc tggacagtcc ccttcggtgc tcgggcttat   1140
gttgagatga tgcaatgtcg tcgggaacct gagccgctcg tgcgagtcct cgttaatgac   1200
cgtgttattc cgctgcacgg ttgcccggtg gataaacttg gccgttgtcg ccgtcgtgat   1260
ttcgtgaaag ggcttacttt cgcacgctct ggcggcgact gggccaggtg ttataaa     1317
```

<210> SEQ ID NO 2
<211> LENGTH: 439
<212> TYPE: PRT
<213> ORGANISM: Penicillium chrysogenum

<400> SEQUENCE: 2

```
Cys Thr Thr Val Asp Gly Gly Tyr Gln Cys Asn Ser Glu Leu Ser His
  1               5                  10                  15

Lys Trp Gly Gln Tyr Ser Pro Tyr Phe Ser Leu Ser Glu Glu Ser Ser
             20                  25                  30

Ile Ser Asn Glu Val Pro His Asp Cys Gln Ile Thr Phe Ala Gln Val
         35                  40                  45

Ile Ser Arg His Gly Ala Arg Phe Pro Ser Ala Lys Lys Ser Lys Val
     50                  55                  60

Tyr Ala Lys Leu Ile Glu Asn Ile Gln Ala Asn Ala Thr Ala Tyr Asn
 65                  70                  75                  80

Gly Asn Thr Lys Phe Leu Arg Ser Tyr Lys Tyr Thr Met Gly Gly Asp
                 85                  90                  95

Asp Leu Val Pro Phe Gly Val Asn Gln Thr Val Asp Ser Gly Thr Lys
            100                 105                 110

Phe Tyr Gln Arg Tyr Glu Ala Leu Ala Lys Lys Ala Val Pro Phe Ile
        115                 120                 125

Arg Ser Ser Asp Ser Gly Arg Val Val Ala Ser Gly Val Asn Phe Ile
    130                 135                 140

Lys Gly Phe Gln Gln Ala Lys Leu Asp Asp Lys Asn Ala Asn His Arg
145                 150                 155                 160

Gln Pro Ser Pro Lys Thr Asn Val Ile Ile Ser Glu Glu Ser Gly Thr
                165                 170                 175
```

```
Asn Asn Thr Leu Asn His Ser Glu Ile Cys Pro Lys Phe Glu Asp Asn
            180                 185                 190

Glu Leu Gly Asp Lys Val Glu Lys Tyr Met Lys Ile Phe Val Pro
        195                 200                 205

Pro Ile Arg Ala Arg Leu Glu Ala Asp Leu Pro Gly Val Lys Leu Glu
    210                 215                 220

Asp Ile Asp Val Val Ser Leu Met Asp Ile Cys Pro Phe Glu Thr Val
225                 230                 235                 240

Ser Ser Ser Asp Asp Ala Ala Glu Leu Ser Pro Phe Cys Asp Leu Phe
                245                 250                 255

Thr Pro Thr Glu Trp Ser Gln Tyr Asp Tyr Leu Gln Ser Leu Ser Lys
            260                 265                 270

Tyr Tyr Gly Tyr Gly Ala Gly Asn Pro Leu Gly Pro Thr Gln Gly Val
        275                 280                 285

Gly Phe Val Asn Glu Leu Ile Ala Arg Leu Thr Arg His Pro Val Arg
    290                 295                 300

Asp His Thr Ser Thr Asn Arg Ala Leu Asp Ala Pro Gly Ala Ala Thr
305                 310                 315                 320

Phe Pro Leu Asn Tyr Thr Met Tyr Ala Asp Phe His Asp Asn Gly
                325                 330                 335

Met Ile Pro Phe Phe Phe Ala Leu Gly Leu Tyr Asn Gly Thr Ala Pro
            340                 345                 350

Leu Ser Leu Thr His Val Gln Ser Pro Ser Gln Thr Asp Gly Phe Ser
            355                 360                 365

Ser Ala Trp Thr Val Pro Phe Gly Ala Arg Ala Tyr Val Glu Met Met
    370                 375                 380

Gln Cys Arg Arg Glu Pro Glu Pro Leu Val Arg Val Leu Val Asn Asp
385                 390                 395                 400

Arg Val Ile Pro Leu His Gly Cys Pro Val Asp Lys Leu Gly Arg Cys
                405                 410                 415

Arg Arg Arg Asp Phe Val Lys Gly Leu Thr Phe Ala Arg Ser Gly Gly
            420                 425                 430

Asp Trp Ala Arg Cys Tyr Lys
            435

<210> SEQ ID NO 3
<211> LENGTH: 446
<212> TYPE: PRT
<213> ORGANISM: Artificial Sequence
<220> FEATURE:
<223> OTHER INFORMATION: chimeric phytase enzyme

<400> SEQUENCE: 3

Ala Ser Arg Asn Gln Ser Thr Cys Thr Thr Val Asp Gly Gly Tyr Gln
1               5                   10                  15

Cys Asn Ser Glu Leu Ser His Lys Trp Gly Gln Tyr Ser Pro Tyr Phe
            20                  25                  30

Ser Leu Ser Glu Glu Ser Ser Ile Ser Asn Glu Val Pro His Asp Cys
        35                  40                  45

Gln Ile Thr Phe Ala Gln Val Ile Ser Arg His Gly Ala Arg Phe Pro
    50                  55                  60

Ser Ala Lys Lys Ser Lys Val Tyr Ala Lys Leu Ile Glu Asn Ile Gln
65                  70                  75                  80

Ala Asn Ala Thr Ala Tyr Asn Gly Asn Thr Lys Phe Leu Arg Ser Tyr
                85                  90                  95
```

Lys Tyr Thr Met Gly Gly Asp Asp Leu Val Pro Phe Gly Val Asn Gln
            100                 105                 110

Thr Val Asp Ser Gly Thr Lys Phe Tyr Gln Arg Tyr Glu Ala Leu Ala
        115                 120                 125

Lys Lys Ala Val Pro Phe Ile Arg Ser Ser Asp Ser Gly Arg Val Val
    130                 135                 140

Ala Ser Gly Val Asn Phe Ile Lys Gly Phe Gln Gln Ala Lys Leu Asp
145                 150                 155                 160

Asp Lys Asn Ala Asn His Arg Gln Pro Ser Pro Lys Thr Asn Val Ile
                165                 170                 175

Ile Ser Glu Glu Ser Gly Thr Asn Asn Thr Leu Asn His Ser Glu Ile
            180                 185                 190

Cys Pro Lys Phe Glu Asp Asn Glu Leu Gly Asp Lys Val Glu Glu Lys
        195                 200                 205

Tyr Met Lys Ile Phe Val Pro Pro Ile Arg Ala Arg Leu Glu Ala Asp
    210                 215                 220

Leu Pro Gly Val Lys Leu Glu Asp Ile Asp Val Val Ser Leu Met Asp
225                 230                 235                 240

Ile Cys Pro Phe Glu Thr Val Ser Ser Ser Asp Ala Ala Glu Leu
                245                 250                 255

Ser Pro Phe Cys Asp Leu Phe Thr Pro Thr Glu Trp Ser Gln Tyr Asp
            260                 265                 270

Tyr Leu Gln Ser Leu Ser Lys Tyr Tyr Gly Tyr Gly Ala Gly Asn Pro
        275                 280                 285

Leu Gly Pro Thr Gln Gly Val Gly Phe Val Asn Glu Leu Ile Ala Arg
    290                 295                 300

Leu Thr Arg His Pro Val Arg Asp His Thr Ser Thr Asn Arg Ala Leu
305                 310                 315                 320

Asp Ala Pro Gly Ala Ala Thr Phe Pro Leu Asn Tyr Thr Met Tyr Ala
                325                 330                 335

Asp Phe Thr His Asp Asn Gly Met Ile Pro Phe Phe Ala Leu Gly
            340                 345                 350

Leu Tyr Asn Gly Thr Ala Pro Leu Ser Leu Thr His Val Gln Ser Pro
        355                 360                 365

Ser Gln Thr Asp Gly Phe Ser Ser Ala Trp Thr Val Pro Phe Gly Ala
    370                 375                 380

Arg Ala Tyr Val Glu Met Met Gln Cys Arg Arg Glu Pro Glu Pro Leu
385                 390                 395                 400

Val Arg Val Leu Val Asn Asp Arg Val Ile Pro Leu His Gly Cys Pro
                405                 410                 415

Val Asp Lys Leu Gly Arg Cys Arg Arg Arg Asp Phe Val Lys Gly Leu
            420                 425                 430

Thr Phe Ala Arg Ser Gly Gly Asp Trp Ala Arg Cys Tyr Lys
        435                 440                 445

<210> SEQ ID NO 4
<211> LENGTH: 1299
<212> TYPE: DNA
<213> ORGANISM: Fusarium javanicum

<400> SEQUENCE: 4
tgtgagtatg acgggagctg taatgacatc tctcggctct ggggacagta ctctgcatac    60
ttcccaatcc cgtctgagct tgatgcctca ac

-continued

```
ctcgtcttgt cccgccatgg agccaggtac ccaacggaca gcaagtctgc agcatacaac    180
gctaccattg cccgcattca aaagtctgct accatgtacg gcaagaacta caagtggctt    240
aaggagtata cctacagtct cggcgctgaa gacctgactg agtttggcca gcggcagatg    300
gtcgactctg gtagggcctt ttatgagcgg tacatgagtc tcgctgagaa gactgagcct    360
tttgttcggg catcgggctc agatcgggtc atcatgtcgt cttacaattt tacgcaaggc    420
ttttacgcat cgcgaggaga gtctggagac gattatactc aggatgttct tatcatccct    480
gaagaacctg gcatcaacaa caccatgttg catggatcgt gcgcctcatt cgaaagcgac    540
agagttccta aagacgcaga tgaaaaggcc gaggttgcat ggggagcaag attcctcccc    600
gagattcgaa ataggttgaa ccaccacctg ccaggagtca acctgacgct ggaggaaacc    660
atctacatga tggacatgtg tccgttcctc gcggctgaca cacctgatgg cgctggtcac    720
tcgaggttct gcgacctctt caccaaggca gactggcgaa gttacgacta ctacatgact    780
ctgagcaagt tctacaagtt tggcaatggc aatgccatgg gaccgacaca aggtgttgga    840
tatgtcaacg aactcatctc acgcttgact gggaagcctg ttgacgacca caccacgacc    900
aacagcacat tggactcatc gccaaagacg ttccctcttg acagggctct atatgcggat    960
tttagccacg acaacagcat ggtctccatc ttctcagcac tgggcttgta caactcgact   1020
accctgctac caaaggacca tattgtgccc gcgatcaagg cgcacggcta ctcatcgaca   1080
tgggtagtcc cctttggagc cagaatgtac gtcgagaagc tcgagtgtgg tgccagcagg   1140
aatgaaaaga gagacgagta cgtgcgagtc ctggtcaacg accgagtgat gtcgctcgaa   1200
acctgcggag gcgacgagta cggctctgc agactagaaa actttgtgga gagtctgtcg    1260
tttgccgcct cgggaggaaa ctgggatcaa tgcggtgga                          1299
```

```

<210> SEQ ID NO 5
<211> LENGTH: 433
<212> TYPE: PRT
<213> ORGANISM: Fusarium javanicum

<400> SEQUENCE: 5

Cys Glu Tyr Asp Gly Ser Cys Asn Asp Ile Ser Arg Leu Trp Gly Gln
 1               5                  10                  15

Tyr Ser Ala Tyr Phe Pro Ile Pro Ser Glu Leu Asp Ala Ser Thr Pro
            20                  25                  30

Asp Asp Cys Asp Val Thr Phe Ala Leu Val Leu Ser Arg His Gly Ala
        35                  40                  45

Arg Tyr Pro Thr Asp Ser Lys Ser Ala Ala Tyr Asn Ala Thr Ile Ala
    50                  55                  60

Arg Ile Gln Lys Ser Ala Thr Met Tyr Gly Lys Asn Tyr Lys Trp Leu
65                  70                  75                  80

Lys Glu Tyr Thr Tyr Ser Leu Gly Ala Glu Asp Leu Thr Glu Phe Gly
                85                  90                  95

Gln Arg Gln Met Val Asp Ser Gly Arg Ala Phe Tyr Glu Arg Tyr Met
            100                 105                 110

Ser Leu Ala Glu Lys Thr Glu Pro Phe Val Arg Ala Ser Gly Ser Asp
        115                 120                 125

Arg Val Ile Met Ser Ser Tyr Asn Phe Thr Gln Gly Phe Tyr Ala Ser
    130                 135                 140

Arg Gly Glu Ser Gly Asp Asp Tyr Thr Gln Asp Val Leu Ile Ile Pro
145                 150                 155                 160

Glu Glu Pro Gly Ile Asn Asn Thr Met Leu His Gly Ser Cys Ala Ser
```

```
                165                 170                 175
Phe Glu Ser Asp Arg Val Pro Lys Asp Ala Asp Glu Lys Ala Glu Val
            180                 185                 190

Ala Trp Gly Ala Arg Phe Leu Pro Glu Ile Arg Asn Arg Leu Asn His
            195                 200                 205

His Leu Pro Gly Val Asn Leu Thr Leu Glu Glu Thr Ile Tyr Met Met
            210                 215                 220

Asp Met Cys Pro Phe Leu Ala Ala Asp Thr Pro Asp Gly Ala Gly His
225                 230                 235                 240

Ser Arg Phe Cys Asp Leu Phe Thr Lys Ala Asp Trp Arg Ser Tyr Asp
                245                 250                 255

Tyr Tyr Met Thr Leu Ser Lys Phe Tyr Lys Phe Gly Asn Gly Asn Ala
            260                 265                 270

Met Gly Pro Thr Gln Gly Val Gly Tyr Val Asn Glu Leu Ile Ser Arg
            275                 280                 285

Leu Thr Gly Lys Pro Val Asp Asp His Thr Thr Thr Asn Ser Thr Leu
            290                 295                 300

Asp Ser Ser Pro Lys Thr Phe Pro Leu Asp Arg Ala Leu Tyr Ala Asp
305                 310                 315                 320

Phe Ser His Asp Asn Ser Met Val Ser Ile Phe Ser Ala Leu Gly Leu
                325                 330                 335

Tyr Asn Ser Thr Thr Leu Leu Pro Lys Asp His Ile Val Pro Ala Ile
            340                 345                 350

Lys Ala His Gly Tyr Ser Ser Thr Trp Val Val Pro Phe Gly Ala Arg
            355                 360                 365

Met Tyr Val Glu Lys Leu Glu Cys Gly Ala Ser Arg Asn Glu Lys Arg
            370                 375                 380

Asp Glu Tyr Val Arg Val Leu Val Asn Asp Arg Val Met Ser Leu Glu
385                 390                 395                 400

Thr Cys Gly Gly Asp Glu Tyr Gly Leu Cys Arg Leu Glu Asn Phe Val
                405                 410                 415

Glu Ser Leu Ser Phe Ala Ala Ser Gly Gly Asn Trp Asp Gln Cys Gly
            420                 425                 430

Gly

<210> SEQ ID NO 6
<211> LENGTH: 440
<212> TYPE: PRT
<213> ORGANISM: Artificial Sequence
<220> FEATURE:
<223> OTHER INFORMATION: chimeric phytase enzyme

<400> SEQUENCE: 6

Ala Ser Arg Asn Gln Ser Thr Cys Glu Tyr Asp Gly Ser Cys Asn Asp
 1               5                  10                  15

Ile Ser Arg Leu Trp Gly Gln Tyr Ser Ala Tyr Phe Pro Ile Pro Ser
            20                  25                  30

Glu Leu Asp Ala Ser Thr Pro Asp Asp Cys Asp Val Thr Phe Ala Leu
        35                  40                  45

Val Leu Ser Arg His Gly Ala Arg Tyr Pro Thr Asp Ser Lys Ser Ala
    50                  55                  60

Ala Tyr Asn Ala Thr Ile Ala Arg Ile Gln Lys Ser Ala Thr Met Tyr
65                  70                  75                  80

Gly Lys Asn Tyr Lys Trp Leu Lys Glu Tyr Thr Tyr Ser Leu Gly Ala
                85                  90                  95
```

```
Glu Asp Leu Thr Glu Phe Gly Gln Arg Gln Met Val Asp Ser Gly Arg
            100                 105                 110

Ala Phe Tyr Glu Arg Tyr Met Ser Leu Ala Glu Lys Thr Glu Pro Phe
        115                 120                 125

Val Arg Ala Ser Gly Ser Asp Arg Val Ile Met Ser Ser Tyr Asn Phe
    130                 135                 140

Thr Gln Gly Phe Tyr Ala Ser Arg Gly Glu Ser Gly Asp Asp Tyr Thr
145                 150                 155                 160

Gln Asp Val Leu Ile Ile Pro Glu Glu Pro Gly Ile Asn Asn Thr Met
                165                 170                 175

Leu His Gly Ser Cys Ala Ser Phe Glu Ser Asp Arg Val Pro Lys Asp
            180                 185                 190

Ala Asp Glu Lys Ala Glu Val Ala Trp Gly Ala Arg Phe Leu Pro Glu
        195                 200                 205

Ile Arg Asn Arg Leu Asn His His Leu Pro Gly Val Asn Leu Thr Leu
    210                 215                 220

Glu Glu Thr Ile Tyr Met Met Asp Met Cys Pro Phe Leu Ala Ala Asp
225                 230                 235                 240

Thr Pro Asp Gly Ala Gly His Ser Arg Phe Cys Asp Leu Phe Thr Lys
                245                 250                 255

Ala Asp Trp Arg Ser Tyr Asp Tyr Tyr Met Thr Leu Ser Lys Phe Tyr
            260                 265                 270

Lys Phe Gly Asn Gly Asn Ala Met Gly Pro Thr Gln Gly Val Gly Tyr
        275                 280                 285

Val Asn Glu Leu Ile Ser Arg Leu Thr Gly Lys Pro Val Asp Asp His
    290                 295                 300

Thr Thr Thr Asn Ser Thr Leu Asp Ser Ser Pro Lys Thr Phe Pro Leu
305                 310                 315                 320

Asp Arg Ala Leu Tyr Ala Asp Phe Ser His Asp Asn Ser Met Val Ser
                325                 330                 335

Ile Phe Ser Ala Leu Gly Leu Tyr Asn Ser Thr Thr Leu Leu Pro Lys
            340                 345                 350

Asp His Ile Val Pro Ala Ile Lys Ala His Gly Tyr Ser Ser Thr Trp
        355                 360                 365

Val Val Pro Phe Gly Ala Arg Met Tyr Val Glu Lys Leu Glu Cys Gly
    370                 375                 380

Ala Ser Arg Asn Glu Lys Arg Asp Glu Tyr Val Arg Val Leu Val Asn
385                 390                 395                 400

Asp Arg Val Met Ser Leu Glu Thr Cys Gly Gly Asp Glu Tyr Gly Leu
                405                 410                 415

Cys Arg Leu Glu Asn Phe Val Glu Ser Leu Ser Phe Ala Ala Ser Gly
            420                 425                 430

Gly Asn Trp Asp Gln Cys Gly Gly
        435                 440

<210> SEQ ID NO 7
<211> LENGTH: 224
<212> TYPE: DNA
<213> ORGANISM: Fusarium vertisillibodes

<400> SEQUENCE: 7
gcggatttta ggcacgataa tagtctgacc tcgatatacg ctgctcttgg tctgtataac      60
ggcacaaagc aactatccaa atcgaggata gaatc

```
gctggctgga cagttccatt tggagcaagg gcgtatgttg agatgatgca atgcccctcg    180
ggggatgaac ctctgattcg agttctggtg aacgatcgcg tcat                    224
```

<210> SEQ ID NO 8
<211> LENGTH: 74
<212> TYPE: PRT
<213> ORGANISM: Fusarium vertisillibodes

<400> SEQUENCE: 8

```
Ala Asp Phe Arg His Asp Asn Ser Leu Thr Ser Ile Tyr Ala Ala Leu
 1               5                  10                  15

Gly Leu Tyr Asn Gly Thr Lys Gln Leu Ser Lys Ser Arg Ile Glu Ser
             20                  25                  30

Thr Asn Gln Thr Asn Gly Tyr Ser Ala Gly Trp Thr Val Pro Phe Gly
         35                  40                  45

Ala Arg Ala Tyr Val Glu Met Met Gln Cys Pro Ser Gly Asp Glu Pro
     50                  55                  60

Leu Ile Arg Val Leu Val Asn Asp Arg Val
 65                  70
```

<210> SEQ ID NO 9
<211> LENGTH: 1326
<212> TYPE: DNA
<213> ORGANISM: Humicola grisea

<400> SEQUENCE: 9

```
tgcgactctg tcgacagagg cttctggtgc gccgccgaca tctcccactc ctggggacag     60
tactcaccat acttctccgt cccctctgac attgacccgg gtttccccaa gggctgcaat    120
gtgacgttcg cacaggtcct ctcacgccac ggcgcccgcg ccccaactac gggccgggcc    180
gcctactacg tcgacgtgat tgaccgcgtc cagcgtcagg cgacctcgta cggccccggc    240
cacgcgttcc tgcgctccta ccgctacacc ctcggcgcca acgagcttac cccgatggga    300
gagcggcagc tggcgtattc cggcgcaagg ttttaccatc gctatcgcga acttgcgcgc    360
gtcgaggcgc cctccgtgcg gtccagtggc gtaagccgcg ttgtagcctc agctgtcaat    420
ttcacccagg gcttccacca ggcgcggctc gccgaccgcg gcgccacgtt gccccccgcca    480 acactgccct atgacatggt gatcatctcg tcagacgaca ccgccaacaa cacccttgcac    540 cacggtctct gcacggtctt cgaggagggg ccctatgccg acattggcga caaggcgcag    600
aaagaatacc tctccaagtt tgtcggtccc atcgtggagc gcattaacgc gcagctgccc    660
ggcgcgaatc tcaacgcgac ggacatcatc gcgctgatgg acctgtgccc gttcgagacg    720
gtcgcgttcc agaaggcac gaagctgtcg cccttctgcc ggctcttcac ggccgccgaa    780
tggcgggcct acgaccggta ccaggacgtc ggcaaatggt tcggctacgg cccgggcaat    840
ccgctcggcc cgactcaggg ggtcgggttc gtcaacgagc tgatcgcgcg gctgtccggc    900
cagccggtga gcgatgggac cagcacgaac cgcacgctgg atgagaaccc ggagaccttc    960
ccgctcggga ggaggctgta tgcggatttc agccatgata cgacatggt gggcatcctc   1020 agcgccttgg ggttgtggga caaccatgaa gaacctggga atgaaatgcc cgctgagggg   1080
gaggaggacg acaatggtcg gttctcgact gctagggccg tgccgttcgg ggcgcgggtg   1140
tatgtcgaaa agctgcggtg tggggggatcg gaggaggatg aagaaatggt gcgcgtgttg   1200
gtcaatgacc gggtgatgcc ccttgcacag tgcggagggg acaagagggg aatgtgcacc   1260
ctcagccggt tcgttgaaag cttgaagttt gcgcggaaca acgggaggtg ggacatgtgt   1320
``` tttgaa 1326

<210> SEQ ID NO 10
<211> LENGTH: 442
<212> TYPE: PRT
<213> ORGANISM: Humicola grisea

<400> SEQUENCE: 10

```
Cys Asp Ser Val Asp Arg Gly Phe Trp Cys Ala Ala Asp Ile Ser His
  1               5                  10                  15

Ser Trp Gly Gln Tyr Ser Pro Tyr Phe Ser Val Pro Ser Asp Ile Asp
             20                  25                  30

Pro Gly Phe Pro Lys Gly Cys Asn Val Thr Phe Ala Gln Val Leu Ser
         35                  40                  45

Arg His Gly Ala Arg Ala Pro Thr Thr Gly Arg Ala Ala Tyr Tyr Val
 50                  55                  60

Asp Val Ile Asp Arg Val Gln Arg Gln Ala Thr Ser Tyr Gly Pro Gly
 65                  70                  75                  80

His Ala Phe Leu Arg Ser Tyr Arg Tyr Thr Leu Gly Ala Asn Glu Leu
                 85                  90                  95

Thr Pro Met Gly Glu Arg Gln Leu Ala Tyr Ser Gly Ala Arg Phe Tyr
            100                 105                 110

His Arg Tyr Arg Glu Leu Ala Arg Val Glu Ala Pro Phe Val Arg Ser
        115                 120                 125

Ser Gly Val Ser Arg Val Ala Ser Ala Val Asn Phe Thr Gln Gly
        130                 135                 140

Phe His Gln Ala Arg Leu Ala Asp Arg Gly Ala Thr Leu Pro Pro Pro
145                 150                 155                 160

Thr Leu Pro Tyr Asp Met Val Ile Ile Ser Asp Asp Thr Ala Asn
                165                 170                 175

Asn Thr Leu His His Gly Leu Cys Thr Val Phe Glu Glu Gly Pro Tyr
            180                 185                 190

Ala Asp Ile Gly Asp Lys Ala Gln Lys Glu Tyr Leu Ser Lys Phe Val
        195                 200                 205

Gly Pro Ile Val Glu Arg Ile Asn Ala Gln Leu Pro Gly Ala Asn Leu
    210                 215                 220

Asn Ala Thr Asp Ile Ile Ala Leu Met Asp Leu Cys Pro Phe Glu Thr
225                 230                 235                 240

Val Ala Phe Pro Glu Gly Thr Lys Leu Ser Pro Phe Cys Arg Leu Phe
                245                 250                 255

Thr Ala Ala Glu Trp Arg Ala Tyr Asp Arg Tyr Gln Asp Val Gly Lys
            260                 265                 270

Trp Phe Gly Tyr Gly Pro Gly Asn Pro Leu Gly Pro Thr Gln Gly Val
        275                 280                 285

Gly Phe Val Asn Glu Leu Ile Ala Arg Leu Ser Gly Gln Pro Val Ser
    290                 295                 300

Asp Gly Thr Ser Thr Asn Arg Thr Leu Asp Glu Asn Pro Glu Thr Phe
305                 310                 315                 320

Pro Leu Gly Arg Arg Leu Tyr Ala Asp Phe Ser His Asp Asn Asp Met
                325                 330                 335

Val Gly Ile Leu Ser Ala Leu Gly Leu Trp Asp Asn His Glu Glu Pro
            340                 345                 350

Gly Asn Glu Met Pro Ala Glu Gly Glu Glu Asp Asp Asn Gly Arg Phe
        355                 360                 365
```

```
Ser Thr Ala Arg Ala Val Pro Phe Gly Ala Arg Val Tyr Val Glu Lys
    370                 375                 380

Leu Arg Cys Gly Gly Ser Glu Glu Asp Glu Glu Met Val Arg Val Leu
385                 390                 395                 400

Val Asn Asp Arg Val Met Pro Leu Ala Gln Cys Gly Gly Asp Lys Arg
                405                 410                 415

Gly Met Cys Thr Leu Ser Arg Phe Val Glu Ser Leu Lys Phe Ala Arg
                420                 425                 430

Asn Asn Gly Arg Trp Asp Met Cys Phe Glu
        435                 440

<210> SEQ ID NO 11
<211> LENGTH: 449
<212> TYPE: PRT
<213> ORGANISM: Artificial Sequence
<220> FEATURE:
<223> OTHER INFORMATION: chimeric phytase enzyme

<400> SEQUENCE: 11

Ala Ser Arg Asn Gln Ser Thr Cys Asp Ser Val Asp Arg Gly Phe Trp
1               5                   10                  15

Cys Ala Ala Asp Ile Ser His Ser Trp Gly Gln Tyr Ser Pro Tyr Phe
                20                  25                  30

Ser Val Pro Ser Asp Ile Asp Pro Gly Phe Pro Lys Gly Cys Asn Val
            35                  40                  45

Thr Phe Ala Gln Val Leu Ser Arg His Gly Ala Arg Ala Pro Thr Thr
        50                  55                  60

Gly Arg Ala Ala Tyr Tyr Val Asp Val Ile Asp Arg Val Gln Arg Gln
65                  70                  75                  80

Ala Thr Ser Tyr Gly Pro Gly His Ala Phe Leu Arg Ser Tyr Arg Tyr
                85                  90                  95

Thr Leu Gly Ala Asn Glu Leu Thr Pro Met Gly Glu Arg Gln Leu Ala
            100                 105                 110

Tyr Ser Gly Ala Arg Phe Tyr His Arg Tyr Arg Glu Leu Ala Arg Val
        115                 120                 125

Glu Ala Pro Phe Val Arg Ser Ser Gly Val Ser Arg Val Val Ala Ser
130                 135                 140

Ala Val Asn Phe Thr Gln Gly Phe His Gln Ala Arg Leu Ala Asp Arg
145                 150                 155                 160

Gly Ala Thr Leu Pro Pro Pro Thr Leu Pro Tyr Asp Met Val Ile Ile
                165                 170                 175

Ser Ser Asp Asp Thr Ala Asn Asn Thr Leu His His Gly Leu Cys Thr
            180                 185                 190

Val Phe Glu Glu Gly Pro Tyr Ala Asp Ile Gly Asp Lys Ala Gln Lys
        195                 200                 205

Glu Tyr Leu Ser Lys Phe Val Gly Pro Ile Val Glu Arg Ile Asn Ala
    210                 215                 220

Gln Leu Pro Gly Ala Asn Leu Asn Ala Thr Asp Ile Ile Ala Leu Met
225                 230                 235                 240

Asp Leu Cys Pro Phe Glu Thr Val Ala Phe Pro Glu Gly Thr Lys Leu
                245                 250                 255

Ser Pro Phe Cys Arg Leu Phe Thr Ala Ala Glu Trp Arg Ala Tyr Asp
            260                 265                 270

Arg Tyr Gln Asp Val Gly Lys Trp Phe Gly Tyr Gly Pro Gly Asn Pro
        275                 280                 285
```

Leu Gly Pro Thr Gln Gly Val Gly Phe Val Asn Glu Leu Ile Ala Arg
    290                 295                 300

Leu Ser Gly Gln Pro Val Ser Asp Gly Thr Ser Thr Asn Arg Thr Leu
305                 310                 315                 320

Asp Glu Asn Pro Glu Thr Phe Pro Leu Gly Arg Arg Leu Tyr Ala Asp
                325                 330                 335

Phe Ser His Asp Asn Asp Met Val Gly Ile Leu Ser Ala Leu Gly Leu
            340                 345                 350

Trp Asp Asn His Glu Glu Pro Gly Asn Glu Met Pro Ala Glu Gly Glu
        355                 360                 365

Glu Asp Asp Asn Gly Arg Phe Ser Thr Ala Arg Ala Val Pro Phe Gly
370                 375                 380

Ala Arg Val Tyr Val Glu Lys Leu Arg Cys Gly Gly Ser Glu Glu Asp
385                 390                 395                 400

Glu Glu Met Val Arg Val Leu Val Asn Asp Arg Val Met Pro Leu Ala
                405                 410                 415

Gln Cys Gly Gly Asp Lys Arg Gly Met Cys Thr Leu Ser Arg Phe Val
            420                 425                 430

Glu Ser Leu Lys Phe Ala Arg Asn Asn Gly Arg Trp Asp Met Cys Phe
        435                 440                 445

Glu

<210> SEQ ID NO 12
<211> LENGTH: 192
<212> TYPE: DNA
<213> ORGANISM: Aspergillus niger

<400> SEQUENCE: 12
atgggcgtct ctgctgttct acttcctttg tatctcctag ctgggtatgc taagcaccgc   60
tatctaagtc tgataaggac cctctctgcc gagggcccct gaagctcgga ctgtgtggga  120
ctactgatcg ctgacaatct gtgcagagtc acctccggac tggcagtccc cgcctcgaga  180
aatcaatcca ct                                                      192

<210> SEQ ID NO 13
<211> LENGTH: 30
<212> TYPE: PRT
<213> ORGANISM: Aspergillus niger

<400> SEQUENCE: 13

Met Gly Val Ser Ala Val Leu Leu Pro Leu Tyr Leu Leu Ala Gly Val
1               5                   10                  15

Thr Ser Gly Leu Ala Val Pro Ala Ser Arg Asn Gln Ser Thr
            20                  25                  30

<210> SEQ ID NO 14
<211> LENGTH: 442
<212> TYPE: PRT
<213> ORGANISM: Aspergillus niger

<400> SEQUENCE: 14

Ala Ser Arg Asn Gln Ser Ser Cys Asp Thr Val Asp Gln Gly Tyr Gln
1               5                   10                  15

Cys Phe Ser Glu Thr Ser His Leu Trp Gly Gln Tyr Ala Pro Phe Phe
            20                  25                  30

Ser Leu Ala Asn Glu Ser Val Ile Ser Pro Glu Val Pro Ala Gly Cys
        35                  40                  45

Arg Val Thr Phe Ala Gln Val Leu Ser Arg His Gly Ala Arg Tyr Pro
    50                  55                  60

```
Thr Asp Ser Lys Gly Lys Lys Tyr Ser Ala Leu Ile Glu Glu Ile Gln
 65                  70                  75                  80

Gln Asn Ala Thr Thr Phe Asp Gly Lys Tyr Ala Phe Leu Lys Thr Tyr
                 85                  90                  95

Asn Tyr Ser Leu Gly Ala Asp Asp Leu Thr Pro Phe Gly Glu Gln Glu
            100                 105                 110

Leu Val Asn Ser Gly Ile Lys Phe Tyr Gln Arg Tyr Glu Ser Leu Thr
        115                 120                 125

Arg Asn Ile Val Pro Phe Ile Arg Ser Ser Gly Ser Ser Arg Val Ile
130                 135                 140

Ala Ser Gly Lys Lys Phe Ile Glu Gly Phe Gln Ser Thr Lys Leu Lys
145                 150                 155                 160

Asp Pro Arg Ala Gln Pro Gly Gln Ser Ser Pro Lys Ile Asp Val Val
                165                 170                 175

Ile Ser Glu Ala Ser Ser Ser Asn Asn Thr Leu Asp Pro Gly Thr Cys
            180                 185                 190

Thr Val Phe Glu Asp Ser Glu Leu Ala Asp Thr Val Glu Ala Asn Phe
        195                 200                 205

Thr Ala Thr Phe Val Pro Ser Ile Arg Gln Arg Leu Glu Asn Asp Leu
210                 215                 220

Ser Gly Val Thr Leu Thr Asp Thr Glu Val Thr Tyr Leu Met Asp Met
225                 230                 235                 240

Cys Ser Phe Asp Thr Ile Ser Thr Ser Thr Val Asp Thr Lys Leu Ser
                245                 250                 255

Pro Phe Cys Asp Leu Phe Thr His Asp Glu Trp Ile Asn Tyr Asp Tyr
            260                 265                 270

Leu Gln Ser Leu Lys Lys Tyr Tyr Gly His Gly Ala Gly Asn Pro Leu
        275                 280                 285

Gly Pro Thr Gln Gly Val Gly Tyr Ala Asn Glu Leu Ile Ala Arg Leu
290                 295                 300

Thr His Ser Pro Val His Asp Asp Thr Ser Ser Asn His Thr Leu Asp
305                 310                 315                 320

Ser Ala Thr Phe Pro Leu Asn Ser Thr Leu Tyr Ala Asp Phe Ser His
                325                 330                 335

Asp Asn Gly Ile Ile Ser Ile Leu Phe Ala Leu Gly Leu Tyr Asn Gly
            340                 345                 350

Thr Lys Pro Leu Ser Thr Thr Val Glu Asn Ile Thr Gln Thr Asp
        355                 360                 365

Gly Phe Ser Ser Ala Trp Thr Val Pro Phe Ala Ser Arg Leu Tyr Val
370                 375                 380

Glu Met Met Gln Cys Gln Ala Glu Gln Glu Pro Leu Val Arg Val Leu
385                 390                 395                 400

Val Asn Asp Arg Val Val Pro Leu His Gly Cys Pro Val Asp Ala Leu
                405                 410                 415

Gly Arg Cys Thr Arg Asp Ser Phe Val Arg Gly Leu Ser Phe Ala Arg
            420                 425                 430

Ser Gly Gly Asp Trp Ala Glu Cys Phe Ala
        435                 440

<210> SEQ ID NO 15
<211> LENGTH: 446
<212> TYPE: PRT
<213> ORGANISM: Penicillium chrysogenum

<400> SEQUENCE: 15
```

-continued

```
Ala Ser Arg Asn Gln Ser Thr Cys Thr Thr Val Asp Gly Gly Tyr Gln
 1               5                  10                  15

Cys Asn Ser Glu Leu Ser His Lys Trp Gly Gln Tyr Ser Pro Tyr Phe
             20                  25                  30

Ser Leu Ser Glu Glu Ser Ser Ile Ser Asn Glu Val Pro His Asp Cys
         35                  40                  45

Gln Ile Thr Phe Ala Gln Val Ile Ser Arg His Gly Ala Arg Phe Pro
     50                  55                  60

Ser Ala Lys Lys Ser Lys Val Tyr Ala Lys Leu Ile Glu Asn Ile Gln
 65                  70                  75                  80

Ala Asn Ala Thr Ala Tyr Asn Gly Asn Thr Lys Phe Leu Arg Ser Tyr
                 85                  90                  95

Lys Tyr Thr Met Gly Gly Asp Asp Leu Val Pro Phe Gly Val Asn Gln
             100                 105                 110

Thr Val Asp Ser Gly Thr Lys Phe Tyr Gln Arg Tyr Glu Ala Leu Ala
         115                 120                 125

Lys Lys Ala Val Pro Phe Ile Arg Ser Ser Asp Ser Gly Arg Val Val
 130                 135                 140

Ala Ser Gly Val Asn Phe Ile Lys Gly Phe Gln Gln Ala Lys Leu Asp
 145                 150                 155                 160

Asp Lys Asn Ala Asn His Arg Gln Pro Ser Pro Lys Thr Asn Val Ile
             165                 170                 175

Ile Ser Glu Glu Ser Gly Thr Asn Asn Thr Leu Asn His Ser Glu Ile
             180                 185                 190

Cys Pro Lys Phe Glu Asp Asn Glu Leu Gly Asp Lys Val Glu Glu Lys
         195                 200                 205

Tyr Met Lys Ile Phe Val Pro Pro Ile Arg Ala Arg Leu Glu Ala Asp
     210                 215                 220

Leu Pro Gly Val Lys Leu Glu Asp Ile Asp Val Val Ser Leu Met Asp
 225                 230                 235                 240

Ile Cys Pro Phe Glu Thr Val Ser Ser Asp Asp Ala Ala Glu Leu
             245                 250                 255

Ser Pro Phe Cys Asp Leu Phe Thr Pro Thr Glu Trp Ser Gln Tyr Asp
             260                 265                 270

Tyr Leu Gln Ser Leu Ser Lys Tyr Tyr Gly Tyr Gly Ala Gly Asn Pro
     275                 280                 285

Leu Gly Pro Thr Gln Gly Val Gly Phe Val Asn Glu Leu Ile Ala Arg
 290                 295                 300

Leu Thr Arg His Pro Val Arg Asp His Thr Ser Thr Asn Arg Ala Leu
 305                 310                 315                 320

Asp Ala Pro Gly Ala Ala Thr Phe Pro Leu Asn Tyr Thr Met Tyr Ala
                 325                 330                 335

Asp Phe Thr His Asp Asn Gly Met Ile Pro Phe Phe Ala Leu Gly
             340                 345                 350

Leu Tyr Asn Gly Thr Ala Pro Leu Ser Leu Thr His Val Gln Ser Pro
     355                 360                 365

Ser Gln Thr Asp Gly Phe Ser Ser Ala Trp Thr Val Pro Phe Gly Ala
 370                 375                 380

Arg Ala Tyr Val Glu Met Met Gln Cys Arg Arg Glu Pro Glu Pro Leu
 385                 390                 395                 400

Val Arg Val Leu Val Asn Asp Arg Val Ile Pro Leu His Gly Cys Pro
                 405                 410                 415
```

-continued

```
Val Asp Lys Leu Gly Arg Cys Arg Arg Arg Asp Phe Val Lys Gly Leu
            420                 425                 430

Thr Phe Ala Arg Ser Gly Gly Asp Trp Ala Arg Cys Tyr Lys
        435                 440                 445

<210> SEQ ID NO 16
<211> LENGTH: 445
<212> TYPE: PRT
<213> ORGANISM: Penicillium chrysogenum

<400> SEQUENCE: 16

Ala Ser Arg Asn Gln Ser Thr Cys Thr Thr Val Asp Gly Gly Tyr Gln
  1               5                  10                  15

Cys Asn Ser Glu Leu Ser His Lys Trp Gly Gln Tyr Ser Pro Tyr Phe
             20                  25                  30

Ser Leu Ser Glu Glu Ser Ser Ile Ser Asn Glu Val Pro His Asp Cys
         35                  40                  45

Gln Ile Thr Phe Ala Gln Val Ile Ser Arg His Gly Ala Arg Phe Pro
     50                  55                  60

Ser Ala Lys Lys Ser Lys Val Tyr Ala Lys Leu Ile Glu Asn Ile Gln
 65                  70                  75                  80

Ala Asn Ala Thr Ala Tyr Asn Gly Asn Thr Lys Phe Leu Arg Ser Tyr
                 85                  90                  95

Lys Tyr Thr Met Gly Gly Asp Leu Val Pro Phe Gly Val Asn Gln
            100                 105                 110

Thr Val Asp Ser Gly Thr Lys Phe Tyr Gln Arg Tyr Glu Ala Leu Ala
        115                 120                 125

Lys Lys Ala Val Pro Phe Ile Arg Ser Ser Asp Ser Gly Arg Val Val
130                 135                 140

Ala Ser Gly Val Asn Phe Ile Lys Gly Phe Gln Gln Ala Lys Leu Asp
145                 150                 155                 160

Asp Lys Asn Ala Asn His Arg Gln Pro Ser Pro Lys Thr Asn Val Ile
                165                 170                 175

Ile Ser Glu Glu Ser Gly Thr Asn Asn Thr Leu Asn His Ser Glu Ile
            180                 185                 190

Cys Pro Lys Phe Glu Asp Asn Glu Leu Gly Asp Lys Val Glu Glu Lys
        195                 200                 205

Tyr Met Lys Ile Phe Val Pro Pro Ile Arg Ala Arg Leu Glu Ala Asp
    210                 215                 220

Leu Pro Gly Val Lys Leu Glu Asp Ile Asp Val Val Ser Leu Met Asp
225                 230                 235                 240

Ile Cys Pro Phe Glu Thr Val Ser Ser Asp Asp Ala Ala Glu Leu
                245                 250                 255

Ser Pro Phe Cys Asp Leu Phe Thr Pro Thr Glu Trp Ser Gln Tyr Asp
            260                 265                 270

Tyr Leu Gln Ser Leu Ser Lys Tyr Tyr Gly Tyr Gly Ala Gly Asn Pro
        275                 280                 285

Leu Gly Pro Thr Gln Gly Val Gly Phe Val Asn Glu Leu Ile Ala Arg
    290                 295                 300

Leu Thr Arg His Pro Val Arg Asp His Thr Ser Thr Asn Arg Ala Leu
305                 310                 315                 320

Asp Ala Pro Gly Ala Ala Thr Phe Pro Leu Asn Tyr Thr Met Tyr Ala
                325                 330                 335

Asp Phe Thr His Asp Asn Gly Met Ile Pro Phe Phe Ala Leu Gly
            340                 345                 350
```

```
Leu Tyr Asn Gly Thr Ala Pro Leu Ser Leu Thr His Val Gln Ser Pro
            355                 360                 365

Ser Gln Thr Asp Gly Phe Ser Ser Ala Trp Thr Val Pro Phe Gly Ala
            370                 375                 380

Arg Ala Tyr Val Glu Met Met Gln Cys Arg Arg Glu Pro Glu Pro Leu
385                 390                 395                 400

Val Arg Val Leu Val Asn Asp Arg Val Ile Pro Leu His Gly Cys Pro
            405                 410                 415

Val Asp Lys Leu Gly Arg Cys Arg Arg Arg Asp Phe Val Lys Gly Leu
            420                 425                 430

Thr Phe Ala Arg Ser Gly Gly Asp Trp Ala Arg Cys Tyr
            435                 440                 445

<210> SEQ ID NO 17
<211> LENGTH: 442
<212> TYPE: PRT
<213> ORGANISM: Aspergillus fumigatus

<400> SEQUENCE: 17

Ser Ser Ala Gly Ser Lys Ser Cys Asp Thr Val Asp Leu Gly Tyr Gln
1               5                   10                  15

Cys Ser Pro Ala Thr Ser His Leu Trp Gly Gln Tyr Ser Pro Phe Phe
            20                  25                  30

Ser Leu Glu Asp Glu Leu Ser Val Ser Ser Lys Leu Pro Lys Asp Cys
            35                  40                  45

Arg Ile Thr Leu Val Gln Val Leu Ser Arg His Gly Ala Arg Tyr Pro
        50                  55                  60

Thr Ser Ser Lys Ser Lys Lys Tyr Lys Lys Leu Val Thr Ala Ile Gln
65                  70                  75                  80

Ala Asn Ala Thr Asp Phe Lys Gly Lys Phe Ala Phe Leu Lys Thr Tyr
                85                  90                  95

Asn Tyr Thr Leu Gly Ala Asp Asp Leu Thr Pro Phe Gly Glu Gln Gln
            100                 105                 110

Leu Val Asn Ser Gly Ile Lys Phe Tyr Gln Arg Tyr Lys Ala Leu Ala
            115                 120                 125

Arg Ser Val Val Pro Phe Ile Arg Ala Ser Gly Ser Asp Arg Val Ile
        130                 135                 140

Ala Ser Gly Glu Lys Phe Ile Glu Gly Phe Gln Gln Ala Lys Leu Ala
145                 150                 155                 160

Asp Pro Gly Ala Thr Asn Arg Ala Ala Pro Ala Ile Ser Val Ile Ile
                165                 170                 175

Pro Glu Ser Glu Thr Phe Asn Asn Thr Leu Asp His Gly Val Cys Thr
            180                 185                 190

Lys Phe Glu Ala Ser Gln Leu Gly Asp Glu Val Ala Ala Asn Phe Thr
            195                 200                 205

Ala Leu Phe Ala Pro Asp Ile Arg Ala Arg Ala Glu Lys His Leu Pro
        210                 215                 220

Gly Val Thr Leu Thr Asp Glu Asp Val Val Ser Leu Met Asp Met Cys
225                 230                 235                 240

Ser Phe Asp Thr Val Ala Arg Thr Ser Asp Ala Ser Gln Leu Ser Pro
                245                 250                 255

Phe Cys Gln Leu Phe Thr His Asn Glu Trp Lys Lys Tyr Asn Tyr Leu
            260                 265                 270

Gln Ser Leu Gly Lys Tyr Tyr Gly Tyr Gly Ala Gly Asn Pro Leu Gly
```

-continued

```
                275                 280                 285
Pro Ala Gln Gly Ile Gly Phe Thr Asn Glu Leu Ile Ala Arg Leu Thr
    290                 295                 300
Arg Ser Pro Val Gln Asp His Thr Ser Thr Asn Ser Thr Leu Val Ser
305                 310                 315                 320
Asn Pro Ala Thr Phe Pro Leu Asn Ala Thr Met Tyr Val Asp Phe Ser
                325                 330                 335
His Asp Asn Ser Met Val Ser Ile Phe Phe Ala Leu Gly Leu Tyr Asn
            340                 345                 350
Gly Thr Glu Pro Leu Ser Arg Thr Ser Val Glu Ser Ala Lys Glu Leu
        355                 360                 365
Asp Gly Tyr Ser Ala Ser Trp Val Val Pro Phe Gly Ala Arg Ala Tyr
    370                 375                 380
Phe Glu Thr Met Gln Cys Lys Ser Glu Lys Glu Pro Leu Val Arg Ala
385                 390                 395                 400
Leu Ile Asn Asp Arg Val Val Pro Leu His Gly Cys Asp Val Asp Lys
                405                 410                 415
Leu Gly Arg Cys Lys Leu Asn Asp Phe Val Lys Gly Leu Ser Trp Ala
            420                 425                 430
Arg Ser Gly Gly Asn Trp Gly Glu Cys Phe
        435                 440

<210> SEQ ID NO 18
<211> LENGTH: 444
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(444)
<223> OTHER INFORMATION: Xaa = Any Amino Acid

<400> SEQUENCE: 18

Xaa Ser Xaa Xaa Xaa Xaa Xaa Cys Xaa Thr Val Asp Xaa Gly Tyr Gln
1               5                   10                  15
Cys Xaa Xaa Xaa Xaa Ser His Xaa Trp Gly Gln Tyr Ser Pro Xaa Phe
            20                  25                  30
Ser Leu Xaa Xaa Glu Xaa Ser Xaa Ser Xaa Xaa Xaa Pro Xaa Asp Cys
        35                  40                  45
Xaa Ile Thr Xaa Xaa Gln Val Xaa Ser Arg His Gly Ala Arg Xaa Pro
    50                  55                  60
Xaa Xaa Xaa Lys Ser Lys Xaa Tyr Xaa Lys Leu Xaa Xaa Xaa Ile Gln
65                  70                  75                  80
Ala Asn Ala Thr Xaa Xaa Xaa Gly Xaa Xaa Xaa Phe Leu Xaa Xaa Tyr
                85                  90                  95
Xaa Tyr Thr Xaa Gly Xaa Asp Asp Leu Xaa Pro Phe Gly Xaa Xaa Gln
            100                 105                 110
Xaa Val Xaa Ser Gly Xaa Lys Phe Tyr Gln Arg Tyr Xaa Ala Leu Ala
        115                 120                 125
Xaa Xaa Xaa Val Pro Phe Ile Arg Xaa Ser Xaa Ser Xaa Arg Val Xaa
    130                 135                 140
Ala Ser Gly Xaa Xaa Phe Ile Xaa Gly Phe Gln Gln Ala Lys Leu Xaa
145                 150                 155                 160
Asp Xaa Xaa Ala Xaa Xaa Arg Xaa Xaa Xaa Pro Xaa Xaa Xaa Val Ile
                165                 170                 175
```

-continued

```
Ile Xaa Glu Xaa Xaa Xaa Xaa Asn Asn Thr Leu Xaa His Xaa Xaa Xaa
            180                 185                 190

Cys Xaa Lys Phe Glu Xaa Xaa Xaa Leu Gly Asp Xaa Val Xaa Xaa Xaa
        195                 200                 205

Xaa Xaa Xaa Xaa Phe Xaa Pro Xaa Ile Arg Ala Arg Xaa Glu Xaa Xaa
    210                 215                 220

Leu Pro Gly Val Xaa Leu Xaa Asp Xaa Asp Val Val Ser Leu Met Asp
225                 230                 235                 240

Xaa Cys Xaa Phe Xaa Thr Val Xaa Xaa Xaa Asp Ala Xaa Xaa Leu
            245                 250                 255

Ser Pro Phe Cys Xaa Leu Phe Thr Xaa Xaa Glu Trp Xaa Xaa Tyr Xaa
            260                 265                 270

Tyr Leu Gln Ser Leu Xaa Lys Tyr Tyr Gly Tyr Gly Ala Gly Asn Pro
        275                 280                 285

Leu Gly Pro Xaa Gln Gly Xaa Gly Phe Xaa Asn Glu Leu Ile Ala Arg
    290                 295                 300

Leu Thr Arg Xaa Pro Val Xaa Asp His Thr Ser Thr Asn Xaa Xaa Leu
305                 310                 315                 320

Xaa Xaa Xaa Xaa Xaa Ala Thr Phe Pro Leu Asn Xaa Thr Met Tyr Xaa
            325                 330                 335

Asp Phe Xaa His Asp Asn Xaa Met Xaa Xaa Xaa Phe Phe Ala Leu Gly
        340                 345                 350

Leu Tyr Asn Gly Thr Xaa Pro Leu Ser Xaa Thr Xaa Val Xaa Ser Xaa
            355                 360                 365

Xaa Xaa Xaa Asp Gly Xaa Ser Xaa Xaa Trp Xaa Val Pro Phe Gly Ala
    370                 375                 380

Arg Ala Tyr Xaa Glu Xaa Met Gln Cys Xaa Xaa Glu Xaa Glu Pro Leu
385                 390                 395                 400

Val Arg Xaa Leu Xaa Asn Asp Arg Val Xaa Pro Leu His Gly Cys Xaa
            405                 410                 415

Val Asp Lys Leu Gly Arg Cys Xaa Xaa Xaa Asp Phe Val Lys Gly Leu
        420                 425                 430

Xaa Xaa Ala Arg Ser Gly Gly Xaa Trp Xaa Xaa Cys
    435                 440
```

<210> SEQ ID NO 19
<211> LENGTH: 442
<212> TYPE: PRT
<213> ORGANISM: Penicillium chrysogenum

<400> SEQUENCE: 19

```
Asn Gln Ser Thr Cys Thr Thr Val Asp Gly Gly Tyr Gln Cys Asn Ser
1               5                   10                  15

Glu Leu Ser His Lys Trp Gly Gln Tyr Ser Pro Tyr Phe Ser Leu Ser
            20                  25                  30

Glu Glu Ser Ser Ile Ser Asn Glu Val Pro His Asp Cys Gln Ile Thr
        35                  40                  45

Phe Ala Gln Val Ile Ser Arg His Gly Ala Arg Phe Pro Ser Ala Lys
    50                  55                  60

Lys Ser Lys Val Tyr Ala Lys Leu Ile Glu Asn Ile Gln Ala Asn Ala
65                  70                  75                  80

Thr Ala Tyr Asn Gly Asn Thr Lys Phe Leu Arg Ser Tyr Lys Tyr Thr
            85                  90                  95

Met Gly Gly Asp Asp Leu Val Pro Phe Gly Val Asn Gln Thr Val Asp
        100                 105                 110
```

```
Ser Gly Thr Lys Phe Tyr Gln Arg Tyr Glu Ala Leu Ala Lys Lys Ala
        115                 120                 125

Val Pro Phe Ile Arg Ser Ser Asp Ser Gly Arg Val Ala Ser Gly
130                 135                 140

Val Asn Phe Ile Lys Gly Phe Gln Gln Ala Lys Leu Asp Asp Lys Asn
145                 150                 155                 160

Ala Asn His Arg Gln Pro Ser Pro Lys Thr Asn Val Ile Ile Ser Glu
                165                 170                 175

Glu Ser Gly Thr Asn Asn Thr Leu Asn His Ser Glu Ile Cys Pro Lys
                180                 185                 190

Phe Glu Asp Asn Glu Leu Gly Asp Lys Val Glu Glu Lys Tyr Met Lys
            195                 200                 205

Ile Phe Val Pro Pro Ile Arg Ala Arg Leu Glu Ala Asp Leu Pro Gly
        210                 215                 220

Val Lys Leu Glu Asp Ile Asp Val Val Ser Leu Met Asp Ile Cys Pro
225                 230                 235                 240

Phe Glu Thr Val Ser Ser Asp Asp Ala Ala Glu Leu Ser Pro Phe
                245                 250                 255

Cys Asp Leu Phe Thr Pro Thr Glu Trp Ser Gln Tyr Asp Tyr Leu Gln
                260                 265                 270

Ser Leu Ser Lys Tyr Tyr Gly Tyr Gly Ala Gly Asn Pro Leu Gly Pro
            275                 280                 285

Thr Gln Gly Val Gly Phe Val Asn Glu Leu Ile Ala Arg Leu Thr Arg
        290                 295                 300

His Pro Val Arg Asp His Thr Ser Thr Asn Arg Ala Leu Asp Ala Pro
305                 310                 315                 320

Gly Ala Ala Thr Phe Pro Leu Asn Tyr Thr Met Tyr Ala Asp Phe Thr
                325                 330                 335

His Asp Asn Gly Met Ile Pro Phe Phe Phe Ala Leu Gly Leu Tyr Asn
                340                 345                 350

Gly Thr Ala Pro Leu Ser Leu Thr His Val Gln Ser Pro Ser Gln Thr
            355                 360                 365

Asp Gly Phe Ser Ser Ala Trp Thr Val Pro Phe Gly Ala Arg Ala Tyr
        370                 375                 380

Val Glu Met Met Gln Cys Arg Arg Glu Pro Glu Pro Leu Val Arg Val
385                 390                 395                 400

Leu Val Asn Asp Arg Val Ile Pro Leu His Gly Cys Pro Val Asp Lys
                405                 410                 415

Leu Gly Arg Cys Arg Arg Asp Phe Val Lys Gly Leu Thr Phe Ala
            420                 425                 430

Arg Ser Gly Gly Asp Trp Ala Arg Cys Tyr
        435                 440

<210> SEQ ID NO 20
<211> LENGTH: 440
<212> TYPE: PRT
<213> ORGANISM: Aspergillus terreus

<400> SEQUENCE: 20

Asn His Ser Asp Cys Thr Ser Val Asp Arg Gly Tyr Gln Cys Phe Pro
1               5                   10                  15

Glu Leu Ser His Lys Trp Gly Leu Tyr Ala Pro Tyr Phe Ser Leu Gln
            20                  25                  30

Asp Glu Ser Pro Phe Pro Leu Asp Val Pro Asp Asp Cys His Ile Thr
```

```
                35                  40                  45
Phe Val Gln Val Leu Ala Arg His Gly Ala Arg Ser Pro Thr Asp Ser
 50                  55                  60
Lys Thr Lys Ala Tyr Ala Ala Thr Ile Ala Ala Ile Gln Lys Asn Ala
 65                  70                  75                  80
Thr Ala Leu Pro Gly Lys Tyr Ala Phe Leu Lys Ser Tyr Asn Tyr Ser
                 85                  90                  95
Met Gly Ser Glu Asn Leu Asn Pro Phe Gly Arg Asn Gln Leu Gln Asp
                100                 105                 110
Leu Gly Ala Gln Phe Tyr Arg Arg Tyr Asp Thr Leu Thr Arg His Ile
                115                 120                 125
Asn Pro Phe Val Arg Ala Ala Asp Ser Ser Arg Val His Glu Ser Ala
130                 135                 140
Glu Lys Phe Val Glu Gly Phe Gln Asn Ala Arg Gln Gly Asp Pro His
145                 150                 155                 160
Ala Asn Pro His Gln Pro Ser Pro Arg Val Asp Val Ile Pro Glu
                165                 170                 175
Gly Thr Ala Tyr Asn Asn Thr Leu Glu His Ser Ile Cys Thr Ala Phe
                180                 185                 190
Glu Ala Ser Thr Val Gly Asp Ala Ala Asp Asn Phe Thr Ala Val
                195                 200                 205
Phe Ala Pro Ala Ile Ala Lys Arg Leu Glu Ala Asp Leu Pro Gly Val
210                 215                 220
Gln Leu Ser Ala Asp Val Val Asn Leu Met Ala Met Cys Pro Phe
225                 230                 235                 240
Glu Thr Val Ser Leu Thr Asp Asp Ala His Thr Leu Ser Pro Phe Cys
                245                 250                 255
Asp Leu Phe Thr Ala Ala Glu Trp Thr Gln Tyr Asn Tyr Leu Leu Ser
                260                 265                 270
Leu Asp Lys Tyr Tyr Gly Tyr Gly Gly Asn Pro Leu Gly Pro Val
                275                 280                 285
Gln Gly Val Gly Trp Ala Asn Glu Leu Ile Ala Arg Leu Thr Arg Ser
                290                 295                 300
Pro Val His Asp His Thr Cys Val Asn Asn Thr Leu Asp Ala Asn Pro
305                 310                 315                 320
Ala Thr Phe Pro Leu Asn Ala Thr Leu Tyr Ala Asp Phe Ser His Asp
                325                 330                 335
Ser Asn Leu Val Ser Ile Phe Trp Ala Leu Gly Leu Tyr Asn Gly Thr
                340                 345                 350
Lys Pro Leu Ser Gln Thr Thr Val Glu Asp Ile Thr Arg Thr Asp Gly
                355                 360                 365
Tyr Ala Ala Ala Trp Thr Val Pro Phe Ala Ala Arg Ala Tyr Ile Glu
                370                 375                 380
Met Met Gln Cys Arg Ala Glu Lys Gln Pro Leu Val Arg Val Leu Val
385                 390                 395                 400
Asn Asp Arg Val Met Pro Leu His Gly Cys Ala Val Asp Asn Leu Gly
                405                 410                 415
Arg Cys Lys Arg Asp Asp Phe Val Glu Gly Leu Ser Phe Ala Arg Ala
                420                 425                 430
Gly Gly Asn Trp Ala Glu Cys Phe
                435                 440

<210> SEQ ID NO 21
```

<211> LENGTH: 442
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(442)
<223> OTHER INFORMATION: Xaa = Any Amino Acid

<400> SEQUENCE: 21

```
Asn Xaa Ser Xaa Cys Thr Xaa Val Asp Xaa Gly Tyr Gln Cys Xaa Xaa
 1               5                  10                  15

Glu Leu Ser His Lys Trp Gly Xaa Tyr Xaa Pro Tyr Phe Ser Leu Xaa
             20                  25                  30

Xaa Glu Ser Xaa Xaa Xaa Xaa Val Pro Xaa Asp Cys Xaa Ile Thr
         35                  40                  45

Phe Xaa Gln Val Xaa Xaa Arg His Gly Ala Arg Xaa Pro Xaa Xaa Xaa
 50                  55                  60

Lys Xaa Lys Xaa Tyr Ala Xaa Xaa Ile Xaa Xaa Ile Gln Xaa Asn Ala
 65                  70                  75                  80

Thr Ala Xaa Xaa Gly Xaa Xaa Xaa Phe Leu Xaa Ser Tyr Xaa Tyr Xaa
                 85                  90                  95

Met Gly Xaa Xaa Xaa Leu Xaa Pro Phe Gly Xaa Asn Gln Xaa Xaa Asp
             100                 105                 110

Xaa Gly Xaa Xaa Phe Tyr Xaa Arg Tyr Xaa Leu Xaa Xaa Xaa Xaa
         115                 120                 125

Xaa Pro Phe Xaa Arg Xaa Xaa Asp Ser Xaa Arg Val Xaa Xaa Ser Xaa
 130                 135                 140

Xaa Xaa Phe Xaa Xaa Gly Phe Gln Xaa Ala Xaa Xaa Xaa Asp Xaa Xaa
145                 150                 155                 160

Ala Asn Xaa Xaa Gln Pro Ser Pro Xaa Xaa Xaa Val Xaa Ile Xaa Glu
                 165                 170                 175

Xaa Xaa Xaa Xaa Asn Asn Thr Leu Xaa His Ser Xaa Ile Cys Xaa Xaa
             180                 185                 190

Phe Glu Xaa Xaa Xaa Xaa Gly Asp Xaa Xaa Xaa Xaa Xaa Xaa Xaa Xaa
         195                 200                 205

Xaa Phe Xaa Pro Xaa Ile Xaa Xaa Arg Leu Glu Ala Asp Leu Pro Gly
 210                 215                 220

Val Xaa Leu Xaa Xaa Xaa Asp Val Val Xaa Leu Met Xaa Xaa Cys Pro
225                 230                 235                 240

Phe Glu Thr Val Ser Xaa Xaa Asp Asp Ala Xaa Xaa Leu Ser Pro Phe
                 245                 250                 255

Cys Asp Leu Phe Thr Xaa Xaa Glu Trp Xaa Gln Tyr Xaa Tyr Leu Xaa
             260                 265                 270

Ser Leu Xaa Lys Tyr Tyr Gly Tyr Gly Xaa Gly Asn Pro Leu Gly Pro
         275                 280                 285

Xaa Gln Gly Val Gly Xaa Xaa Asn Glu Leu Ile Ala Arg Leu Thr Arg
 290                 295                 300

Xaa Pro Val Xaa Asp His Thr Xaa Xaa Asn Xaa Xaa Leu Asp Ala Xaa
305                 310                 315                 320

Xaa Xaa Ala Thr Phe Pro Leu Asn Xaa Thr Xaa Tyr Ala Asp Phe Xaa
                 325                 330                 335

His Asp Xaa Xaa Xaa Xaa Xaa Phe Xaa Ala Leu Gly Leu Tyr Asn
             340                 345                 350

Gly Thr Xaa Pro Leu Ser Xaa Thr Xaa Val Xaa Xaa Xaa Xaa Xaa Thr
```

```
                 355                 360                 365
Asp Gly Xaa Xaa Xaa Ala Trp Thr Val Pro Phe Xaa Ala Arg Ala Tyr
        370                 375                 380
Xaa Glu Met Met Gln Cys Arg Xaa Glu Xaa Xaa Pro Leu Val Arg Val
385                 390                 395                 400
Leu Val Asn Asp Arg Val Xaa Pro Leu His Gly Cys Xaa Val Asp Xaa
                405                 410                 415
Leu Gly Arg Cys Xaa Arg Xaa Asp Phe Val Xaa Gly Leu Xaa Phe Ala
            420                 425                 430
Arg Xaa Gly Gly Xaa Trp Ala Xaa Cys Xaa
        435                 440

<210> SEQ ID NO 22
<211> LENGTH: 439
<212> TYPE: PRT
<213> ORGANISM: Penicillium chrysogenum

<400> SEQUENCE: 22

Thr Cys Thr Thr Val Asp Gly Gly Tyr Gln Cys Asn Ser Glu Leu Ser
1               5                   10                  15
His Lys Trp Gly Gln Tyr Ser Pro Tyr Phe Ser Leu Ser Glu Glu Ser
            20                  25                  30
Ser Ile Ser Asn Glu Val Pro His Asp Cys Gln Ile Thr Phe Ala Gln
        35                  40                  45
Val Ile Ser Arg His Gly Ala Arg Phe Pro Ser Ala Lys Lys Ser Lys
    50                  55                  60
Val Tyr Ala Lys Leu Ile Glu Asn Ile Gln Ala Asn Ala Thr Ala Tyr
65                  70                  75                  80
Asn Gly Asn Thr Lys Phe Leu Arg Ser Tyr Lys Tyr Thr Met Gly Gly
                85                  90                  95
Asp Asp Leu Val Pro Phe Gly Val Asn Gln Thr Val Asp Ser Gly Thr
            100                 105                 110
Lys Phe Tyr Gln Arg Tyr Glu Ala Leu Ala Lys Lys Ala Val Pro Phe
        115                 120                 125
Ile Arg Ser Ser Asp Ser Gly Arg Val Val Ala Ser Gly Val Asn Phe
    130                 135                 140
Ile Lys Gly Phe Gln Gln Ala Lys Leu Asp Asp Lys Asn Ala Asn His
145                 150                 155                 160
Arg Gln Pro Ser Pro Lys Thr Asn Val Ile Ile Ser Glu Glu Ser Gly
                165                 170                 175
Thr Asn Asn Thr Leu Asn His Ser Glu Ile Cys Pro Lys Phe Glu Asp
            180                 185                 190
Asn Glu Leu Gly Asp Lys Val Glu Glu Lys Tyr Met Lys Ile Phe Val
        195                 200                 205
Pro Pro Ile Arg Ala Arg Leu Glu Ala Asp Leu Pro Gly Val Lys Leu
    210                 215                 220
Glu Asp Ile Asp Val Val Ser Leu Met Asp Ile Cys Pro Phe Glu Thr
225                 230                 235                 240
Val Ser Ser Ser Asp Asp Ala Ala Glu Leu Ser Pro Phe Cys Asp Leu
                245                 250                 255
Phe Thr Pro Thr Glu Trp Ser Gln Tyr Asp Tyr Leu Gln Ser Leu Ser
            260                 265                 270
Lys Tyr Tyr Gly Tyr Gly Ala Gly Asn Pro Leu Gly Pro Thr Gln Gly
        275                 280                 285
```

```
Val Gly Phe Val Asn Glu Leu Ile Ala Arg Leu Thr Arg His Pro Val
    290                 295                 300

Arg Asp His Thr Ser Thr Asn Arg Ala Leu Asp Ala Pro Gly Ala Ala
305                 310                 315                 320

Thr Phe Pro Leu Asn Tyr Thr Met Tyr Ala Asp Phe Thr His Asp Asn
                325                 330                 335

Gly Met Ile Pro Phe Phe Phe Ala Leu Gly Leu Tyr Asn Gly Thr Ala
            340                 345                 350

Pro Leu Ser Leu Thr His Val Gln Ser Pro Ser Gln Thr Asp Gly Phe
        355                 360                 365

Ser Ser Ala Trp Thr Val Pro Phe Gly Ala Arg Ala Tyr Val Glu Met
370                 375                 380

Met Gln Cys Arg Arg Glu Pro Glu Pro Leu Val Arg Val Leu Val Asn
385                 390                 395                 400

Asp Arg Val Ile Pro Leu His Gly Cys Pro Val Asp Lys Leu Gly Arg
                405                 410                 415

Cys Arg Arg Arg Asp Phe Val Lys Gly Leu Thr Phe Ala Arg Ser Gly
            420                 425                 430

Gly Asp Trp Ala Arg Cys Tyr
            435

<210> SEQ ID NO 23
<211> LENGTH: 434
<212> TYPE: PRT
<213> ORGANISM: Emericella nidulans

<400> SEQUENCE: 23

Ser Cys Asn Thr Ala Asp Gly Gly Tyr Gln Cys Phe Pro Asn Val Ser
1               5                   10                  15

His Val Trp Gly Gln Tyr Ser Pro Tyr Phe Ser Ile Glu Gln Glu Ser
            20                  25                  30

Ala Ile Ser Glu Asp Val Pro His Gly Cys Glu Val Thr Phe Val Gln
        35                  40                  45

Val Leu Ser Arg His Gly Ala Arg Tyr Pro Thr Glu Ser Lys Ser Lys
    50                  55                  60

Ala Tyr Ser Gly Leu Ile Glu Ala Ile Gln Lys Asn Ala Thr Ser Phe
65                  70                  75                  80

Trp Gly Gln Tyr Ala Phe Leu Glu Ser Tyr Asn Tyr Thr Leu Gly Ala
                85                  90                  95

Asp Asp Leu Thr Ile Phe Gly Glu Asn Gln Met Val Ser Gly Ala
            100                 105                 110

Lys Phe Tyr Arg Arg Tyr Lys Asn Leu Ala Arg Lys Asn Thr Pro Phe
        115                 120                 125

Ile Arg Ala Ser Gly Ser Asp Arg Val Val Ala Ser Ala Glu Lys Phe
130                 135                 140

Ile Asn Gly Phe Arg Lys Ala Gln Leu His Asp His Gly Ser Lys Arg
145                 150                 155                 160

Ala Thr Pro Val Val Asn Val Ile Ile Pro Glu Ile Asp Gly Phe Asn
                165                 170                 175

Asn Thr Leu Asp His Ser Thr Cys Val Ser Phe Glu Asn Asp Glu Arg
            180                 185                 190

Ala Asp Glu Ile Glu Ala Asn Phe Thr Ala Ile Met Gly Pro Pro Ile
        195                 200                 205

Arg Lys Arg Leu Glu Asn Asp Leu Pro Gly Ile Lys Leu Thr Asn Glu
210                 215                 220
```

```
Asn Val Ile Tyr Leu Met Asp Met Cys Ser Phe Asp Thr Met Ala Arg
225                 230                 235                 240

Thr Ala His Gly Thr Glu Leu Ser Pro Phe Cys Ala Ile Phe Thr Glu
            245                 250                 255

Lys Glu Trp Leu Gln Tyr Asp Tyr Leu Gln Ser Leu Ser Lys Tyr Tyr
                260                 265                 270

Gly Tyr Gly Ala Gly Ser Pro Leu Gly Pro Ala Gln Gly Ile Gly Phe
            275                 280                 285

Thr Asn Glu Leu Ile Ala Arg Leu Thr Gln Ser Pro Val Gln Asp Asn
290                 295                 300

Thr Ser Thr Asn His Thr Leu Asp Ser Asn Pro Ala Thr Phe Pro Leu
305                 310                 315                 320

Asp Arg Lys Leu Tyr Ala Asp Phe Ser His Asp Asn Ser Met Ile Ser
                325                 330                 335

Ile Phe Phe Ala Met Gly Leu Tyr Asn Gly Thr Gln Pro Leu Ser Met
                340                 345                 350

Asp Ser Val Glu Ser Ile Gln Glu Met Asp Gly Tyr Ala Ala Ser Trp
            355                 360                 365

Thr Val Pro Phe Gly Ala Arg Ala Tyr Phe Glu Leu Met Gln Cys Glu
370                 375                 380

Lys Lys Glu Pro Leu Val Arg Val Leu Val Asn Asp Arg Val Val Pro
385                 390                 395                 400

Leu His Gly Cys Ala Val Asp Lys Phe Gly Arg Cys Thr Leu Asp Asp
                405                 410                 415

Trp Val Glu Gly Leu Asn Phe Ala Arg Ser Gly Gly Asn Trp Lys Thr
                420                 425                 430

Cys Phe

<210> SEQ ID NO 24
<211> LENGTH: 439
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(439)
<223> OTHER INFORMATION: Xaa = Any Amino Acid

<400> SEQUENCE: 24

Xaa Cys Xaa Thr Xaa Asp Gly Gly Tyr Gln Cys Xaa Xaa Xaa Xaa Ser
1               5                   10                  15

His Xaa Trp Gly Gln Tyr Ser Pro Tyr Phe Ser Xaa Xaa Xaa Glu Ser
                20                  25                  30

Xaa Ile Ser Xaa Xaa Val Pro His Xaa Xaa Xaa Xaa Thr Phe Xaa Gln
                35                  40                  45

Val Xaa Ser Arg His Gly Ala Arg Xaa Pro Xaa Xaa Xaa Lys Ser Lys
            50                  55                  60

Xaa Tyr Xaa Xaa Leu Ile Glu Xaa Ile Gln Xaa Asn Ala Thr Xaa Xaa
65                  70                  75                  80

Xaa Gly Xaa Xaa Xaa Phe Leu Xaa Ser Tyr Xaa Tyr Thr Xaa Gly Xaa
                85                  90                  95

Asp Asp Leu Xaa Xaa Phe Gly Xaa Asn Gln Xaa Val Asp Ser Gly Xaa
                100                 105                 110

Lys Phe Tyr Xaa Arg Tyr Xaa Xaa Leu Ala Xaa Lys Xaa Xaa Pro Phe
                115                 120                 125
```

Ile Arg Xaa Ser Xaa Ser Xaa Arg Val Val Ala Ser Xaa Xaa Xaa Phe
130                 135                 140

Ile Xaa Gly Phe Xaa Xaa Ala Xaa Leu Xaa Asp Xaa Xaa Xaa Xaa
145                 150                 155                 160

Xaa Xaa Xaa Xaa Pro Xaa Xaa Asn Val Ile Xaa Glu Xaa Xaa Gly
                165                 170                 175

Xaa Asn Asn Thr Leu Xaa His Ser Xaa Xaa Cys Xaa Xaa Phe Glu Xaa
            180                 185                 190

Xaa Glu Xaa Xaa Asp Xaa Xaa Glu Xaa Xaa Xaa Xaa Ile Xaa Xaa
        195                 200                 205

Pro Pro Ile Arg Xaa Arg Leu Glu Xaa Asp Leu Pro Gly Xaa Lys Leu
210                 215                 220

Xaa Xaa Xaa Xaa Val Xaa Xaa Leu Met Asp Xaa Cys Xaa Phe Xaa Thr
225                 230                 235                 240

Xaa Xaa Xaa Xaa Xaa Xaa Xaa Glu Leu Ser Pro Phe Cys Xaa Xaa
            245                 250                 255

Phe Thr Xaa Xaa Glu Trp Xaa Gln Tyr Asp Tyr Leu Gln Ser Leu Ser
            260                 265                 270

Lys Tyr Tyr Gly Tyr Gly Ala Gly Xaa Pro Leu Gly Pro Xaa Gln Gly
            275                 280                 285

Xaa Gly Phe Xaa Asn Glu Leu Ile Ala Arg Leu Thr Xaa Xaa Pro Val
290                 295                 300

Xaa Asp Xaa Thr Ser Thr Asn Xaa Xaa Leu Asp Xaa Xaa Xaa Xaa Ala
305                 310                 315                 320

Thr Phe Pro Leu Xaa Xaa Xaa Xaa Tyr Ala Asp Phe Xaa His Asp Asn
                325                 330                 335

Xaa Met Ile Xaa Xaa Phe Ala Xaa Gly Leu Tyr Asn Gly Thr Xaa
            340                 345                 350

Pro Leu Ser Xaa Xaa Xaa Val Xaa Ser Xaa Xaa Xaa Xaa Asp Gly Xaa
            355                 360                 365

Xaa Xaa Xaa Trp Thr Val Pro Phe Gly Ala Arg Ala Tyr Xaa Glu Xaa
370                 375                 380

Met Gln Cys Xaa Xaa Xaa Xaa Glu Pro Leu Val Arg Val Leu Val Asn
385                 390                 395                 400

Asp Arg Val Xaa Pro Leu His Gly Cys Xaa Val Asp Lys Xaa Gly Arg
                405                 410                 415

Cys Xaa Xaa Xaa Asp Xaa Val Xaa Gly Leu Xaa Phe Ala Arg Ser Gly
            420                 425                 430

Gly Xaa Trp Xaa Xaa Cys Xaa
        435

<210> SEQ ID NO 25
<211> LENGTH: 444

<212> TYPE: PRT
<213> ORGANISM: Aspergillus niger

<400> SEQUENCE: 25

Ala Ser Arg Asn Gln Ser Ser Cys Asp Thr Val Asp Gln Gly Tyr Gln
1               5                   10                  15

Cys Phe Ser Glu Thr Ser His Leu Trp Gly Gln Tyr Ala Pro Phe Phe
            20                  25                  30

Ser Leu Ala Asn Glu Ser Val Ile Ser Pro Glu Val Pro Ala Gly Cys

-continued

```
                35                  40                  45
Arg Val Thr Phe Ala Gln Val Leu Ser Arg His Gly Ala Arg Tyr Pro
 50                  55                  60

Thr Asp Ser Lys Gly Lys Lys Tyr Ser Ala Leu Ile Glu Glu Ile Gln
 65                  70                  75                  80

Gln Asn Ala Thr Thr Phe Asp Gly Lys Tyr Ala Phe Leu Lys Thr Tyr
                 85                  90                  95

Asn Tyr Ser Leu Gly Ala Asp Asp Leu Thr Pro Phe Gly Glu Gln Glu
                100                 105                 110

Leu Val Asn Ser Gly Ile Lys Phe Tyr Gln Arg Tyr Glu Ser Leu Thr
                115                 120                 125

Arg Asn Ile Val Pro Phe Ile Arg Ser Ser Gly Ser Ser Arg Val Ile
130                 135                 140

Ala Ser Gly Lys Lys Phe Ile Glu Gly Phe Gln Ser Thr Lys Leu Lys
145                 150                 155                 160

Asp Pro Arg Ala Gln Pro Gly Gln Ser Ser Pro Lys Ile Asp Val Val
                165                 170                 175

Ile Ser Glu Ala Ser Ser Asn Asn Thr Leu Asp Pro Gly Thr Cys
                180                 185                 190

Thr Val Phe Glu Asp Ser Glu Leu Ala Asp Thr Val Glu Ala Asn Phe
                195                 200                 205

Thr Ala Thr Phe Val Pro Ser Ile Arg Gln Arg Leu Glu Asn Asp Leu
210                 215                 220

Ser Gly Val Thr Leu Thr Asp Thr Glu Val Thr Tyr Leu Met Asp Met
225                 230                 235                 240

Cys Ser Phe Asp Thr Ile Ser Thr Ser Thr Val Asp Thr Lys Leu Ser
                245                 250                 255

Pro Phe Cys Asp Leu Phe Thr His Asp Glu Trp Ile Asn Tyr Asp Tyr
                260                 265                 270

Leu Gln Ser Leu Lys Lys Tyr Gly His Gly Ala Gly Asn Pro Leu
                275                 280                 285

Gly Pro Thr Gln Gly Val Gly Tyr Ala Asn Glu Leu Ile Ala Arg Leu
290                 295                 300

Thr His Ser Pro Val His Asp Asp Thr Ser Ser Asn His Thr Leu Asp
305                 310                 315                 320

Ser Ser Pro Ala Thr Phe Pro Leu Asn Ser Thr Leu Tyr Ala Asp Phe
                325                 330                 335

Ser His Asp Asn Gly Ile Ile Ser Ile Leu Phe Ala Leu Gly Leu Tyr
                340                 345                 350

Asn Gly Thr Lys Pro Leu Ser Thr Thr Thr Val Glu Asn Ile Thr Gln
                355                 360                 365

Thr Asp Gly Phe Ser Ser Ala Trp Thr Val Pro Phe Ala Ser Arg Leu
370                 375                 380

Tyr Val Glu Met Met Gln Cys Gln Ala Glu Gln Pro Leu Val Arg
385                 390                 395                 400

Val Leu Val Asn Asp Arg Val Val Pro Leu His Gly Cys Pro Val Asp
                405                 410                 415

Ala Leu Gly Arg Cys Thr Arg Asp Ser Phe Val Arg Gly Leu Ser Phe
                420                 425                 430

Ala Arg Ser Gly Gly Asp Trp Ala Glu Cys Phe Ala
                435                 440
```

<210> SEQ ID NO 26

<211> LENGTH: 440
<212> TYPE: PRT
<213> ORGANISM: Fusarium javanicum

<400> SEQUENCE: 26

```
Ala

```
385                 390                 395                 400
Asp Arg Val Met Ser Leu Glu Thr Cys Gly Gly Asp Glu Tyr Gly Leu
                405                 410                 415

Cys Arg Leu Glu Asn Phe Val Glu Ser Leu Ser Phe Ala Ala Ser Gly
                420                 425                 430

Gly Asn Trp Asp Gln Cys Gly Gly
            435                 440

<210> SEQ ID NO 27
<211> LENGTH: 440
<212> TYPE: PRT
<213> ORGANISM: Fusarium javanicum

<400> SEQUENCE: 27

Ala Ser Arg Asn Gln Ser Thr Cys Glu Tyr Asp Gly Ser Cys Asn Asp
 1               5                  10                  15

Ile Ser Arg Leu Trp Gly Gln Tyr Ser Ala Tyr Phe Pro Ile Pro Ser
                20                  25                  30

Glu Leu Asp Ala Ser Thr Pro Asp Asp Cys Asp Val Thr Phe Ala Leu
            35                  40                  45

Val Leu Ser Arg His Gly Ala Arg Tyr Pro Thr Asp Ser Lys Ser Ala
50                  55                  60

Ala Tyr Asn Ala Thr Ile Ala Arg Ile Gln Lys Ser Ala Thr Met Tyr
65                  70                  75                  80

Gly Lys Asn Tyr Lys Trp Leu Lys Glu Tyr Thr Tyr Ser Leu Gly Ala
                85                  90                  95

Glu Asp Leu Thr Glu Phe Gly Gln Arg Gln Met Val Asp Ser Gly Arg
            100                 105                 110

Ala Phe Tyr Glu Arg Tyr Met Ser Leu Ala Glu Lys Thr Glu Pro Phe
        115                 120                 125

Val Arg Ala Ser Gly Ser Asp Arg Val Ile Met Ser Ser Tyr Asn Phe
    130                 135                 140

Thr Gln Gly Phe Tyr Ala Ser Arg Gly Glu Ser Gly Asp Asp Tyr Thr
145                 150                 155                 160

Gln Asp Val Leu Ile Ile Pro Glu Glu Pro Gly Ile Asn Asn Thr Met
                165                 170                 175

Leu His Gly Ser Cys Ala Ser Phe Glu Ser Asp Arg Val Pro Lys Asp
            180                 185                 190

Ala Asp Glu Lys Ala Glu Val Ala Trp Gly Ala Arg Phe Leu Pro Glu
        195                 200                 205

Ile Arg Asn Arg Leu Asn His His Leu Pro Gly Val Asn Leu Thr Leu
    210                 215                 220

Glu Glu Thr Ile Tyr Met Met Asp Met Cys Pro Phe Leu Ala Ala Asp
225                 230                 235                 240

Thr Pro Asp Gly Ala Gly His Ser Arg Phe Cys Asp Leu Phe Thr Lys
                245                 250                 255

Ala Asp Trp Arg Ser Tyr Asp Tyr Tyr Met Thr Leu Ser Lys Phe Tyr
            260                 265                 270

Lys Phe Gly Asn Gly Asn Ala Met Gly Pro Thr Gln Gly Val Gly Tyr
        275                 280                 285

Val Asn Glu Leu Ile Ser Arg Leu Thr Gly Lys Pro Val Asp Asp His
    290                 295                 300

Thr Thr Thr Asn Ser Thr Leu Asp Ser Ser Pro Lys Thr Phe Pro Leu
305                 310                 315                 320
```

```
Asp Arg Ala Leu Tyr Ala Asp Phe Ser His Asp Asn Ser Met Val Ser
            325                 330                 335

Ile Phe Ser Ala Leu Gly Leu Tyr Asn Ser Thr Thr Leu Leu Pro Lys
        340                 345                 350

Asp His Ile Val Pro Ala Ile Lys Ala His Gly Tyr Ser Ser Thr Trp
    355                 360                 365

Val Val Pro Phe Gly Ala Arg Met Tyr Val Glu Lys Leu Glu Cys Gly
370                 375                 380

Ala Ser Arg Asn Glu Lys Arg Asp Glu Tyr Val Arg Val Leu Val Asn
385                 390                 395                 400

Asp Arg Val Met Ser Leu Glu Thr Cys Gly Asp Glu Tyr Gly Leu
                405                 410                 415

Cys Arg Leu Glu Asn Phe Val Glu Ser Leu Ser Phe Ala Ala Ser Gly
            420                 425                 430

Gly Asn Trp Asp Gln Cys Gly Gly
        435                 440

<210> SEQ ID NO 28
<211> LENGTH: 463
<212> TYPE: PRT
<213> ORGANISM: Emericella nidulans

<400> SEQUENCE: 28

Met Ala Phe Phe Thr Val Ala Leu Ser Leu Tyr Tyr Leu Leu Ser Arg
1               5                   10                  15

Val Ser Ala Gln Ala Pro Val Val Gln Asn His Ser Cys Asn Thr Ala
            20                  25                  30

Asp Gly Gly Tyr Gln Cys Phe Pro Asn Val Ser His Val Trp Gly Gln
        35                  40                  45

Tyr Ser Pro Tyr Phe Ser Ile Glu Gln Glu Ser Ala Ile Ser Glu Asp
    50                  55                  60

Val Pro His Gly Cys Glu Val Thr Phe Val Gln Val Leu Ser Arg His
65                  70                  75                  80

Gly Ala Arg Tyr Pro Thr Glu Ser Lys Ser Lys Ala Tyr Ser Gly Leu
                85                  90                  95

Ile Glu Ala Ile Gln Lys Asn Ala Thr Ser Phe Trp Gly Gln Tyr Ala
            100                 105                 110

Phe Leu Glu Ser Tyr Asn Tyr Thr Leu Gly Ala Asp Asp Leu Thr Ile
        115                 120                 125

Phe Gly Glu Asn Gln Met Val Asp Ser Gly Ala Lys Phe Tyr Arg Arg
    130                 135                 140

Tyr Lys Asn Leu Ala Arg Lys Asn Thr Pro Phe Ile Arg Ala Ser Gly
145                 150                 155                 160

Ser Asp Arg Val Val Ala Ser Ala Glu Lys Phe Ile Asn Gly Phe Arg
                165                 170                 175

Lys Ala Gln Leu His Asp His Gly Ser Lys Arg Ala Thr Pro Val Val
            180                 185                 190

Asn Val Ile Ile Pro Glu Ile Asp Gly Phe Asn Asn Thr Leu Asp His
        195                 200                 205

Ser Thr Cys Val Ser Phe Glu Asn Asp Glu Arg Ala Asp Glu Ile Glu
    210                 215                 220

Ala Asn Phe Thr Ala Ile Met Gly Pro Pro Ile Arg Lys Arg Leu Glu
225                 230                 235                 240

Asn Asp Leu Pro Gly Ile Lys Leu Thr Asn Glu Asn Val Ile Tyr Leu
                245                 250                 255
```

```
Met Asp Met Cys Ser Phe Asp Thr Met Ala Arg Thr Ala His Gly Thr
            260                 265                 270

Glu Leu Ser Pro Phe Cys Ala Ile Phe Thr Glu Lys Glu Trp Leu Gln
        275                 280                 285

Tyr Asp Tyr Leu Gln Ser Leu Ser Lys Tyr Tyr Gly Tyr Ala Gly
        290                 295                 300

Ser Pro Leu Gly Pro Ala Gln Gly Ile Gly Phe Thr Asn Glu Leu Ile
305                 310                 315                 320

Ala Arg Leu Thr Gln Ser Pro Val Gln Asp Asn Thr Ser Thr Asn His
                325                 330                 335

Thr Leu Asp Ser Asn Pro Ala Thr Phe Pro Leu Asp Arg Lys Leu Tyr
            340                 345                 350

Ala Asp Phe Ser His Asp Asn Ser Met Ile Ser Ile Phe Ala Met
            355                 360                 365

Gly Leu Tyr Asn Gly Thr Gln Pro Leu Ser Met Asp Ser Val Glu Ser
        370                 375                 380

Ile Gln Glu Met Asp Gly Tyr Ala Ala Ser Trp Thr Val Pro Phe Gly
385                 390                 395                 400

Ala Arg Ala Tyr Phe Glu Leu Met Gln Cys Glu Lys Lys Glu Pro Leu
                405                 410                 415

Val Arg Val Leu Val Asn Asp Arg Val Val Pro Leu His Gly Cys Ala
            420                 425                 430

Val Asp Lys Phe Gly Arg Cys Thr Leu Asp Asp Trp Val Glu Gly Leu
            435                 440                 445

Asn Phe Ala Arg Ser Gly Gly Asn Trp Lys Thr Cys Phe Thr Leu
            450                 455                 460

<210> SEQ ID NO 29
<211> LENGTH: 422
<212> TYPE: PRT
<213> ORGANISM: Fusarium javanicum

<400> SEQUENCE: 29

Ile Ser Arg Leu Trp Gly G

```
                    165                 170                 175
Ala Asp Glu Lys Ala Glu Val Ala Trp Gly Ala Arg Phe Leu Pro Glu
                180                 185                 190

Ile Arg Asn Arg Leu Asn His His Leu Pro Gly Val Asn Leu Thr Leu
            195                 200                 205

Glu Glu Thr Ile Tyr Met Met Asp Met Cys Pro Phe Leu Ala Ala Asp
        210                 215                 220

Thr Pro Asp Gly Ala Gly His Ser Arg Phe Cys Asp Leu Phe Thr Lys
225                 230                 235                 240

Ala Asp Trp Arg Ser Tyr Asp Tyr Tyr Met Thr Leu Ser Lys Phe Tyr
                245                 250                 255

Lys Phe Gly Asn Gly Asn Ala Met Gly Pro Thr Gln Gly Val Gly Tyr
                260                 265                 270

Val Asn Glu Leu Ile Ser Arg Leu Thr Gly Lys Pro Val Asp Asp His
            275                 280                 285

Thr Thr Thr Asn Ser Thr Leu Asp Ser Ser Pro Lys Thr Phe Pro Leu
        290                 295                 300

Asp Arg Ala Leu Tyr Ala Asp Phe Ser His Asp Asn Ser Met Val Ser
305                 310                 315                 320

Ile Phe Ser Ala Leu Gly Leu Tyr Asn Ser Thr Thr Leu Leu Pro Lys
                325                 330                 335

Asp His Ile Val Pro Ala Ile Lys Ala His Gly Tyr Ser Ser Thr Trp
                340                 345                 350

Val Val Pro Phe Gly Ala Arg Met Tyr Val Lys Leu Glu Cys Gly
            355                 360                 365

Ala Ser Arg Asn Glu Lys Arg Asp Glu Tyr Val Arg Val Leu Val Asn
        370                 375                 380

Asp Arg Val Met Ser Leu Glu Thr Cys Gly Gly Asp Glu Tyr Gly Leu
385                 390                 395                 400

Cys Arg Leu Glu Asn Phe Val Glu Ser Leu Ser Phe Ala Ala Ser Gly
                405                 410                 415

Gly Asn Trp Asp Gln Cys
                420

<210> SEQ ID NO 30
<211> LENGTH: 447
<212> TYPE: PRT
<213> ORGANISM: Myceliopthora thermophila

<400> SEQUENCE: 30

Ile Ser His Phe Trp Gly Gln Tyr Ser Pro Tyr Phe Ser Val Pro Ser
1               5                   10                  15

Glu Leu Asp Ala Ser Ile Pro Asp Asp Cys Glu Val Thr Phe Ala Gln
                20                  25                  30

Val Leu Ser Arg His Gly Ala Arg Ala Pro Thr Leu Lys Arg Ala Ala
            35                  40                  45

Ser Tyr Val Asp Leu Ile Asp Arg Ile His His Gly Ala Ile Ser Tyr
        50                  55                  60

Gly Pro Gly Tyr Glu Phe Leu Arg Thr Tyr Asp Tyr Thr Leu Gly Ala
65                  70                  75                  80

Asp Glu Leu Thr Arg Thr Gly Gln Gln Gln Met Val Asn Ser Gly Ile
                85                  90                  95

Lys Phe Tyr Arg Arg Tyr Arg Ala Leu Ala Arg Lys Ser Ile Pro Phe
                100                 105                 110
```

-continued

```
Val Arg Thr Ala Gly Gln Asp Arg Val Val His Ser Ala Glu Asn Phe
        115                 120                 125
Thr Gln Gly Phe His Ser Ala Leu Leu Ala Asp Arg Gly Ser Thr Val
    130                 135                 140
Arg Pro Thr Leu Pro Tyr Asp Met Val Val Ile Pro Glu Thr Ala Gly
145                 150                 155                 160
Ala Asn Asn Thr Leu His Asn Asp Leu Cys Thr Ala Phe Glu Glu Gly
            165                 170                 175
Pro Tyr Ser Thr Ile Gly Asp Ala Gln Asp Thr Tyr Leu Ser Thr
            180                 185                 190
Phe Ala Gly Pro Ile Thr Ala Arg Val Asn Ala Asn Leu Pro Gly Ala
            195                 200                 205
Asn Leu Thr Asp Ala Asp Thr Val Ala Leu Met Asp Leu Cys Pro Phe
    210                 215                 220
Glu Thr Val Ala Ser Ser Ser Asp Pro Ala Thr Ala Asp Ala Gly
225                 230                 235                 240
Gly Gly Asn Gly Arg Pro Leu Ser Pro Phe Cys Arg Leu Phe Ser Glu
            245                 250                 255
Ser Glu Trp Arg Ala Tyr Asp Tyr Leu Gln Ser Val Gly Lys Trp Tyr
            260                 265                 270
Gly Tyr Gly Pro Gly Asn Pro Leu Gly Pro Thr Gln Gly Val Gly Phe
        275                 280                 285
Val Asn Glu Leu Leu Ala Arg Leu Ala Gly Val Pro Val Arg Asp Gly
    290                 295                 300
Thr Ser Thr Asn Arg Thr Leu Asp Gly Asp Pro Arg Thr Phe Pro Leu
305                 310                 315                 320
Gly Arg Pro Leu Tyr Ala Asp Phe Ser His Asp Asn Asp Met Met Gly
            325                 330                 335
Val Leu Gly Ala Leu Gly Ala Tyr Asp Gly Val Pro Pro Leu Asp Lys
            340                 345                 350
Thr Ala Arg Arg Asp Pro Glu Glu Leu Gly Gly Tyr Ala Ala Ser Trp
        355                 360                 365
Ala Val Pro Phe Ala Ala Arg Ile Tyr Val Glu Lys Met Arg Cys Ser
    370                 375                 380
Gly Gly Gly Gly Gly Gly Gly Glu Gly Arg Gln Glu Lys Asp
385                 390                 395                 400
Glu Glu Met Val Arg Val Leu Val Asn Asp Arg Val Met Thr Leu Lys
            405                 410                 415
Gly Cys Gly Ala Asp Glu Arg Gly Met Cys Thr Leu Glu Arg Phe Ile
            420                 425                 430
Glu Ser Met Ala Phe Ala Arg Gly Asn Gly Lys Trp Asp Leu Cys
        435                 440                 445
```

<210> SEQ ID NO 31
<211> LENGTH: 448
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(448)
<223> OTHER INFORMATION: Xaa = Any Amino Acid

<400> SEQUENCE: 31

```
Ile Ser Xaa Xaa Trp Gly Gln Tyr Ser Xaa Tyr Phe Xaa Xaa Pro Ser
1               5                   10                  15
```

-continued

```
Glu Leu Asp Ala Ser Xaa Pro Asp Asp Cys Xaa Val Thr Phe Ala Xaa
             20                  25                  30

Val Leu Ser Arg His Gly Ala Arg Xaa Pro Thr Xaa Xaa Xaa Xaa Ala
         35                  40                  45

Xaa Tyr Xaa Xaa Xaa Ile Xaa Arg Ile Xaa Xaa Ala Xaa Xaa Tyr
     50                  55                  60

Gly Xaa Xaa Tyr Xaa Xaa Leu Xaa Xaa Tyr Xaa Tyr Xaa Leu Gly Ala
 65                  70                  75                  80

Xaa Xaa Leu Thr Xaa Xaa Gly Gln Xaa Gln Met Val Xaa Ser Gly Xaa
                 85                  90                  95

Xaa Phe Tyr Xaa Arg Tyr Xaa Xaa Leu Ala Xaa Lys Xaa Xaa Pro Phe
            100                 105                 110

Val Arg Xaa Xaa Gly Xaa Asp Arg Val Xaa Xaa Ser Xaa Xaa Asn Phe
            115                 120                 125

Thr Gln Gly Phe Xaa Xaa Xaa Xaa Ala Xaa Arg Gly Xaa Xaa Xaa
            130                 135                 140

Xaa Xaa Xaa Xaa Xaa Xaa Asp Xaa Xaa Xaa Ile Pro Glu Xaa Xaa Gly
145                 150                 155                 160

Xaa Asn Asn Thr Xaa Xaa Xaa Xaa Xaa Cys Xaa Xaa Phe Glu Xaa Xaa
                165                 170                 175

Xaa Xaa Xaa Xaa Xaa Asp Xaa Xaa Ala Xaa Xaa Xaa Xaa Xaa
                180                 185                 190

Xaa Phe Xaa Xaa Xaa Ile Xaa Xaa Arg Xaa Asn Xaa Xaa Leu Pro Gly
        195                 200                 205

Xaa Asn Leu Thr Xaa Xaa Xaa Thr Xaa Xaa Xaa Met Asp Xaa Cys Pro
210                 215                 220

Phe Xaa Xaa Xaa Ala Xaa Xaa Xaa Asp Xaa Xaa Xaa Xaa Xaa Xaa
225                 230                 235                 240

Gly Xaa Gly Xaa Xaa Arg Xaa Xaa Xaa Xaa Phe Cys Xaa Leu Phe Xaa
            245                 250                 255

Xaa Xaa Xaa Trp Arg Xaa Tyr Asp Tyr Xaa Xaa Xaa Xaa Xaa Lys Xaa
            260                 265                 270

Tyr Xaa Xaa Gly Xaa Gly Asn Xaa Xaa Gly Pro Thr Gln Gly Val Gly
     275                 280                 285

Xaa Val Asn Glu Leu Xaa Xaa Arg Leu Xaa Gly Xaa Pro Val Xaa Asp
    290                 295                 300

Xaa Thr Xaa Thr Asn Xaa Thr Leu Asp Xaa Xaa Pro Xaa Thr Phe Pro
305                 310                 315                 320

Leu Xaa Arg Xaa Leu Tyr Ala Asp Phe Ser His Asp Asn Xaa Met Xaa
        325                 330                 335

Xaa Xaa Xaa Xaa Ala Leu Gly Xaa Tyr Xaa Xaa Xaa Xaa Xaa Leu Xaa
            340                 345                 350

Lys Xaa Xaa Xaa Xaa Xaa Xaa Xaa Xaa Gly Tyr Xaa Xaa Xaa
    355                 360                 365

Trp Xaa Val Pro Phe Xaa Ala Arg Xaa Tyr Val Glu Lys Xaa Xaa Cys
370                 375                 380

Xaa Xaa Xaa Xaa Xaa Xaa Xaa Xaa Gly Xaa Xaa Arg Xaa Glu Lys
385                 390                 395                 400

Xaa Xaa Glu Xaa Val Arg Val Leu Val Asn Asp Arg Val Met Xaa Leu
        405                 410                 415

Xaa Xaa Cys Gly Xaa Asp Glu Xaa Gly Xaa Cys Xaa Leu Glu Xaa Phe
            420                 425                 430
```

Xaa Glu Ser Xaa Xaa Phe Ala Xaa Xaa Gly Xaa Trp Asp Xaa Cys
                435                 440                 445

<210> SEQ ID NO 32
<211> LENGTH: 449
<212> TYPE: PRT
<213> ORGANISM: Humicola grisea

<400> SEQUENCE: 32

Ala Ser Arg Asn Gln Ser Thr Cys Asp Ser Val Asp Arg Gly Phe Trp
 1               5                  10                  15

Cys Ala Ala Asp Ile Ser His Ser Trp Gly Gln Tyr Ser Pro Tyr Phe
                20                  25                  30

Ser Val Pro Ser Asp Ile Asp Pro Gly Phe Pro Lys Gly Cys Asn Val
            35                  40                  45

Thr Phe Ala Gln Val Leu Ser Arg His Gly Ala Arg Ala Pro Thr Thr
50                  55                  60

Gly Arg Ala Ala Tyr Tyr Val Asp Val Ile Asp Arg Val Gln Arg Gln
65                  70                  75                  80

Ala Thr Ser Tyr Gly Pro Gly His Ala Phe Leu Arg Ser Tyr Arg Tyr
                85                  90                  95

Thr Leu Gly Ala Asn Glu Leu Thr Pro Met Gly Glu Arg Gln Leu Ala
            100                 105                 110

Tyr Ser Gly Ala Arg Phe Tyr His Arg Tyr Arg Glu Leu Ala Arg Val
        115                 120                 125

Glu Ala Pro Phe Val Arg Ser Ser Gly Val Ser Arg Val Val Ala Ser
130                 135                 140

Ala Val Asn Phe Thr Gln Gly Phe His Gln Ala Arg Leu Ala Asp Arg
145                 150                 155                 160

Gly Ala Thr Leu Pro Pro Thr Leu Pro Tyr Asp Met Val Ile Ile
                165                 170                 175

Ser Ser Asp Asp Thr Ala Asn Asn Thr Leu His His Gly Leu Cys Thr
            180                 185                 190

Val Phe Glu Glu Gly Pro Tyr Ala Asp Ile Gly Asp Lys Ala Gln Lys
        195                 200                 205

Glu Tyr Leu Ser Lys Phe Val Gly Pro Ile Val Glu Arg Ile Asn Ala
210                 215                 220

Gln Leu Pro Gly Ala Asn Leu Asn Ala Thr Asp Ile Ile Ala Leu Met
225                 230                 235                 240

Asp Leu Cys Pro Phe Glu Thr Val Ala Phe Pro Glu Gly Thr Lys Leu
                245                 250                 255

Ser Pro Phe Cys Arg Leu Phe Thr Ala Ala Glu Trp Arg Ala Tyr Asp
            260                 265                 270

Arg Tyr Gln Asp Val Gly Lys Trp Phe Gly Tyr Gly Pro Gly Asn Pro
        275                 280                 285

Leu Gly Pro Thr Gln Gly Val Gly Phe Val Asn Glu Leu Ile Ala Arg
290                 295                 300

Leu Ser Gly Gln Pro Val Ser Asp Gly Thr Ser Thr Asn Arg Thr Leu
305                 310                 315                 320

Asp Glu Asn Pro Glu Thr Phe Pro Leu Gly Arg Arg Leu Tyr Ala Asp
                325                 330                 335

Phe Ser His Asp Asn Asp Met Val Gly Ile Leu Ser Ala Leu Gly Leu
            340                 345                 350

Trp Asp Asn His Glu Glu Pro Gly Asn Glu Met Pro Ala Glu Gly Glu
        355                 360                 365

Glu Asp Asp Asn Gly Arg Phe Ser Thr Ala Arg Ala Val Pro Phe Gly
            370                 375                 380

Ala Arg Val Tyr Val Glu Lys Leu Arg Cys Gly Gly Ser Glu Glu Asp
385                 390                 395                 400

Glu Glu Met Val Arg Val Leu Val Asn Asp Arg Val Met Pro Leu Ala
                405                 410                 415

Gln Cys Gly Gly Asp Lys Arg Gly Met Cys Thr Leu Ser Arg Phe Val
            420                 425                 430

Glu Ser Leu Lys Phe Ala Arg Asn Asn Gly Arg Trp Asp Met Cys Phe
            435                 440                 445

Glu

<210> SEQ ID NO 33
<211> LENGTH: 487
<212> TYPE: PRT
<213> ORGANISM: Myceliopthora thermophila

<400> SEQUENCE: 33

Met Thr Gly Leu Gly Val Met Val Met Val Gly Phe Leu Ala Ile
1               5                   10                  15

Ala Ser Leu Gln Ser Glu Ser Arg Pro Cys Asp Thr Pro Asp Leu Gly
                20                  25                  30

Phe Gln Cys Gly Thr Ala Ile Ser His Phe Trp Gly Gln Tyr Ser Pro
            35                  40                  45

Tyr Phe Ser Val Pro Ser Glu Leu Asp Ala Ser Ile Pro Asp Asp Cys
 50                 55                  60

Glu Val Thr Phe Ala Gln Val Leu Ser Arg His Gly Ala Arg Ala Pro
65                  70                  75                  80

Thr Leu Lys Arg Ala Ala Ser Tyr Val Asp Leu Ile Asp Arg Ile His
                85                  90                  95

His Gly Ala Ile Ser Tyr Gly Pro Gly Tyr Glu Phe Leu Arg Thr Tyr
            100                 105                 110

Asp Tyr Thr Leu Gly Ala Asp Glu Leu Thr Arg Thr Gly Gln Gln Gln
            115                 120                 125

Met Val Asn Ser Gly Ile Lys Phe Tyr Arg Arg Tyr Arg Ala Leu Ala
            130                 135                 140

Arg Lys Ser Ile Pro Phe Val Arg Thr Ala Gly Gln Asp Arg Val Val
145                 150                 155                 160

His Ser Ala Glu Asn Phe Thr Gln Gly Phe His Ser Ala Leu Leu Ala
                165                 170                 175

Asp Arg Gly Ser Thr Val Arg Pro Thr Leu Pro Tyr Asp Met Val Val
            180                 185                 190

Ile Pro Glu Thr Ala Gly Ala Asn Asn Thr Leu His Asn Asp Leu Cys
            195                 200                 205

Thr Ala Phe Glu Glu Gly Pro Tyr Ser Thr Ile Gly Asp Asp Ala Gln
            210                 215                 220

Asp Thr Tyr Leu Ser Thr Phe Ala Gly Pro Ile Thr Ala Arg Val Asn
225                 230                 235                 240

Ala Asn Leu Pro Gly Ala Asn Leu Thr Asp Ala Asp Thr Val Ala Leu
                245                 250                 255

Met Asp Leu Cys Pro Phe Glu Thr Val Ala Ser Ser Ser Asp Pro
            260                 265                 270

Ala Thr Ala Asp Ala Gly Gly Asn Gly Arg Pro Leu Ser Pro Phe
            275                 280                 285

```
Cys Arg Leu Phe Ser Glu Ser Glu Trp Arg Ala Tyr Asp Tyr Leu Gln
        290                 295                 300

Ser Val Gly Lys Trp Tyr Gly Tyr Gly Pro Gly Asn Pro Leu Gly Pro
305                 310                 315                 320

Thr Gln Gly Val Gly Phe Val Asn Glu Leu Leu Ala Arg Leu Ala Gly
                325                 330                 335

Val Pro Val Arg Asp Gly Thr Ser Thr Asn Arg Thr Leu Asp Gly Asp
            340                 345                 350

Pro Arg Thr Phe Pro Leu Gly Arg Pro Leu Tyr Ala Asp Phe Ser His
        355                 360                 365

Asp Asn Asp Met Met Gly Val Leu Gly Ala Leu Gly Ala Tyr Asp Gly
    370                 375                 380

Val Pro Pro Leu Asp Lys Thr Ala Arg Arg Asp Pro Glu Glu Leu Gly
385                 390                 395                 400

Gly Tyr Ala Ala Ser Trp Ala Val Pro Phe Ala Ala Arg Ile Tyr Val
                405                 410                 415

Glu Lys Met Arg Cys Ser Gly Gly Gly Gly Gly Gly Gly Gly Gly Glu
            420                 425                 430

Gly Arg Gln Glu Lys Asp Glu Glu Met Val Arg Val Leu Val Asn Asp
        435                 440                 445

Arg Val Met Thr Leu Lys Gly Cys Gly Ala Asp Glu Arg Gly Met Cys
    450                 455                 460

Thr Leu Glu Arg Phe Ile Glu Ser Met Ala Phe Ala Arg Gly Asn Gly
465                 470                 475                 480

Lys Trp Asp Leu Cys Phe Ala
                485

<210> SEQ ID NO 34
<211> LENGTH: 444
<212> TYPE: PRT
<213> ORGANISM: Aspergillus niger

<400> SEQUENCE: 34

Ala Ser Arg Asn Gln Ser Ser Cys Asp Thr Val Asp Gln Gly Tyr Gln
  1               5                  10                  15

Cys Phe Ser Glu Thr Ser His Leu Trp Gly Gln Tyr Ala Pro Phe Phe
             20                  25                  30

Ser Leu Ala Asn Glu Ser Val Ile Ser Pro Glu Val Pro Ala Gly Cys
         35                  40                  45

Arg Val Thr Phe Ala Gln Val Leu Ser Arg His Gly Ala Arg Tyr Pro
     50                  55                  60

Thr Asp Ser Lys Gly Lys Lys Tyr Ser Ala Leu Ile Glu Glu Ile Gln
 65                  70                  75                  80

Gln Asn Ala Thr Thr Phe Asp Gly Lys Tyr Ala Phe Leu Lys Thr Tyr
                 85                  90                  95

Asn Tyr Ser Leu Gly Ala Asp Asp Leu Thr Pro Phe Gly Glu Gln Glu
            100                 105                 110

Leu Val Asn Ser Gly Ile Lys Phe Tyr Gln Arg Tyr Glu Ser Leu Thr
        115                 120                 125

Arg Asn Ile Val Pro Phe Ile Arg Ser Gly Ser Ser Arg Val Ile
    130                 135                 140

Ala Ser Gly Lys Lys Phe Ile Glu Gly Phe Gln Ser Thr Lys Leu Lys
145                 150                 155                 160

Asp Pro Arg Ala Gln Pro Gly Gln Ser Ser Pro Lys Ile Asp Val Val
```

-continued

```
                165                 170                 175
Ile Ser Glu Ala Ser Ser Asn Asn Thr Leu Asp Pro Gly Thr Cys
            180                 185                 190

Thr Val Phe Glu Asp Ser Glu Leu Ala Asp Thr Val Glu Ala Asn Phe
        195                 200                 205

Thr Ala Thr Phe Val Pro Ser Ile Arg Gln Arg Leu Glu Asn Asp Leu
    210                 215                 220

Ser Gly Val Thr Leu Thr Asp Thr Glu Val Thr Tyr Leu Met Asp Met
225                 230                 235                 240

Cys Ser Phe Asp Thr Ile Ser Ser Thr Val Asp Thr Lys Leu Ser
                245                 250                 255

Pro Phe Cys Asp Leu Phe Thr His Asp Glu Trp Ile Asn Tyr Asp Tyr
            260                 265                 270

Leu Gln Ser Leu Lys Lys Tyr Tyr Gly His Gly Ala Gly Asn Pro Leu
        275                 280                 285

Gly Pro Thr Gln Gly Val Gly Tyr Ala Asn Glu Leu Ile Ala Arg Leu
    290                 295                 300

Thr His Ser Pro Val His Asp Asp Thr Ser Ser Asn His Thr Leu Asp
305                 310                 315                 320

Ser Ser Pro Ala Thr Phe Pro Leu Asn Ser Thr Leu Tyr Ala Asp Phe
                325                 330                 335

Ser His Asp Asn Gly Ile Ile Ser Ile Leu Phe Ala Leu Gly Leu Tyr
            340                 345                 350

Asn Gly Thr Lys Pro Leu Ser Thr Thr Val Glu Asn Ile Thr Gln
        355                 360                 365

Thr Asp Gly Phe Ser Ser Ala Trp Thr Val Pro Phe Ala Ser Arg Leu
    370                 375                 380

Tyr Val Glu Met Met Gln Cys Gln Ala Glu Gln Pro Leu Val Arg
385                 390                 395                 400

Val Leu Val Asn Asp Arg Val Val Pro Leu His Gly Cys Pro Val Asp
                405                 410                 415

Ala Leu Gly Arg Cys Thr Arg Asp Ser Phe Val Arg Gly Leu Ser Phe
            420                 425                 430

Ala Arg Ser Gly Gly Asp Trp Ala Glu Cys Phe Ala
        435                 440
```

<210> SEQ ID NO 35
<211> LENGTH: 449
<212> TYPE: PRT
<213> ORGANISM: Humicola grisea

<400> SEQUENCE: 35

```
Ala Ser Arg Asn Gln Ser Thr Cys Asp Ser Val Asp Arg Gly Phe Trp
1               5                   10                  15

Cys Ala Asp Ile Ser His Ser Trp Gly Gln Tyr Ser Pro Tyr Phe
            20                  25                  30

Ser Val Pro Ser Asp Ile Asp Pro Gly Phe Pro Lys Gly Cys Asn Val
        35                  40                  45

Thr Phe Ala Gln Val Leu Ser Arg His Gly Ala Arg Ala Pro Thr Thr
    50                  55                  60

Gly Arg Ala Ala Tyr Tyr Val Asp Val Ile Asp Arg Val Gln Arg Gln
65                  70                  75                  80

Ala Thr Ser Tyr Gly Pro Gly His Ala Phe Leu Arg Ser Tyr Arg Tyr
                85                  90                  95
```

```
Thr Leu Gly Ala Asn Glu Leu Thr Pro Met Gly Glu Arg Gln Leu Ala
            100                 105                 110

Tyr Ser Gly Ala Arg Phe Tyr His Arg Tyr Arg Glu Leu Ala Arg Val
        115                 120                 125

Glu Ala Pro Phe Val Arg Ser Ser Gly Val Ser Arg Val Val Ala Ser
    130                 135                 140

Ala Val Asn Phe Thr Gln Gly Phe His Gln Ala Arg Leu Ala Asp Arg
145                 150                 155                 160

Gly Ala Thr Leu Pro Pro Thr Leu Pro Tyr Asp Met Val Ile Ile
                165                 170                 175

Ser Ser Asp Asp Thr Ala Asn Asn Thr Leu His His Gly Leu Cys Thr
                180                 185                 190

Val Phe Glu Glu Gly Pro Tyr Ala Asp Ile Gly Asp Lys Ala Gln Lys
            195                 200                 205

Glu Tyr Leu Ser Lys Phe Val Gly Pro Ile Val Glu Arg Ile Asn Ala
        210                 215                 220

Gln Leu Pro Gly Ala Asn Leu Asn Ala Thr Asp Ile Ile Ala Leu Met
225                 230                 235                 240

Asp Leu Cys Pro Phe Glu Thr Val Ala Phe Pro Glu Gly Thr Lys Leu
                245                 250                 255

Ser Pro Phe Cys Arg Leu Phe Thr Ala Ala Glu Trp Arg Ala Tyr Asp
            260                 265                 270

Arg Tyr Gln Asp Val Gly Lys Trp Phe Gly Tyr Gly Pro Gly Asn Pro
        275                 280                 285

Leu Gly Pro Thr Gln Gly Val Gly Phe Val Asn Glu Leu Ile Ala Arg
    290                 295                 300

Leu Ser Gly Gln Pro Val Ser Asp Gly Thr Ser Thr Asn Arg Thr Leu
305                 310                 315                 320

Asp Glu Asn Pro Glu Thr Phe Pro Leu Gly Arg Arg Leu Tyr Ala Asp
                325                 330                 335

Phe Ser His Asp Asn Asp Met Val Gly Ile Leu Ser Ala Leu Gly Leu
            340                 345                 350

Trp Asp Asn His Glu Glu Pro Gly Asn Glu Met Pro Ala Glu Gly Glu
        355                 360                 365

Glu Asp Asp Asn Gly Arg Phe Ser Thr Ala Arg Ala Val Pro Phe Gly
    370                 375                 380

Ala Arg Val Tyr Val Glu Lys Leu Arg Cys Gly Gly Ser Glu Glu Asp
385                 390                 395                 400

Glu Glu Met Val Arg Val Leu Val Asn Asp Arg Val Met Pro Leu Ala
                405                 410                 415

Gln Cys Gly Gly Asp Lys Arg Gly Met Cys Thr Leu Ser Arg Phe Val
            420                 425                 430

Glu Ser Leu Lys Phe Ala Arg Asn Asn Gly Arg Trp Asp Met Cys Phe
        435                 440                 445

Glu
```

<210> SEQ ID NO 36
<211> LENGTH: 441
<212> TYPE: PRT
<213> ORGANISM: Humicola grisea
<220> FEATURE:
<221> NAME/KEY: VARIANT
<222> LOCATION: (126)...(139)
<223> OTHER INFORMATION: Xaa = Any Amino Acid

<400> SEQUENCE: 36

```
Cys Asp Ser Val Asp Arg Gly Phe Trp Cys Ala Asp Ile Ser His
  1               5                  10                 15

Ser Trp Gly Gln Tyr Ser Pro Tyr Phe Ser Val Pro Ser Asp Ile Asp
                 20                  25                  30

Pro Gly Phe Pro Lys Gly Cys Asn Val Thr Phe Ala Gln Val Leu Ser
             35                  40                  45

Arg His Gly Ala Arg Ala Pro Thr Thr Gly Arg Ala Ala Tyr Tyr Val
     50                  55                  60

Asp Val Ile Asp Arg Val Gln Arg Gln Ala Thr Ser Tyr Gly Pro Gly
 65              70                  75                  80

His Ala Phe Leu Arg Ser Tyr Arg Tyr Thr Leu Gly Ala Asn Glu Leu
                 85                  90                  95

Thr Pro Met Gly Glu Arg Gln Leu Ala Tyr Ser Gly Ala Arg Phe Tyr
            100                 105                 110

His Arg Tyr Arg Glu Leu Ala Arg Val Glu Ala Pro Phe Xaa Xaa Xaa
            115                 120                 125

Xaa Xaa Xaa Xaa Xaa Xaa Xaa Xaa Xaa Xaa Asn Phe Thr Gln Gly
        130                 135                 140

Phe His Gln Ala Arg Leu Ala Asp Arg Gly Ala Thr Leu Pro Pro Pro
145                 150                 155                 160

Thr Leu Pro Tyr Asp Met Val Ile Ser Ser Asp Thr Ala Asn
                165                 170                 175

Asn Thr Leu His His Gly Leu Cys Thr Val Phe Glu Glu Gly Pro Tyr
                180                 185                 190

Ala Asp Ile Gly Asp Lys Ala Gln Lys Glu Tyr Leu Ser Lys Phe Val
            195                 200                 205

Gly Pro Ile Val Glu Arg Ile Asn Ala Gln Leu Pro Gly Ala Asn Leu
            210                 215                 220

Asn Ala Thr Asp Ile Ile Ala Leu Met Asp Leu Cys Pro Phe Glu Thr
225                 230                 235                 240

Val Ala Phe Pro Glu Gly Thr Lys Leu Ser Pro Phe Cys Arg Leu Phe
            245                 250                 255

Thr Ala Ala Glu Trp Arg Ala Tyr Asp Arg Tyr Gln Asp Val Gly Lys
            260                 265                 270

Trp Phe Gly Tyr Gly Pro Gly Asn Pro Leu Gly Pro Thr Gln Gly Val
            275                 280                 285

Gly Phe Val Asn Glu Leu Ile Ala Arg Leu Ser Gly Gln Pro Val Ser
            290                 295                 300

Asp Gly Thr Ser Thr Asn Arg Thr Leu Asp Glu Asn Pro Glu Thr Phe
305                 310                 315                 320

Pro Leu Gly Arg Arg Leu Tyr Ala Asp Phe Ser His Asp Asn Asp Met
            325                 330                 335

Val Gly Ile Leu Ser Ala Leu Gly Leu Trp Asp Asn His Glu Glu Pro
            340                 345                 350

Gly Asn Glu Met Pro Ala Glu Gly Glu Asp Asp Asn Gly Arg Phe
            355                 360                 365

Ser Thr Ala Arg Ala Val Pro Phe Gly Ala Arg Val Tyr Val Glu Lys
        370                 375                 380

Leu Arg Cys Gly Gly Ser Glu Glu Asp Glu Met Val Arg Val Leu
385                 390                 395                 400

Val Asn Asp Arg Val Met Pro Leu Ala Gln Cys Gly Gly Asp Lys Arg
                405                 410                 415
```

-continued

```
Gly Met Cys Thr Leu Ser Arg Phe Val Glu Ser Leu Lys Phe Ala Arg
            420                 425                 430

Asn Asn Gly Arg Trp Asp Met Cys Phe
            435                 440

<210> SEQ ID NO 37
<211> LENGTH: 461
<212> TYPE: PRT
<213> ORGANISM: Myceliopthora thermophila

<400> SEQUENCE: 37

Cys Asp Thr Pro Asp Leu Gly Phe Gln Cys Gly Thr Ala Ile Ser His
  1               5                  10                  15

Phe Trp Gly Gln Tyr Ser Pro Tyr Phe Ser Val Pro Ser Glu Leu Asp
             20                  25                  30

Ala Ser Ile Pro Asp Cys Glu Val Thr Phe Ala Gln Val Leu Ser
         35                  40                  45

Arg His Gly Ala Arg Ala Pro Thr Leu Lys Arg Ala Ser Tyr Val
     50                  55                  60

Asp Leu Ile Asp Arg Ile His His Gly Ala Ile Ser Tyr Gly Pro Gly
 65                  70                  75                  80

Tyr Glu Phe Leu Arg Thr Tyr Asp Tyr Thr Leu Gly Ala Asp Glu Leu
                 85                  90                  95

Thr Arg Thr Gly Gln Gln Gln Met Val Asn Ser Gly Ile Lys Phe Tyr
            100                 105                 110

Arg Arg Tyr Arg Ala Leu Ala Arg Lys Ser Ile Pro Phe Val Arg Thr
        115                 120                 125

Ala Gly Gln Asp Arg Val Val His Ser Ala Glu Asn Phe Thr Gln Gly
    130                 135                 140

Phe His Ser Ala Leu Leu Ala Asp Arg Gly Ser Thr Val Arg Pro Thr
145                 150                 155                 160

Leu Pro Tyr Asp Met Val Val Ile Pro Glu Thr Ala Gly Ala Asn Asn
                165                 170                 175

Thr Leu His Asn Asp Leu Cys Thr Ala Phe Glu Glu Gly Pro Tyr Ser
            180                 185                 190

Thr Ile Gly Asp Asp Ala Gln Asp Thr Tyr Leu Ser Thr Phe Ala Gly
        195                 200                 205

Pro Ile Thr Ala Arg Val Asn Ala Asn Leu Pro Gly Ala Asn Leu Thr
    210                 215                 220

Asp Ala Asp Thr Val Ala Leu Met Asp Leu Cys Pro Phe Glu Thr Val
225                 230                 235                 240

Ala Ser Ser Ser Asp Pro Ala Thr Ala Asp Ala Gly Gly Asn
                245                 250                 255

Gly Arg Pro Leu Ser Pro Phe Cys Arg Leu Phe Ser Glu Ser Glu Trp
            260                 265                 270

Arg Ala Tyr Asp Tyr Leu Gln Ser Val Gly Lys Trp Tyr Gly Tyr Gly
        275                 280                 285

Pro Gly Asn Pro Leu Gly Pro Thr Gln Gly Val Gly Phe Val Asn Glu
    290                 295                 300

Leu Leu Ala Arg Leu Ala Gly Val Pro Val Arg Asp Gly Thr Ser Thr
305                 310                 315                 320

Asn Arg Thr Leu Asp Gly Asp Pro Arg Thr Phe Pro Leu Gly Arg Pro
                325                 330                 335

Leu Tyr Ala Asp Phe Ser His Asp Asn Asp Met Met Gly Val Leu Gly
            340                 345                 350
```

Ala Leu Gly Ala Tyr Asp Gly Val Pro Pro Leu Asp Lys Thr Ala Arg
            355                 360                 365

Arg Asp Pro Glu Glu Leu Gly Gly Tyr Ala Ala Ser Trp Ala Val Pro
        370                 375                 380

Phe Ala Ala Arg Ile Tyr Val Glu Lys Met Arg Cys Ser Gly Gly Gly
385                 390                 395                 400

Gly Gly Gly Gly Gly Glu Gly Arg Gln Glu Lys Asp Glu Glu Met
                405                 410                 415

Val Arg Val Leu Val Asn Asp Arg Val Met Thr Leu Lys Gly Cys Gly
            420                 425                 430

Ala Asp Glu Arg Gly Met Cys Thr Leu Glu Arg Phe Ile Glu Ser Met
            435                 440                 445

Ala Phe Ala Arg Gly Asn Gly Lys Trp Asp Leu Cys Phe
            450                 455                 460

<210> SEQ ID NO 38
<211> LENGTH: 464
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(464)
<223> OTHER INFORMATION: Xaa = Any Amino Acid

<400> SEQUENCE: 38

Cys Asp Xaa Xaa Asp Xaa Gly Phe Xaa Cys Xaa Xaa Xaa Ile Ser His
1               5                   10                  15

Xaa Trp Gly Gln Tyr Ser Pro Tyr Phe Ser Val Pro Ser Xaa Xaa Asp
            20                  25                  30

Xaa Xaa Xaa Pro Xaa Xaa Cys Xaa Val Thr Phe Ala Gln Val Leu Ser
        35                  40                  45

Arg His Gly Ala Arg Ala Pro Thr Xaa Xaa Arg Ala Ala Xaa Tyr Val
    50                  55                  60

Asp Xaa Ile Asp Arg Xaa Xaa Xaa Ala Xaa Ser Tyr Gly Pro Gly
65              70                  75                  80

Xaa Xaa Phe Leu Arg Xaa Tyr Xaa Tyr Thr Leu Gly Ala Xaa Glu Leu
            85                  90                  95

Thr Xaa Xaa Gly Xaa Xaa Gln Xaa Xaa Xaa Ser Gly Xaa Xaa Phe Tyr
            100                 105                 110

Xaa Arg Tyr Arg Xaa Leu Ala Arg Xaa Xaa Xaa Pro Phe Xaa Xaa Xaa
        115                 120                 125

Xaa Xaa Xaa Xaa Xaa Xaa Xaa Xaa Xaa Asn Phe Thr Gln Gly
    130                 135                 140

Phe His Xaa Ala Xaa Leu Ala Asp Arg Gly Xaa Thr Xaa Xaa Xaa Pro
145                 150                 155                 160

Thr Leu Pro Tyr Asp Met Val Xaa Ile Xaa Xaa Xaa Xaa Ala Asn
            165                 170                 175

Asn Thr Leu His Xaa Xaa Leu Cys Thr Xaa Phe Glu Glu Gly Pro Tyr
            180                 185                 190

Xaa Xaa Ile Gly Asp Xaa Ala Gln Xaa Xaa Tyr Leu Ser Xaa Phe Xaa
            195                 200                 205

Gly Pro Ile Xaa Xaa Arg Xaa Asn Ala Xaa Leu Pro Gly Ala Asn Leu
        210                 215                 220

Xaa Xaa Xaa Asp Xaa Xaa Ala Leu Met Asp Leu Cys Pro Phe Glu Thr

-continued

```
                225                 230                 235                 240
        Val Ala Xaa Xaa Xaa Xaa Xaa Xaa Xaa Xaa Xaa Xaa Xaa Xaa
                        245                 250                 255

Xaa Gly Xaa Xaa Leu Ser Pro Phe Cys Arg Leu Phe Xaa Xaa Xaa Glu
                260                 265                 270

Trp Arg Ala Tyr Asp Xaa Xaa Gln Xaa Val Gly Lys Trp Xaa Gly Tyr
                    275                 280                 285

Gly Pro Gly Asn Pro Leu Gly Pro Thr Gln Gly Val Gly Phe Val Asn
                290                 295                 300

Glu Leu Xaa Ala Arg Leu Xaa Gly Xaa Pro Val Xaa Asp Gly Thr Ser
        305                 310                 315                 320

Thr Asn Arg Thr Leu Asp Xaa Xaa Pro Xaa Thr Phe Pro Leu Gly Arg
                        325                 330                 335

Xaa Leu Tyr Ala Asp Phe Ser His Asp Asn Asp Met Xaa Gly Xaa Leu
                    340                 345                 350

Xaa Ala Leu Gly Xaa Xaa Asp Xaa Xaa Xaa Xaa Pro Xaa Xaa Xaa Xaa
                355                 360                 365

Xaa Ala Xaa Xaa Xaa Xaa Xaa Xaa Gly Xaa Xaa Xaa Xaa Xaa Xaa Xaa
                370                 375                 380

Ala Val Pro Phe Xaa Ala Arg Xaa Tyr Val Glu Lys Xaa Arg Cys Xaa
        385                 390                 395                 400

Gly Xaa Xaa Xaa Xaa Xaa Xaa Xaa Xaa Xaa Xaa Xaa Glu Xaa Asp
                        405                 410                 415

Glu Glu Met Val Arg Val Leu Val Asn Asp Arg Val Met Xaa Leu Xaa
                    420                 425                 430

Xaa Cys Gly Xaa Asp Xaa Arg Gly Met Cys Thr Leu Xaa Arg Phe Xaa
                        435                 440                 445

Glu Ser Xaa Xaa Phe Ala Arg Xaa Asn Gly Xaa Trp Asp Xaa Cys Phe
                450                 455                 460

<210> SEQ ID NO 39
<211> LENGTH: 1449
<212> TYPE: DNA
<213> ORGANISM: Emericella desertorum

<400> SEQUENCE: 39 atggttctt  tcacggtctc  cctttcgctg  tactacctac  ttacgaggtg  agatctctac      60
agtagctgct  tgtttagttg  agttggtact  tacctacaca  gcgtctctgc  tcaggccgtg     120
gtggcgcagg  aatattcatg  taattcggcc  gacgctgggt  atcaatgttt  ccccaatgtc     180
tcgcacgtct  ggggccagta  ctcgccgtac  ttctcactcg  agcatgagtc  tgccatttct     240
caggacgtgc  ctcatggctg  tgaggttacc  ttcgtgcagg  tgctctcgcg  acatgggggct    300 agatatcctt  cggagtcaaa  aagcaaggcg  tatgcgaagt  tgattgacgc  tatcaagaag     360
aatgctactt  cgttttcggg  acagtatgct  tttctggaga  gttataatta  tactctcggc     420
gcggaagact  tgactacttt  tggtgagaac  cagatggtcg  actcgggtgc  caagttttac     480
cggcggtata  agaatttggc  caggaaaaat  actccattca  tacgtgcatc  agggtctgac     540
cgtgtcgttg  cgtccgcgga  gaagtttatt  gacggacttc  gagacgccca  gacccacgac     600
cagggctcca  aacgtgttgc  cccagttgtc  aatgtggtta  tccctgaaac  tgatggattt     660
aacaacaccc  tggatcatag  cacttgcgtg  tctttttgaga  atgatgagcg  ggcggacgaa     720
attgaagcca  acttcgccgc  gatcattgga  cctccgattc  gcaaacgtct  ggaaaacgac     780
cttcctggcg  ttgagcttac  aaatgagcat  gtggaatact  tgatggatat  gtgctcgttc     840
```

-continued

```
gacaccatgg cgcgcaccgc ccatggaacc gagctgtctc cattctgcgc catcttcact   900
gaaaaggagt ggctgcagta cgactaccta caatctctgt caaagtacta cggctacggt   960
gccgggaacc cccttggccc agctcaggga attggcttca ccaacgagct gattgcccga  1020
ctgacgcagt cgcctgtcca ggacaacacg agcaccaacc acactctaga ctctgacccg  1080
gccacgttcc ccctcgacag gaagctctac gccgacttct cccacgacaa taacatgatt  1140
tctatattct tcgccatggg cctgtacaac ggcacccagc cgctgtccat ggacactgtg  1200
gagtcgattg aggagatgga tggctacgcg cgtcttgga ctgtcccgtt tggtgcgagg   1260
gcttactttg aggtgatgca gtgccaaaaa aagaaggagc cacttgtgcg ggtattagtg   1320
aatgatcgcg ttgttcctct ccatggctgt gctgttgaca agctcggacg atgcactttg   1380
gacgattggg tcgagggctt gagttttgcg agggccggtg ggaactggaa ggcttgtttt   1440
actgcctaa                                                           1449
```

<210> SEQ ID NO 40
<211> LENGTH: 464
<212> TYPE: PRT
<213> ORGANISM: Emericella desertorum

<400> SEQUENCE: 40

```
Met Val Leu Phe Thr Val Ser Leu Ser Leu Tyr Tyr Leu Leu Thr Ser
  1               5                  10                  15

Val Ser Ala Gln Ala Val Val Ala Gln Glu Tyr Ser Cys Asn Ser Ala
                 20                  25                  30

Asp Ala Gly Tyr Gln Cys Phe Pro Asn Val Ser His Val Trp Gly Gln
             35                  40                  45

Tyr Ser Pro Tyr Phe Ser Leu Glu His Glu Ser Ala Ile Ser Gln Asp
         50                  55                  60

Val Pro His Gly Cys Glu Val Thr Phe Val Gln Val Leu Ser Arg His
 65                  70                  75                  80

Gly Ala Arg Tyr Pro Ser Glu Ser Lys Ser Lys Ala Tyr Ala Lys Leu
                 85                  90                  95

Ile Asp Ala Ile Lys Lys Asn Ala Thr Ser Phe Ser Gly Gln Tyr Ala
            100                 105                 110

Phe Leu Glu Ser Tyr Asn Tyr Thr Leu Gly Ala Glu Asp Leu Thr Thr
        115                 120                 125

Phe Gly Glu Asn Gln Met Val Asp Ser Gly Ala Lys Phe Tyr Arg Arg
    130                 135                 140

Tyr Lys Asn Leu Ala Arg Lys Asn Thr Pro Phe Ile Arg Ala Ser Gly
145                 150                 155                 160

Ser Asp Arg Val Val Ala Ser Ala Glu Lys Phe Ile Asp Gly Leu Arg
                165                 170                 175

Asp Ala Gln Thr His Asp Gln Gly Ser Lys Arg Val Ala Pro Val Val
            180                 185                 190

Asn Val Val Ile Pro Glu Thr Asp Gly Phe Asn Asn Thr Leu Asp His
        195                 200                 205

Ser Thr Cys Val Ser Phe Glu Asn Asp Glu Arg Ala Asp Glu Ile Glu
    210                 215                 220

Ala Asn Phe Ala Ala Ile Ile Gly Pro Pro Ile Arg Lys Arg Leu Glu
225                 230                 235                 240

Asn Asp Leu Pro Gly Val Glu Leu Thr Asn Glu His Val Glu Tyr Leu
                245                 250                 255
```

```
Met Asp Met Cys Ser Phe Asp Thr Met Ala Arg Thr Ala His Gly Thr
            260                 265                 270

Glu Leu Ser Pro Phe Cys Ala Ile Phe Thr Glu Lys Glu Trp Leu Gln
        275                 280                 285

Tyr Asp Tyr Leu Gln Ser Leu Ser Lys Tyr Tyr Gly Tyr Gly Ala Gly
        290                 295                 300

Asn Pro Leu Gly Pro Ala Gln Gly Ile Gly Phe Thr Asn Glu Leu Ile
305                 310                 315                 320

Ala Arg Leu Thr Gln Ser Pro Val Gln Asp Asn Thr Ser Thr Asn His
                325                 330                 335

Thr Leu Asp Ser Asp Pro Ala Thr Phe Pro Leu Asp Arg Lys Leu Tyr
            340                 345                 350

Ala Asp Phe Ser His Asp Asn Asn Met Ile Ser Ile Phe Phe Ala Met
            355                 360                 365

Gly Leu Tyr Asn Gly Thr Gln Pro Leu Ser Met Asp Thr Val Glu Ser
        370                 375                 380

Ile Glu Glu Met Asp Gly Tyr Ala Ala Ser Trp Thr Val Pro Phe Gly
385                 390                 395                 400

Ala Arg Ala Tyr Phe Glu Val Met Gln Cys Gln Lys Lys Lys Glu Pro
                405                 410                 415

Leu Val Arg Val Leu Val Asn Asp Arg Val Val Pro Leu His Gly Cys
            420                 425                 430

Ala Val Asp Lys Leu Gly Arg Cys Thr Leu Asp Asp Trp Val Glu Gly
            435                 440                 445

Leu Ser Phe Ala Arg Ala Gly Gly Asn Trp Lys Ala Cys Phe Thr Ala
        450                 455                 460

<210> SEQ ID NO 41
<211> LENGTH: 2270
<212> TYPE: DNA
<213> ORGANISM: Fusarium javanicum

<400> SEQUENCE: 41
ttaagactgc ctagagcagc ttttaaata cgaatcgcct agtgcgatct attattctca      60
agatatttat tgactcacat gaagtgaagt tgaatgagag aagatgtctg agtgaatcat     120
gcatgcgtgg ccgagacatt gcgtggtgca gggtatttac aagccaagcg atgaatgcgt     180
ccatcactca gagtttaagc taattgaatc cactcaatta atcaaccttg acagaaacat     240
cggacatatt cttcaattga cttcaagta taaaatcaaa atcacagcac aagacgccct     300
tgtacatcaa ctcatgtgca gggtgctcaa agtggctgac aaagtgcctc gttcgttgac     360
caaccacgtg gtccacctca aggccatgtc ttcaacgtca acattcagg atagccgag      420 cagctcgttc atctcattca ccctcagccc cgcaacctga ctcgatggaa ccatcccttg     480
acaatcacat taacgcgcgc gactctacag catcttttac tgaaattcaa tcagccagag     540
ctgctgagct gatgggtctc gccgccagtg ggagctagca tatccctgtc acgattaccg     600
aatcactgga gatggtgcat cttgggcggc gcgacggcga agaggaagac gcgcctccca     660
tcgcggatca tcgggacgac gacaacgacg acatgtctga ttctgatccc gagaggggac     720
gcctgcttca taatgacgac gatgatggtg ttgatactga gagccgctcg gacgctgagc     780
ggcttgagag ctggcatgag gagcaccgac gtcgtgagac gagacgatgg agttacctcg     840
tcatggtcat cagcaccatc gcattgatca cagttcttgg attttgggtc cagaatgggt     900
gagttatatg agttgatgct catcttttaa atcaaactga cacgcctgat agaactcgac     960
```

-continued

```
cggctgggtg tgagtatgac gggagctgta atgacatctc tcggctctgg ggacagtact    1020
ctgcatactt cccaatcccg tctgagcttg atgcctcaac accagacgat tgtgatgtga    1080
cttttgcact cgtcttgtcc cgccatggag ccaggtaccc aacggacagc aagtctgcag    1140
catacaacgc taccattgcc cgcattcaaa agtctgctac catgtacggc aagaactaca    1200
agtggcttaa ggagtatacc tacagtctcg gcgctgaaga cctgactgag tttggccagc    1260
ggcagatggt cgactctggt agggccttt atgagcggta catgagtctc gctgagaaga    1320
ctgagccttt tgttcgggca tcgggctcag atcgggtcat catgtcgtct tacaatttta    1380
cgcaaggctt ttacgcatcg cgaggagagt ctggagacga ttatactcag gatgttctta    1440
tcatccctga gaacctggc atcaacaaca ccatgttgca tggatcgtgc gcctcattcg    1500
aaagcgacag agttcctaaa gacgcagatg aaaaggccga ggttgcatgg ggagcaagat    1560
tcctccccga gattcgaaat aggttgaacc accacctgcc aggagtcaac ctgacgctgg    1620
aggaaaccat ctacatgatg gacatgtgtc cgttcctcgc ggctgacaca cctgatggcg    1680
ctggtcactc gaggttctgc gacctcttca ccaaggcaga ctggcgaagt tacgactact    1740
acatgactct gagcaagttc tacaagtttg caatggcaa tgccatggga ccgacacaag    1800
gtgttggata tgtcaacgaa ctcatctcac gcttgactgg gaagcctgtt gacgaccaca    1860
ccacgaccaa cagcacattg gactcatcgc caaagacgtt ccctcttgac agggctctat    1920
atgcggattt tagccacgac aacagcatgg tctccatctt ctcagcactg gcttgtaca    1980 actcgactac cctgctacca aaggaccata ttgtgcccgc gatcaaggcg cacggctact    2040
catcgacatg ggtagtcccc tttggagcca gaatgtacgt cgagaagctc gagtgtggtg    2100
ccagcaggaa tgaaaagaga gacgagtacg tgcgagtcct ggtcaacgac cgagtgatgt    2160
cgctcgaaac ctgcggaggc gacgagtacg ggctctgcag actagaaaac tttgtggaga    2220
gtctgtcgtt tgccgcctcg ggaggaaact gggatcaatg cggtggataa    2270
```

<210> SEQ ID NO 42
<211> LENGTH: 457
<212> TYPE: PRT
<213> ORGANISM: Fusarium javanicum

<400> SEQUENCE: 42

```
Met Val Ile Ser Thr Ile Ala Leu Ile Thr Val Leu Gly Phe Trp Val
 1               5                   10                  15

Gln Asn Gly Thr Arg Pro Ala Gly Cys Glu Tyr Asp Gly Ser Cys Asn
            20                  25                  30

Asp Ile Ser Arg Leu Trp Gly Gln Tyr Ser Ala Tyr Phe Pro Ile Pro
        35                  40                  45

Ser Glu Leu Asp Ala Ser Thr Pro Asp Asp Cys Asp Val Thr Phe Ala
    50                  55                  60

Leu Val Leu Ser Arg His Gly Ala Arg Tyr Pro Thr Asp Ser Lys Ser
65                  70                  75                  80

Ala Ala Tyr Asn Ala Thr Ile Ala Arg Ile Gln Lys Ser Ala Thr Met
                85                  90                  95

Tyr Gly Lys Asn Tyr Lys Trp Leu Lys Glu Tyr Thr Tyr Ser Leu Gly
            100                 105                 110

Ala Glu Asp Leu Thr Glu Phe Gly Gln Arg Gln Met Val Asp Ser Gly
        115                 120                 125

Arg Ala Phe Tyr Glu Arg Tyr Met Ser Leu Ala Glu Lys Thr Glu Pro
    130                 135                 140
```

-continued

```
Phe Val Arg Ala Ser Gly Ser Asp Arg Val Ile Met Ser Ser Tyr Asn
145                 150                 155                 160
Phe Thr Gln Gly Phe Tyr Ala Ser Arg Gly Glu Ser Gly Asp Asp Tyr
                165                 170                 175
Thr Gln Asp Val Leu Ile Ile Pro Glu Glu Pro Gly Ile Asn Asn Thr
            180                 185                 190
Met Leu His Gly Ser Cys Ala Ser Phe Glu Ser Asp Arg Val Pro Lys
        195                 200                 205
Asp Ala Asp Glu Lys Ala Glu Val Ala Trp Gly Ala Arg Phe Leu Pro
    210                 215                 220
Glu Ile Arg Asn Arg Leu Asn His His Leu Pro Gly Val Asn Leu Thr
225                 230                 235                 240
Leu Glu Glu Thr Ile Tyr Met Met Asp Met Cys Pro Phe Leu Ala Ala
                245                 250                 255
Asp Thr Pro Asp Gly Ala Gly His Ser Arg Phe Cys Asp Leu Phe Thr
            260                 265                 270
Lys Ala Asp Trp Arg Ser Tyr Asp Tyr Tyr Met Thr Leu Ser Lys Phe
        275                 280                 285
Tyr Lys Phe Gly Asn Gly Asn Ala Met Gly Pro Thr Gln Gly Val Gly
    290                 295                 300
Tyr Val Asn Glu Leu Ile Ser Arg Leu Thr Gly Lys Pro Val Asp Asp
305                 310                 315                 320
His Thr Thr Asn Ser Thr Leu Asp Ser Ser Pro Lys Thr Phe Pro
                325                 330                 335
Leu Asp Arg Ala Leu Tyr Ala Asp Phe Ser His Asp Asn Ser Met Val
            340                 345                 350
Ser Ile Phe Ser Ala Leu Gly Leu Tyr Asn Ser Thr Thr Leu Leu Pro
        355                 360                 365
Lys Asp His Ile Val Pro Ala Ile Lys Ala His Gly Tyr Ser Ser Thr
    370                 375                 380
Trp Val Val Pro Phe Gly Ala Arg Met Tyr Val Glu Lys Leu Glu Cys
385                 390                 395                 400
Gly Ala Ser Arg Asn Glu Lys Arg Asp Glu Tyr Val Arg Val Leu Val
                405                 410                 415
Asn Asp Arg Val Met Ser Leu Glu Thr Cys Gly Gly Asp Glu Tyr Gly
            420                 425                 430
Leu Cys Arg Leu Glu Asn Phe Val Glu Ser Leu Ser Phe Ala Ala Ser
        435                 440                 445
Gly Gly Asn Trp Asp Gln Cys Gly Gly
    450                 455
```

<210> SEQ ID NO 43
<211> LENGTH: 1697

<212> TYPE: DNA
<213> ORGANISM: Penicillium chrysogenum

<400> SEQUENCE: 43

```
actatagggc acgcgtggtc gacggcccgg gctggtaaat atgaactggt tttcccctct    60
tcgcattcta tatgctcaca ggtgtcacgg actagtcaag ctgtgatttc gtgtattcac   120
cggtgtgatg gcggctttct ctaaaaacca tggagaggaa gagggccttc tcggagagaa   180
acaagagcga cgctggaaac agcaacgcca gcaatcttcc cgaagatgga cagcgttgac   240
```

```
catcatgtcc ctgctgggca ctttcgccct ggttgtgtac ttcgcgaagg gaacccagtg    300
caaccctcct ccacgtgcgc acaacccagc ctgacctacc tctgacttcc cccgtgaaca    360
tgtcgaagag atctgactgc actactgtcg atggcggtta ccaatgcaat tccgagctct    420
cacacaagtg gggccagtat tcgccctatt tctctctttc cgaagaatca tccatctcga    480
atgaggtacc tcatgattgt cagatcactt ttgctcaagt gatctcccgt catggtgctc    540
gattcccgtc cgcgaagaag agcaaggtat atgccaagct cattgaaaat atccaagcga    600
acgcgactgc atacaatggc aacacgaagt tcctccgctc atacaagtac accatgggcg    660
gtgatgattt ggtacccttc ggagtgaacc agacggtgga ctcggggacc aaattctacc    720
agcgctacga ggcgttggcg aagaaagctg tgcccttcat tcggtcatct gactcagggc    780
gggttgtggc ttcaggcgtg aactttatca agggattcca gcaggcaaag ttggatgata    840
aaaatgccaa tcaccgtcag ccaagcccca aaccaacgt catcatctca gaagagtctg    900
gcaccaacaa cactctgaac cacagcgaga tctgtcctaa gttcgaagac aatgagctgg    960
gcgacaaggt cgaagaaaaa tacatgaaaa tctttgtgcc gcccatccga gctcgtctcg   1020
aggccgatct ccctggcgtt aaacttgaag acatcgatgt tgtcagtctg atggacatct   1080
gccctttcga cagtgtctt tcaagtgacg acgcagccga gctatctcca ttctgcgacc   1140
tcttcacccc gaccgaatgg agccaatatg actacctcca gtcgttaagc aagtactatg   1200
gttatggcgc cggcaatcct ctcggcccga cccagggtgt cggtttcgta acgaactga   1260
ttgcccgact cactcgccac ccagtgagag accacacaag cacaaaccgt gcgctcgatg   1320
cccccggcgc tgcgacattc cccctcaact acaccatgta tgccgacttc acgcatgaca   1380
acggaatgat cccgttcttc tttgctttgg ggctgtacaa cggcaccgct ccactctcgc   1440
tcacccacgt ccagtctcct agccaaacag acgggttctc atccgcctgg acagtcccct   1500
tcggtgctcg ggcttatgtt gagatgatgc aatgtcgtcg ggaacctgag ccgctcgtgc   1560
gagtcctcgt taatgaccgt gttattccgc tgcacggttg cccggtggat aaacttggcc   1620
gttgtcgccg tcgtgatttc gtgaaagggc ttactttcgc acgctctggc ggcgactggg   1680
ccaggtgtta taaatag                                                  1697
```

```
<210> SEQ ID NO 44
<211> LENGTH: 464
<212> TYPE: PRT
<213> ORGANISM: Penicillium chrysogenum

<400> SEQUENCE: 44

Met Ser Leu Leu Gly Thr Phe Ala Leu Val Val Tyr Phe Ala Lys Gly
 1               5                  10                  15

Thr Gln Cys Asn Pro Pro Ser Asp Cys Thr Thr Val Asp Gly Gly
                20                  25                  30

Tyr Gln Cys Asn Ser Glu Leu Ser His Lys Trp Gly Gln Tyr Ser Pro
            35                  40                  45

Tyr Phe Ser Leu Ser Glu Glu Ser Ser Ile Ser Asn Glu Val Pro His
        50                  55                  60

Asp Cys Gln Ile Thr Phe Ala Gln Val Ile Ser Arg His Gly Ala Arg
65                  70                  75                  80

Phe Pro Ser Ala Lys Lys Ser Lys Val Tyr Ala Lys Leu Ile Glu Asn
                85                  90                  95

Ile Gln Ala Asn Ala Thr Ala Tyr Asn Gly Asn Thr Lys Phe Leu Arg
            100                 105                 110
```

```
Ser Tyr Lys Tyr Thr Met Gly Gly Asp Asp Leu Val Pro Phe Gly Val
            115                 120                 125

Asn Gln Thr Val Asp Ser Gly Thr Lys Phe Tyr Gln Arg Tyr Glu Ala
        130                 135                 140

Leu Ala Lys Lys Ala Val Pro Phe Ile Arg Ser Ser Asp Ser Gly Arg
145                 150                 155                 160

Val Val Ala Ser Gly Val Asn Phe Ile Lys Gly Phe Gln Gln Ala Lys
                165                 170                 175

Leu Asp Asp Lys Asn Ala Asn His Arg Gln Pro Ser Pro Lys Thr Asn
            180                 185                 190

Val Ile Ile Ser Glu Glu Ser Gly Thr Asn Asn Thr Leu Asn His Ser
            195                 200                 205

Glu Ile Cys Pro Lys Phe Glu Asp Asn Glu Leu Gly Asp Lys Val Glu
            210                 215                 220

Glu Lys Tyr Met Lys Ile Phe Val Pro Pro Ile Arg Ala Arg Leu Glu
225                 230                 235                 240

Ala Asp Leu Pro Gly Val Lys Leu Glu Asp Ile Asp Val Val Ser Leu
                245                 250                 255

Met Asp Ile Cys Pro Phe Glu Thr Val Ser Ser Ser Asp Asp Ala Ala
            260                 265                 270

Glu Leu Ser Pro Phe Cys Asp Leu Phe Thr Pro Thr Glu Trp Ser Gln
            275                 280                 285

Tyr Asp Tyr Leu Gln Ser Leu Ser Lys Tyr Tyr Gly Tyr Gly Ala Gly
            290                 295                 300

Asn Pro Leu Gly Pro Thr Gln Gly Val Gly Phe Val Asn Glu Leu Ile
305                 310                 315                 320

Ala Arg Leu Thr Arg His Pro Val Arg Asp His Thr Ser Thr Asn Arg
                325                 330                 335

Ala Leu Asp Ala Pro Gly Ala Ala Thr Phe Pro Leu Asn Tyr Thr Met
            340                 345                 350

Tyr Ala Asp Phe Thr His Asp Asn Gly Met Ile Pro Phe Phe Ala
            355                 360                 365

Leu Gly Leu Tyr Asn Gly Thr Ala Pro Leu Ser Leu Thr His Val Gln
            370                 375                 380

Ser Pro Ser Gln Thr Asp Gly Phe Ser Ser Ala Trp Thr Val Pro Phe
385                 390                 395                 400

Gly Ala Arg Ala Tyr Val Glu Met Met Gln Cys Arg Arg Glu Pro Glu
                405                 410                 415

Pro Leu Val Arg Val Leu Val Asn Asp Arg Val Ile Pro Leu His Gly
            420                 425                 430

Cys Pro Val Asp Lys Leu Gly Arg Cys Arg Arg Asp Phe Val Lys
            435                 440                 445

Gly Leu Thr Phe Ala Arg Ser Gly Gly Asp Trp Ala Arg Cys Tyr Lys
            450                 455                 460

<210> SEQ ID NO 45
<211> LENGTH: 2030
<212> TYPE: DNA
<213> ORGANISM: Humicola grisea

<400> SEQUENCE: 45
gccgctagcc atcgtcacaa agaaaacctg cttcggcagc tcccacgtcg tctgcggatt      60
cctcctcccc tatttcccca tcggctcttt acgtgaccac cttctccaac ctgacttcca     120
```

```
caccgccacc gccctgacct tcttcatgtt aggcctcgtc gccgtcactt tcttgtgagt    180
ttgggctccc ttttctgcca tcgctggtga actaaccgtt cggaaggcaa caaccgcacc    240
actcttgcga ctctgtcgac agaggcttct ggtgcgccgc cgacatctcc cactcctggg    300
gacagtactc accatacttc tccgtcccct ctgacattga cccgggtttc cccaagggct    360
gcaatgtgac gttcgcacag gtcctctcac gccacggcgc ccgcgcccca actacgggcc    420
gggccgccta ctacgtcgac gtgattgacc gcgtccagcg tcaggcgacc tcgtacggcc    480
ccggccacgc gttcctgcgc tcctaccgct acaccctcgg cgccaacgag cttaccccga    540
tgggagagcg gcagctggcg tattccggcg caaggtttta ccatcgctat cgcgaacttg    600
cgcgcgtcga ggcgcccttc gtgcggtcca gtggcgtaag ccgcgttgta gcctcagctg    660
tcaatttcac ccagggcttc caccaggcgc ggctcgccga ccgcggcgcc acgttgcccc    720
cgccaacact gccctatgac atggtgatca tctcgtcaga cgacaccgcc aacaacacct    780
tgcaccacgg tctctgcacg tcttcgagg aggggcccta tgccgacatt ggcgacaagg    840
cgcagaaaga ataccctctc aagtttgtcg gtcccatcgt ggagcgcatt aacgcgcagc    900
tgcccggcgc gaatctcaac gcgacggaca tcatcgcgct gatggacctg tgcccgttcg    960
agacggtcgc gttcccagaa ggcacgaagc tgtcgccctt ctgccggctc ttcacggccg   1020
ccgaatggcg ggcctacgac cggtaccagg acgtcggcaa atggttcggc tacggcccgg   1080
gcaatccgct cggcccgact caggggtcg ggttcgtcaa cgagctgatc gcgcggctgt   1140
ccggccagcc ggtgagcgat gggaccagca cgaaccgcac gctggatgag aacccggaga   1200
ccttcccgct cgggaggagg ctgtatgcgg atttcagcca tgataacgac atggtgggca   1260
tcctcagcgc cttggggttg tgggacaacc atgaagaacc tgggaatgaa atgcccgctg   1320
agggggagga ggacgacaat ggtcggttct cgactgctag ggccgtgccg ttcggggcgc   1380
gggtgtatgt cgaaaagctg cggtgtgggg gatcggagga ggatgaagaa atggtgcgcg   1440
tgttggtcaa tgaccgggtg atgccccttg cacagtgcgg aggggacaag aggggaatgt   1500
gcaccctcag ccggttcgtt gaaagcttga gtttgcgcg aacaacggg aggtgggaca   1560
tgtgttttga atgatgagag atgacacagg ctcaggttgg ggaggcgcgt tgtgagtttt   1620
ggagtatgga gtatgcggc aggaattgga tacctgatac cttttggata gagcttttg   1680
cgagggaaa acgcagtggt ttgaatactc ggagattctt tgatgatgta agttgatcga   1740
tttcagttgt gaggtgtagg acataaggat atacagcaag ttcagggtaa gggttcggag   1800
atcgggaagc ttgcccggat ctgcggcttg gcagcggggc tgaagtagcc gttttcagag   1860
gtctgcaacg gccaaagcca cactgggctg cggcgtcacc caacttgatg caacttgttg   1920
gaggttccag gttcccttc gatccgagac cccctccatg ccacgaaatc cctccttctt   1980
cgtttcccag atttcccagg cgcaaacccg tccaracgtg ctcggaattc                2030
```

<210> SEQ ID NO 46
<211> LENGTH: 458
<212> TYPE: PRT
<213> ORGANISM: Humicola grisea

<400> SEQUENCE: 46

Met Leu Gly Leu Val Ala Val Thr Phe Leu Gln Gln Pro His His Ser
1               5                   10                  15

Cys Asp Ser Val Asp Arg Gly Phe Trp Cys Ala Ala Asp Ile Ser His
            20                  25                  30

Ser Trp Gly Gln Tyr Ser Pro Tyr Phe Ser Val Pro Ser Asp Ile Asp

-continued

```
            35                  40                  45
Pro Gly Phe Pro Lys Gly Cys Asn Val Thr Phe Ala Gln Val Leu Ser
        50                  55                  60
Arg His Gly Ala Arg Ala Pro Thr Thr Gly Arg Ala Ala Tyr Tyr Val
 65                  70                  75                  80
Asp Val Ile Asp Arg Val Gln Arg Gln Ala Thr Ser Tyr Gly Pro Gly
                85                  90                  95
His Ala Phe Leu Arg Ser Tyr Arg Tyr Thr Leu Gly Ala Asn Glu Leu
            100                 105                 110
Thr Pro Met Gly Glu Arg Gln Leu Ala Tyr Ser Gly Ala Arg Phe Tyr
            115                 120                 125
His Arg Tyr Arg Glu Leu Ala Arg Val Glu Ala Pro Phe Val Arg Ser
            130                 135                 140
Ser Gly Val Ser Arg Val Val Ala Ser Ala Val Asn Phe Thr Gln Gly
145                 150                 155                 160
Phe His Gln Ala Arg Leu Ala Asp Arg Gly Ala Thr Leu Pro Pro Pro
                165                 170                 175
Thr Leu Pro Tyr Asp Met Val Ile Ile Ser Ser Asp Thr Ala Asn
            180                 185                 190
Asn Thr Leu His His Gly Leu Cys Thr Val Phe Glu Glu Gly Pro Tyr
            195                 200                 205
Ala Asp Ile Gly Asp Lys Ala Gln Lys Glu Tyr Leu Ser Lys Phe Val
            210                 215                 220
Gly Pro Ile Val Glu Arg Ile Asn Ala Gln Leu Pro Gly Ala Asn Leu
225                 230                 235                 240
Asn Ala Thr Asp Ile Ile Ala Leu Met Asp Leu Cys Pro Phe Glu Thr
                245                 250                 255
Val Ala Phe Pro Glu Gly Thr Lys Leu Ser Pro Phe Cys Arg Leu Phe
            260                 265                 270
Thr Ala Ala Glu Trp Arg Ala Tyr Asp Arg Tyr Gln Asp Val Gly Lys
            275                 280                 285
Trp Phe Gly Tyr Gly Pro Gly Asn Pro Leu Gly Pro Thr Gln Gly Val
            290                 295                 300
Gly Phe Val Asn Glu Leu Ile Ala Arg Leu Ser Gly Gln Pro Val Ser
305                 310                 315                 320
Asp Gly Thr Ser Thr Asn Arg Thr Leu Asp Glu Asn Pro Glu Thr Phe
                325                 330                 335
Pro Leu Gly Arg Arg Leu Tyr Ala Asp Phe Ser His Asp Asn Asp Met
            340                 345                 350
Val Gly Ile Leu Ser Ala Leu Gly Leu Trp Asp Asn His Glu Glu Pro
            355                 360                 365
Gly Asn Glu Met Pro Ala Glu Gly Glu Glu Asp Asn Gly Arg Phe
            370                 375                 380
Ser Thr Ala Arg Ala Val Pro Phe Gly Ala Arg Val Tyr Val Glu Lys
385                 390                 395                 400
Leu Arg Cys Gly Gly Ser Glu Glu Asp Glu Glu Met Val Arg Val Leu
                405                 410                 415
Val Asn Asp Arg Val Met Pro Leu Ala Gln Cys Gly Gly Asp Lys Arg
            420                 425                 430
Gly Met Cys Thr Leu Ser Arg Phe Val Glu Ser Leu Lys Phe Ala Arg
            435                 440                 445
Asn Asn Gly Arg Trp Asp Met Cys Phe Glu
            450                 455
```

<210> SEQ ID NO 47
<211> LENGTH: 1146
<212> TYPE: DNA
<213> ORGANISM: Emericella desertorum

<400> SEQUENCE: 47

```
tatccttcgg agtcagaaag caaggcgtat gcgaagttga ttgacgctat caagaagaat      60
gctacttcgt tttcgggaca gtatgctttt ctggagagtt ataattatac tctcggcgcg     120
gaagacttga ctactttttgg tgagaaccag atggtcgact cgggtgccaa gttttaccgg    180
cggtataaga atttggccag gaaaaatact ccattcatac gtgcatcagg gtctgaccgt     240
gtcgttgcgt ccgcggagaa gtttattgac ggacttcgag acgcccagac ccacgaccag     300
ggctccaaac gtgttgcccc agttgtcaat gtggttatcc ctgaaactga tggatttaac     360
aacaccctgg atcatagcac ttgcgtgtct tttgagaatg atgagcgggc ggacgaaatt     420
gaagccaact tcgccgcgat cattggacct ccgattcgca acgtctgga aaacgacctt      480
cctggcgttg agcttacaaa tgagcatgtg aatacttga tggatatgtg ctcgttcgac      540
accatggcgc gcaccgccca tggaaccgag ctgtctccat tctgcgccat cttcactgaa     600
aaggagtggc tgcagtacga ctacctacaa tctctgtcaa agtactacgg ctacggtgcc     660
gggaacccccc ttgcccagc tcagggaatt ggcttcacca acgagctgat tgcccgactg     720
acgcagtcgc ctgtccagga caacacgagc accaaccaca ctctagactc tgacccggcc     780
acgttccccc tcgacaggaa gctctacgcc gacttctccc acgacaataa catgatttct     840
atattcttcg ccatgggcct gtacaacggc acccagccgc tgtccatgga cactgtggag     900
tcgattgagg agatgagatgg ctacgcggcg tcttggactg tcccgtttgg tgcgagggct    960
tactttgagg tgatgcagtg ccaaaaaaag aaggagccac ttgtgcgggt attagtgaat   1020
gatcgcgttg ttcctctcca tggctgtgct gttgacaagc tcggacgatg cactttggac   1080
gattgggtcg agggcttgag ttttgcgagg gccggtggga actggaaggc ttgttttact   1140
gcctaa                                                              1146
```

<210> SEQ ID NO 48
<211> LENGTH: 381
<212> TYPE: PRT
<213> ORGANISM: Emericella desertorum

<400> SEQUENCE: 48

```
Tyr Pro Ser Glu Ser Glu Ser Lys Ala Tyr Ala Lys Leu Ile Asp Ala
1               5                   10                  15

Ile Lys Lys Asn Ala Thr Ser Phe Ser Gly Gln Tyr Ala Phe Leu Glu
            20                  25                  30

Ser Tyr Asn Tyr Thr Leu Gly Ala Glu Asp Leu Thr Thr Phe Gly Glu
        35                  40                  45

Asn Gln Met Val Asp Ser Gly Ala Lys Phe Tyr Arg Arg Tyr Lys Asn
    50                  55                  60

Leu Ala Arg Lys Asn Thr Pro Phe Ile Arg Ala Ser Gly Ser Asp Arg
65                  70                  75                  80

Val Val Ala Ser Ala Glu Lys Phe Ile Asp Gly Leu Arg Asp Ala Gln
                85                  90                  95

Thr His Asp Gln Gly Ser Lys Arg Val Ala Pro Val Val Asn Val Val
            100                 105                 110

Ile Pro Glu Thr Asp Gly Phe Asn Asn Thr Leu Asp His Ser Thr Cys
```

-continued

```
        115                 120                 125

Val Ser Phe Glu Asn Asp Glu Arg Ala Asp Glu Ile Glu Ala Asn Phe
    130                 135                 140

Ala Ala Ile Ile Gly Pro Pro Ile Arg Lys Arg Leu Glu Asn Asp Leu
145                 150                 155                 160

Pro Gly Val Glu Leu Thr Asn Glu His Val Glu Tyr Leu Met Asp Met
                165                 170                 175

Cys Ser Phe Asp Thr Met Ala Arg Thr Ala His Gly Thr Glu Leu Ser
            180                 185                 190

Pro Phe Cys Ala Ile Phe Thr Glu Lys Glu Trp Leu Gln Tyr Asp Tyr
        195                 200                 205

Leu Gln Ser Leu Ser Lys Tyr Tyr Gly Tyr Gly Ala Gly Asn Pro Leu
    210                 215                 220

Gly Pro Ala Gln Gly Ile Gly Phe Thr Asn Glu Leu Ile Ala Arg Leu
225                 230                 235                 240

Thr Gln Ser Pro Val Gln Asp Asn Thr Ser Thr Asn His Thr Leu Asp
                245                 250                 255

Ser Asp Pro Ala Thr Phe Pro Leu Asp Arg Lys Leu Tyr Ala Asp Phe
            260                 265                 270

Ser His Asp Asn Asn Met Ile Ser Ile Phe Phe Ala Met Gly Leu Tyr
        275                 280                 285

Asn Gly Thr Gln Pro Leu Ser Met Asp Thr Val Glu Ser Ile Glu Glu
    290                 295                 300

Met Asp Gly Tyr Ala Ala Ser Trp Thr Val Pro Phe Gly Ala Arg Ala
305                 310                 315                 320

Tyr Phe Glu Val Met Gln Cys Gln Lys Lys Lys Glu Pro Leu Val Arg
                325                 330                 335

Val Leu Val Asn Asp Arg Val Val Pro Leu His Gly Cys Ala Val Asp
            340                 345                 350

Lys Leu Gly Arg Cys Thr Leu Asp Asp Trp Val Glu Gly Leu Ser Phe
        355                 360                 365

Ala Arg Ala Gly Gly Asn Trp Lys Ala Cys Phe Thr Ala
    370                 375                 380
```

<210> SEQ ID NO 49
<211> LENGTH: 1257
<212> TYPE: DNA
<213> ORGANISM: Fusarium javanicum

<400> SEQUENCE: 49

```
cagtactctg catacttccc aatcccgtct gagcttgatg cctcaacacc acacgattgt     60
gatgtgactt ttgcactcgt cttgtcccgc catggagcca ggtacccaac ggacagcaag    120
tctgcagcat acaacgctac cattgcccgc attcaaaagt ctgctaccat gtacggcaag    180
aactacaagt ggcttaagga gtatacctac agtctcggcg ctgaagacct gactgagttt    240
ggccagcggc agatggtcga ctctggtagg gccttttatg agcggtacat gagtctcgct    300
gagaagactg agccttttgt tcgggcatcg ggctcagatc gggtcatcat gtcgtcttac    360
aattttacgc aaggctttta cgcatcgcga ggagagtctg gagacgatta tactcaggat    420
gttcttatca tccctgaaga acctggcatc aacaacacca tgttgcatgg atcgtgcgcc    480
tcattcgaaa gcgacagagt tcctaaagac gcagatgaaa aggccgaggt tgcatgggga    540
gcaagattcc tccccgagat tcgaaatagg ttgaaccacc acctgccagg agtcaacctg    600
acgctggagg aaaccatcta catgatggac atgtgtccgt tcctcgcggc tgacacacct    660
```

-continued

```
gatggcgctg gtcactcgag gttctgcgac ctcttcacca aggcagactg gcgaagttac   720
gactactaca tgactctgag caagttctac aagtttggca atggcaatgc catgggaccg   780
acacaaggtg ttggatatgt caacgaactc atctcacgct tgactgggaa gcctgttgac   840
gaccacacca cgaccaacag cacattggac tcatcgccaa agacgttccc tcttgacagg   900
gctctatatg cggattttag ccacgacaac agcatggtct ccatcttctc agcactgggc   960
ttgtacaact cgactaccct gctaccaaag gaccatattg tgcccgcgat caaggcgcac  1020
ggctactcat cgacatgggt agtccccttt ggagccagaa tgtacgtcga aagctcgag   1080 tgtggtgcca gcaggaatga aaagagagac gagtacgtgc gagtcctggt caacgaccga  1140
gtgatgtcgc tcgaaacctg cggaggcgac gagtacgggc tctgcagact agaaaacttt  1200
gtggagagtc tgtcgtttgc cgcctcggga ggaaactggg atcaatgcgg tggataa     1257
```

<210> SEQ ID NO 50
<211> LENGTH: 418
<212> TYPE: PRT
<213> ORGANISM: Fusarium javanicum

<400> SEQUENCE: 50

```
Gln Tyr Ser Ala Tyr Phe Pro Ile Pro Ser Glu Leu Asp Ala Ser Thr
1               5                   10                  15

Pro His Asp Cys Asp Val Thr Phe Ala Leu Val Leu Ser Arg His Gly
            20                  25                  30

Ala Arg Tyr Pro Thr Asp Ser Lys Ser Ala Ala Tyr Asn Ala Thr Ile
        35                  40                  45

Ala Arg Ile Gln Lys Ser Ala Thr Met Tyr Gly Lys Asn Tyr Lys Trp
    50                  55                  60

Leu Lys Glu Tyr Thr Tyr Ser Leu Gly Ala Glu Asp Leu Thr Glu Phe
65                  70                  75                  80

Gly Gln Arg Gln Met Val Asp Ser Gly Arg Ala Phe Tyr Glu Arg Tyr
                85                  90                  95

Met Ser Leu Ala Glu Lys Thr Glu Pro Phe Val Arg Ala Ser Gly Ser
            100                 105                 110

Asp Arg Val Ile Met Ser Ser Tyr Asn Phe Thr Gln Gly Phe Tyr Ala
        115                 120                 125

Ser Arg Gly Glu Ser Gly Asp Asp Tyr Thr Gln Asp Val Leu Ile Ile
    130                 135                 140

Pro Glu Glu Pro Gly Ile Asn Asn Thr Met Leu His Gly Ser Cys Ala
145                 150                 155                 160

Ser Phe Glu Ser Asp Arg Val Pro Lys Asp Ala Asp Glu Lys Ala Glu
                165                 170                 175

Val Ala Trp Gly Ala Arg Phe Leu Pro Glu Ile Arg Asn Arg Leu Asn
            180                 185                 190

His His Leu Pro Gly Val Asn Leu Thr Leu Glu Glu Thr Ile Tyr Met
        195                 200                 205

Met Asp Met Cys Pro Phe Leu Ala Ala Asp Thr Pro Asp Gly Ala Gly
    210                 215                 220

His Ser Arg Phe Cys Asp Leu Phe Thr Lys Ala Asp Trp Arg Ser Tyr
225                 230                 235                 240

Asp Tyr Tyr Met Thr Leu Ser Lys Phe Tyr Lys Phe Gly Asn Gly Asn
                245                 250                 255

Ala Met Gly Pro Thr Gln Gly Val Gly Tyr Val Asn Glu Leu Ile Ser
            260                 265                 270
```

```
Arg Leu Thr Gly Lys Pro Val Asp Asp His Thr Thr Asn Ser Thr
        275                 280                 285

Leu Asp Ser Ser Pro Lys Thr Phe Pro Leu Asp Arg Ala Leu Tyr Ala
290                 295                 300

Asp Phe Ser His Asp Asn Ser Met Val Ser Ile Phe Ser Ala Leu Gly
305                 310                 315                 320

Leu Tyr Asn Ser Thr Thr Leu Leu Pro Lys Asp His Ile Val Pro Ala
                325                 330                 335

Ile Lys Ala His Gly Tyr Ser Ser Thr Trp Val Val Pro Phe Gly Ala
                340                 345                 350

Arg Met Tyr Val Glu Lys Leu Glu Cys Gly Ala Ser Arg Asn Glu Lys
                355                 360                 365

Arg Asp Glu Tyr Val Arg Val Leu Val Asn Asp Arg Val Met Ser Leu
        370                 375                 380

Glu Thr Cys Gly Gly Asp Glu Tyr Gly Leu Cys Arg Leu Glu Asn Phe
385                 390                 395                 400

Val Glu Ser Leu Ser Phe Ala Ala Ser Gly Gly Asn Trp Asp Gln Cys
                405                 410                 415

Gly Gly

<210> SEQ ID NO 51
<211> LENGTH: 8
<212> TYPE: PRT
<213> ORGANISM: Artificial Sequence
<220> FEATURE:
<223> OTHER INFORMATION: conserved BOX1 sequence
<220> FEATURE:
<221> NAME/KEY: VARIANT
<222> LOCATION: 1
<223> OTHER INFORMATION: Xaa = Val or Leu
<220> FEATURE:
<221> NAME/KEY: VARIANT
<222> LOCATION: 3
<223> OTHER INFORMATION: Xaa = Ala or Ser

<400> SEQUENCE: 51

Xaa Leu Xaa Arg His Gly Ala Arg
 1               5

<210> SEQ ID NO 52
<211> LENGTH: 23
<212> TYPE: DNA
<213> ORGANISM: Artificial Sequence
<220> FEATURE:
<221> NAME/KEY: misc_feature
<222> LOCATION: 3, 6, 9, 12, 18, 21
<223> OTHER INFORMATION: n = inosine
<220> FEATURE:
<223> OTHER INFORMATION: primer

<400> SEQUENCE: 52
btnytnkcnm gncayggnhc nmg                                           23

<210> SEQ ID NO 53
<211> LENGTH: 23
<212> TYPE: DNA
<213> ORGANISM: Artificial Sequence
<220> FEATURE:
<221> NAME/KEY: misc_feature
<222> LOCATION: 3, 6, 12, 18, 21
<223> OTHER INFORMATION: n = inosine
<220> FEATURE:
<223> OTHER INFORMATION: primer

<400> SEQUENCE: 53
```
btnytnagym gncayggnhc nmg 23

```
<210> SEQ ID NO 54
<211> LENGTH: 5
<212> TYPE: PRT
<213> ORGANISM: Artificial Sequence
<220> FEATURE:
<223> OTHER INFORMATION: conserved BOX2 sequence
<220> FEATURE:
<221> NAME/KEY: VARIANT
<222> LOCATION: 5
<223> OTHER INFORMATION: Xaa = Asp, Glu or His

<400> SEQUENCE: 54
```

Asn Asn Thr Leu Xaa
 1               5

```
<210> SEQ ID NO 55
<211> LENGTH: 14
<212> TYPE: DNA
<213> ORGANISM: Artificial Sequence
<220> FEATURE:
<221> NAME/KEY: misc_feature
<222> LOCATION: 9, 12
<223> OTHER INFORMATION: n = inosine
<220> FEATURE:
<223> OTHER INFORMATION: primer

<400> SEQUENCE: 55
```
aayaayacny tnsa 14

```
<210> SEQ ID NO 56
<211> LENGTH: 14
<212> TYPE: DNA
<213> ORGANISM: Artificial Sequence
<220> FEATURE:
<221> NAME/KEY: misc_feature
<222> LOCATION: 3, 6
<223> OTHER INFORMATION: n = inosine
<220> FEATURE:
<223> OTHER INFORMATION: primer

<400> SEQUENCE: 56
```
tsnarngtrt trtt 14

```
<210> SEQ ID NO 57
<211> LENGTH: 5
<212> TYPE: PRT
<213> ORGANISM: Artificial Sequence
<220> FEATURE:
<223> OTHER INFORMATION: conserved BOX3 sequence

<400> SEQUENCE: 57
```

Leu Ser Pro Phe Cys
 1               5

```
<210> SEQ ID NO 58
<211> LENGTH: 15
<212> TYPE: DNA
<213> ORGANISM: Artificial Sequence
<220> FEATURE:
<221> NAME/KEY: misc_feature
<222> LOCATION: 6, 9
<223> OTHER INFORMATION: n = inosine
<220> FEATURE:
<223> OTHER INFORMATION: primer

<400> SEQUENCE: 58
```
ytttcnccnt tytgy 15

```
<210> SEQ ID NO 59
<211> LENGTH: 15
<212> TYPE: DNA
<213> ORGANISM: Artificial Sequence
<220> FEATURE:
<221> NAME/KEY: misc_feature
<222> LOCATION: 3, 9
<223> OTHER INFORMATION: n = inosine
<220> FEATURE:
<223> OTHER INFORMATION: primer

<400> SEQUENCE: 59
ytnagyccnt tytgy                                                    15

<210> SEQ ID NO 60
<211> LENGTH: 15
<212> TYPE: DNA
<213> ORGANISM: Artificial Sequence
<220> FEATURE:
<221> NAME/KEY: misc_feature
<222> LOCATION: 7, 10, 13
<223> OTHER INFORMATION: n = inosine
<220> FEATURE:
<223> OTHER INFORMATION: primer

<400> SEQUENCE: 60
rcaraanggn ganar                                                    15

<210> SEQ ID NO 61
<211> LENGTH: 15
<212> TYPE: DNA
<213> ORGANISM: Artificial Sequence
<220> FEATURE:
<221> NAME/KEY: misc_feature
<222> LOCATION: 7, 13
<223> OTHER INFORMATION: n = inosine
<220> FEATURE:
<223> OTHER INFORMATION: primer

<400> SEQUENCE: 61
rcaraanggr ctnar                                                    15

<210> SEQ ID NO 62
<211> LENGTH: 6
<212> TYPE: PRT
<213> ORGANISM: Artificial Sequence
<220> FEATURE:
<223> OTHER INFORMATION: conserved BOX4 sequence
<220> FEATURE:
<221> NAME/KEY: VARIANT
<222> LOCATION: 2
<223> OTHER INFORMATION: Xaa = Asn or Ser

<400> SEQUENCE: 62

Gly Xaa Pro Leu Gly Pro
 1               5

<210> SEQ ID NO 63
<211> LENGTH: 17
<212> TYPE: DNA
<213> ORGANISM: Artificial Sequence
<220> FEATURE:
<221> NAME/KEY: misc_feature
<222> LOCATION: 3, 6, 9, 12, 15
<223> OTHER INFORMATION: n = inosine
<220> FEATURE:
<223> OTHER INFORMATION: primer

<400> SEQUENCE: 63
```

```
ggnwvnccny tnggncc                                                    17
```

<210> SEQ ID NO 64
<211> LENGTH: 14
<212> TYPE: DNA
<213> ORGANISM: Artificial Sequence
<220> FEATURE:
<221> NAME/KEY: misc_feature
<222> LOCATION: 3, 6, 9, 12
<223> OTHER INFORMATION: n = inosine
<220> FEATURE:
<223> OTHER INFORMATION: primer

<400> SEQUENCE: 64

```
ccnarnggnb wncc                                                       14
```

<210> SEQ ID NO 65
<211> LENGTH: 5
<212> TYPE: PRT
<213> ORGANISM: Artificial Sequence
<220> FEATURE:
<223> OTHER INFORMATION: conserved BOX5 sequence

<400> SEQUENCE: 65

Asp Phe Ser His Asp
 1               5

<210> SEQ ID NO 66
<211> LENGTH: 15
<212> TYPE: DNA
<213> ORGANISM: Artificial Sequence
<220> FEATURE:
<221> NAME/KEY: misc_feature
<222> LOCATION: 9
<223> OTHER INFORMATION: n = inosine
<220> FEATURE:
<223> OTHER INFORMATION: primer

<400> SEQUENCE: 66

```
gayttytcnc aygay                                                      15
```

<210> SEQ ID NO 67
<211> LENGTH: 15
<212> TYPE: DNA
<213> ORGANISM: Artificial Sequence
<220> FEATURE:
<223> OTHER INFORMATION: primer

<400> SEQUENCE: 67

```
gayttyagyc aygay                                                      15
```

<210> SEQ ID NO 68
<211> LENGTH: 15
<212> TYPE: DNA
<213> ORGANISM: Artificial Sequence
<220> FEATURE:
<221> NAME/KEY: misc_feature
<222> LOCATION: 7
<223> OTHER INFORMATION: n = inosine
<220> FEATURE:
<223> OTHER INFORMATION: primer

<400> SEQUENCE: 68

```
rtcrtgngar aartc                                                      15
```

<210> SEQ ID NO 69
<211> LENGTH: 15
<212> TYPE: DNA

-continued

<213> ORGANISM: Artificial Sequence
<220> FEATURE:
<223> OTHER INFORMATION: primer

<400> SEQUENCE: 69
rtcrtgrctr aartc                                                         15

<210> SEQ ID NO 70
<211> LENGTH: 8
<212> TYPE: PRT
<213> ORGANISM: Artificial Sequence
<220> FEATURE:
<223> OTHER INFORMATION: conserved BOX6 sequence
<220> FEATURE:
<221> NAME/KEY: VARIANT
<222> LOCATION: 3
<223> OTHER INFORMATION: Xaa = Ala or Val
<220> FEATURE:
<221> NAME/KEY: VARIANT
<222> LOCATION: 5
<223> OTHER INFORMATION: Xaa = Ile or Val

<400> SEQUENCE: 70

Val Arg Xaa Ile Xaa Asn Asp Arg
 1               5

<210> SEQ ID NO 71
<211> LENGTH: 23
<212> TYPE: DNA
<213> ORGANISM: Artificial Sequence
<220> FEATURE:
<221> NAME/KEY: misc_feature
<222> LOCATION: 9, 12, 15, 18, 21
<223> OTHER INFORMATION: n = inosine
<220> FEATURE:
<223> OTHER INFORMATION: primer

<400> SEQUENCE: 71
ckrtcrttna ynarnrcnck nac                                                23

<210> SEQ ID NO 72
<211> LENGTH: 7
<212> TYPE: PRT
<213> ORGANISM: Artificial Sequence
<220> FEATURE:
<223> OTHER INFORMATION: conserved BOX2.5 sequence

<400> SEQUENCE: 72

Met Asp Met Cys Ser Phe Asp
 1               5

<210> SEQ ID NO 73
<211> LENGTH: 20
<212> TYPE: DNA
<213> ORGANISM: Artificial Sequence
<220> FEATURE:
<221> NAME/KEY: misc_feature
<222> LOCATION: 15
<223> OTHER INFORMATION: n = A,T,C or G
<220> FEATURE:
<223> OTHER INFORMATION: primer

<400> SEQUENCE: 73
atggayatgt gytcnttyga                                                    20

<210> SEQ ID NO 74
<211> LENGTH: 6
<212> TYPE: PRT
<213> ORGANISM: Artificial Sequence

```
<220> FEATURE:
<223> OTHER INFORMATION: conserved BOX4' sequence

<400> SEQUENCE: 74

Tyr Gly His Gly Ala Gly
 1               5

<210> SEQ ID NO 75
<211> LENGTH: 20
<212> TYPE: DNA
<213> ORGANISM: Artificial Sequence
<220> FEATURE:
<221> NAME/KEY: misc_feature
<222> LOCATION: 15
<223> OTHER INFORMATION: n = A,T,C or G
<220> FEATURE:
<223> OTHER INFORMATION: primer

<400> SEQUENCE: 75
ttrccrgcrc crtgnccrta                                              20

<210> SEQ ID NO 76
<211> LENGTH: 7
<212> TYPE: PRT
<213> ORGANISM: Aspergillus niger

<400> SEQUENCE: 76

Arg His Gly Ala Arg Tyr Pro
 1               5

<210> SEQ ID NO 77
<211> LENGTH: 7
<212> TYPE: PRT
<213> ORGANISM: Aspergillus niger

<400> SEQUENCE: 77

Arg His Gly Glu Arg Tyr Pro
 1               5

<210> SEQ ID NO 78
<211> LENGTH: 8
<212> TYPE: PRT
<213> ORGANISM: Aspergillus niger

<400> SEQUENCE: 78

Arg His Gly Ala Arg Tyr Pro Thr
 1               5

<210> SEQ ID NO 79
<211> LENGTH: 7
<212> TYPE: PRT
<213> ORGANISM: Aspergillus niger

<400> SEQUENCE: 79

Phe Thr His Asp Glu Trp Ile
 1               5

<210> SEQ ID NO 80
<211> LENGTH: 7
<212> TYPE: PRT
<213> ORGANISM: Aspergillus niger

<400> SEQUENCE: 80

Phe Thr Gln Asp Glu Trp Val
 1               5
```

PHYTASE ENZYMES, NUCLEIC ACID SEQUENCES ENCODING PHYTASE ENZYMES AND VECTORS AND HOST CELLS INCORPORATING SAME

The present application is a divisional application of U.S. patent application Ser. No. 10/492,782, filed on Apr. 14, 2004 (now U.S. Pat. No. 7,220,445), which is a 371 of PCT/US02/34256, filed on Oct. 25, 2002, which claims priority to U.S. Provisional Patent Application Ser. No. 60/339,552, filed on October 26, 2001.

FIELD OF THE INVENTION

The present invention relates to phytase, nucleic acid sequences encoding phytase, as well as is the production of phytase and its use.

REFERENCES

Al-Batshan et al., Poultry Science 73(10):1590-1596 (1994).

Altschul, S. F., Gish, W., Miller, W., Myers, E. W. & Lipman, D. J. (1990) "Basic local alignment search tool." J. Mol. Biol. 215:403-410.

Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402.

Aplin and Wriston, Crit. Rev. Biochem., pp. 259-306 (1981).

ASC Symposium Series 580, "Carbohydrate Modifications in Antisense Research", Chapters 2, 3, 6 and 7, Ed. Y. S. Sanghui and P. Dan Cook.

Ausubel et al. (eds.) (1995) Current Protocols In Molecular Biology, 3rd edition, John Wiley & Sons, Inc.

Baker et al., U.S. Pat. No. 5,571,706 (1996).

Beaucage et al. (1993) Tetrahedron 49(10):1925.

Benner, Steven A., U.S. Pat. No. 5,216,141 (1993).

Bennett & Lasure, More Gene Manipulations in Fungi, Academic Press, San Diego, pp. 70-76 (1991).

Benton, W. and Davis, R., 1977, Science 196:180.

Berger and Kimmel, (1987), Guide to Molecular Cloning Techniques, Methods in Enzymology, Vol. 152, Academic Press, San Diego Calif.

Birnboim, H. C. and Doly, J. (1979). Nucleic Acids Research 7: 1513-23.

Botstein, D. and Shortle, D. (1985) Science 229:1193-1201.

Bowen et al., U.S. Pat. No. 5,736,369 (1998).

Bremel et al., U.S. Pat. No. 6,291,740 (2001).

Bremel et al., U.S. Pat. No. 6,080,912 (2000).

Brisson et al. (1984) Nature 310:511-514.

Briu et al. (1989) J. Am. Chem. Soc. 111:2321.

Broglie et al. (1984) Science 224:838-843).

Cadwell, R. C. and Joyce, G. F., 1992, PCR Methods Applic. 2: 28-33.

Canadian Journal of Animal Science 75(3):439-444 (1995).

Committee on Food Chemicals Codex, Institute of Medicine, Food Chemicals Codex, 4th Edition, National Academy Press, Washington, D.C., 1996.

Carlsson et al., Nature 380:207 (1996).

Clark, H. Fred, U.S. Pat. No. 5,610,049 (1997).

Conklin et al., U.S. Pat. No. 5,750,386 (1998).

Cook et al., U.S. Pat. No. 5,637,684 (1997).

Coruzzi et al. (1984) EMBO J. 3:1671-1680.

Creighton, T. E., Proteins: Structure and Molecular Properties, W.H. Freeman & Co., San Francisco, pp. 79-86 (1983)

Cromwell, G. L. T., T. S. Stahly, R. D. Coffey, H. J. Monegue, and J. H. Randolph. 1993. Efficacy of phytase in improving bioavailability of phosphorus in soybean and corn-soybean meal diets for pigs. J. Anim. Sci. 71:1831.

Damron et al., Poultry Science 74(5):784-787 (1995).

Dayhoff, M. O., Schwartz, R. M. & Orcutt, B. C. (1978) "A model of evolutionary change in proteins." In "Atlas of Protein Sequence and Structure, vol. 5, suppl. 3." M. O. Dayhoff (ed.), pp. 345-352, Natl. Biomed. Res. Found., Washington, D.C. Deutscher, Methods in Enzymology, 182 (1990).

DeBoer et al., U.S. Pat. No. 6,066,725 (2000).

De Clercq et al., U.S. Pat. No. 5,589,615 (1996).

De Mesmaeker et al., U.S. Pat. No. 5,602,240 (1997).

De Mesmaeker et al., Bioorganic & Medicinal Chem. Lett. 4:395 (1994).

Denpcy et al., Proc. Natl. Acad. Sci. USA 92:6097 (1995).

Devlin, Robert H., U.S. Pat. No. 5,998,697 (1999).

Dieffenbach C W and Dveksler G S, 1995, PCR Primer, a Laboratory Manual, Cold Spring Harbor Press, Plainview N.Y.

Eckert, K. A. and Kunkel, T. A., 1991, PCR Methods Applic. 1: 17-24.

Eckstein, Oligonucleotides and Analogues: A Practical Approach, Oxford University Press.

Edge et al., Anal. Biochem., 118:131 (1981).

Egholm (1992) J. Am. Chem. Soc. 114:1895.

Ehrlich, K. C., Montalbano, B. G., Mullaney, E. J., Dischinger Jnr., H. C. & Ullah, A. H. J. (1993). Identification and cloning of a second phytase gene (phy B) from Aspergillus niger (ficum). Biochemical and Biophysical Research Communications 195, 53-57.

Elander, R. P., Microbial screening, Selection and Strain Improvement, in Basic Biotechnology, J. Bullock and B. Kristiansen Eds., Academic Press, New York, 1987, 217.

Evan et al., Molecular and Cellular Biology, 5:3610-3616 (1985).

Field et al., Mol. Cell. Biol., 8:2159-2165 (1988).

Finkelstein, D B 1992 Transformation. In Biotechnology of Filamentous Fungi. Technology and Products (eds by Finkelstein & Bill) 113-156.

Fiske, C. H. and SubbaRow, Y. (1925). Journal of Biological Chemistry 66:375-392.

Fungaro et al. (1995) Transformation of Aspergillus nidulans by microprojection bombardment on intact conidia, FEMS Microbiology Letters 125 293-298.

Gelvin et al., J. Bacteriol. 172(3):1600-1608 (1990).

Gish, W. & States, D. J. (1993) "Identification of protein coding regions by database similarity search." Nature Genet. 3:266-272.

Glover, D M and Hames, B D (Eds.), DNA Cloning: A Practical Approach, Vols 1 and 2, Second Edition.

Glover, D M and Hames, B D (Eds.), 1995, DNA Cloning 1: A Practical Approach, Oxford University Press, Oxford).

Glover, D M and Hames, B D (Eds.), 1995, DNA Cloning 2: A Practical Approach, Oxford University Press, Oxford).

Groot et al. (1998) Agrobacterium tumefaciens-mediated transformation of filamentous fungi, Nature Biotechnology 16 839-842.

Grunstein, M. and Hogness, D., 1975, Proc. Natl. Acad. Sci. USA 72:3961.

Hakimuddin, et al., Arch. Biochem. Biophys., 259:52 (1987).

Hale & Marham, THE HARPER COLLINS DICTIONARY OF BIOLOGY, Harper Perennial, N.Y. (1991).

Henikoff & Henikoff, Proc. Natl. Acad. Sci. USA 89:10915 (1989).

Hershey et al., U.S. Pat. No. 5,268,526 (1993).

Higgins D. G., Bleasby A. J., Fuchs R. (1992) CLUSTAL V: improved software for multiple sequence alignment. Comput. Appl. Biosci. 8:189-191.

Hobbs S or Murry L E (1992) in McGraw Hill Yearbook of Science and Technology, McGraw Hill, New York, N.Y., pp 191-196.

Hodges et al., U.S. Pat. No. 5,677,175 (1997).

Hopp et al., BioTechnology, 6:1204-1210 (1988).

Houdebine et al., U.S. Pat. No. 6,268,545 (2001).

Jaynes et al., U.S. Pat. No. 5,597,945 (1997).

Jeffs et al., J. Biomolecular NMR 34:17 (1994).

Jenkins et al., Chem. Soc. Rev. (1995) pp 169-176.

Jeroch et al., Bodenkultur Vo. 45(4):361-368 (1994).

Karatzas et al., U.S. Pat. No. 5,907,080 (1999).

Karlin & Altschul, Proc. Nat'l. Acad. Sci. USA 90:5873-5787 (1993).

Kerovuo, J., Lauraeus, M., Nurminen, P., Kalkkinen, N., Apajalahti, J. (1988) Isolation, characterization and molecular gene cloning, and sequencing of a novel phytase from *Bacillus subtilis*. Appl. Environ. Micro., 64, 6, 2079-2085.

Kiedrowski et al., Angew. Chem. Intl. Ed. English 30:423 (1991).

Kornegay, E. T., D. M. Denbow, Z. Yi., and V. Ravindran. 1996. Response of broilers to graded levels of Natuphosa phytase added to corn-soybean meal-based diets containing three levels of nonphytate phosphorus. Br. J. Nutr.

Lebrun et al., U.S. Pat. No. 5,510,471 (1996).

Letsinger, J. Org. Chem. 35:3800 (1970).

Letsinger et al., Nucleoside & Nucleotide 13:1597 (1994).

Letsinger et al. (1988) J. Am. Chem. Soc. 110:4470.

Letsinger et al. (1986) Nucl. Acids Res. 14:3487.

Leung, D. W., Chen, E., and Goeddel, D. V., 1989, Technique 1: 11-15.

Lubon et al., U.S. Pat. No. 6,262,336 (2001).

Lundquist et al., U.S. Pat. No. 5,780,708 (1998).

Lundquist et al., U.S. Pat. No. 5,538,880 (1996); Lutz-Freyermuth et al., Proc. Natl. Acad. Sci. USA, 87:6393-6397 (1990).

Madden, T. L., Tatusov, R. L. & Zhang, J. (1996) "Applications of network BLAST server" Meth. Enzymol. 266:131-141.

Mag et al. (1991) Nucleic Acids Res. 19:1437.

Martin et al., Science, 255:192-194 (1992).

Meier et al. (1992) Chem. Int. Ed. Engl. 31:1008.

The Merck Veterinary Manual (Seventh Edition, Merck & Co., Inc., Rahway, N.J., USA, 1991, page 1268).

Myers, R. M., Lerman, L. S., and Maniatis, T., 1985, Science 229: 242-247.

Mitchell, D. B., Vogel, K., Weimann, B. J., Pasamontes, L. and van Loon, A. P., Microbiology 143 (Pt 1), 245-252 (1997)).

Moloney et al., U.S. Pat. No. 5,750,871(1998).

Mullis, Kary B., U.S. Pat. No. 4,683,202 (1990).

Needleman & Wunsch, J. Mol. Biol. 48:443 (1970).

Nielsen (1993) Nature, 365:566.

Oakley et al., Gene 61(3): 385-99 (1987).

Paborsky et al., Protein Engineering, 3(6):547-553 (1990).

Pasamontes, L., Haiker, M., Henriquez-Huecas, M., Mitchell, D. B. and van Loon, A. P., Cloning of the phytases from *Emericella nidulans* and the thermophilic fungus *Talaromyces thermophilus*, Biochim. Biophys. Acta 1353 (3), 217-223 (1997).

Pasamontes, L., Haiker, M., Wyss, M., Tessier, M. and van Loon, A. P., Gene cloning, purification, and characterization of a heat-stable phytase from the fungus *Aspergillus fumigatus*, Appl. Environ. Microbiol. 63 (5), 1696-1700 (1997).

Pauwels et al. (1986) Chemica Scripta 26:141.

Pearson & Lipman, Proc. Nat'l. Acad. Sci. USA 85:2444 (1988).

Piedrahita et al., U.S. Pat. No. 6,271,436 (2001).

Piddington, C. S., Houston, C. S., Paloheimo, M., Cantrell, M., Miettinen-Oinonen, A., Nevalainen, H. & Rambosek, J. (1993). The cloning and sequencing of the genes encoding phytase (PhyA) and pH 2,5-optimum acid phosphatase (aph) from *Aspergillus niger* var. *awamori*. Gene 133, 55-62.

Powar, V. K. and Jagannathan V., (1982) J. Bacteriology, 151 (3), 1102-1108.

Rawls, C & E News Jun. 2, 1997 page 35.

Roland et al., Poultry Science, 75(1):62-68 (1996).

Sambrook, J., Fritsch, E. F. and Maniatis, T. (1989). Molecular Cloning—A Laboratory Manual, $2^{nd}$ Ed. Cold Spring Harbour Press.

Sambrook et al. (2001). Molecular Cloning, A Laboratory Manual, 3d Ed., Cold Spring Harbor Laboratory Press, Cold Spring Harbor, N.Y.

Sanchez, O. and J. Aguirre. 1996. Efficient transformation of *Aspergillus nidulans* by electroporation of germinated conidia. Fungal Genetics Newsletter 43: 48-51.

Sanger, F., Nilken, S, and Coulson, A. R. (1977). Proc. Nat'l. Acad. Sci. USA, 74: 5463-5467.

Sanghvi et al. U.S. Pat. No. 5,386,023 (1995)

Sawai et al. (1984) Chem. Lett. 805.

Schwartz, R. M. & Dayhoff, M. O. (1978) "Matrices for detecting distant relationships." In "Atlas of Protein Sequence and Structure, vol. 5, suppl. 3." M. O. Dayhoff (ed.), pp. 353-358, Natl. Biomed. Res. Found., Washington, D.C.

Scopes, Protein Purification: Principles and Practice, Springer-Verlag, New York (1982).

Shimizu, M., (1992) Biosci. Biotech. Biochem., 56 (8), 1266-1269.

Shimizu, M., Japanese Patent Application 6-38745 (1994).

Singleton, et al., DICTIONARY OF MICROBIOLOGY AND MOLECULAR BIOLOGY, 2D ED., John Wiley and Sons, New York (1994).

Skinner et al., J. Biol. Chem., 266:15163-15166 (1991).

Smith & Waterman, Adv. Appl. Math. 2:482 (1981).

Somers et al., U.S. Pat. No. 5,773,269 (1998).

Sprinzl et al. (1977) Eur. J. Biochem. 81:579.

Summerton et al., U.S. Pat. No. 5,235,033 (1993).

Summerton et al., U.S. Pat. No. 5,034,506 (1991).

Takamatsu et al. (1987) EMBO J. 6:307-311

Thotakura et al., Meth. Enzymol., 138:350 (1987).

T'so et al., U.S. Pat. No. 4,469,863 (1984).

Ullah, H. J. and Gibson, D. M., Preparative Biochemistry, 17 (1) (1987), 63-91.

van Gorcom, Robert Franciscus Maria; van Hartingsveldt, Willem; van Paridon, Peter Andreas; Veenstra, Annemarie Eveline; Luiten, Rudolf Gijsbertus Marie; Selten, Gerardus Cornelis Maria; EP 420 358 (1991).

van Hartingsveldt, W., van Zeijl, C. M. J., Harteveld, G. M., Gouka, R. J., Suykerbuyk, M. E. G., Luiten, R. G. M., van Paridon, P. A., Selten, C. G. M., Veenstra, A. E., van Gorcom, R. F. M. & van den Hondel, C. A. J. J. (1993). Cloning, characterization and over expression of the phytase-encoding gene (PhyA) of *Aspergillus niger*. Gene 127:87-94.

Van Loon, A. and Mitchell, D.; EP 684 313 (1995).

Weber, K. L. et al., *Biotechniques* 25(3): 415-9 (1998).

Weidner, G., d'Enfert, C., Koch, A., Mol, P., and Brakhage, A. A. (1998) Development of a homologous transformation system for the human pathogenic fungus *Aspergillus furnigatus* based on the pyrG gene encoding orotidine monophosphate decarboxylase. Current Genet. 33: 378-385.

Weissbach and Weissbach (1988) Methods for Plant Molecular Biology, Academic Press, New York, N.Y., pp 421-463.

Wheeler, Mathew B., U.S. Pat. No. 5,942,435 (1999).

Winter J and Sinibaldi R M (1991) Results Probl Cell Differ 17:85-105.

Yau, Eric K., U.S. Pat. No. 5,644,048 (1997).

Yamada et al., Agr. Biol. Chem., 32 (10) (1968), 1275-1282.

BACKGROUND OF THE INVENTION

Phosphorous (P) is an essential element for growth. A substantial amount of the phosphorous found in conventional livestock feed, e.g., cereal grains, oil seed meal, and by products that originate from seeds, is in the form of phosphate which is covalently bound in a molecule know as phytate (myo-inositol hexakisphosphate). The bioavailability of phosphorus in this form is generally quite low for non-ruminants, such as poultry and swine, because they lack digestive enzymes for separating phosphorus from the phytate molecule.

Several important consequences of the inability of non-ruminants to utilize phytate may be noted. For example, expense is incurred when inorganic phosphorus (e.g., dicalcium phosphate, defluorinated phosphate) or animal products (e.g., meat and bone meal, fish meal) are added to meet the animals' nutritional requirements for phosphorus. Additionally, phytate can bind or chelate a number of minerals (e.g., calcium, zinc, iron, magnesium, copper) in the gastrointestinal tract, thereby rendering them unavailable for absorption. Furthermore, most of the phytate present in feed passes through the gastrointestinal tract, elevating the amount of phosphorous in the manure. This leads to an increased ecological phosphorous burden on the environment.

Ruminants, such as cattle, in contrast, readily utilize phytate thanks to an enzyme produced by rumen microorganisms known as phytase. Phytase catalyzes the hydrolysis of phytate to (1) myo-inositol and/or (2) mono-, di-, tri-, tetra- and/or penta-phosphates thereof and (3) inorganic phosphate. Two different types of phytases are known: (1) a so-called 3-phytase (myo-inositol hexaphosphate 3-phosphohydrolase, EC 3.1.3.8) and (2) a so-called 6-phytase (myo-inositol hexaphosphate 6-phosphohydrolase, EC 3.1.3.26). The 3-phytase preferentially hydrolyzes first the ester bond at the 3-position, whereas the 6-phytase preferentially hydrolyzes first the ester bond at the 6-position.

Microbial phytase, as a feed additive, has been found to improve the bioavailability of phytate phosphorous in typical non-ruminant diets (See, e.g., Cromwell, et al., 1993). The result is a decreased need to add inorganic phosphorous to animal feeds, as well as lower phosphorous levels in the excreted manure (See, e.g., Kornegay, et al., 1996).

Despite such advantages, few of the known phytases have gained widespread acceptance in the feed industry. The reasons for this vary from enzyme to enzyme. Typical concerns relate to high is manufacture costs and/or poor stability/activity of the enzyme in the environment of the desired application (e.g., the pH/temperature encountered in the processing of feedstuffs, or in the digestive tracts of animals).

It is, thus, generally desirable to discover and develop novel enzymes having good stability and phytase activity for use in connection with animal feed, and to apply advancements in fermentation technology to the production of such enzymes in order to make them commercially viable. It is also desirable to ascertain nucleotide sequences which can be used to produce more efficient genetically engineered organisms capable of expressing such phytases in quantities suitable for industrial production. It is still further desirable to develop a phytase expression system via genetic engineering which will enable the purification and utilization of working quantities of relatively pure enzyme.

SUMMARY OF THE INVENTION

The present invention provides for a purified enzyme having phytase activity which is derived from a microbial source, and preferably from a fungal source, such as, a *Penicillium* species, e.g., *P. chrysogenum* (deposit no. NRRL 1951), a *Fusarium* species, e.g. *F. javanicum* (deposit no. CBS 203.32) or *F. vertisillibodes*, a *Humicola* species, e.g., *H. grisea* (deposit no. ATCC 22081 or CBS 225.63), or an *Emericella* species, e.g., *E. desertorum* (deposit no. CBS 653.73).

The present invention further provides a polynucleotide sequence coding for the enzyme comprising a DNA as shown in FIG. 1(SEQ ID NO:1) or FIGS. 19A-19C (SEQ ID NO:43); a polynucleotide which encodes the amino acid sequence shown in FIG. 2 (SEQ ID NO:2), 3 (SEQ ID NO:3) or 19A-19C (SEQ ID NO:44); a polynucleotide which encodes a phytase which comprises an amino acid segment which differs from the sequence in FIG. 2 (SEQ ID NO:2) or FIG. 3 (SEQ ID NO:3) or FIGS. 19A-19C (SEQ ID NO:44), provided that the polynucleotide encodes a derivative of the phytase specifically described herein; and a polynucleotide which encodes a phytase that comprises an amino acid sequence which differs from the sequence in FIG. 2 (SEQ ID NO:2) or FIG. 3 (SEQ ID NO:3) or FIGS. 19A-19C (SEQ ID NO:44), provided that the polynucleotide hybridizes under medium to high stringency conditions with a nucleic acid sequence comprising all or part of the nucleic acid sequence in FIG. 1 (SEQ ID NO:1) or FIGS. 19A-19C (SEQ ID NO:43).

The present invention also provides a polynucleotide encoding an enzyme having phytate hydrolyzing activity and including a nucleotide sequence as shown in FIG. 4, 7, 18A-18C or 21 (SEQ ID NO:4, 7, 41 and 7, respectively); a polynucleotide which encodes the amino acid sequence shown in FIG. 5, 6, 8, 18A-18C or 21 (SEQ ID NO:5, 6, 8, 42, and 8, respectively); a polynucleotide which encodes a phytase which comprises an amino acid segment which differs from the sequence in FIG. 5, 6, 8, 18A-18C or 21 (SEQ ID NO:5, 6, 8, 42, and 8, respectively), provided that the polynucleotide encodes a derivative of the phytase specifically described herein; and a polynucleotide which encodes a phytase that comprises an amino acid segment which differs from the sequence in FIG. 5, 6, 8, 18A-18C or 21 (SEQ ID NO:5, 6, 8, 42, and 8, respectively), provided that the polynucleotide hybridizes under medium to high stringency conditions with a nucleotide sequence as shown in FIG. 4, 7, 18A-18C or 21 (SEQ ID NO:4, 7,41 and 7, respectively).

The present invention further provides a polynucleotide encoding an enzyme having phytate hydrolyzing activity and including a nucleotide sequence as shown in FIG. 9 or FIGS. 20A-20C (SEQ ID NO:9 or 45, respectively); a polynucleotide which encodes the amino acid sequence shown in FIG. 10, 11, or 20A-20B (SEQ ID NO:10, 11, and 46, respectively); a polynucleotide which encodes a phytase which comprises an amino acid segment which differs from the sequence in FIG. 10, 11, or 20A-20B (SEQ ID NO:10, 11, and 46, respectively), provided that the polynucleotide encodes a derivative of the phytase specifically described herein; and a polynucleotide which encodes a phytase that comprises an amino acid segment which differs from the sequence in FIG.

10, 11, or 20A-20B (SEQ ID NO:10, 11, and 46, respectively), provided that the polynucleotide hybridizes under medium to high stringency conditions with a nucleotide sequence as shown in FIG. 9 or FIGS. 20A-20C (SEQ ID NO:9 or 45, respectively).

The present invention further provides a polynucleotide encoding an enzyme having phytate hydrolyzing activity and including a nucleotide sequence as shown in FIG. 17A (SEQ ID NO:39); a polynucleotide which encodes the amino acid sequence shown in FIG. 17B (SEQ ID NO:40); a polynucleotide which encodes a phytase which comprises an amino acid segment which differs from the sequence in FIG. 17B (SEQ ID NO:40), provided that the polynucleotide encodes a derivative of the phytase specifically described herein; and a polynucleotide which encodes a phytase that comprises an amino acid segment which differs from the sequence in FIG. 17B (SEQ ID NO:40), provided that the polynucleotide hybridizes under medium to high stringency conditions with a nucleotide sequence as shown in FIG. 17A (SEQ ID NO:39).

Additionally, the present invention encompasses vectors which include the polynucleotide sequences described above, host cells which have been transformed with such polynucleotides or vectors, fermentation broths comprising such host cells and phytase proteins encoded by such polynucleotides which are expressed by the host cells. Preferably, the polynucleotide of the invention is in purified or isolated form and is used to prepare a transformed host cell capable of producing the encoded protein product thereof. Additionally, polypeptides which are the expression product of the polynucleotide sequences described above are within the scope of the present invention.

In one embodiment, the present invention provides an isolated or purified polynucleotide derived from a fungal source of the genus *Penicillium*, which polynucleotide comprises a nucleotide is sequence encoding an enzyme having phytase activity. The fungal source can be, for example, from *Penicillium chrysogenum*. In another embodiment, the invention provides an isolated or purified polynucleotide derived from a fungal source of the genus *Fusarium*, which polynucleotide comprises a nucleotide sequence encoding an enzyme having phytase activity. The fungal source can be selected, for example, from the group consisting of *Fusarium javanicum* and *Fusarium vertisillibodes*. In yet another embodiment, the present invention provides an isolated or purified polynucleotide derived from a fungal source of the genus *Humicola*, which polynucleotide comprises a nucleotide sequence encoding an enzyme having phytase activity. The fungal source can be, for example, from *Humicola grisea*. In still another embodiment, the present invention provides an isolated or purified polynucleotide derived from a fungal source of the genus *Emericella*, which polynucleotide comprises a nucleotide sequence encoding an enzyme having phytase activity. The fungal source can be, for example, from *Emericella desertorum*.

According to one embodiment, the polynucleotide encodes a phytate-hydrolyzing enzyme including an amino acid sequence having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to an amino acid sequence as disclosed in FIG. 2, 3 or 19A-19C (SEQ ID NO:2, 3, and 44, respectively).

One embodiment of the present invention provides an isolated polynucleotide comprising a nucleotide sequence (i) having at least 55% identity, preferably at least 60% identity, more preferably at least 65% identity, still more preferably at least 70% identity, yet more preferably at least 75% identity, even more preferably at least 80% identity, again more preferably at least 85% identity, yet more preferably at least 90% identity, and most preferably at least 95% up to about 100% identity to a nucleotide sequence as disclosed in FIG. 1 or 19A-19C (SEQ ID NO:1 and 43, respectively), or (ii) being capable of hybridizing to a probe derived from the nucleotide sequence disclosed in FIG. 1 or 19A-19C (SEQ ID NO:1 and 43, respectively) under conditions of intermediate to high stringency, or (iii) being complementary to the nucleotide sequence disclosed in FIG. 1 or 19A-19C (SEQ ID NO:1 and 43, respectively).

Another aspect of the present invention provides an isolated polynucleotide encoding an enzyme having phytase activity, wherein the enzyme is derived from a *Penicillium* source. The source can be, for example, *Penicillium chrysogenum*.

In one embodiment, the polynucleotide encodes a phytate-hydrolyzing enzyme that includes an amino acid sequence having at least 55% identity, preferably at least 60% identity, more preferably at least 65% identity, still more preferably at least 70% identity, yet more preferably at least 75% is identity, even more preferably at least 80% identity, again more preferably at least 85% identity, yet again more preferably at least 90% identity, and most preferably at least 95% up to about 100% identity to an amino acid sequence as disclosed in FIG. 5, 6, 8, 18A-18C or 21 (SEQ ID NO:5, 6, 8, 42, and 8, respectively).

In another embodiment, the polynucleotide encoding a phytate-hydrolyzing enzyme has at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to a nucleotide sequence as disclosed in FIG. 1 or 19A-19C (SEQ ID NO:1 and 43, respectively), or (ii) is capable of hybridizing to a probe derived from the nucleotide sequence disclosed in FIG. 1 or 19A-19C (SEQ ID NO:1 and 43, respectively) under conditions of medium to high stringency, or (iii) is complementary to the nucleotide sequence disclosed in FIG. 1 or 19A-19C (SEQ ID NO:1 and 43, respectively).

Yet a further aspect of the present invention provides an expression construct including a polynucleotide sequence (i) having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to a nucleotide sequence as disclosed in FIG. 1 or 19A-19C (SEQ ID NO:1 and 43, respectively), or (ii) being capable of hybridizing to a probe derived from the nucleotide sequence disclosed in FIG. 1 or 19A-19C (SEQ ID NO:1 and 43, respectively) under conditions of medium to high stringency, or (iii) being complementary to the nucleotide sequence disclosed in FIG. 1 or 19A-19C (SEQ ID NO:1 and 43, respectively). Also provided are a vector (e.g., a plasmid) including such expression construct, and a host cell (such as an *Aspergillus*, e.g., *Aspergillus niger* or *Aspergillus nidulans*) transformed with such a vector.

In another of its aspects, the present invention provides a probe for use in detecting nucleic acid sequences coding for an enzyme having phytase activity derived from a microbial source, comprising: a nucleotide sequence (i) having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to a nucleotide sequence as disclosed in FIG. 1 or 19A-19C (SEQ ID NO:1 and 43, respectively), or (ii) being capable of hybridizing to a polynucleotide including a sequence as disclosed in FIG. 1 or 19A-19C (SEQ ID NO:1 and 43, respectively) under conditions of medium to high stringency, or (iii) being complementary to the nucleotide sequence disclosed in FIG. 1 or 19A-19C (SEQ ID NO:1 and 43, respectively).

In one embodiment, the microbial source is a fungal source, e.g., a *Penicillium* species, such as *Penicillium chrysogenum*.

The present invention additionally provides a food or animal feed including an enzyme having phytase activity, wherein the enzyme comprises an amino acid sequence having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to an amino acid sequence as disclosed in FIG. 2, 3 or 19A-19C (SEQ ID NO:2, 3, and 44, respectively).

The present invention provides food or animal feed including an enzyme having phytase activity, wherein the enzyme is derived from a fungal source such as *Penicillium chrysogenum*.

Another aspect of the present invention provides a method of producing an enzyme having phytase activity, comprising:
  (a) providing a host cell transformed with an expression vector comprising a polynucleotide as described herein;
  (b) cultivating the transformed host cell under conditions suitable for the host cell to produce the phytase; and
  (c) recovering the phytase.

According to one embodiment, the host cell is an *Aspergillus* species, such as *A. niger* or *A. nidulans*.

In one embodiment, the host cell is a plant cell. In this embodiment, cells or entire transformed plants may be grown and used.

Another aspect of the present invention provides a method of producing an enzyme having phytase activity, comprising:
  (a) providing a host cell transformed with an expression vector comprising a polynucleotide as described herein;
  (b) cultivating the transformed host cell under conditions suitable for the host cell to produce the phytase. The transformed cells, as well as organisms grown from such cells, may be used without further isolation of the enzyme.

In another aspect, the invention provides a purified enzyme having phytase activity, produced by the methods described above.

In yet another of its aspects, the present invention provides a method of separating phosphorous from phytate, comprising the step of treating the phytate with an enzyme comprising an amino acid sequence having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to an amino acid sequence as disclosed in FIG. 2, 3 or 19A-19C (SEQ ID NO:2, 3, and 44, respectively).

The present invention further provides a method of separating phosphorous from phytate, comprising the step of treating the phytate with an enzyme as defined above.

Another aspect of the present invention provides a phytate-hydrolyzing enzyme that includes an amino acid sequence having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to an amino acid sequence as disclosed in FIG. 5, 6, 8, 18A-18C or 21 (SEQ ID NO:5, 6, 8, 42, and 8, respectively). In a different embodiment, the sequence compares in the same way to the sequence as disclosed in FIG. 10, 11 or 20A-20B (SEQ ID NO:10, 11, and 46, respectively).

A further aspect of the present invention provides an isolated polynucleotide including a nucleotide sequence (i) having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to a nucleotide sequence as disclosed in FIG. 5, 6, 8, 18A-18C or 21 (SEQ ID NO:5, 6, 8, 42, and 8, respectively), or (ii) being capable of hybridizing to a probe derived from the nucleotide sequence disclosed in FIG. 5, 6, 8, 18A-18C or 21 (SEQ ID NO:5, 6, 8, 42, and 8, respectively) under conditions of intermediate to high stringency, or (iii) being complementary to the nucleotide sequence disclosed in FIG. 5, 6, 8, 18A-18C or 21 (SEQ ID NO:5, 6, 8, 42, and 8, respectively).

In another embodiment, the invention provides an isolated polynucleotide including a nucleotide sequence (i) having at least 55% identity, preferably at least 60% identity, more preferably at least 65% identity, still more preferably at least 70% identity, yet more preferably at least 75% is identity, even more preferably at least 80% identity, again more preferably at least 85% identity, yet again more preferably at least 90% identity, and most preferably at least 95% up to about 100% identity to a nucleotide sequence as disclosed in FIG. 10, 11 or 20A-20B (SEQ ID NO:10, 11, and 46, respectively), or (ii) being capable of hybridizing to a probe derived from the nucleotide sequence disclosed in FIG. 10, 11 or 20A-20B (SEQ ID NO:10, 11, and 46, respectively) under conditions of intermediate to high stringency, or (iii) being complementary to the nucleotide sequence disclosed in FIG. 10, 11 or 20A-20B (SEQ ID NO:10,11, and 46, respectively).

In one embodiment, the isolated polynucleotide encodes a phytate-hydrolyzing enzyme derived from a member of the *Fusarium* genus, preferably from *F. javanicum* or *F. vertisillibodes*. The enzyme includes, according to one embodiment, an amino acid sequence having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to an amino acid sequence as disclosed in FIG. 5, 6, 8, 18A-18C or 21 (SEQ ID NO:5, 6, 8, 42, and 8, respectively).

In a different embodiment, the isolated polynucleotide encodes a phytate-hydrolyzing enzyme derived from a member of the *Humicola* genus, preferably from *H. grisea*. The enzyme includes, according to one embodiment, an amino acid sequence having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to an amino acid sequence as disclosed in FIG. 10, 11 or 20A-20B (SEQ ID NO:10, 11, and 46, respectively).

In still another embodiment, the isolated polynucleotide encodes a phytate-hydrolyzing enzyme derived from a member of the *Emericella* genus, preferably from *E. desertorum*. The enzyme includes, according to one embodiment, an amino acid sequence having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to an amino acid sequence as disclosed in FIG. 17B (SEQ ID NO:40).

In another embodiment, the polynucleotide encoding a phytate-hydrolyzing enzyme includes a nucleotide sequence (i) having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to a nucleotide sequence as disclosed in FIG. 4, 7, 18A-18C, and 21 (SEQ ID NO:4, 7, 41, and 7, respectively), or (ii) capable of hybridizing to a probe derived from the nucleotide sequence disclosed in FIG. 4, 7, 18A-18C, and 21 (SEQ ID NO:4, 7,41, and 7, respectively) under conditions of medium to high stringency, or (iii) complementary to the nucleotide sequence disclosed in FIG. 4, 7, 18A-18C, and 21 (SEQ ID NO:4, 7, 41, and 7, respectively).

In still another embodiment, the polynucleotide encoding a phytate-hydrolyzing enzyme includes a nucleotide sequence (i) having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to a nucleotide sequence as disclosed in FIG. 9 or 20A-20C (SEQ ID NO:9 and 45, respectively), or (ii) capable of hybridizing to a probe derived from the nucleotide sequence disclosed in FIG. 9 or 20A-20C (SEQ ID NO:9 and 45, respectively) under conditions of medium to high stringency, or (iii) complementary to the nucleotide sequence disclosed in FIG. 9 or 20A-20C (SEQ ID NO:9 and 45, respectively).

In still another embodiment, the polynucleotide encoding a phytate-hydrolyzing enzyme includes a nucleotide sequence (i) having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to a nucleotide sequence as disclosed in FIG. 17A (SEQ ID NO:39), or (ii) capable of hybridizing to a probe derived from the nucleotide sequence disclosed in FIG. 17A (SEQ ID NO:39) under conditions of medium to high stringency, or (iii) complementary to the nucleotide sequence disclosed in FIG. 17A (SEQ ID NO:39).

Another aspect of the present invention provides an expression construct comprising a polynucleotide including a nucleotide sequence (i) having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to a nucleotide sequence as disclosed in FIG. 4, 7, 18A-18C, and 21 (SEQ ID NO:4, 7, 41, and 7, respectively), or (ii) being capable of hybridizing to a probe derived from the nucleotide sequence disclosed in FIG. 4, 7, 18A-18C, and 21 (SEQ ID NO:4, 7, 41, and 7, respectively) under conditions of medium to high stringency, or (iii) being complementary to the nucleotide sequence disclosed in FIG. 4, 7, 18A-18C, and 21 (SEQ ID NO:4, 7, 41, and 7, respectively).

Alternatively, the present invention provides an expression construct comprising a polynucleotide including a nucleotide sequence (i) having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to a nucleotide sequence as disclosed in FIG. 9 or 20A-20C (SEQ ID NO:9 and 45, respectively), or (ii) being capable of hybridizing to a probe derived from the nucleotide sequence disclosed in FIG. 9 or 20A-20C (SEQ ID NO:9 and 45, respectively) under conditions of medium to high stringency, or (iii) being complementary to the nucleotide sequence disclosed in FIG. 9 or 20A-20C (SEQ ID NO:9 and 45, respectively).

In another embodiment, the present invention provides an expression construct comprising a polynucleotide including a nucleotide sequence (i) having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to a nucleotide sequence as disclosed in FIG. 17A (SEQ ID NO:39), or (ii) being capable of hybridizing to a probe derived from the nucleotide sequence disclosed in FIG. 17A (SEQ ID NO:39) under conditions of medium to high stringency, or (iii) being complementary to the nucleotide sequence disclosed in FIG. 17A (SEQ ID NO:39).

The present invention further provides a vector (e.g., plasmid) including such an expression construct, as well as a host cell (e.g., *Aspergillus niger* or *Aspergillus nidulans*) transformed with a vector as described above.

The present invention additionally provides a probe for use in detecting nucleic acid sequences coding for an enzyme having phytase activity derived from a microbial source, comprising: a nucleotide sequence (i) having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to a nucleotide sequence as disclosed in FIG. 4, 7, 18A-18C, and 21 (SEQ ID NO:4, 7, 41, and 7, respectively), or (ii) being capable of hybridizing to a polynucleotide including a sequence as disclosed in FIG. 4, 7, 18A-18C, and 21 (SEQ ID NO:4, 7, 41, and 7, respectively) under conditions of medium to high stringency, or (iii) being complementary to the nucleotide sequence disclosed in FIG. 4, 7, 18A-18C, and 21 (SEQ ID NO:4, 7, 41, and 7, respectively).

In another aspect, the invention provides a probe for use in detecting nucleic acid sequences coding for an enzyme having phytase activity derived from a microbial source, comprising: a nucleotide sequence (i) having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to a nucleotide sequence as disclosed in FIG. 9 or 20A-20C (SEQ ID NO:9 and 45, respectively), or (ii) being capable of hybridizing to a polynucleotide including a sequence as disclosed in FIG. 9 or 20A-20C (SEQ ID NO:9 and 45, respectively) under conditions of medium to high stringency, or (iii) being complementary to the nucleotide sequence disclosed in FIG. 9 or 20A-20C (SEQ ID NO:9 and 45, respectively).

In another aspect, the invention provides a probe for use in detecting nucleic acid sequences coding for an enzyme having phytase activity derived from a microbial source, comprising: a nucleotide sequence (i) having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to a nucleotide sequence as disclosed in FIG. 17A (SEQ ID NO:39), or (ii) being capable of hybridizing to a polynucleotide including a sequence as disclosed in FIG. 17A (SEQ ID NO:39) under conditions of medium to high stringency, or (iii) being complementary to the nucleotide sequence disclosed in FIG. 17A (SEQ ID NO:39).

In one embodiment, the microbial source is a fungal source, e.g., a *Penicillium* species, such as *P. chrysogenum*, a *Fusarium* species, such as *F. javanicum* or *F. vertisillibodes*, an *Emericella* species such as *E. desertorum* or a *Humicola* species, such as *H. grisea*.

The present invention further provides a food or animal feed including an enzyme having phytase activity, wherein the enzyme includes an amino acid sequence having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to an amino acid sequence as disclosed in FIG. 5, 6, 8, 10, 11, 17B, 18A-18C, 19A-19C, 20A-20B or 21 (SEQ ID NO:5, 6, 8, 10, 11, 40, 42, 44, and 46, respectively).

Still further, the present invention provides a method of separating phosphorous from phytate, comprising the step of treating the phytate with an enzyme (i) having phytate hydrolyzing activity and (ii) including an amino acid sequence having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to an amino acid sequence as disclosed in FIG. 5, 6, 8, 18A-18C or 21 (SEQ ID NO:5, 6, 8, 42 and 8, respectively). In another aspect, the invention provides a method of separating phosphorous from phytate, comprising the step of treating the phytate with an enzyme (i) having phytate hydrolyzing activity and (ii) including an amino acid sequence having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to an amino acid sequence as disclosed in FIG. 10, 11 or 20A-20B (SEQ ID NO:10, 11, and 46, respectively), or as disclosed in FIG. 17B (SEQ ID NO:40).

As will be appreciated, an advantage of the present invention is that a polynucleotide has been isolated which provides the capability of isolating further polynucleotides which encode proteins having phytase activity.

Another advantage of the present invention is that, by virtue of providing a polynucleotide encoding a protein having phytase activity, it is possible to produce, through recombinant means, a host cell which is capable of producing the protein having phytase activity in relatively large quantities.

Yet another advantage of the present invention is that commercial application of proteins having phytase activity is made practical. For example, the present invention provides animal feed incorporating the phytase described herein.

Other objects and advantages of the present invention will become apparent from the following detailed specification.

BRIEF DESCRIPTION OF THE DRAWINGS

FIG. 1 shows a nucleic acid sequence (SEQ ID NO:1) corresponding to 1317 base pairs of a gene encoding a phytase hydrolyzing enzyme derived from *Penicillium chrysogenum*.

FIG. 2 shows an amino acid sequence (SEQ ID NO:2) of a phytase enzyme encoded by the nucleic acid sequence of FIG. 1 (SEQ ID NO:1).

FIG. 3 shows an amino acid sequence (SEQ ID NO:3) of a mature chimeric phytase enzyme, produced via the expression of a nucleic acid sequence encoding an *Aspergillus* signal sequence, linked to a nucleic acid sequence encoding a phytase hydrolyzing enzyme derived from *Penicillium chrysogenum*.

FIG. 4 shows a nucleic acid sequence (SEQ ID NO:4) corresponding to 1299 base pairs of a gene encoding a phytase hydrolyzing enzyme derived from *Fusarium javanicum*.

FIG. 5 shows an amino acid sequence (SEQ ID NO:5) of a phytase enzyme encoded by the nucleic acid sequence of FIG. 4 (SEQ ID NO:4).

FIG. 6 shows an amino acid sequence (SEQ ID NO:6) of a mature chimeric phytase enzyme, produced via the expression of a nucleic acid sequence encoding an *Aspergillus* signal sequence, linked to a nucleic acid sequence encoding a phytase hydrolyzing enzyme derived from *Fusarium javanicum*.

FIG. 7 shows a nucleic acid sequence (SEQ ID NO:7) corresponding to 224 base pairs of a gene encoding a phytase hydrolyzing enzyme derived from *Fusarium vertisillibodes*.

FIG. 8 shows an amino acid sequence (SEQ ID NO:8) of a phytase enzyme encoded by the nucleic acid sequence of FIG. 7 (SEQ ID NO:7).

FIG. 9 shows a nucleic acid sequence (SEQ ID NO:9) corresponding to 224 base pairs of a gene encoding a phytase hydrolyzing enzyme derived from *Humicola grisea*.

FIG. 10 shows an amino acid sequence (SEQ ID NO:10) of a phytase enzyme encoded by the nucleic acid sequence of FIG. 9 (SEQ ID NO:9).

FIG. 11 shows an amino acid sequence (SEQ ID NO:11) of a mature chimeric phytase enzyme, produced via the expression of a nucleic acid sequence encoding an *Aspergillus* signal sequence, linked to a nucleic acid sequence encoding a phytase hydrolyzing enzyme derived from *Humicola grisea*.

FIG. 12 shows a nucleic acid sequence (SEQ ID NO:12) corresponding to 192 base pairs of a gene fragment encoding the amino end, including a signal sequence, for a phytase hydrolyzing enzyme derived from *Aspergillus niger*. This sequence includes an ATG start codon at the 5□ end and an intron extending from residues 46 to 147.

FIG. 13 shows an amino acid sequence (SEQ ID NO:13) of the amino end, including a signal sequence, of a phytase enzyme encoded by the nucleic acid sequence of FIG. 12 (SEQ ID NO:12).

FIGS. 14A-14D show alignments of amino acid sequences disclosed herein with published amino acid sequences of known phytase enzymes. FIG. 14A shows a GAP alignment, as further described below, of the amino acid sequence of a mature (i.e., lacking the signal sequence corresponding to amino acids 1-23) phytase from *A. niger* (accession number P34752, 444 amino acids; top row of each pair, SEQ ID NO:14) and a phytase derived from *P. chrysogenum* (FIG. 3, 446 amino acids; bottom row of each pair, SEQ ID NO:15). Straight lines between the aligned sequences indicate identical residues, dots between the aligned sequences indicate similar residues. The two sequences show 65% identity, 70% similarity.

FIG. 14B shows a BLAST alignment (TBLASTN 2.0.5 program, SEQ ID NO:18), as further described below, of residues 1-445 of the amino acid sequence (SEQ ID NO:16) from *P. chrysogenum* (P.c.) disclosed in FIG. 3 and the amino acid sequence determined from nucleic acid residues 407 to 1732 of a cDNA sequence encoding an *Aspergillus fumigatus* (A.f.) phytase (accession number U59804, SEQ ID NO:17). Letters between the aligned sequences indicate identical amino acid residues, pluses indicate similar residues. These portions of the two sequences show 62% identity, 75% similarity.

FIG. 14C shows a BLAST alignment of (SEQ ID NO:21) residues 4-445 of the amino acid sequence (SEQ ID NO:19) from *P. chrysogenum* (P.c.) disclosed in FIG. 3 and the amino acid sequence determined from nucleic acid residues 411 to 1730 of a cDNA sequence encoding an *Aspergillus terreus* (A.t.) phytase (accession number U60412, SEQ ID NO:20). These portions of the two sequences show 60% identity, 73% similarity.

FIG. 14D shows a BLAST alignment (SEQ ID NO:24) of residues 7-445 of the amino acid sequence (SEQ ID NO:22) from *P. chrysogenum* (P.c.) disclosed in FIG. 3 and the amino acid sequence determined from nucleic acid residues 293 to 1594 of a cDNA sequence encoding an *Emericella nidulans* (*Aspergillus nidulans*; A.t.) phytase (accession number U59803, SEQ ID NO:23). These portions of the two sequences show 60% identity, 75% similarity.

FIGS. 15A-15C show alignments of amino acid sequences disclosed herein with published amino acid sequences of known phytase enzymes. FIG. 15A shows a GAP alignment of the 444 amino acid sequence of a mature phytase from *A. niger* (accession number P34752, SEQ ID NO:25) and a 440 amino acid phytase sequence derived from *F. javanicum* (disclosed in FIG. 6, SEQ ID NO:26). The two sequences show 50% identity, 56% similarity.

FIG. 15B shows a GAP alignment of a 440 amino acid phytase sequence derived from *F. javanicum* (disclosed in FIG. 6, SEQ ID NO:27) and the 463 amino acid sequence of a phytase from *Emericella nidulans* (E.n.) (*Aspergillus nidulans*; accession number U59803, SEQ ID NO:28). The two sequences show 52% identity, 60% similarity.

FIG. 15C shows a BLAST alignment (SEQ ID NO:31) of residues 7-438 of a phytase amino acid sequence (SEQ ID NO:29) from *F. javanicum* (F.j.) disclosed in FIG. 6 and the amino acid sequence (SEQ ID NO:30) determined from nucleic acid residues 2379 to 3719 of a cDNA sequence encoding an *Myceliopthora thermophila* (M.t.) phytase (accession number U59806). These portions of the two sequences show 52% identity, 68% similarity.

FIGS. 16A-16C show alignments of amino acid sequences disclosed herein with published amino acid sequences of known phytase enzymes. FIG. 16A shows a GAP alignment of a 487 amino acid sequence of a phytase from *M. thermophila* (accession number U59806, SEQ ID NO:33) and a 449 amino acid phytase sequence derived from *H. grisea* (disclosed in FIG. 11, SEQ ID NO:32). The two sequences show 66% identity, 72% similarity.

FIG. 16B shows a GAP alignment of a 449 amino acid phytase sequence derived from *H. grisea* (disclosed in FIG. 11, SEQ ID NO:35) and the 444 amino acid sequence of a mature phytase from *A. niger* (accession number P34752, SEQ ID NO:34). The two sequences show 51% identity, 59% similarity.

FIG. 16C shows a BLAST alignment (SEQ ID NO:38) of residues 8-448 of a phytase amino acid sequence from *H. grisea* (H.g) (SEQ ID NO:36) disclosed in FIG. 11 and the amino acid sequence determined from nucleic acid residues 2340 to 3722 of a cDNA sequence encoding an *Myceliopthora thermophila* (M.t.) phytase (accession number U59806, SEQ ID NO:37). These portions of the two sequences show 65% identity, 74% similarity.

FIGS. 17A and 17B show the DNA encoding and amino acid sequence of a phytase from *E. desertorum*. FIG. 17A shows the sequence of genomic DNA (SEQ ID NO:39) encoding the gene for the phytase. Lower case lettering depicts a putative intron. FIG. 17B shows the putative amino acid sequence (SEQ ID NO:40) encoded by the E desertorum phytase gene.

FIGS. 18A-18C show the genomic DNA sequence (SEQ ID NO:41) encoding a phytase from *F. javanicum*. The putative amino acid sequence (SEQ ID NO:42) of the phytase is indicated below the DNA sequence. A putative intron is indicated below the DNA sequence by a horizontal line. Box arrows below the DNA sequence indicate sequences of primers useful for amplifying the gene. Restriction sites are indicated above the sequence in bold.

FIGS. 19A-19C show the genomic DNA sequence (SEQ ID NO:43) encoding a phytase from *P. chrysogenum*. The putative amino acid sequence (SEQ ID NO:44) of the phytase is indicated below the DNA sequence. A putative intron is indicated below the DNA sequence by a horizontal box. Box arrows below the DNA sequence indicate sequences of primers useful for amplifying the gene. Restriction sites are indicated above the sequence in bold.

FIGS. 20A-20C show the genomic DNA sequence (SEQ ID NO:45) encoding a phytase from *H. grisea*. The putative amino acid sequence (SEQ ID NO:46) of the phytase is indicated below the DNA sequence. A putative intron is indicated below the DNA sequence by a horizontal line. Restriction sites are indicated above the sequence in bold.

FIG. 21 shows a partial genomic DNA sequence (SEQ ID NO:7) encoding a phytase from *F. vertisillibodes*. The putative amino acid sequence (SEQ ID NO:8) of the phytase is indicated below the DNA sequence. A putative intron is indicated below the DNA sequence by a horizontal line. Restriction sites are indicated above the sequence in bold.

FIG. 22 shows the DNA sequence (SEQ ID NO:47) of a gene encoding a phytase from *E. desertorum* obtained using the procedure described in Example 1. Below the DNA sequence is indicated the putative amino acid sequence (SEQ ID NO:48) of the phytase. The arrows above the DNA sequence indicate ligation sequences (primers GSP1 rev: fyt037 and GSP2rev:fyt036) used to obtain upstream sequences of the gene (see FIG. 17A).

FIG. 23 shows the DNA sequence (SEQ ID NO:49) of a gene encoding a phytase from *F. javanicum* obtained using the procedure described in Example 1. The putative amino acid sequence (SEQ ID NO:50) of the phytase is indicated below the DNA sequence. The arrows above the DNA sequence indicate ligation sequences (primers GSP1rev: fyt039 and GSP2rev:fyt038) used to obtain upstream sequences of the gene (see FIGS. 18A-18B).

FIG. 24 shows results of expression of recombinantly produced phytase described herein. FIG. 24A shows an isoelectric focusing (IEF) gel stained with Comassie blue. This gel sows protein present in the supernatant from cultures of *Aspergillus niger* which had been transformed with a vector encoding chimeric phytase from *P. chrysogenum* (lanes 5-8) and *F. javanicum* (lanes 9-12), as described in Examples 3 and 4. The transformed host cells were grown under conditions designed to facilitate expression of the proteins encoded in the expression vector. Lanes 1-3 (as marked) have nothing in them. Lane 4 has fermentation broth from an *A. nigertrans* formed with the same vector as used for the *F. javanicum* and *P. chrysogenum* phytases, but comprising a nucleic acid sequence encoding the native *A. niger* phytase enzyme. Lanes 5-8 have fermentation broth from four different clones transformed with vector comprising the *P. chrysogenum* chimeric phytase, selected for their apparent high (lanes 5 and 8), moderate (lane 7) and low (lane 6) phytase activity, as determined in a preliminary test. Lanes 9-12 have fermentation broth from four different clones transformed with vector comprising the *F. javanicum* chymeric phytase, selected for their apparent high (lane 11), moderate (lanes 9 and 10) and low (lane 12) phytase activity, as determined in a preliminary test. The Comassie stained gel indicates novel protein bands corresponding to phytase activity, as shown in the zymogram described in FIG. 24B, for each of the transformant types and no such novel protein bands for clones in which no activity was found.

FIG. 24B shows a zymogram produced as an overlay of the IEF gel described in FIG. 24A, made prior to staining of the gel, showing the phosphatase activity of the proteins in the gel. The zymogram indicates phytase activity associated with the novel Comassie stained bands from the hosts transformed with chimeric phytase.

DETAILED DESCRIPTION OF THE INVENTION

I. Definitions

Figure 19C:

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acid sequences are written left to right in 5' to 3' orientation; amino acid sequences are written left to right in amino to carboxy orientation, respectively. The headings provided herein are not limitations of the various aspects or embodiments of the invention which can be had by reference to the specification as a whole. Accordingly, the terms defined immediately below are more fully defined by reference to the specification as a whole.

"Protein", as used herein, includes proteins, polypeptides, and peptides. As will be appreciated by those in the art, the nucleic acid sequences of the invention, as defined below and further described herein, can be used to generate protein sequences.

As used herein, the term "phytase" or "phytase activity" refers to a protein or polypeptide which is capable of catalyzing the hydrolysis of phytate to (1) myo-inositol and/or (2) mono-, di-, tri-, tetra- and/or penta-phosphates thereof and (3) inorganic phosphate. For example, enzymes having catalytic activity as defined in Enzyme Commission EC number 3.1.3.8, or EC number 3.1.3.26.

In the broadest sense, by "nucleic acid sequence", "polynucleotide" or "oligonucleotide" or grammatical equivalents herein means at least two nucleotides covalently linked together. A nucleic acid sequence of the present invention will generally contain phosphodiester bonds, although in some cases, as outlined below, nucleic acid sequence analogs are included that may have alternate backbones, comprising, for example, phosphoramidate (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al., Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644, 048), phosphorodithioate (Briu et al., J. Am. Chem. Soc. 111:2321 (1989)), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386, 023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within one definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done for a variety of reasons, for example to increase the stability and half-life of such molecules in physiological or food processing environments.

As will be appreciated by those in the art, all of these nucleic acid analogs may find use in the present invention. In addition, mixtures of naturally occurring nucleic acids and analogs can be made; alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop is closer to 7-9° C. Similarly, due to their non-ionic nature, hybridization of the bases attached to these backbones is relatively insensitive to salt concentration. In addition, PNAs are not degraded by cellular enzymes, and thus can be more stable.

The nucleic acid sequences may be single stranded or double stranded, as specified, or contain portions of both double stranded or single stranded sequence. As will be appreciated by those in the art, the depiction of a single strand ("Watson") also defines the sequence of the other strand ("Crick"); thus the sequences described herein also includes the complement of the sequence. The nucleic acid sequence may be DNA, both genomic and cDNA, RNA or a hybrid, where the nucleic acid sequence contains any combination of deoxyribo- and ribo-nucleotides, and any combination of bases, including uracil, adenine, thymine, cytosine, guanine, inosine, xanthine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid sequence, each containing a base, are referred to herein as a nucleoside.

The term "identical" in the context of two nucleic acid sequences or polypeptide sequences refers to the residues in the two sequences that are the same when aligned for maximum correspondence, as measured using one of the following sequence comparison or analysis algorithms.

"Optimal alignment" is defined as an alignment giving the highest percent identity score. Such alignment can be performed using a variety of commercially available sequence analysis programs, such as the local alignment program LALIGN using a ktup of 1, default parameters and the default PAM. A preferred alignment is the pairwise alignment performed using the CLUSTAL-W program in MACVECTOR, operated in "slow" alignment mode using default parameters, including an open gap penalty of 10.0, an extend gap penalty of 0.1, and a BLOSUM30 similarity matrix. If a gap needs to be inserted into a first sequence to optimally align it with a second sequence, the percent identity is calculated using only the residues that are paired with a corresponding amino acid residue (i.e., the calculation does not consider residues in the second sequences that are in the "gap" of the first sequence).

Optimal alignment of sequences for comparison can also be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

"Percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two optimally aligned polypeptide sequences are identical.

Percent identity can be determined, for example, by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in "Atlas of Protein Sequence and Structure", M. O. Dayhoff ed.,* 5 Suppl. 3:353-358, National Biomedical Research Foundation, Washington, D.C., which adapts the local homology algorithm of Smith and Waterman (1981) Advances in Appl. Math. 2:482-489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above.

An example of an algorithm that is suitable for determining sequence similarity is the BLAST algorithm, which is described in Altschul, et al., J. Mol. Biol. 215:403-410 (1990). Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, Proc. Natl. Acad. Sci. USA 89:10915 (1989)) alignments (B) of 50, expectation (E) of 10, M'5, N'-4, and a comparison of both strands.

The BLAST algorithm then performs a statistical analysis of the similarity between two sequences (see, e.g., Karlin &

Altschul, *Proc. Nat'l. Acad. Sci. USA* 90.5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid sequence is considered similar to a phytase nucleic acid sequence of this invention if the smallest sum probability in a comparison of the test nucleic acid sequence to a phytase nucleic acid sequence is less than about 0.1, more preferably less than about 0.01, and most preferably less than about 0.001. Where the test nucleic acid sequence encodes a phytase polypeptide, it is considered similar to a specified phytase nucleic acid sequence if the comparison results in a smallest sum probability of less than about 0.5, and more preferably less than about 0.2.

The phrase "substantially identical" in the context of two nucleic acid sequences or polypeptides thus typically means that a polynucleotide or polypeptide comprises a sequence that has at least 60% sequence identity, preferably at least 80%, more preferably at least 90% and most preferably at least 95%, compared to a reference sequence using the programs described above (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

"Hybridization" includes any process by which a strand of a nucleic acid sequence joins with a second nucleic acid sequence strand through base-pairing. Thus, strictly speaking, the term refers to the ability of a target sequence to bind to a test sequence, or vice-versa.

"Hybridization conditions" are typically classified by degree of "stringency" of the conditions under which hybridization is measured. The degree of stringency can be based, for example, on the calculated (estimated) melting temperature (Tm) of the nucleic acid sequence binding complex or probe. Calculation of Tm is well known in the art (see, e.g. page 9.50-9.51 of Sambrook (1989), below). For example, "maximum stringency" typically occurs at about Tm–5° C. (50 below the Tm of the probe); "high stringency" at about 5-10° below the Tm; "intermediate stringency" at about 10-20° below the Tm of the probe; and "low stringency" at about 20-25° below the Tm. In general, hybridization conditions are carried out under high ionic strength conditions, for example, using 6×SSC or 6×SSPE. Under high stringency conditions, hybridization is followed by two washes with low salt solution, for example 0.5×SSC, at the calculated temperature. Under medium stringency conditions, hybridization is followed by two washes with medium salt solution, for example 2×SSC. Under low stringency conditions, hybridization is followed by two washes with high salt solution, for example 6×SSC. Functionally, maximum stringency conditions may be used to identify nucleic acid sequences having strict identity or near-strict identity with the hybridization probe; while high stringency conditions are used to identify nucleic acid sequences having about 80% or more sequence identity with the probe.

For applications requiring high selectivity, one will typically desire to employ relatively stringent conditions to form the hybrids, e.g., one will select relatively high temperature conditions. Hybridization conditions, including moderate stringency and high stringency, are provided in Sambrook et al., Molecular Cloning: A Laboratory Manual, Second Edition, Cold Spring Harbor Press (1989); Sambrook et al., Molecular Cloning, A Laboratory Manual, 3d Ed., Cold Spring Harbor Laboratory Press, Cold Spring Harbor, N.Y. (2001) incorporated herein by reference.

The term "complementary", in the context of a nucleic acid sequence, means a nucleic acid sequence having a sequence relationship to a second nucleic acid sequence such that there is perfect alignment of Watson-Crick base pairs along the entire length of both nucleic acid sequences.

The term "isolated" or "purified" means that a material is removed from its original environment (e.g., the natural environment if it is naturally occurring). For example, the material is said to be "purified" when it is present in a particular composition in a higher or lower concentration than exists in a naturally occurring or wild type organism or in combination with components not normally present upon expression from a naturally occurring or wild type organism. For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector, and/or such polynucleotides or polypeptides could be part of a composition, and still be isolated in that such vector or composition is not part of its natural environment. A nucleic acid sequence or protein is said to be purified, for example, if it gives rise to essentially one band in an electrophoretic gel.

The present invention provides for the production of recombinant nucleic acids and proteins. By "recombinant" and grammatical equivalents thereof is meant produced using recombinant technology, whereby novel nucleic acids are made (recombinant nucleic acids) and proteins are produced therefrom (recombinant proteins). Such techniques are well known in the art and many are described in great detail herein. In a broad sense, a recombinant nucleic acid sequence may be any nucleic acid sequence not in its naturally occurring form, whether it be a sequence isolated from its naturally occurring adjoining sequence, or combined with other sequences with which it was not joined in nature to form a new nucleic acid sequence, such as in a vector. Recombinant nucleic acid sequences also include those that are produced from recombinant nucleic acid sequences, for example complementary sequences made through polymerization, additional copies made though replication, or RNA transcribed from recombinant DNA. Recombinant protein is protein produced by translation of recombinant nucleic acid sequences.

As used herein in referring to phytate hydrolyzing enzymes (phytases), the term "derived from" is intended not only to indicate a phytase produced or producible by a strain of the organism in question, but also a phytase encoded by a DNA sequence isolated from such strain and produced in a host organism containing such DNA sequence. Additionally, the term is intended to indicate a phytase which is encoded by a DNA sequence of synthetic and/or cDNA origin and which has the identifying characteristics of the phytase in question. To exemplify, "phytases derived from *Penicillium*" refers to those enzymes having phytase activity which are naturally-produced by *Penicillium*, as well as to phytases like those produced by *Penicillium* sources but which through the use of genetic engineering techniques are produced by non-*Penicillium* organisms transformed with a nucleic acid sequence encoding said phytases. The present invention encompasses phytate hydrolyzing enzymes that are equivalent to those that are derived from the particular microbial strain mentioned.

Being "equivalent," in this context, means that the phytate hydrolyzing enzymes are encoded by a polynucleotide capable of hybridizing to the polynucleotide having the sequence as shown in any one of FIGS. 1, 4, 7 and 9 (SEQ ID NO:1, 4, 7, and 9, respectively) under conditions of medium to high stringency. Being equivalent means that the phytate hydrolyzing enzyme comprises at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to the phytate hydrolyzing enzyme having the amino acid sequence disclosed in one of FIGS. 2, 3, 5, 6, 8, 10 and 11 (SEQ ID NO:2, 3, 5, 6, 8, 10, and 11, respectively). The present invention also encompasses mutants, variants and derivatives of the phytate hydrolyzing enzymes of the present invention as long as the mutant, variant or derivative phytate hydrolyzing enzyme is able to retain at least one characteristic activity of the naturally occurring phytate hydrolyzing enzyme. As used herein, the term "mutants and variants", when referring to phytate hydrolyzing enzymes, refers to phytate hydrolyzing enzymes obtained by alteration of the naturally occurring amino acid sequence and/or structure thereof, such as by alteration of the DNA nucleotide sequence of the structural gene and/or by direct substitution and/or alteration of the amino acid sequence and/or structure of the phytate hydrolyzing enzyme.

The term "derivative" or "functional derivative" as it relates to phytase is used herein to indicate a derivative of phytase which has the functional characteristics of phytase of the present invention. Functional derivatives of phytase encompass naturally occurring, synthetically or recombinantly produced peptides or peptide fragments, mutants or variants which may have one or more amino acid deletions, substitutions or insertions which have the general characteristics of the phytase of the present invention.

The term "functional derivative" as it relates to nucleic acid sequences encoding phytase is used throughout the specification to indicate a derivative of a nucleic acid sequence which has the functional characteristics of a nucleic acid sequence which encodes phytase. Functional derivatives of a nucleic acid sequence which encode phytase of the present invention encompass naturally occurring, synthetically or recombinantly produced nucleic acid sequences or fragments, mutants or variants thereof which may have one or more nucleic acid deletions, substitutions or insertions and encode phytase characteristic of the present invention. Variants of nucleic acid sequences encoding phytase according to the invention include alleles and variants based on the degeneracy of the genetic code known in the art. Mutants of nucleic acid sequences encoding phytase according to the invention include mutants produced via site-directed mutagenesis techniques (see for example, Botstein, D. and Shortle, D., 1985, Science 229:1193-1201 and Myers, R. M., Lerman, L. S., and Maniatis, T., 1985, Science 229: 242-247), error-prone PCR (see for example, Leung, D. W., Chen, E., and Goeddel, D. V., 1989, Technique 1: 11-15; Eckert, K. A. and Kunkel, T. A., 1991, PCR Methods Applic. 1: 17-24; and Cadwell, R. C. and Joyce, G. F., 1992, PCR Methods Applic. 2: 28-33) and/or chemical-induced mutagenesis techniques known in the art (see for example, Elander, R. P., Microbial screening, Selection and Strain Improvement, in Basic Biotechnology, J. Bullock and B. Kristiansen Eds., Academic Press, New York, 1987, 217).

"Expression vector" means a DNA construct comprising a DNA sequence which is operably linked to a suitable control sequence capable of effecting the expression of the DNA in a suitable host. Such control sequences may include a promoter to effect transcription, an optional operator sequence to control such transcription, a sequence encoding suitable ribosome-binding sites on the mRNA, and sequences which control termination of transcription and translation. Different cell types are preferably used with different expression vectors. A preferred promoter for vectors used in *Bacillus subtilis* is the AprE promoter; a preferred promoter used in *E. coli* is the Lac promoter and a preferred promoter used in *Aspergillus niger* is glaA. The vector may be a plasmid, a phage particle, or simply a potential genomic insert. Once transformed into a suitable host, the vector may replicate and function independently of the host genome, or may, under suitable conditions, integrate into the genome itself.

In the present specification, plasmid and vector are sometimes used interchangeably. However, the invention is intended to include other forms of expression vectors which serve equivalent functions and which are, or become, known in the art. Thus, a wide variety of host/expression vector combinations may be employed in expressing the DNA sequences of this invention. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC19 and their derivatives, wider host range plasmids, e.g., RP4, phage DNAs e.g., the numerous derivatives of phage 1, e.g., NM989, and other DNA phages, e.g., M13 and filamentous single stranded DNA phages, yeast plasmids such as the 2 m plasmid or derivatives thereof, vectors useful in eukaryotic cells, such as vectors useful in animal cells and vectors derived from combinations of plasmids and phage DNAs, such as plasmids which have been modified to employ phage DNA or other expression control sequences.

Expression techniques using the expression vectors of the present invention are known in the art and are described generally in, for example, Sambrook et al., Molecular Cloning: A Laboratory Manual, Second Edition, Cold Spring Harbor Press (1989); Sambrook et al., Molecular Cloning, A Laboratory Manual, 3d Ed., Cold Spring Harbor Laboratory Press, Cold Spring Harbor, N.Y. (2001). Often, such expression vectors including the DNA sequences of the invention are transformed into a unicellular host by direct insertion into the genome of a particular species through an integration event (see e.g., Bennett & Lasure, More Gene Manipulations in Fungi, Academic Press, San Diego, pp. 70-76 (1991) and articles cited therein describing targeted genomic insertion in fungal hosts, incorporated herein by reference).

"Host strain" or "host cell" means a suitable host for an expression vector comprising DNA according to the present invention. Host cells useful in the present invention are generally procaryotic or eucaryotic hosts, including any transformable microorganism in which expression can be achieved. For example, host strains can be *Bacillus subtilis, Escherichia coli, Trichoderma iongibrachiatum, Saccharomyces cerevisiae, Aspergillus niger,* and *Aspergillus nidulans.* Host cells are transformed or transfected with vectors constructed using recombinant DNA techniques. Such transformed host cells are capable of both replicating vectors encoding phytase and its variants (mutants) or expressing the desired peptide product.

Examples of appropriate expression hosts include: bacterial cells, such as *E. coli, Streptomyces, Salmonella typhimurium*; fungal cells, such as *Aspergillus* and *Penicillium*; insect cells such as *Drosophila* and *Spodoptera* Sf9; animal cells such as CHO, COS, HEK 293 or Bowes melanoma; plant cells, etc. The selection of an appropriate host is deemed to be within the scope of those skilled in the art from the teachings herein. It should be noted that the invention is not limited by the particular host cells employed.

II. Phytase Enzymes and Nucleic Acid Sequences Encoding Phytase Enzymes

One aspect of the present invention provides proteins or polypeptides which are capable of catalyzing the hydrolysis of phytate and releasing inorganic phosphate; for example, enzymes having catalytic activity as defined in Enzyme Commission EC number 3.1.3.8, or in EC number 3.1.3.26. In one preferred embodiment, the invention provides a so-called 3-phytase. The present invention additionally encompasses polynucleotides (e.g., DNA) which encode such phytate hydrolyzing proteins or polypeptides.

Preferably, the phytase and/or polynucleotides encoding the phytase according to the present invention is derived from a fungus, preferably from an anaerobic fungus or thermophilic fungus and most preferably from *Penicillium* sp., e.g., *Penicillium chrysogenum*, *Fusarium* sp., e.g., *Fusarium javanicum* or *Fusarium vertisillibodes* or *Humicola* sp., e.g. *Humicola grisea*. Thus, it is contemplated that the phytase or the DNA encoding the phytase according to the invention can be derived from *Absidia* sp.; *Acremonium* sp.; *Actinomycetes* sp.; *Agaricus* sp.; *Anaeromyces* sp.; *Aspergillus* sp., including *A. auculeatus*, *A. awamori*, *A. flavus*, *A. foetidus*, *A. fumaricus*, *A. fumigatus*, *A. nidulans*, *A. niger*, *A. oryzae*, *A. terreus* and *A. versicolor; Aeurobasidium* sp.; *Cephalosporum* sp.; *Chaetomium* sp.; *Coprinus* sp.; *Dactyllum* sp.; *Fusarium* sp., including *F. conglomerans*, *F. decemcellulare*, *F. javanicum*, *F. lini*, *F. oxysporum* and *F. solani; Gliocladium* sp.; *Humicola* sp., including *H. insolens* and *H. lanuginosa; Mucor* sp.; *Myceliopthora* ssp., including *M. thermophila; Neurospora* sp., including *N. crassa* and *N. sitophila; Neocallimastix* sp.; *Orpinomyces* sp.; *Penicillium* spp; *Phanerochaete* sp.; *Phlebia* sp.; *Piromyces* sp.; *Pseudomonas* sp.; *Rhizopus* sp.; *Schizophyllum* sp.; *Streptomyces* spp; *Trametes* sp.; and *Trichbderma* sp., including *T. reesei*, *T. longibrachiatum* and *T. viride*; and *Zygorhynchus* sp. Similarly, it is envisioned that a phytase and/or DNA encoding a phytase as described herein may be derived from bacteria such as *Streptomyces* sp., including *S. olivochromogenes*; specifically fiber degrading ruminal bacteria such as *Fibrobacter succinogenes*; and in yeast including *Candida torresii; C. parapsllosis; C. sake; C. zeylanoides; Pichia minuta; Rhodotorula glutinis; R. mucilaginosa*; and *Sporobolomyces holsaticus*.

In one preferred embodiment, the phytase and/or polynucleotides encoding the phytase according to the present invention is/are derived from (i) a grain-spoilage fungus, such as *Penicillium hordei, Penicillium piceum*, or *Penicillium brevi-compactum*; or (ii) an ectomycorrhizal fungus associated with tree roots, e.g., *Laccaria laccata, Laccaria rufus, Paxillus involutus, Hebeloma crustuliniforme, Amanita rubescens*, or *Amanita muscaria*. According to a preferred embodiment, the phytase and/or polynucleotide encoding the phytase of the present invention is in a purified form, i.e., present in a particular composition in a higher or lower concentration than exists in a naturally occurring or wild type organism or in combination with components not normally present upon expression from a naturally occurring or wild type organism.

The invention encompasses phytate hydrolyzing proteins and peptides comprising at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to the phytate hydrolyzing enzyme having the amino acid sequence disclosed in FIGS. 2, 3, 5, 6, 8, 10 or 11 (SEQ ID NO:2, 3, 5, 6, 8, 10, and 11, respectively).

The invention further encompasses polynucleotides, e.g., DNA, which encode phytate hydrolyzing enzymes derived from fungal sources, such as *Penicillium* sp., which polynucleotides include a sequence having at least 65% identity, at least 70% identity, at least 75% identity, at least 80% identity, at least 85% identity, at least 90% identity and at least 9.5% identity to the polynucleotide sequence disclosed in any one of FIGS. 1, 4, 7 and 9 (SEQ ID NO:1, 4, 7, and 9, respectively), as long as the enzyme encoded by the polynucleotide is capable of catalyzing the hydrolysis of phytate and releasing inorganic phosphate. In a preferred embodiment, the polynucleotide encoding the phytate hydrolyzing enzyme has the polynucleotide sequence as shown in any one of FIGS. 1, 4, 7 and 9 (SEQ ID NO:1, 4, 7, and 9, respectively), or is capable of hybridizing to the polynucleotide sequence as shown in any one of FIGS. 1, 4, 7 and 9 (SEQ ID NO:1, 4, 7, and 9, respectively) or its complement, or is complementary to the polynucleotide sequence as shown in any one of FIGS. 1, 4, 7 and 9 (SEQ ID NO:1, 4, 7, and 9, respectively). As will be understood by the skilled artisan, due to the degeneracy of the genetic code, a variety of polynucleotides can encode the phytate hydrolyzing enzyme disclosed in any one of FIGS. 2, 3, 5, 6, 8, 10 and 11 (SEQ ID NO:2, 3, 5, 6, 8, 10, and 11, respectively). The present invention encompasses all such polynucleotides.

III. Obtaining Polynucleotides Encoding a Phytate Hydrolyzing Enzyme

The nucleic acid sequence encoding a phytate hydrolyzing enzyme may be obtained by standard procedures known in the art from, for example, cloned DNA (e.g., a DNA "library"), by chemical synthesis, by cDNA cloning, by PCR, or by the cloning of genomic DNA, or fragments thereof, purified from a desired cell, such as a fungal species (See, for example, Sambrook et al., 2001, Molecular Cloning, A Laboratory Manual, 3d Ed., Cold Spring Harbor Laboratory Press, Cold Spring Harbor, N.Y.; Glover, D M and Hames, B D (Eds.), 1995, DNA Cloning 1: A Practical Approach and DNA Cloning 2: A Practical Approach, Oxford University Press, Oxford). Nucleic acid sequences derived from genomic DNA may contain regulatory regions in addition to coding regions.

In the molecular cloning of the gene from genomic DNA, DNA fragments are generated, some of which will comprise at least a portion of the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis, PCR and column chromatography.

Once nucleic acid sequence fragments are generated, identification of the specific DNA fragment encoding a phytate hydrolyzing enzyme may be accomplished in a number of ways. For example, a phytate hydrolyzing enzyme encoding gene of the present invention or its specific RNA, or a fragment thereof, such as a probe or primer, may be isolated and labeled and then used in hybridization assays to detect a generated gene. (Benton, W. and Davis, R., 1977, *Science* 196:180; Grunstein, M. and Hogness, D., 1975, *Proc. Natl. Acad. Sci. USA* 72:3961). Those DNA fragments sharing substantial sequence similarity to the probe will hybridize under medium to high stringency.

The present invention encompasses phytate hydrolyzing enzymes derived from fungal species (esp., *Penicillium, Fusarium* and *Humicola* species) which are identified through nucleic acid sequence hybridization techniques using one of the sequences disclosed in FIGS. 1, 4, 7 and 9 (SEQ ID NO:1, 4, 7, and 9, respectively), or a suitable portion or fragment thereof (e.g., at least about 10-15 contiguous nucleotides), as a probe or primer and screening nucleic acid sequences of either genomic or cDNA origin. Nucleic acid sequences encoding phytate hydrolyzing enzymes derived from fungal species and having at least 65% identity to the sequence of one of FIGS. 1, 4, 7 and 9 (SEQ ID NO:1, 4, 7, and 9, respectively) or a portion or fragment thereof can be detected by DNA-DNA or DNA-RNA hybridization or amplification using probes, portions or fragments of the disclosed sequences. Accordingly, the present invention provides a method for the detection of nucleic acid sequences encoding a phytate hydrolyzing enzyme encompassed by the present invention which comprises hybridizing part or all of a nucleic acid sequence of FIG. 1, 4, 7 or 9 (SEQ ID NO:1, 4, 7, and 9, respectively) with a nucleic acid sequence of either genomic or cDNA origin.

Also included within the scope of the present invention are polynucleotide sequences that are capable of hybridizing to the nucleotide sequence disclosed in FIGS. 1, 4, 7 or 9 (SEQ ID NO:1, 4, 7, and 9, respectively) under conditions of medium to high stringency. In one embodiment, hybridization conditions are based on the melting temperature (Tm) of the nucleic acid sequence binding complex, as taught in Berger and Kimmel (1987, Guide to Molecular Cloning Techniques, Methods in Enzymology, Vol 152, Academic Press, San Diego Calif.) incorporated herein by reference, and confer a defined stringency. In this embodiment, "maximum stringency" typically occurs at about Tm−5° C. (5° C. below the Tm of the probe); "high stringency" at about 5° C. to 10° C. below Tm; "medium" or "intermediate stringency" at about 10° C. to 20° C. below Tm; and "low stringency" at about 20° C. to 25° C. below Tm. A maximum stringency hybridization can be used to identify or detect identical or near-identical polynucleotide sequences, while an intermediate or low stringency hybridization can be used to identify or detect polynucleotide sequence homologs.

The process of amplification as carried out in polymerase chain reaction (PCR) technologies is described in Dieffenbach C W and G S Dveksler (1995, PCR Primer, a Laboratory Manual, Cold Spring Harbor Press, Plainview N.Y.). A nucleic acid sequence of at least about 10 nucleotides and as many as about 60 nucleotides from the sequences of FIG. 1, 4, 7 or 9 (SEQ ID NO:1, 4, 7, and 9, respectively), preferably about 12 to 30 nucleotides, and more preferably about 25 nucleotides can be used as a probe or PCR primer.

A preferred method of isolating a nucleic acid sequence construct of the invention from a cDNA or genomic library is by use of polymerase chain reaction (PCR) using degenerate oligonucleotide probes prepared on the basis of the amino acid sequence of the protein having the amino acid sequence shown in any one of FIGS. 2, 3, 5, 6, 8, 10 and 11 (SEQ ID NO:2, 3, 5, 6, 8, 10, and 11, respectively). For instance, the PCR may be carried out using the techniques described in U.S. Pat. No. 4,683,202.

In view of the above, it will be appreciated that the polynucleotide sequences provided in FIGS. 1, 4, 7 and 9 (SEQ ID NO:1, 4, 7, and 9, respectively) are useful for obtaining identical or homologous fragments of polynucleotides from other species, and particularly from fungi (e.g., the grain-spoilage fungi, or the *Ectomycorrhizae*) which encode enzymes having phytase activity.

IV. Obtaining Derivative or Variant Phytate Hydrolyzing Enzymes

In one embodiment, the phytase proteins are derivative or variant phytase as compared to the wild-type sequence. That is, as outlined more fully below, the derivative phytase peptide will contain at least one amino acid substitution, deletion or insertion, with amino acid substitutions being particularly preferred. The amino acid substitution, insertion or deletion may occur at any residue within the phytase peptide.

Also included in an embodiment of phytase proteins of the present invention are amino acid sequence variants. These variants fall into one or more of three classes: substitutional, insertional or deletional variants. These variants ordinarily are prepared by site specific mutagenesis of nucleotides in the DNA encoding the phytase protein, using cassette or PCR mutagenesis or other techniques well known in the art, to produce DNA encoding the variant, and thereafter expressing the DNA in recombinant cell culture as outlined above. However, variant phytase protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the phytase protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed variants screened for the optimal combination of desired activity. Techniques for making substitution mutations at predetermined sites in DNA having a known sequence are well known, for example, M13 primer mutagenesis and PCR mutagenesis. Screening of the mutants is done using assays of phytase protein activities.

Amino acid substitutions are typically of single residues; insertions usually will be on the order of from about 1 to 20 amino acids, although considerably larger insertions may be tolerated, and may occur internally or at either terminus of the encoded protein. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the phytase are desired, substitutions are generally made in accordance with the following chart of conservative substitution residues:

CHART I

| Original Residue | Exemplary Substitutions |
|---|---|
| Ala | Ser |
| Arg | Lys |
| Asn | Gln, His |
| Asp | Glu |
| Cys | Ser |

CHART I-continued

| Original Residue | Exemplary Substitutions |
| --- | --- |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and may elicit the same immune response as the naturally-occurring analogue, although variants also are selected to modify the characteristics of the phytase proteins as needed. Alternatively, the variant may be designed such that the biological activity of the phytase is altered. For example, glycosylation sites may be altered or removed. Such alterations may result in altered immunogenicity, as well.

Covalent modifications of phytase polypeptides are included within the scope of this invention. One type of covalent modification includes reacting targeted amino acid residues of a phytase polypeptide with an organic derivatizing agent that is capable of reacting with selected side chains or the N- or C-terminal residues of a phytase polypeptide. Derivatization with bifunctional agents is useful, for instance, for crosslinking a phytase to another protein. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl, threonyl or tyrosyl residues, methylation of the α-amino groups of lysine, arginine, and histidine side chains [T.E. Creighton, Proteins: Structure and Molecular Properties, W.H. Freeman & Co., San Francisco, pp. 79-86 (1983)], acetylation of the N-terminal amine, and amidation of any C-terminal carboxyl group.

Another type of covalent modification of the phytase polypeptide included within the scope of this invention comprises altering the native glycosylation pattern of the polypeptide. "Altering the native glycosylation pattern" is intended for purposes herein to mean deleting one or more carbohydrate moieties found in native phytase, and/or adding one or more glycosylation sites that are not present in the native polypeptide.

Addition of glycosylation sites to polypeptides may be accomplished by altering the amino acid sequence thereof. The alteration may be made, for example, by the addition of, or substitution by, one or more serine or threonine residues to the native sequence phytase polypeptide (for O-linked glycosylation sites). The phytase amino acid sequence may optionally be altered through changes at the DNA level, particularly by mutating the DNA encoding the phytase polypeptide at preselected bases such that codons are generated that will translate into the desired amino acids.

Another means of increasing the number of carbohydrate moieties on the phytase polypeptide is by chemical or enzymatic coupling of glycosides to the polypeptide. Such methods are described in the art, e.g., in WO 87/05330 published 11 Sep. 1987, and in Aplin and Wriston, Crit. Rev. Biochem., pp. 259-306 (1981).

Removal of carbohydrate moieties present on the phytase may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of phytase comprises linking the phytase polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Phytases of the present invention may also be modified to form chimeric molecules comprising a phytase polypeptide fused to another, heterologous polypeptide or amino acid sequence. In one embodiment, such a chimeric molecule comprises a fusion of a phytase polypeptide with a tag polypeptide which provides an epitope to which an anti-tag antibody can selectively bind. The epitope tag is generally placed at the amino-or carboxyl-terminus of the phytase polypeptide. The presence of such epitope-tagged forms of a phytase can be detected using an antibody against the tag polypeptide. Also, provision of the epitope tag enables the phytase to be readily purified by affinity purification using an anti-tag antibody or another type of affinity matrix that binds to the epitope tag. In preferred embodiment, the chimeric molecule may comprise a fusion of a phytase polypeptide with an initial sequence or signal polypeptide, such as a secretion signal, of a different phytase or other protein. The fusion may involve the addition of a sequence from a protein, such as a phytase, which is native to the host cell in which the phytase is being expressed. Specific examples of this are provided in the Examples section, below.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology, 6:1204-1210 (1988)]; the KT3 epitope peptide [Martin et al., Science, 255:192-194 (1992)]; tubulin epitope peptide [Skinner et al., J. Biol. Chem., 266: 15163-15166 (1991)]; and the T7 gene 10 protein peptide tag [Lutz-Freyermuth et al., Proc. Natl. Acad. Sci. USA, 87:6393-6397 (1990)].

Also included with the definition of phytase in one embodiment are other phytase proteins from other organisms, which are cloned and expressed as outlined below. Thus, probe or degenerate polymerase chain reaction (PCR) primer sequences may be used to find other related phytases from fungi or other organisms. As will be appreciated by those in the art, particularly useful probe and/or PCR primer sequences include the highly conserved amino acid sequences and the known binding or catalytic sequences. For example, the phosphate binding region of phytase produced in various fungi is highly conserved. As is generally known in the art, preferred PCR primers are from about 15 to about 35 nucleotides in length, with from about 20 to about 30 being preferred, and may contain inosine as needed. The conditions for the PCR reaction are well known in the art.

V. Expression and Recovery of Phytate Hydrolyzing Enzymes

The polynucleotide sequences of the present invention may be expressed by operatively linking them to an expression control sequence in an appropriate expression vector and employed in that expression vector to transform an appropriate host according to techniques well established in the art. The polypeptides produced on expression of the DNA sequences of this invention can be isolated from the fermentation of cell cultures and purified in a variety of ways according to well established techniques in the art. One of skill in the art is capable of selecting the most appropriate isolation and purification techniques.

More particularly, the present invention provides host cells, expression methods and systems for the production of phytate hydrolyzing enzymes derived from microorganisms, such as *Penicillium, Fusarium* and *Humicola* species. Once a nucleic acid sequence encoding a phytate hydrolyzing enzyme of the present invention is obtained, recombinant host cells containing the nucleic acid sequence may be constructed using techniques well known in the art. Molecular biology techniques are disclosed in Sambrook et al., Molecular Biology Cloning: A Laboratory Manual, Second Edition (1989) Cold Spring Harbor Laboratory Press, Cold Spring Harbor, N.Y. (1989) and Sambrook et al., Molecular Cloning, A Laboratory Manual, 3d Ed., Cold Spring Harbor Laboratory Press, Cold Spring Harbor, N.Y. (2001).

In one embodiment, nucleic acid sequences encoding phytate hydrolyzing enzymes derived from *Penicillium, Fusarium* and *Humicola* species and having at least 65%, at least 70%, at least 75%, at least 80%, at least 85%, at least 90% and at least 95% identity to the nucleic acid sequence of any one of FIGS. 1, 4, 7 and 9 (SEQ ID NO:1, 4, 7, and 9, respectively) or a functional derivative thereof, or which is capable of hybridizing under conditions of intermediate to high stringency to the nucleic acid sequence of any one of FIGS. 1, 4, 7 and 9 (SEQ ID NO:1, 4, 7, and 9, respectively), or which is complementary to the nucleic acid sequence of any one of FIGS. 1, 4, 7 and 9 (SEQ ID NO:1, 4, 7, and 9, respectively) is obtained and transformed into a host cell using appropriate vectors.

The nucleic acid sequences encoding phytate hydrolyzing enzymes can include a leader sequence capable of providing for the secretion of the encoded phytase. Depending on whether the phytase is to be expressed intracellularly or is secreted, a DNA sequence or expression vector of the invention can be engineered such that the mature form of the phytase is expressed with or without a natural phytase signal sequence or a signal sequence which functions in a fungus (e.g., *Aspergillus niger*, other prokaryotes or eukaryotes. Expression can also be achieved by either removing or partially removing said signal sequence.

A variety of vectors and transformation and expression cassettes suitable for the cloning, transformation and expression in fungus, yeast, bacteria, insect and plant cells are known by those of skill in the art. Typically, the vector or cassette contains sequences directing transcription and translation of the nucleic acid sequence, a selectable marker, and sequences allowing autonomous replication or chromosomal integration. Suitable vectors comprise a region 5' of the gene which harbors transcriptional initiation controls and a region 3' of the DNA fragment which controls transcriptional termination. These control regions may be derived from genes homologous or heterologous to the host as long as the control region selected is able to function in the host cell.

Initiation control regions or promoters, which are useful to drive expression of the phytate hydrolyzing enzymes in a host cell are known to those skilled in the art. A nucleic acid sequence encoding the phytate hydrolyzing enzyme is linked operably through initiation codons to selected expression control regions for effective expression of such enzyme. Once suitable cassettes are constructed, they are used to transform the host cell.

In cases where plant expression vectors are used, the expression of a sequence encoding phytase may be driven by any of a number of promoters. For example, viral promoters such as the 35S and 19S promoters of CaMV (Brisson et al. (1984) Nature 310:511-514) may be used alone or in combination with the omega leader sequence from TMV (Takamatsu et al. (1987) EMBO J. 6:307-311). Alternatively, plant promoters such as the small subunit of RUBISCO (Coruzzi et al. (1984) EMBO J. 3:1671-1680; Broglie et al. (1984) Science 224:838-843); or heat shock promoters (Winter J and Sinibaldi R M (1991) Results Probl Cell Differ 17:85-105) may be used. These constructs can be introduced into plant cells by direct DNA transformation or pathogen-mediated transfection. For reviews of such techniques, see Hobbs S or Murry L E (1992) in McGraw Hill Yearbook of Science and Technology, McGraw Hill, New York, N.Y., pp 191-196; or Weissbach and Weissbach (1988) Methods for Plant Molecular Biology, Academic Press, New York, N.Y., pp 421-463.

General transformation procedures are taught in Current Protocols In Molecular Biology (3rd edition, edited by Ausubel et al., John Wiley & Sons, Inc. 1995, Chapter 9) and include calcium phosphate methods, transformation using PEG and electroporation.

For *Aspergillus* and *Trichoderma*, PEG and Calcium mediated protoplast transformation can be used (Finkelstein, D B 1992 Transformation. In Biotechnology of Filamentous Fungi. Technology and Products (eds by Finkelstein & Bill) 113-156. Electroporation of protoplast is disclosed in Finkelstein, D B 1992 Transformation. In Biotechnology of Filamentous Fungi. Technology and Products (eds by Finkelstein & Bill) 113-156. Microprojection bombardment on conidia is described in Fungaro et al. (1995) Transformation of *Aspergillus nidulans* by microprojection bombardment on intact conidia, FEMS Microbiology Letters 125 293-298. *Agrobacterium* mediated transformation is disclosed in Groot et al. (1998) *Agrobacterium tumefaciens*-mediated transformation of filamentous fungi, Nature Biotechnology 16 839-842 and U.S. Pat. No. 6,255,115. For transformation of *Saccharomyces*, lithium acetate mediated transformation and PEG and calcium mediated protoplast transformation as well as electroporation techniques are known by those of skill in the art.

Host cells which contain the coding sequence for a phytate hydrolyzing enzyme of the present invention and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid sequence or protein.

It should also be noted that the invention contemplates in vitro expression of the phytase enzymes described herein.

In preferred embodiments of the invention, phytase is produced in fungal cells. In one embodiment of the present invention, a polynucleotide sequence encoding a phytate hydrolyzing enzyme derived from *Penicillium chrysogenum* (deposit No. NRRL 1951) is isolated and expressed in *Aspergillus niger*, and in another embodiment is expressed in *Aspergillus nidulans*. In another embodiment, a polynucleotide sequence encoding a phytate hydrolyzing enzyme derived from *Fusarium javanicum* (deposit No. CBS 203.32) or *Fusarium vertisillibodes* is isolated and expressed. In yet another embodiment, a polynucleotide sequence encoding a phytate hydrolyzing enzyme derived from *Humicola grisea* (deposit No. ATCC 22081) is isolated and expressed. The expressed phytase can then be recovered, e.g., as described below.

In preferred embodiments of the invention, the phytase is expressed in plants. Transgenic plant, as used herein, refers to a plant that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually). It is understood that the term transgenic plant encompasses the entire plant and parts of said plant, for instance grains, seeds, flowers, leaves, roots, fruit, pollen, stems, etc.

The present invention is applicable to both dicotyledonous plants (e.g. tomato, potato, soybean, cotton, tobacco, etc.) and monocotyledonous plants, including, but not limited to graminaceous monocots such as wheat (*Triticum* spp.), rice (*Oryza* spp.), barley (*Hordeum* spp.), oat (*Avena* spp.), rye (*Secale* spp.), corn (*Zea mays*), sorghum (*Sorghum* spp.) and millet (*Pennisetum* spp). For example, the present invention can be employed with barley genotypes including, but not limited to Morex, Harrington, Crystal, Stander, Moravian III, Galena, Salome, Steptoe, Klages, Baronesse, and with wheat genotypes including, but not limited to Yecora Rojo, Bobwhite, Karl and Anza. In general, the invention is particularly useful in cereals.

Standard molecular biology methods and plant transformation techniques can be used to produce transgenic plants that produce seeds containing phytase protein. The following description provides general guidance as to the selection of particular constructs and transformation procedures.

The present invention utilizes recombinant constructs that are suitable for obtaining expression of phytase in plant seeds relative to non-transformed plant seeds. In their most basic form, these constructs may be represented as Pr-Ph, wherein Pr is a seed-specific promoter and Ph is a nucleic acid sequence encoding phytase. In another embodiment, a peptide signal sequence that targets expression of the phytase polypeptide to an intracellular body may be employed. Such constructs may be represented as Pr-SS-Ph, wherein SS is the signal peptide. Nucleic acid molecules that may be used as the source of each of these components are described in the Definitions section above.

Each component is operably linked to the next. For example, where the construct comprises the hordein D-promoter (P), the hordein D-signal sequence (SS) encoding the hordein signal peptide, and an open reading frame encoding a phytase (Ph), the hordein promoter is linked to the 5' end of the sequence encoding the hordein signal sequence, and the hordein signal sequence is operably linked to the 5' end of the phytase open reading frame, such that C terminus of the signal peptide is joined to the N-terminus of the encoded protein.

The construct will also typically include a transcriptional termination region following the 3' end of the encoded protein ORF. Illustrative transcriptional termination regions include the nos terminator from *Agrobacterium* Ti plasmid and the rice alpha-amylase terminator.

Standard molecular biology methods, such as the polymerase chain reaction, restriction enzyme digestion, and/or ligation may be employed to produce these constructs comprising any nucleic acid molecule or sequence encoding a phytase protein or polypeptide.

Introduction of the selected construct into plants is typically achieved using standard transformation techniques. The basic approach is to: (a) clone the construct into a transformation vector; which (b) is then introduced into plant cells by one of a number of techniques (e.g., electroporation, microparticle bombardment, *Agrobacterium* infection); (c) identify the transformed plant cells; (d) regenerate whole plants from the identified plant cells, and (d) select progeny plants containing the introduced construct. Preferably all or part of the transformation vector will stably integrate into the genome of the plant cell. That part of the transformation vector which integrates into the plant cell and which contains the introduced Pr-Ph or Pr-SS-Ph sequence (the introduced "phytase transgene") may be referred to as the recombinant expression cassette.

Selection of progeny plants containing the introduced transgene may be made based upon the detection of phytase expression in seeds, or upon enhanced resistance to a chemical agent (such as an antibiotic) as a result of the inclusion of a dominant selectable marker gene incorporated into the transformation vector.

Successful examples of the modification of plant characteristics by transformation with cloned nucleic acid sequences are replete in the technical and scientific literature. Selected examples, which serve to illustrate the knowledge in this field of technology include:

U.S. Pat. No. 5,571,706 ("Plant Virus Resistance Gene and Methods");

U.S. Pat. No. 5,677,175 ("Plant Pathogen Induced Proteins");

U.S. Pat. No. 5,510,471 ("Chimeric Gene for the Transformation of Plants");

U.S. Pat. No. 5,750,386 ("Pathogen-Resistant Transgenic Plants");

U.S. Pat. No. 5,597,945 ("Plants Genetically Enhanced for Disease Resistance");

U.S. Pat. No. 5,589,615 ("Process for the Production of Transgenic Plants with Increased Nutritional Value Via the Expression of Modified 2S Storage Albumins");

U.S. Pat. No. 5,750,871 ("Transformation and Foreign Gene Expression in *Brassica* Species");.

U.S. Pat. No. 5,268,526 ("Over expression of Phytochrome in Transgenic Plants");

U.S. Pat. No. 5,780,708 ("Fertile Transgenic Corn Plants");

U.S. Pat. No. 5,538,880 ("Method For Preparing Fertile Transgenic Corn Plants");

U.S. Pat. No. 5,773,269 ("Fertile Transgenic Oat Plants");

U.S. Pat. No. 5,736,369 ("Method For Producing Transgenic Cereal Plants");

U.S. Pat. No. 5,610,049 ("Methods For Stable Transformation of Wheat").

These examples include descriptions of transformation vector selection, transformation techniques and the construction of constructs designed to express an introduced transgene.

The transgene-expressing constructs of the present invention may be usefully expressed in a wide range of higher plants to obtain seed- or grain-specific expression of selected polypeptides. The invention is expected to be particularly applicable to monocotyledonous cereal plants including barley, wheat, rice, rye, maize, triticale, millet, sorghum, oat, forage, and turf grasses. In particular, the transformation methods described herein will enable the invention to be used with genotypes of barley including Morex, Harrington, Crystal, Stander, Moravian III, Galena, Golden Promise, Steptoe, Klages and Baronesse, and commercially important wheat genotypes including Yecora Rojo, Bobwhite, Karl and Anza.

The invention may also be applied to dicotyledenous plants, including, but not limited to, soybean, sugar beet, cotton, beans, rape/canola, alfalfa, flax, sunflower, safflower, *brassica*, cotton, flax, peanut, clover; vegetables such as lettuce, tomato, cucurbits, cassaya, potato, carrot, radish, pea, lentils, cabbage, cauliflower, broccoli, Brussels sprouts, peppers; and tree fruits such as citrus, apples, pears, peaches, apricots, and walnuts.

A number of recombinant vectors suitable for stable transformation of plant cells or for the establishment of transgenic plants have been described including those described in Weissbach and Weissbach, (1988), and Gelvin et al., J. Bacteriol. 172(3):1600-1608 (1990). Typically, plant transformation vectors include one or more ORFs under the transcriptional control of 5' and 3' regulatory sequences and a dominant selectable marker with 5' and 3' regulatory sequences. The selection of suitable 5' and 3' regulatory sequences for constructs of the present invention is discussed above. Dominant selectable marker genes that allow for the ready selection of transformants include those encoding antibiotic resistance genes (e.g., resistance to hygromycin, kanamycin, bleomycin, G418, streptomycin or spectinomycin) and herbicide resistance genes (e.g, phosphinothricin acetyltransferase).

Methods for the transformation and regeneration of both monocotyledonous and dicotyledonous plant cells are known, and the appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium* mediated transformation. Typical procedures for transforming and regenerating plants are described in the patent documents listed at the beginning of this section.

Following transformation, transformants are preferably selected using a dominant selectable marker. Typically, such a marker will confer antibiotic or herbicide resistance on the seedlings of transformed plants, and selection of transformants can be accomplished by exposing the seedlings to appropriate concentrations of the antibiotic or herbicide. After transformed plants are selected and grown to maturity to allow seed set, the seeds can be harvested and assayed for expression of phytase.

The phytase of the invention can be recovered from culture medium or from host cell lysates. If membrane-bound, it can be released from the membrane using a suitable detergent solution (e.g. Triton-X 100) or by enzymatic cleavage. Cells employed in expression of phytase can be disrupted by various physical or chemical means, such as freeze-thaw cycling, sonication, mechanical disruption, or cell lysing agents. It may be desired to purify the phytase from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants; and metal chelating columns to bind epitope-tagged forms of the phytase. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular form of phytase produced.

In a preferred embodiment, the phytase(s) is/are produced in transgenic non-human animals. Methods of producing such transgenic animals are described, for example, in U.S. Pat. No. 6,291,740. Methods for the successful production of transgenic bovine (e.g., U.S. Pat. Nos. 6,080,912 and 6,066,725), swine (e.g., U.S. Pat. Nos. 6,271,436 and 5,942,435), goats (e.g., U.S. Pat. No. 5,907,080) and fish (e.g., U.S. Pat. No. 5,998,697) are available in the art. Furthermore, organ-specific expression, particularly expression in milk produced by the transgenic animals, is within the skill of the ordinary artisan (e.g., e.g., U.S. Pat. Nos. 6,268,545 and 6,262,336). The disclosure of each of these patents is incorporated herein in its entirety.

VI. Assaying for Phytase Activity

Assays for phytase activity are well known in the art. Perhaps the most widely used is the classic assay for liberation of inorganic phosphate developed by Fiske and SubbaRow, *Journal of Biological Chemistry* 66:375-392 (1925). A variation of this method is found in Mitchell et al., *Microbiol.* 143:245-252 (1997). A preferred method is described in *Food Chemicals Codex*, 4th Edition, Committee on Food Chemicals Codex, Institute of Medicine, National Academy Press, Washington, D.C., 1996 at pages 809-810. Each of these references are incorporated herein.

Generally, the assay involves allowing a measured weight or volume of a phytase sample to react with phytate in solution for a measured period of time. The reaction is stopped and a color solution containing ammonium molybdate (AM) is added to the reaction solution. Colorimetry is then performed using a spectrophotometer and compared to controls of known concentration of inorganic phosphate ($P_i$) and/or controls produced by reactions with enzymes having known phytase activity. A Unit of activity is determined as the amount of enzyme sample required to liberate 1 μmol $P_i$ per minute from phytate under defined reaction conditions.

Enzyme reactions are frequently run at pH 5.5 and 37° C. However, pH and temperature conditions may be varied to determine optimum reaction conditions and tolerances for a given phytase. When different reaction conditions are tested, Units of activity should still be related to a single specific set of reaction conditions.

The reaction may be stopped and then the color solution added, or a stop/color solution may be used that both arrests the enzyme activity and adds a product whose spectral absorbance is measurably affected by the concentration of $P_i$ in a predictable and calculatable manner. As discussed above, the color solutions generally contain AM. Various examples of such solutions are available in the relevant literature. In U.S. Pat. No. 6,039,942, the reaction is stopped using trichloroactetate (TCA) and the color solution added thereafter contained ferrous sulfate and AM. In other examples wherein the reaction was first stopped with TCA, different color solution contained sulfuric acid, AM and ascorbic acid (U.S. Pat. No. 6,221,644) and sulfuric acid, AM and ferrous sulfate (U.S. Pat. No. 6,190,897). In other cases, the color and stop solution are the same. For example, in both U.S. Pat. Nos. 6,139,902 and 6,261,592, the solution contained sulfuric acid, AM and acetone, after which a solution containing acetic acid was added. In a preferred embodiment, the color/stop solution contains ammonium vanadate, AM and nitric acid (see *Food Chemicals Codex*, above).

Wavelength-specific absorption by the final solution, containing the reaction solution and stop/color solution(s), is measured using a spectrophotometer. Many such instruments are available and their use is routine in the art. The wavelength used for absorption measurement can vary with the components of the color solution. For example, the references cited above measured absorbance at 380, 415, 690, 700 or 750 nm. Any of these may provide adequate indication of $P_i$ concentration in these solutions. However, the wavelength used should generally be the one described in a given protocol. The skilled artisan can easily determine empirically which wavelength provides optimum discrimination of differences in $P_i$ concentration by comparing the linearity of absorption change between serially diluted control solutions of known $P_i$ concentration at different wavelengths.

VII. Applications of Phytate Hydrolyzing Enzymes

The phytase and derivatives thereof as taught herein can be used in a variety of applications where it is desirable to separate phosphorous from phytate. Several exemplary applications are set forth below.

For example, the invention provides for the use of cells or spores capable of producing phytase according to the invention as a probiotic or direct fed microbial product. Preferred embodiments for said uses are phytase-producing *Aspergillus* sp. of the invention.

In addition, the invention contemplates the use of phytase as described herein in food or animal feed.

The present invention provides food or animal feed including phytase as described herein. Preferably, said food or animal feed comprises phytase as an additive which is active in the digestive tract, preferably the crop and/or small intestine, of livestock, such as poultry and swine, and aquatic farm animals including fish and shrimp. Said additive is also preferably active in food or feed processing.

In an alternative embodiment, phytase or phytase producing organisms are added as a pretreatment to food or animal feed, such as in the processing of the food or feed. In this embodiment, the phytase is active prior to consumption of the food or feed, but may or may not be active at the time the food or animal feed is consumed.

Compositions comprising polypeptides or proteins possessing phytase activity may be prepared in accordance with methods known in the art and may be in the form of a liquid or a dry composition. The polypeptide to be included in the composition may be stabilized in accordance with methods known in the art.

The invention additionally provides food or animal feed comprising cells, spores or plant parts, including seeds, capable of expressing phytase as described herein.

Still further, the present invention contemplates a method for the production of a food or animal feed, characterized in that phytase according to the invention is mixed with said food or animal feed. Said phytase is added as a dry product or as a liquid, before or after processing. According to one embodiment, wherein a dry powder is used, the enzyme is diluted as a liquid onto a dry carrier such as milled grain.

Liquid compositions need not contain anything more than the phytase enzyme, preferably in a purified form. Usually, however, a stabilizer such as glycerol, sorbitol or mono propylene glycol is also added. The liquid composition may also comprise one or more other additives, such as salts, sugars, preservatives, pH-adjusting agents (i.e., buffering agents), proteins, or phytate (a phytase substrate). Typical liquid composition are aqueous or oil-based slurries.

The liquid compositions can be added to a food or feed after an optional pelleting thereof. Dry compositions may be spray-dried compositions, in which case the composition need not contain anything more than the enzyme in a dry form. Usually, however, dry compositions are so-called granulates which may readily be mixed with for example food or feed components, or more preferably, form a component of a pre-mix. The particle size of the enzyme granulates preferably is compatible with that of the other components of the mixture. This provides a safe and convenient means of incorporating enzymes into for example an animal feed.

Agglomeration granules are prepared using agglomeration techniques in a high shear mixer (e.g., Lodige) during which a filler material and the enzyme are co-agglomerated to form granules. Absorption granulates are prepared by having cores of a carrier material to adsorb/be coated by the enzyme.

Typical filler materials are salts such as disodium sulphate. Other fillers are kaolin, talc, magnesium aluminum silicate and cellulose fibers. Optionally, binders such as dextrins are also included in agglomeration granules.

Typical carrier materials are starch, e.g., in the form of cassaya, corn, potato, rice and wheat. Salts may also be used.

Optionally, the granulates are coated with a coating mixture. Such mixture comprises coating agents, preferably hydrophobic coating agents, such as hydrogenated palm oil and beef tallow, and if desired other additives, such as calcium carbonate or kaolin.

Additionally, phytase compositions may contain other substituents such as coloring agents, aroma compounds, stabilizers, vitamins, minerals other feed or food enhancing enzymes and the like. This is so in particular for the so-called pre-mixes.

A "feed" and a "food," respectively, means any natural or artificial diet, meal or the like or components of such meals intended or suitable for being eaten, taken in, digested, by an animal and a human being, respectively.

A "food or feed additive" is an essentially pure compound or a multi component composition intended for or suitable for being added to food or feed. It usually comprises one or more compounds such as vitamins, minerals or feed enhancing enzymes and suitable carriers and/or excipients, and it is usually provided in a form that is suitable for being added to animal feed.

The phytases of the invention can also be used in poultry food to improve egg shell quality (reduction of losses due to breaking), see for example, The Merck Veterinary Manual (Seventh Edition, Merck & Co., Inc., Rahway, N.J., USA, 1991, page 1268); Jeroch et al. Bodenkultur Vo. 45(4):361-368 (1994); Poultry Science, 75(1):62-68 (1996); Canadian Journal of Animal Science 75(3):439-444 (1995); Poultry Science 74(5):784-787 (1995) and Poultry Science 73(10): 1590-1596 (1994).

An effective amount of the polypeptide in food or feed is typically from about 10 to 50,000 U/kg feed or food; preferably from about 10 to 15,000, more preferably from about 10 to 10,000, in particular from about 100 to 5,000, especially from about 100 to about 2,000 U/kg feed or food.

The present invention also provides a method for the production of a food or animal feed, characterized in that cells, plant parts, including seeds, and/or spores capable of expressing phytase according to the invention are added to said food or animal feed. Such cells or spores, may be of any origin, bacterial, plant, or animal.

Further, the present invention provides for the use of the phytase described herein with or without accessory phosphatases in the production of inositol and inorganic phosphate, and phytate intermediates.

Also provided is a method for the reduction of levels of phosphorous in animal manure, characterized in that an animal is fed an animal feed according to the invention in an amount effective in converting phytate contained in said animal feed.

In one embodiment, the transgene protein, for example phytase expressed in plants, especially seeds or grains, using the methods described herein, is used in the production and synthesis of phytase. The phytase transgene expressed by the recombinant nucleic acid of the invention may be harvested at any point after expression of the protein has commenced. When harvesting from the seed or grain or other part of a plant for example, it is not necessary for the seed or grain or other part of the plant to have undergone maturation prior to harvesting. For example, transgene expression may occur prior to seed or grain maturation or may reach optimal levels prior to seed or grain maturation. The transgene protein may be isolated from the seeds or grain, if desired, by conventional protein purification methods. For example, the seed or grain can be milled, then extracted with an aqueous or organic extraction medium, followed by purification of the extracted phytase protein. Alternatively, depending on the nature of the intended use, the transgene protein may be partially purified, or the seed or grain may be used directly without purification of the transgene protein for food or animal feed, food processing or other purposes.

Alpha-amylases break down starch 1-4 linkages. Amylases are enzymes fundamental to the brewing and baking industries. Amylases are required to break down starch in malting and in certain baking procedures carried out in the absence of added sugars or other carbohydrates. Obtaining adequate activity of these enzymes is problematic especially in the malting industry. It has been known for some time that phytate has an inhibitory effect on amylases. A method of adequately increasing the activity of amylases with a physiologically acceptable system, leads to more rapid malting methods and, owing to increased sugar availability, to alcoholic beverages such as beers with reduced carbohydrate content.

Accordingly, seeds or grains with phytase expression provide advantages in the production of malt and beverages produced by a fermentation process. Enhanced activity of amylases in grain increases the speed and efficiency of germination, important in malting, where malt is produced having increased enzymatic activity resulting in enhanced hydrolysis of starch to fermentable carbohydrates, thereby, improving the efficiency of fermentation in the production of alcoholic beverages, for example, beer and scotch whiskey. Enhanced fermentation processes also find use in the production of alcohols that are not intended for human consumption, i.e., industrial alcohols.

The phytase and phytate-derived intermediates of the invention also find use in many other agricultural, industrial, medical and nutritional applications. For example phytase and phytate-derived intermediates can be used in grain wet milling. Phytate is used in cleaning products, rust removal products and in the removal of metals and other polycations from such diverse materials as waste products and carbonated beverages. Phytate and phytases may be used in the isolation and recovery of rare metals. Phytase may be used to produce lower phosphate homologs of phytate, which may be used in dentifrice and other dental care products as well as potential treatments or preventatives of bone resorption (e.g., in osteoporosis) and renal calculi (kidney stones). Phytate and derivatives have found use in the production of tofu, and chelation of minerals (e.g., iron, zinc, calcium or magnesium) with phytate, followed by release with addition of phytase may provide a unique means of providing these nutrients. Phytases may be used in the production of inositol from phytate its use in food products. Phytases may also be used in the chemical and biochemical synthesis of phosphate containing materials. Phytase, phytate and lower phosphate phytate derivatives find many other uses in personal care products, medical products and food and nutritional products, as well as various industrial applications, particularly in the cleaning, textile, lithographic and chemical arts.

The following examples are offered for illustrative purposes only, and are not intended to limit the scope of the present invention in any way. The skilled artisan will appreciate that the methods disclosed may be applied to any number of different species, including to obtain all sequences disclosed herein. All patent and literature references cited in the present specification are hereby incorporated by reference in their entirety.

EXAMPLES

Example 1

Preparation of Genomic DNA Encoding Phytases

Genomic DNA was prepared for several different microorganisms for the purpose of undertaking a PCR reaction to determine whether phytases are encoded by the DNA for a particular organism.

Genomic DNA is obtained from *Penicillium chrysogenum* (deposit no. NRRL 1951); *Fusarium javanicum* (deposit no. CBS 203.32); *Fusarium vertisillibodes; Humicola grisea* var. *thermoidia* deposit no. CBS 225.63 or ATCC 22081; and *Emericella desertorum* deposit no. CBS 653.73 and isolated according to standard methods.

Alignments were performed for several known phytase sequences, including those from *Aspergillus Niger/Aspergillus ficum*, *Aspergillus terreus* 59, *Aspergillus terreus* 60, *Aspergillus fumigatus*, *Aspergillus niger*, *Emericella nidulans*, *Talaromyces thermophylus* and *Myceliopthora thermophila*. From these, several "boxes" were identified as being largely conserved, and from these primers were developed.

The following DNA primers were constructed for use in amplification of phytase genes from the libraries constructed from the various microorganisms. All symbols used herein for protein and DNA sequences correspond to IUPAC IUB Biochemical Nomenclature Commission codes.

```
BOX1: primers coding for (V/L)L(A/S)RHGAR
(SEQ ID NO:51)
forward primer
BTIYTIKCIMGICAYGGIHCIMG      (SEQ ID NO:52)

forward primer
BTIYTIAGYMGICAYGGIHCIMG      (SEQ ID NO:53)

BOX2: primers coding for NNTL(D/E/H)
(SEQ ID NO:54)
forward primer
AAYAAYACIYTISA               (SEQ ID NO:55)

reverse primer
TSIARIGTRTTRTT               (SEQ ID NO:56)

BOX3: primers coding for LSPFC
(SEQ ID NO:57)
forward primer
YTTTCICCITTYTGY              (SEQ ID NO:58)

forward primer
YTIAGYCCITTYTGY              (SEQ ID NO:59)

reverse primer
RCARAAIGGIGAIAR              (SEQ ID NO:60)

reverse primer
RCARAAIGGRCTIAR              (SEQ ID NO:61)

BOX4: primers coding for G(N/S)PLGP
(SEQ ID NO:62)
forward primer
GGIWVICCIYTIGGICC            (SEQ ID NO:63)

reverse primer
CCIARIGGIBWICC               (SEQ ID NO:64)

BOX5: primers coding for DFSHD
(SEQ ID NO:65)
forward primer
GAYTTYTCICAYGAY              (SEQ ID NO:66)

forward primer
GAYTTYAGYCAYGAY              (SEQ ID NO:67)

reverse primer
RTCRTGIGARAARTC              (SEQ ID NO:68)

reverse primer
RTCRTGRCTRAARTC              (SEQ ID NO:69)

BOX6: primers coding for VR(A/V)I(I/V)NDR
(SEQ ID NO:70)
reverse primer
CKRTCRTTIAYIARIRCICKIAC      (SEQ ID NO:71)
```

Boxes were also developed according to the methods of Pasamontes et al. *Appl. Evir. Microbial.* 63(5):1696-1700 (1997) (expressly incorporated herein) to provide the following primers.

```
BOX2.5: coding for MDMCSFD (SEQ ID NO:72)
forward primer
ATGGAYATGTGYTCNTTYGA         (SEQ ID NO:73)

BOX4': coding for YGHGAG (SEQ ID NO:74)
reverse primer
TTRCCRGCRCCRTGNCCRTA         (SEQ ID NO:75)
```

PCR is performed on a standard PCR machine such as the PTC-150 Mini Cycler from MJ Research Inc. (Watertown, Mass.) or an Eppendorf Mastercycler (Hamburg, Germany). In the experiments described below, PCR was performed using a Hybaid Touchdown thermocycler (Middlesex, UK).

PCR conditions for Pwo polymerase (Boehringer Mannheim, Cat # 1644-947) comprise a 100 microliter solution made of 10 microliter of 10× reaction buffer (10× reaction buffer comprising 100 mM Tris HCl, pH 8-8.5; 250 mM KCl; 50 mM $(NH_4)_2SO_4$; 20 mM $MgSO_4$); 0.2 mM each of dATP, dTTP, dGTP, dCTP (final concentration), 1 microliter of 100 nanogram/microliter genomic DNA, 1 microliter of PWO at 1 unit per microliter, 500 mM primers (final concentration) and water to 100 microliters. The solution is overlaid with mineral oil.

Two approaches were developed for amplification of phytase genes from the genomic DNA:

A) A first PCR is run using BOX1 and BOX6 primers; the products are run on an agarose gel and approximately 1 kb fragments are isolated and run in a second PCR using nested primers. For the second PCR run, best results were obtained using primers from BOX1-BOX5 or from BOX5-BOX6 or BOX2.5/BOX4'.

Protocol A:
PCR1:
2' at 94° C. (1 cycle)
45" at 94° C.; 1'30" at 40° C.; 1'30" at 72° C. (30 cycles)
7' at 72° C. (1 cycle)
hold at 4° C.

Fragments were put on a 1% low melting gel and fragments around the expected size (0.0-1.2 kb) were sliced from the gel, isolated and used as a template for the second PCR run (PCR2). PCR 2 followed the same cycling protocol as PCR1.

B) Touchdown PCR was performed using BOX2.5/BOX4' primers. Using this technique, a specific fragment could be isolated, cloned into a TOPO vector (Invitrogen Corp., Carlsbad, Calif.), and sequenced without further processing.

Protocol B:
3' at 95° C. (1 cycle)
1' at 95° C.; 1' at 60° C., decreasing to 50° C.; 30" at 72° C. (20 cycles, so that the temperature dropped 0.5° C. each cycle in the annealing step)
1' at 95° C.; 1' at 50° C.; 30" at 72° C. (10 cycles)
hold at 4° C.

From the sequenced fragments, it was possible to use the RAGE technique (rapid amplification of genomic ends) to rapidly obtain the sequence of the full length gene. Using the GenomeWalker™ Kit from Clontech Laboratories, Inc (Palo Alto, Calif.) and manufacturer's protocol (GenomeWalker™ Kits User Manual, published Nov. 10, 1999, expressly incorporated herein), adapter ligations were derived from the fragment sequences to further determine upstream gene sequence. Sequences of phytase genes were determined from chromosomal DNA of various species.

FIG. 22 shows the phytase polynucleotide sequence of E desertorum (SEQ ID NO:47) obtained by the above methods and the sequences therein from which adapter ligations (primers GSP1 rev:fyt037 and GSP2rev:fyt036) were derived to obtain the upstream sequences encoding this phytase (see FIG. 17A).

FIG. 23 shows the phytase sequence of *F. javanicum* (SEQ ID NO:49) obtained by the above methods and the sequences therein from which adapter ligations (primers GSP1 rev: fyt039 and GSP2rev:fyt038) were derived to obtain the upstream sequences encoding this phytase (see FIGS. 18A-18B).

Example 5

Evidence of Phytate Hydrolyzing Activity in Liquid Culture

A selected fungal species is grown in defined media containing various concentrations of inorganic phosphate, and growth characteristics and phytase production are assayed and compared. Spore suspensions are used ($2 \times 10^6$ spores/ml final con) to inoculate a minimal media (Vogels) where the phosphate concentration is altered to see how this will affect growth and phytase production. Cultures are grown in 50 ml of medium in shake flask culture at 25° C. to 30° C. Cultures are harvested at 24, 48, 72 and 96 hours. Culture supernatants are assayed for phytase activity using the method of Fiske and SubbaRow, *Journal of Biological Chemistry* 66:375-392 (1925). Growth may be determined: by dry weight or OD readings.

5A. Effect of Different Media Conditions on Growth and Morphology

A series of fungal growth curves are produced to look at the effect of available P in the medium on growth and phytase production. In some instances, when the P level is reduced, morphological changes in the growth of the fungus are observed which are associated with a stressed condition (e.g., mycelial fragmentation, pelleting, heterogeneous growth and an overall appearance of a pale yellow color). This physiological strain may be related to the appearance of phytase activity at a point in the growth curve, for example approaching late exponential phase. Morphological evidence of phytic acid utilization may be observed in cultures of low P (e.g., 0.57 mM) supplemented after 24 hours growth with 1 mM phytate as a phosphorus source. The morphological changes seen without added phytate may not be apparent, indeed the supplement samples may resemble cultures in media of higher P which were not limiting. This response would indicate that a phytic acid specific hydrolyzing activity was being produced so that P could be supplied to the growing fungus. As a caveat, it is possible that higher concentrations of phytate (e.g., 5 mM) supplementing the cultures result in a lack of cell growth. Such a result would suggest that the high level of phytate in the medium chelates essential minerals resulting in a medium that cannot support fungal growth and nutrition.

In an exemplary study, the fungus is grown in media containing
High phosphate (1.14 mM)
Low phosphate (0.57 mM)
Low phosphate plus 1 mM supplemented phytate.

Growth is monitored over 0, 24, 48, 72 and 96 hours by dry weight measurements, and the morphological characteristics in response to the different media conditions are also observed. In a situation where phytate hydrolyzing activity which allows the fungus to access phosphate from phytate, and so circumvent phosphate starvation stresses that the culture may otherwise experience, the major observations that would be expected are:

1. Good growth in high phosphate, consistent fungal morphology indicative of healthy culture.
2. Markedly poorer growth in low phosphate condition, fungal morphology heterogenous with evidence of clumping and mycelial fragmentation. The culture may have a sickly yellow appearance.
3. Similar cultures as for (2), when supplemented with phytate (the substrate), no longer appear to be under the same physiological stress. Biomass growth is similar to condition (1) and the fungal morphology is the same as for the high phosphate condition.
4. Growth curves and photographic evidence support these observations.

5B. Phytase Activity in Culture Supernatants

Phytase activity in the supernatants of fungi growing on media with variable levels of inorganic P can be measured. Supernatant samples are used to compare activities at a specified time post inoculation. Phytase activity may be expressed as the number of mmoles P released per minute per ml culture supernatant. Sample activities are calculated from triplicate culture flasks where supernatants are assayed for phytase in duplicate. Activities are shown as mean_SD. Along with the observations above, a clear physiological stress associated with cultures where phosphate is limited, which adversely affected growth, may be observed and linked to the appearance of phytase activity.

5C. Concentration of Culture Supernatants

Additional evidence of phytase activity can be expected from concentrated supernatant (concentrated protein). For example, concentrated protein samples can be obtained from:
1. Cultures of fungus from conditions of stress and low phosphate (where phytase is expected to be expressed),
2. Cultures of fungus of high phosphate and no stress, where phytase is not expected to be produced, and
3. Cultures supplemented with low phosphate and supplemental phytate.

Silver stained SDS-PAGE gels of these concentrated protein samples are expected to show a protein profile demonstrating the appearance of a protein band (putative phytase band) in concentrated protein from condition 1 (above) which is not present in condition 2. A similar appearance of this band is also expected in condition 3, albeit at a lower level. Based on the amino acid sequence of a specific phytase, and on whether it appears to be an extracellular enzyme, the size of the protein may be approximated. It should be noted, however, that glycosylation modification on the extracellular enzyme may increase the MW.

Example 6

PCR Amplification of Phytase Gene Fragments

6A Degenerate Primer Design

Based on alignments of published phytase amino acid sequences, a range of degenerate primers are designed against conserved structural and catalytic regions. Such regions included those that are highly conserved among the phytases, as well as those known to be important for enzyme structure and function.

For example, amino acid sequences for published phytases are aligned. It should be noted that many phytase sequences are publicly available from GenBank, and each is incorporated herein by reference.

Particular regions are chosen to meet the criteria above, and a range of forward and reverse primers designed from the amino acid sequences. Using the genetic code for codon usage, degenerate nucleotide PCR primers are synthesized.

As another example, primers are designed from the published amino acid sequence for different phytases from a single species (e.g., *A. niger*). These primers may be designed as follows:
1. Primer 1: Forward (5'-3') primer from, for example, the phosphate binding domain of a phytase, which should be essential for catalytic activity.
2. Primer 2: Reverse primer from a central phytase region which seems to be conserved relatively well.

All primers may be synthesized in the 5'-3' direction. The standard genetic code is used to change from amino acid to triplet codon, and standard IUB code for mixed base sites are used (e.g. to designate I for A/C/T/G).

As can be seen from the alignment of sequences for *A. niger* PhyA and PhyB, the phosphate-binding domain is well conserved with only a single amino acid difference between PhyA (RHGARYP; van Hartingsveldt et al., 1993, SEQ ID NO:76) and PhyB (RHGERYP; Piddington et al., 1993, SEQ ID NO:77). A degenerate primer may be designed complementary to this region in the PhyA version of the sequence only, i.e. using RHGARYPT (SEQ ID NO:78) as the basis for primer design. This would be to bias the primer towards a PhyA type phosphate binding domain. A second conserved region, which may serve as the basis for primer 2 for *A. niger*-derived primers, occurs in the middle of the PhyA and PhyB amino acid sequence. This conserved central phytase-specific domain in PhyA (FTHDEWI, SEQ ID NO:79) corresponds to amino acids 285-291. In PhyB, the amino acid sequence (FTQDEWV, SEQ ID NO:80) corresponds to amino acids 280-286.

Degenerate primers developed as described above may be used to amplify a phytase encoding region from other species by PCR, as described next.

6B. PCR amplification of Phytase Gene Fragments

Genomic DNA from a species of interest may be used as a template for PCR amplification of putative phytase gene fragments using combinations of primers made as described above. PCR is carried out using the PCR Ready-to-go Beads from Amersham Pharmacia. Conditions are determined by individual experiments, but typically thirty cycles are run in a Techne thermal cycler. Successful amplification is verified by electrophoresis of the PCR reaction on a 1% agarose gel. A PCR phytase product that is amplified by the primers may be anticipated by a correct expected size. The product is then purified by gel extraction using the Qiaquick Spin Gel Extraction kit from Qiagen. The purified PCR product is ligated into the commercial pGEM-T Easy vector System (Promega Corporation) to facilitate cloning. Ligation reactions are incubated at 4° C. overnight in a total volume of 10 ml containing 0.1 volumes of 10× ligase buffer and 1 ml (1 U.ml$^-$) of T4 DNA ligase. Typically insert DNA is used in the reaction in a 1-4:1 molar ratio of insert to vector DNA. A 100 ml aliquot of $CaCl_2$ competent *E. coli* XL-1 Blue cells are removed from −80° C. storage and thawed on ice for transformation. 3 ml of ligation mix is added to the cells and the mixture incubated on ice for 20 min. The cells are then heat shocked at 42° C. for 1 min. and returned to ice for 5 min. The transformation mixture is added to 0.9 mL of L-broth, and the cells incubated with shaking and without selection to allow expression of the ampicillin resistance gene product before selection is applied (37° C., 1 h). Aliquots of 200, 300 and 400 ml of this culture are then spread directly on selective agar plates. Plates are incubated at 37° C. overnight. Colonies containing recombinant plasmids are visualized using blue/white selection. For rapid screening of recombinant transformants, plasmid DNA is prepared from cultures of putative positive (white) colonies. DNA is isolated by the method of Birnboim and Doly following the protocol in Sambrook et al. (1989). The presence of the correct insert (650 bp) in the recombinant plasmid is confirmed by restriction analysis. DNA is digested with restriction enzymes (e.g., Not1-pPst1) overnight at 37° C., and digest products visualized by agarose gel electrophoresis. A number of clones may contain the correct sized insert and can be selected for manual sequencing to see if the insert is a phytase gene fragment. Inserts are sequenced using the dideoxy chain termination method of Sanger et al (1977) with a modified form of T7 DNA polymerase (Sequenase version 2.0). The reactions are carried out using reagents supplied in the Sequenase version 2;0 kit (Amersham Life Science-United States Biochemical Corporation), following the manufacturer's protocol. Partial sequence from the ends clones may indicate that a phytase gene fragment had been cloned. Full sequencing of the double-stranded inserts is performed on plasmid DNA from these clones.

6C. Sequence Analysis

The sequences are analyzed by BLAST and protein translation sequence tools. BLAST comparison at the nucleotide level may show various levels of homology to published phytase sequences. Initially, nucleotide sequences are submitted to BLAST (Basic BLAST version 2.0) by accessing the BLAST database on the world wide web. The web site used is at ncbi.nlm.nih.gov/cgi-bin/BLAST. The program chosen is blastn, and the database chosen is nr. Standard/default parameter values are employed. Sequence data for putative gene fragments are entered as sequence in FASTA format and the query submitted to BLAST to compare these sequences to those already in the database.

The sequences are then subjected to a DNA-to-protein translation tool called Protein machine. This tool is also available on the web at medkem.gu.se/edu/translat.html. Another suitable translation tool is known as Translation Machine, available on the web at www2.ebi.ac.uk/translate/. The DNA sequences of putative phytase gene fragments are inserted into the analysis block, and the standard genetic code is used as the basis for the translation. Translations are carried out in all three frames and on forward and reverse strands. The translated amino acid sequence is delivered on the screen by the analysis tool as amino acid sequence in one letter code. Ideally, analysis of the amino acid sequence will show that the fragment contains both correct ends (as used to design the primers), contains the essential P binding motif and perhaps other residues which are also present in published phytase sequences. From this, it may be concluded that the fragment cloned is a phytase gene fragment.

Sequence alignments and analysis of those alignments is carried out at the nucleotide and amino acid level using the ALIGN program (Alignment Editor Version 4/97; Dominick Hepperle, Fontanestr. 9c, D016775, Neuglobsow, Germany). In performing the analysis, subject sequences are pasted in, and the PHYLIP Interleaved format employed. The homology analysis is carried out using the "Analyze" section of the program, and specifically the option entitled "Distance Analysis." This calculates % homologies and the number of different sites between species, using a minimum of two amino acid sequences (i.e., two "species"). Minimal and maximal homologies are calculated as %. The basis for homology analysis is done as % identity, on the calculation of "number of identical amino acids (or bases) divided by the total number of amino acids (or bases) multiplied by 100" to give a percentage value. Amino acid sequences are placed into the ALIGN program along with published phytase sequences and a manual alignment at the amino acid level is carried out. From this, the deduced translation for the PCR product obtained using degenerate primers may be obtained.

Example 7

Southern Analysis for Library Production

Genomic DNA from different species is digested with a range of restriction enzymes overnight at 37° C. Successfully digested DNA is run out on a 1% agarose gel in preparation for transfer to the nylon membrane. After completion of electrophoresis, the agarose gel is soaked for 10 min. in 0.2M HCl to depurinate the DNA and then rinsed briefly in ddH$_2$O. The DNA is transferred to the Hybond-N+ membrane (Amersham International PLC) by alkali capillary blotting. The blot is set up so that the nylon filter is sandwiched between the gel and a stack of absorbent paper towels. A wick of Whatman 3 MM paper (Schleicher and Schuell, Dassel, Germany) is prepared on a glass plate over a reservoir of transfer buffer (0.4M NaOH). The gel is inverted on the wick, taking care to avoid the formation of air bubbles, and surrounded by strips of Nescofilm to prevent the blotting action of the paper towels from by-passing the gel at its edges. The gel is covered with an equal sized piece of Hybond-N+ membrane which had been cut in the corner to match the gel and pre-wetted in 3×SSC. Next, 3-5 pieces of 3 MM paper are placed on top of the filter and the blot completed by adding a 10 cm stack of blotting paper followed by a 0.5 kg weight. The blot is left for 8-24 h to transfer the DNA. The membrane is then washed briefly in 2×SSC at RT and baked in a vacuum oven at 80° C. to fix the DNA to the membrane. An isolated fragment from the procedures above is used to probe the Southern blot. It is firstly labeled with $^{32}$P isotope by use of the High Prime DNA Labeling Kit (Boehringer Mannheim). Denatured fragment is added into a random primed labeling reaction which incorporates radio-labeled adenine. The Southern blot is prehybridised for 1 hour at 42° C. in 12 mL of Easy-Hyb buffer (Boehringer Mannheim) in a hybridization tube. Radiolabeled probe is denatured and added to 5 mL of Easy-Hyb hybridization buffer and left to hybridize overnight at 42° C. Following hybridization, the blot is washed by incubation in 40 mL 3×SSC, 0.1% SDS for 15 min at 42° C. This low stringency wash is repeated with fresh wash solution. After stringency washing, the lot is rinsed in 3×SSC, sealed in clear plastic and exposed to x-ray film. This is left for 2 hours and the film developed.

Strong hybridizing bands may be observed for a given species digest. Such results indicate that the fragment can be used as a probe for library screening.

Example 8

Isolation of a Polynucleotide Sequence from the Genome of a Species of Interest Encoding a Phytase 8A. Genomic Library Generation and Screening Following the Southern hybridization analysis, a partial genomic library may be made in order to try and clone a full-length phytase gene. A size restricted plasmid library targeting a digestion fragment (as estimated from Southern analysis) is generated. Digested genomic DNA is run out on a 1.25% agarose gel. The digested fragments of a preferred approximate size are extracted from the gel, and purified by Glass-Max (Gibco-BRL, Scotland). Purified genomic fragments are used in a shotgun ligation reaction with restriction nuclease linearized pSK II Bluescript vector (Stratagene). The vector is first dephosphorylated before ligation, and the ligation reaction is carried out at 14° C. overnight. The library is produced by transformation of *E. coli* XL-10 Gold ultra-competent cells (Stratagene). 100 ml aliquots cells are removed from −80° C. storage and thawed on ice for transformation. 4 mL of b-mercaptoethanol is added to the cells on ice. 3 ml of ligation mix is added to the mixture and the mixture incubated on ice for 20 min. The cells are then heat shocked at 42° C. for 30 sec and returned to ice for 2 min. The transformation mixture is added to 0.9 mL of NZY-broth, and the cells incubated with shaking and without selection to allow expression of the ampicillin resistance gene. The transformed cells are plated out on blue/white selection LB-agar plates, and left to incubate overnight at 37° C. The colonies are lifted onto nitrocellulose filters by the method of Maniatis (10% SDS—lysis, 3 min; 1.5M NaOH-denaturation, 5 min; 1.5M TricHCl—neutralisation, 5 min; 3×SSC—rinse, 5 min). The filters are then baked for 2 hours at 80° C. under vacuum to fix the DNA. The library is screened with $^{32}$P radiolabeled 636 bp probe in the same manner as for Southern hybridization. After hybridization the filters are washed twice in 3×SSC, 0.1% SDS, 42° C., 15 min. The filters are then rinsed in 3×SSC, sealed in plastic and exposed to X-ray film overnight at −80° C. Positive hybridizing spots are identified on the film. These are aligned to the agar plates containing the transformants. The hybridizing spots are matched up single colonies on the agar plates. All colonies in the radius of the hybridizing spot are picked up using sterile loops and used to inoculate 2 mL of Luria broth. The cultures are grown at 37° C. for 2 hours. Dilutions of the cultures are made from $10^{-1}$ to $10^{-5}$ and 100 mL of each sample is plated out on LB-amp agar plates and incubated overnight at 37° C. The plates which have between 10 and 150 colonies on them are chosen to go forward for a secondary screen. Colony lifts are done as before, and filters are processed using the same procedures. Fresh $^{32}$P labeled probe is prepared, and the filters screened in the same way as outlined previously. Stringency washes are carried out using 2×SSC, 0.1% SDS at 42° C. for 15 min. Filters are then rinsed in 2×SSC, sealed in plastic and exposed to X-ray film for 2 hours. The developed film should shows hybridizing spots, consistent with amplification of the positive colonies from the primary screen. The film is then aligned to the plates, and the spots co-ordinated to see if they corresponded to single isolated colonies. The best positives that match up to single colonies are picked and used to inoculate Luria broth for plasmid DNA preparations. Plasmid DNA is purified by Qiaspin Mini-Prep kit (Qiagen) and restriction analysis carried out to estimate the size of the inserts. All clones giving the same restriction profile can be used to suggest an insert size. Clones may be partially sequenced to determine if they are the correct gene/gene fragment. The full sequence of these clones is then determined.

8B. Percentage Identity Comparison Between Fungal Phytases

The deduced polypeptide product of the cloned phytase gene fragment is used for homology analysis with published phytases. The analysis shows percent identities and, together with analysis of the translated sequence, may provided evidence that the gene fragment cloned is a homolog of a specific phytase.

8C. Generation and Screening of a Restriction Enzyme-Based Size-Restricted Genomic Library to Isolate Remainder of Phytase Gene In order to isolate the remaining portion of a gene, a second restriction enzyme may be used to generate a second partial genomic library, and fragments may then be subcloned together. The restriction endonuclease recognition sites present within a cloned phytase sequence are identified using Webcutter. Of particular interest are sites for enzymes that are used in the Southern analysis discussed above. Very large fragments (e.g., 8 Kb), would be difficult to clone in a plasmid-based library a low degree of hybridization with a specific restriction enzyme band argues against use of such in a library screen, and the presence of two bands in a restriction enzyme lane is likely to complicate the screening process. The library is made as before in pBluecript SKII, and screened using the same probe. A selection of positive hybridizing colonies are chosen and aligned to colonies on the plates. Matching colonies are picked for plasmid DNA preparations. Restriction analysis may show how many clones have inserts. These clones are then fully sequenced.

8D. Amplification of Contiguous Phytase Gene for Heterologous Expression

A composite phytase sequence is produced from genomic clones and used to design a number of upstream and downstream primers which could be used to amplify a contiguous phytase gene sequence. PCR amplification is also designed to facilitate cloning and expression of the complete phytase gene in to a heterologous expression vector (e.g., pGAPT-PG, a 5.1 Kb construct provided by Genencor International, Inc.). Restriction enzyme sites within the multiple cloning site of the vector which are not present within the phytase gene sequence are determined. A number of 5' and 3' flanking primers may be designed using the phytase gene sequence, and modified to include the restriction enzyme recognition sites for these enzymes.

Restriction enzyme recognition sites are designed into the primer sequences to facilitate cloning into the expression vector. The upstream and downstream flanking regions used to design the primers are arbitrarily chosen at approximately 100 bp upstream from the ATG (start) codon and downstream from the TAG (stop) codon respectively. The gene sequence used is also chosen to contain as equal balance of bases as possible.

Amplification of the phytase gene by PCR may be done using genomic DNA combinations of primers. PCR should amplify a region corresponding to the full-length phytase gene. The desired product produced by amplification with the primers is cloned into a vector and several clones which contain the correct size of insert are selected for sequencing. Homology analysis of the clone sequences is then performed and a full length phytase sequence determined.

PCR amplification genomic DNA is carried out using a combination of 5' primers and 3' primers, and using a high fidelity DNA polymerase, Pfu, to minimize error for expression of the phytase gene. This polymerase is Pfu DNA polymerase (Stratagene) and comes as part of the Pfu DNA polymerase kit for PCR. For these reactions, reaction buffer, dNTPs, target DNA and primers are mixed together, and 2.5 units of Pfu polymerase added in a final reaction volume of 50 µL. After amplification, a 5 µL aliquot of the reaction mixture is analyzed by gel electrophoresis. Selected fragments are cloned directly into the vector pCR-Blunt II TOPO (Invitrogen), and a select number of clones analyzed to confirm the presence of the correct insert. (Blunt-ended PCR products that are generated by Pfu DNA polymerase are cloned into the Zero Blunt®TOPO®PCR cloning kit (Invitrogen). This vector contains a MCS site and a kanamycin gene for antibiotic resistance, but also allows selection based on disruption of the lethal E. coli gene ccdb, as opposed to blue-white selection. Purified PCR product (50-200 ng) is added to 1 µL of pCR-BluntII-TOPO vector and the reaction volume made up to 5 µL with sterile water. This is mixed gently and left to incubate for 5 min at room temperature. 1 µL of 6×TOPO Cloning Stop Solution is added, and the reaction left on ice or frozen at –20° C. for up to 24 hours for transformation.) The integrity of the engineered restriction sites are also confirmed by this analysis. A number of clones are prepared and sequenced. Sequence analysis may confirm the presence of a full-length phytase gene. This gene may then be taken forward for expression in a heterologous system, and subsequent biochemical characterisation of the enzyme.

8E. Analysis of Phytase Sequence

An alignment is made of the isolated sequence and published phytases and homology analysis done, on a % identity basis.

Example 9

Cloning, Expression and Characterization of the Phytase

Over-expression of the phytase gene in a heterologous host may be done to produce enough protein to carry out characterization of the enzyme.

9A. Cloning of Phytase Gene Into Expression Vector and Transformation in to a Host The full-length phytase gene is amplified with a high-fidelity DNA polymerase, is produced using primers that are engineered to contain two restriction enzyme sites (e.g., EcoRV and AgeI). These sites are used to facilitate cloning into the expression vector (e.g., pGAPT-PG). The phytase clones are digested with the enzymes to produce a single insert fragment. The vector is also digested with these enzymes and linearize. The phytase gene fragment is ligated to the expression vector, and a number of transformants produced. A selection of these clones is analyzed to confirm the presence of the insert. The phytase clones are then used to transform swollen spores of A. nidulans by electroporation.

The transformation of host such as A. niger strain FGSC A767 and A. nidulans FGSC A1032 by electroporation is adapted from the protocol of O, Sanchez and J. Aguirre developed for A. nidulans. 50 mL of YG medium (0.5% yeast extract, 2% glucose, supplemented with 10 mM uridine and 10 mM uracil) is inoculated at $10^7$ spores/mL with appropriate spore suspension. The cultures are grown for 4 hr at 25° C. at 300 rpm on rotary shaker. Swollen spores are collected by centrifugation at 400 rpm for 5 min at 4° C. Spores are resuspended in 200 mL ice-cold sterile water and centrifuged at 4000 rpm for 5 min at 4° C. The supernatant is poured off and the spores are resuspended in 12.5 ml YED media pH 8.0 (1% yeast extract, 1% glucose, 20 mM HEPES) and incubated for 60 min at 30° C. at 100 rpm on rotary shaker. The spores are collected by centrifugation at 400 rpm for 5 min, then resuspended in 1 mL of ice-cold EB buffer (10 mM tris-HCl, pH 7.5, 270 mM sucrose, 1 mM Lithium acetate) at a concentration of $10^9$ conidia.mL$^{-1}$ and kept on ice. 50 µl of the swollen spore suspension is mixed with 1 to 2 µg DNA in a total volume of 60 µl in sterile Eppendorf and kept on ice for 15 min. The suspension is transferred to 0.2 cm electroporation cuvette. Electroporation is carried out in a BioRad electroporation device (settings 1 kV, 400 W, 25 µF). 1 mL of ice-cold YED is added to the suspension after electroporation, and the combined mix is transferred to a pre-chilled sterile 15 mL Falcon tube and kept on ice for 15 min. This is then incubate at 30° C. for 90 min at 100 rpm on rotary shaker, with the tubes in a horizontal position. The spores are plated out and transformants are observed after 36-48 hours.

Circular plasmid DNA may be used. A. niger strain FGSC A767 and A. nidulans strain FGSC A1032 can be obtained from the Fungal Genetics Stock Center, University of Kansas Medical Center, 3901 Rainbow Boulevard, Kansas City, Kans., USA.

9B. Preliminary Characterization of Transformants

Transformants are selected for further analysis. Spores from each of these transformants are used to inoculate selective media, and spore suspensions of each clone are made. These are used to inoculate liquid cultures of the transformants which are screened for phytase activity. Cultures are grown over 72 hours, and the supernatants collected. Samples are desalted in PD-10 columns, and the protein samples eluted in 0.25 M sodium acetate. Phytase assays are carried out in the standard conditions (pH 5.5, 37° C. for 30 min). Clones are identified having phytase activity. These are taken forward for further analysis.

9C. Time of Maximal Expression of Phytase in Liquid Culture

In order to assess when the level of phytase production is at its highest for subsequent biochemical characterisation, a series of liquid cultures of clones are generated over a 2-day to 7-day period. Cultures are inoculated with spore suspension of the appropriate transformants, and harvested at each day over this period. Culture supernatants are processed as standard, and the desalted culture supernatant is assayed under standard phytase conditions. The time point of highest phytase activity is then determined Liquid cultures are harvested at each time point, desalted and eluted in 0.25 mM sodium acetate pH 5.5. Phytase assays are carried out under standard conditions (pH 5.5, 37° C., 30 min) in duplicate. Activity is expressed in phytase units per mL of culture supernatant (μmoles of Pi released min-1 mL-1).

Untransformed host may also be assayed across these timepoints as a control. Protein samples from selected supernatant samples (day 4 and day 6), both before and after desalting are analyzed by SDS-PAGE to determine levels of secretion.

9D. Southern Analysis of Transformants

Although there may be evidence that the phytase gene has been successfully cloned into the expression vector, and that expression of an active enzyme had been achieved, molecular evidence may also be obtained. Genomic DNA preparations are made from the transformed host, and from the original untransformed host. The DNA is digested with a restriction enzyme, preferably one where there is no internal site within the phytase gene, and Southern hybridization analysis of the transformants is carried out. The Southern blots are analyzed with a phytase probe from species under investigation. Single strong hybridizing bands seen for the transformants under conditions of medium to high stringency (3×SSC) indicate successful cloning. If there is no evidence of any other hybridizing bands, it can be concluded that a single-copy of the phytase gene is present in the transformed host. A lack of hybridizing bands in the untransformed sample indicates that there is no homology between the phytase of interest and any phytases present in the host genome.

9E. Biochemical Characterization of a Phytase

To prove that the cloned gene represents a specific phytase activity, and to characterize that activity, a range of biochemical analyses are carried out on the over-expressed enzyme. Preliminary characterization may indicate that the gene is producing a phytic-acid hydrolyzing activity. This analysis can be extended to examine activity at different pHs, temperatures and against different substrates.

Transformants are taken forward for these analyses, and cultures are harvested at optimum expression time, as determined above. With phytic acid as the substrate, the pH effect on enzyme activity can be shown. The purified enzyme sample is desalted from culture supernatant, and eluted in 0.025 mM sodium acetate pH 5.0. This is then added to substrate which is made in solutions of the following buffers: pH 3.0:0.4M glycine-HCl, pH 4.0: 0.4M Sodium acetate, pH 5.0:0.4M Sodium acetate, pH 6.0:0.4M imidazole-HCl, pH 7.0:0.4M Tris-HCl, pH 8.0:0.4M Tris-HCl pH 9.0:0.4M Tris-HCl. An optimum pH for the phytase activity may be determined, as well. Little activity seen when 4-nitrophenyl-phosphate is used as the substrate indicates a high level of specificity for the phytic-acid substrate.

The temperature profile of the enzyme is characterized using pH 5.0 buffer, over a range of temperatures, using phytic acid as the substrate. The phytase temperature activity range and optimum activity temperature can be determined.

Preliminary stability studies may also be carried out on the phytase. Samples of the protein are left at −20° C., 4° C., and 37° C. overnight and then assayed under standard conditions. Samples may also be exposed to high temperature (e.g., 80-105° C. for 5-25 minutes) to determine the thermostability of the phytase activity. Residual activity is based on comparison to phytase activity determinations taken from the samples before exposure to each condition. Samples may be assayed afterwards in the same assay conditions.

Of course, it should be understood that a wide range of changes and modifications can be made to the preferred embodiment described above. It is therefore intended that the foregoing detailed description be understood in the context of the following claims, including all equivalents, which are intended to define the scope of this invention.

The Sequence Listing is contained on a separately submitted CD-ROM entitled GC645-2-US-seqlist.TXT (151 KB) created Sep. 15, 2004 which is incorporated in its entirety by reference herewith.

The invention claimed is:

1. An isolated polynucleotide encoding an enzyme, said enzyme having phytase activity and comprising an amino acid sequence having at least 95% identity to the amino acid sequence of SEQ ID NO: 8.

2. An isolated polynucleotide encoding an enzyme having phytase activity, comprising a polynucleotide sequence (i) having at least 95% identity to the nucleotide sequence of SEQ ID NO: 7, or (ii) the full complement of the sequence of (i).

3. An expression construct comprising the polynucleotide of claim 1.

4. A vector comprising the expression construct of claim 3.

5. A host cell transformed with the vector of claim 4.

6. A method of producing an enzyme having phytase activity, comprising:
  (a) providing a host cell transformed with an expression vector comprising the polynucleotide of in claim 1;
  (b) cultivating said transformed host cell under conditions suitable for said host cell to produce said phytase; and
  (c) recovering said phytase.

7. The method of claim 6, wherein said host cell is an *Aspergillus* species.

8. An expression construct comprising the polynucleotide of claim 2.

9. A vector comprising the expression construct of claim 8.

10. A host cell transformed with the vector of claim 9.

11. A method of producing an enzyme having phytase activity, comprising:
  (a) providing a host cell transformed with an expression vector comprising the polynucleotide of claim 2;
  (b) cultivating said transformed host cell under conditions suitable for said host cell to produce said phytase; and
  (c) recovering said phytase.

12. The method of claim 11, wherein said host cell is an *Aspergillus* species.

* * * * *